(12) United States Patent
Wabnitz et al.

(10) Patent No.: US 8,507,498 B2
(45) Date of Patent: *Aug. 13, 2013

(54) 4, 6-DISUBSTITUTED AMINOPYRIMIDINE DERIVATIVES AS INHIBITORS OF PROTEIN KINASES

(75) Inventors: Philipp Wabnitz, Dusseldorf (DE); Heike Schauerte, Munich (DE); Hans Allgeier, Loerrach-Haagen (DE); Martin Augustin, Seefeld-Hechendorf (DE); Lutz Zeitlmann, Munich (DE); Michael A. Pleiss, Sunnyvale, CA (US); Gabriele Stumm, Unterhaching (DE); Anke Mueller, Germering (DE); Axel Choidas, Herdecke (DE); Bert Klebl, Dortmund (DE); Gerhard Mueller, Utting (DE); Wilfried Schwab, Velbert (DE); Joelle Le, Saffron Walden (GB); Jackie Macritchie, Saffron Walden (GB); Don Simpson, Saffron Walden (GB)

(73) Assignee: Ingenium Pharmaceuticals GmbH, Martinsried (DE)

( * ) Notice: Subject to any disclaimer, the term of this patent is extended or adjusted under 35 U.S.C. 154(b) by 357 days.

This patent is subject to a terminal disclaimer.

(21) Appl. No.: 12/451,039

(22) PCT Filed: Apr. 24, 2008

(86) PCT No.: PCT/EP2008/055017
§ 371 (c)(1),
(2), (4) Date: Jul. 2, 2010

(87) PCT Pub. No.: WO2008/129080
PCT Pub. Date: Oct. 30, 2008

(65) Prior Publication Data
US 2011/0306602 A1    Dec. 15, 2011

(30) Foreign Application Priority Data
Apr. 24, 2007 (WO) ................. PCT/EP2007/003608
Apr. 25, 2007 (EP) ..................................... 07106951

(51) Int. Cl.
*A01N 43/54* (2006.01)
*C07D 239/42* (2006.01)
*C07D 401/04* (2006.01)

(52) U.S. Cl.
USPC ........................................ 514/256; 544/327

(58) Field of Classification Search
USPC ........................................................ 544/327
See application file for complete search history.

(56) References Cited

U.S. PATENT DOCUMENTS

| 5,908,848 | A | 6/1999 | Miller et al. | |
|---|---|---|---|---|
| 2006/0106023 | A1 | 5/2006 | Guzi et al. | |
| 2007/0191344 | A1 | 8/2007 | Choidas et al. | |
| 2009/0221581 | A1* | 9/2009 | Wabnitz et al. | 514/235.8 |
| 2010/0168144 | A1* | 7/2010 | Schauerte et al. | 514/275 |
| 2010/0184780 | A1* | 7/2010 | Schauerte et al. | 514/256 |
| 2010/0184789 | A1* | 7/2010 | Wabnitz et al. | 514/275 |

FOREIGN PATENT DOCUMENTS

| WO | 0172745 A | 10/2001 |
|---|---|---|
| WO | 02079197 A | 10/2002 |
| WO | 03076436 A | 9/2003 |
| WO | 2004041164 A2 | 5/2004 |
| WO | 2005009980 A | 2/2005 |
| WO | 2005012262 A | 2/2005 |
| WO | 2005026129 A | 3/2005 |
| WO | 2005027902 A | 3/2005 |
| WO | WO 2005026129 A1 * | 3/2005 |
| WO | 2005070900 A | 8/2005 |
| WO | 2005121106 A | 12/2005 |
| WO | 2006125616 A | 11/2006 |
| WO | WO 2006125616 A2 * | 11/2006 |

OTHER PUBLICATIONS

S.R. Byrn et al, Solid-State Chemistry of Drugs, 233-247, 516 (2nd ed., 1999).*
J.H. Poupaert, Drug Design: Basic Principles and Applications, in 2 Encyclopedia of Pharmaceutical Technology 1362-1369, 1367 (James Swarbrick ed., 3rd ed., 2007).*
Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*
Ulrich, Chapter 4: Crystallization, Kirk-Othmer Encyclopedia of Chemical Technology, pp. 1-7, Aug. 2002.
Vippagunta et al., Crystalline Solids, Advanced Drug Delivery Reviews, 48, pp. 3-26, 2001.
West, Solid Solutions, Solid State Chemistry and its Applications, pp. 358 & 365, 1988.
Gura et al., Systems for Identifying new Drugs are Often Faulty, Science, 278: 1041-1042, 1997.
Banker et al., Prodrugs, Modern Pharmaceutics, Third Edition, Revised and Expanded, pp. 451 and 596, 1996.
Bundgaard, Design of Prodrugs, p. 1, 1985.

(Continued)

*Primary Examiner* — James O Wilson
*Assistant Examiner* — Alexander R Pagano
(74) *Attorney, Agent, or Firm* — Olson & Cepuritis, Ltd.

(57) ABSTRACT

The present invention relates to inhibitors of general Formula (I) of cyclin-dependent kinases and therapeutic applications thereof. Furthermore, the invention relates to compounds for preventing and/or treating any type of pain, inflammatory disorders, immunological diseases, proliferative diseases, infectious diseases, cardiovascular diseases and neurodegenerative diseases.

24 Claims, 5 Drawing Sheets

(56) References Cited

OTHER PUBLICATIONS

Wolff, Some Consideration for Prodrug Design, Burger's Medicinal Chemistry and Drug Discovery, 5th Edition, vol. 1: Principles and Practice, pp. 975-977, 1995.
Traxler, Protein Tyrosine Kinase Inhibitors in Cancer Treatment, Expert Opinion on Therapeutic Patents, 7(6): 571-588, 1997.
Simone, Oncology: Introduction, Cecil Textbook of Medicine, 20th Edition, vol. 1, pp. 1004-1010, 1996.
LuValle et al., Cell Cycle Control in Growth Plate Chondocytes, Frontiers in Bioscience 5, d493-503 (May 2000).
Douglas, Jr., Introduction to Viral Diseases, Cecil Textbook of Medicine, 20th Edition, vol. 2, pp. 1739-1747, 1996.
Blain et al., Different Integration of the Cyclin-Dependent Kinase (CDK) Inhibitor p27Kipi with Cyclin A-Cdk2 and Cyclin D2-Cdk4, The Journal of Biological Chemistry, 272(41): 25863-72 (1997).
Damasio, Alzheimer's Disease and Related Dementias, Cecil Textbook of Medicine, 20th Edition, vol. 2, 1992-6, 1996.
Layzer, Degenerative Diseases of the Nervous System, Cecil Textbook of Medicine, 20th Edition, vol. 2, 2050-7, 1996.
Johnson et al., Relationships Between Drug Activity in NCI Preclinical In Vitro and In Vivo Models and Early Clinical Trials, British Journal of Cancer, 84 (10): 1424-1431, 2001.
Nonomura et al., Gene Transfer of a Cell Cycle Modulator Exerts Anti-Inflammatory Effects in the Treatment of Arthritis, J. Immunol., Nov. 1, 2003; 171 (9) 4913-9.

* cited by examiner

4, 6-DISUBSTITUTED AMINOPYRIMIDINE DERIVATIVES AS INHIBITORS OF PROTEIN KINASES

This application is the National Stage of PCT/EP2008/055017, filed on Apr. 24, 2008, which is incorporated herein by reference in its entirety.

BACKGROUND OF THE INVENTION

One of the most important and fundamental processes in biology is the division of cells during the cell cycle. This process ensures the controlled production of subsequent generations of cells with defined biological function. It is a highly regulated phenomenon and responds to a diverse set of cellular signals both within the cell and from external sources. Cyclin-dependent protein kinases ("CDKs"), constitute a family of well-conserved enzymes that play multiple roles within the cell, such as cell cycle regulation and transcriptional control (*Science* 1996, Vol. 274:1643-1677; *Ann. Rev. Cell Dev. Biol.*, 1997, 13:261-291).

Some members of the family, such as CDK1, 2, 3, 4, and 6 regulate the transition between different phases of the cell cycle, such as the progression from a quiescent stage in G1 (the gap between mitosis and the onset of DNA replication for a new round of cell division) to S (the period of active DNA synthesis), or the progression from G2 to M phase, in which active mitosis and cell division occur. Other members of this family of proteins, including CDK7, 8, and 9 regulate key points in the transcription cycle, whereas CDK5 plays a role in neuronal and secretory cell function.

CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). To date, thirteen kinase subunits have been identified in humans (Chen et al., *Biochem. Biophys. Res. Commun.*, 2007, 354:735-40; S. Mani et al., *Exp. Opin. Invest. Drugs*, 2000, 9(8):1849-1870; J. C. Sergere et al., *Biochem. Biophys. Res. Commun.*, 2000, 276:271-277; D. Hu et al, *J. Biochem. Chem.*, 2003, 278(10):8623-8629). As the name implies, the CDKs display an absolute dependence on the cyclin subunit in order to phosphorylate their target substrates, and different kinase/cyclin pairs function to regulate progression through specific portions of the cell cycle.

CDK9 in association with its cyclin partners (cyclin T1, T2a, T2b, or K) constitutes the catalytic component of the positive P-TEFb protein kinase complex that functions during the elongation phase of transcription by phosphorylating the carboxyl-terminal domain (CTD) of the largest subunit of RNA polymerase II. P-TEFb acts in concert with positive transcription factor NfkB as well as negative transcription factors, thus overcoming a block of transcriptional elongation (Liu and Herrmann 2005).

It is known that cell-cycle dysregulation, which is one of the cardinal characteristics of neoplastic cells, is closely associated with genetic alteration and deregulation of CDKs and their regulators, suggesting that inhibitors of CDKs may be useful as therapeutics for proliferative diseases, such as cancer. Thus, small molecule inhibitors targeting CDKs have been the focus of extensive interest in cancer therapy (*Current Opinion in Pharmacology*, 2003, 3:362-370). The ability of inhibiting cell cycle progression suggests a general role for small molecule inhibitors of CDKs as therapeutics for proliferative diseases, such as cancer, neuro-fibromatosis, psoriasis, fungal infections, endotoxic shock, transplantation rejection, vascular smooth cell proliferation associated with artherosclerosis, pulmonary fibrosis, arthritis, glomerulonephritis and post-surgical stenosis and restenosis (U.S. Pat. No. 6,114,365). While inhibition of cell cycle-related CDKs is clearly relevant in oncology applications, this may not be the case for the inhibition of RNA polymerase-regulating CDKs. Recently, inhibition of CDK9/cyclin T function was linked to prevention of HIV replication and the discovery of new CDK biology thus continues to open up new therapeutic indications for CDK inhibitors (Sausville, E. A. Trends Molec. Med. 2002, 8, S32-S37), such as, for example, viral infections (WO 02/100401). CDK inhibitors could conceivably also be used to treat other conditions such as immunological diseases and neurodegenerative diseases, amongst others.

More than 50 pharmacological CDK inhibitors have been described, some of which have potent antitumor activity (Current Opinion in Pharmacology, 2003(3): 362-370). A comprehensive review about the known CDK inhibitors may be found in Angew. Chem. Int. Ed. Engl. 2003, 42(19):2122-2138.

The use of 2-anilino-4-phenylpyrimidine derivatives as cyclin-dependent kinase inhibitors for the treatment of e.g. cancer has been reported in WO 2005/012262. Furthermore, 2-pyridinylamino-4-thiazolyl-pyrimidine derivatives for the treatment of cancer etc. have been described in WO 2005/012298. The use of 4,5-dihydro-thiazolo, oxazolo and imidazolo[4,5-h]quinazolin-8-ylamines as protein kinase inhibitors is known from WO 2005/005438. Furthermore, indolinone derivatives and induribin derivatives, which are useful as cyclin-dependent kinase inhibitors have been disclosed in WO 02/081445 and WO 02/074742. Additionally, CDK inhibitors for various therapeutic applications have been described in WO2005/026129.

Known CDK inhibitors may be classified according to their ability to inhibit CDKs in general or according to their selectivity for a specific CDK. Flavopiridol, for example, acts as a "pan" CDK antagonist and is not particularly selective for a specific CDK (Current Opinion in Pharmacology, 2003(3): 362-370). Purine-based CDK inhibitors, such as olomoucine, roscovitine, purvanolols and CGP74514A are known to exhibit a greater selectivity for CDKs 1, 2 and 5, but show no inhibitory activity against CDKs 4 and 6 (Current Opinion in Pharmacology, 2003(3): 362-370). Furthermore, it has been demonstrated that purine-based CDK inhibitors such as roscovitine can exert anti-apoptotic effects in the nervous system (Pharmacol Ther 2002, 93:135-143) or prevent neuronal death in neurodegenerative diseases, such as Alzheimers's disease (Biochem Biophys Res Commun 2002 (297):1154-1158; Trends Pharmacol Sci 2002 (23):417-425).

Given the tremendous potential of targeting CDKs for the therapy of conditions such as proliferative, immunological, infectious, cardiovascular and neurodegenerative diseases, the development of small molecules as selective inhibitors of particular CDKs constitutes a desirable goal.

The present invention provides novel small molecule inhibitors of cyclin-dependent kinases. Preferably, said small molecule inhibitors show an increased potency to inhibit a particular CDK, in particular CDK9. Said small molecule inhibitors may have a therapeutic utility for the treatment of conditions such as proliferative, immunological, neurodegenerative, infectious and cardiovascular diseases. Furthermore, the small molecule inhibitors of the present invention have surprisingly been shown to exert a beneficial effect in the treatment of inflammatory diseases and of any type of pain.

Current treatments for pain are only partially effective, and many also cause debilitating or dangerous side effects. For example, many of the traditional analgesics used to treat severe pain induce debilitating side effects such as nausea, dizziness, constipation, respiratory depression, and cognitive dysfunction (Brower, 2000).

Although there is already a broad panel of approved pain medications like non-narcotic analgesics, opioid analgesics, calcium channel blockers, muscle relaxants, and systemic corticosteroids available, said treatments remain merely empirical and, while they may relieve the symptoms of pain, they do not lead to complete relief in most cases. This is also due to fact that the mechanisms underlying the development of the different types of pain are still only poorly understood. Researchers are only just beginning to appreciate the complexity and diversity of the signaling systems used to relay nerve impulses for each type of pain.

Generally, pain is defined as an unpleasant sensory and emotional experience associated with actual or potential tissue damage, or described in terms of such damage, according to the International Association for the Study of Pain (IASP). Specifically, pain may occur as acute or chronic pain.

Acute pain occurs for brief periods of time, typically less than 1 month and is associated with temporary disorders. It is a natural body response to let the host be aware of physiological or biochemical alteration that could result in further damage within a short period of time. It is felt when noxious stimuli activate high threshold mechanical and/or thermal nociceptors in peripheral nerve endings and the evoked action potentials in thinly myelinated (Aδ) and/or unmyelinated (C) afferent fibres reach a conscious brain. Said noxious stimuli may be provided by injury, surgery, illness, trauma or painful medical procedures. Acute pain usually disappears when the underlying cause has been treated or has healed. Unrelieved acute pain, however, may lead to chronic pain problems that may result in long hospital stays, rehospitalizations, visits to outpatient clinics and emergency departments, and increased health care costs.

In contrast to acute pain, chronic pain persists long after the initial injury has healed and often spreads to other parts of the body, with diverse pathological and psychiatric consequences. Chronic somatic pain results from inflammatory responses to trauma in peripheral tissues (e.g., nerve entrapment, surgical procedures, cancer, or arthritis), which leads to oversensitization of nociceptors and intense searing pain responses to normally non-noxious stimuli (hyperalgesia). Chronic pain is continuous and recurrent and its intensity will vary from mild to severe disabling pain that may significantly reduce quality of life.

Chronic pain is currently treated with conventional analgesics such as NSAIDs (Ibuprofen, Naproxen), Cox-2 inhibitors (Celecoxib, Valdecoxib, Rofecoxib) and opiates (codeine, morphin, thebain, papaverin, noscapin). For a significant number of patients however, these drugs provide insufficient pain relief.

Another subtype of pain, inflammatory pain, can occur as acute as well as chronic pain. Resulting injuries of tissue and neurons must not but may develop into long-lasting chronic neuropathic pain effects in succession to such inflammatory events.

Inflammatory pain is mediated by noxious stimuli like e.g. inflammatory mediators (e.g. cytokines, such as TNF α, prostaglandins, substance P, bradykinin, purines, histamine, and serotonine), which are released following tissue injury, disease, or inflammation and other noxious stimuli (e.g. thermal, mechanical, or chemical stimuli). In addition, cytokines and growth factors can influence neuronal phenotype and function (Besson 1999). These mediators are detected by nociceptors (sensory receptors) that are distributed throughout the periphery of the tissue. Said nociceptors are sensitive to noxious stimuli (e.g. mechanical, thermal, or chemical), which would damage tissue if prolonged (Koltzenburg 2000). A special class of so called C-nociceptors represent a class of "silent" nociceptors that do not respond to any level of mechanical or thermal stimuli but are activated in presence of inflammation only.

Current approaches for the treatment of especially inflammatory pain aim at cytokine inhibition (e.g. IL1β) and suppression of pro-inflammatory TNFα. Current approved anti-cytokine/anti-TNFalpha treatments are based on chimeric antibodies such as Infliximab and Etanercept which reduce TNFα circulation in the bloodstream. TNFα is one of the most important inflammatory mediators that induces synthesis of important enzymes such as COX-2, MMP, iNOS, cPLa$_2$ and others. The main drawbacks of these "biologicals", however, reside in their immunogenic potential with attendant loss of efficacy and their kinetics that lead to a more or less digital all-or-nothing reduction of circulating TNFα. The latter can result in severe immune suppressive side effects.

A distinct form of chronic pain, neuropathic (or neurogenic) pain, arises as a result of peripheral or central nerve dysfunction and includes a variety of conditions that differ in etiology as well as location. Generally, the causes of neuropathic pain are diverse, but share the common symptom of damage to the peripheral nerves or components of central pathways. The causative factors might be metabolic, viral or mechanical nerve lesion. Neuropathic pain is believed to be sustained by aberrant somatosensory processes in the peripheral nervous system, the CNS, or both. Neuropathic pain is not directly linked to stimulation of nociceptors, but instead, is thought to arise e.g. from oversensitization of glutamate receptors on postsynaptic neurons in the gray matter (dorsal horn) of the spinal cord.

Neuropathic pain is associated with conditions such as nerve degeneration in diabetes and postherpetic neuralgia (shingles). Neuropathic pain conditions are the consequence of a number of diseases and conditions, including diabetes, AIDS, multiple sclerosis, stump and phantom pain after amputation, cancer-related neuropathy, post-herpetic neuralgia, traumatic nerve injury, ischemic neuropathy, nerve compression, stroke, spinal cord injury.

Management of neuropathic pain remains a major clinical challenge, partly due to an inadequate understanding of the mechanisms involved in the development and maintenance of neuropathic pain. Many existing analgesics are ineffective in treating neuropathic pain and most of current narcotic and non-narcotic drugs do not control the pain. Current clinical practice includes the use of a number of drug classes for the management of neuropathic pain, for example anticonvulsants, tricyclic antidepressants, and systemic local anaesthetics. However, the usual outcome of such treatment is partial or unsatisfactory pain relief, and in some cases the adverse effects of these drugs outweigh their clinical usefulness. Classic analgesics are widely believed to be poorly effective or ineffective in the treatment of neuropathic pain. Few clinical studies on the use of non steroidal anti-inflammatory drugs (NSAIDs) or opiates in the treatment of neuropathic pain have been conducted, but in those which have, the results appear to indicate that NSAIDs are poorly effective or ineffective and opiates only work at high doses. A review analysing the controlled clinical data for peripheral neuropathic pain (PNP) (Pain, November, 1997 73(2), 123-39) reported that NSAIDs were probably ineffective as analgesics for PNP and that there was no long-term data supporting the analgesic effectiveness of any drug.

Available analgesic drugs often produce insufficient pain relief. Although tricyclic antidepressants and some antiepileptic drugs, for example gabapentin, lamotrigine and carbamazepine, are efficient in some patients, there remains a large unmet need for efficient drugs for the treatment of these conditions.

In conclusion, there is a high unmet need for safe and effective methods of pain treatment, in particular of chronic inflammatory and neuropathic pain.

SUMMARY OF THE INVENTION

The present invention is directed to inhibitors of cyclin-dependent kinases and to methods and compositions for treating and/or preventing any type of pain, inflammatory disorders, immunological diseases, proliferative diseases, infectious diseases, cardiovascular diseases and neurodegenerative diseases comprising: administering an effective amount of at least one inhibitor of a cyclin-dependent kinase (cdk, CDK) to a subject in need thereof.

The inhibitors of the present invention fall within general formula (I):

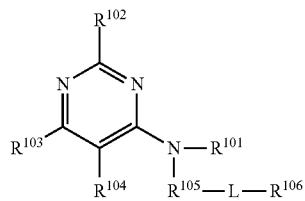

(I)

wherein
$R^{101}$ is selected from the group consisting of:
hydrogen, linear or branched $C_1$-$C_6$ substituted or unsubstituted alkyl, linear or branched $C_2$-$C_6$ alkenyl, and linear or branched $C_2$-$C_6$ alkynyl;
$R^{102}$ is selected from the group consisting of:
hydrogen, linear or branched substituted or unsubstituted $C_1$-$C_6$ alkyl, linear or branched $C_2$-$C_6$ alkenyl, linear or branched $C_2$-$C_6$ alkynyl, —F, —Cl, —Br, —I, —CN, —NH$_2$, N(C$_1$-C$_4$alkyl)$_2$, and —NO$_2$;
$R^{104}$ is selected from the group consisting of:
hydrogen, linear or branched substituted or unsubstituted $C_1$-$C_6$ alkyl, linear or branched $C_2$-$C_6$ alkenyl, linear or branched $C_2$-$C_6$ alkynyl, —F, —Cl, —Br, —I, —CN, —NH$_2$ and —NO$_2$;
$R^{103}$ is selected from substituted or unsubstituted phenyl or pyridine, wherein each substituent is independently selected from the group consisting of linear or branched $C_1$-$C_6$ substituted or unsubstituted alkyl, linear or branched substituted or unsubstituted $C_1$-$C_6$ alkoxy, linear or branched $C_2$-$C_6$ alkenyl, substituted or unsubstituted $C_{2-4}$ alkenyloxy, linear or branched $C_2$-$C_6$ alkynyl, substituted or unsubstituted $C_{3-7}$cycloalkyl, substituted or unsubstituted heterocycloalkyl, substituted or unsubstituted —O-heterocycloalkyl, substituted or unsubstituted $C_{1-4}$alkylsulfonyl, substituted or unsubstituted mono- and di-($C_1$-$C_4$alkyl)sulfonamido, —F, —Cl, —Br, —I, —COOH, —CN, —NH$_2$, —OH, —NO$_2$, —NR$^{20}$R$^{21}$, —CO—R$^{20}$, —CO—O—R$^{20}$, or —CO—NR$^{20}$R$^{21}$, wherein R$^{20}$ and R$^{21}$ are independently of each other selected from hydrogen, linear or branched substituted or unsubstituted $C_1$-$C_6$ alkyl, acetyl, or substituted or unsubstituted amino;
$R^{105}$ is selected from substituted or unsubstituted phenyl or pyridine, wherein each substituent is independently selected from the group consisting of linear or branched $C_1$-$C_6$ substituted or unsubstituted alkyl, linear or branched substituted or unsubstituted $C_1$-$C_6$ alkoxy, linear or branched $C_2$-$C_6$ alkenyl, linear or branched $C_2$-$C_6$ alkynyl, —F, —Cl, —Br, —I, —CN, —NH$_2$, —NO$_2$, —NR$^{20}$R$^{21}$, —CO—R$^{20}$ or —CO—NR$^{20}$R$^{21}$, wherein R$^{20}$ and R$^{21}$ are independently of each other selected from hydrogen, linear or branched substituted or unsubstituted $C_1$-$C_6$ alkyl, acetyl, or substituted or unsubstituted amino;
$R^{106}$ is selected from hydrogen, linear or branched substituted or unsubstituted $C_1$-$C_8$ alkyl, substituted or unsubstituted $C_{3-4}$alkenyl, substituted or unsubstituted $C_{3-8}$-cycloalkyl, substituted or unsubstituted aryl, substituted or unsubstituted heteroaryl, substituted or unsubstituted heterocyclyl, substituted or unsubstituted $C_3$-$C_8$ cycloalkyl or —(CH$_2$)$_q$-A, wherein q is an integer selected from 0 to 5 and A is selected from hydrogen, —F, —Cl, —Br, —I, —CN, —NH$_2$, —NO$_2$, linear or branched substituted or unsubstituted $C_1$-$C_6$ alkyl, linear or branched substituted or unsubstituted $C_1$-$C_6$ alkoxy, linear or branched $C_2$-$C_6$ alkenyl, linear or branched $C_2$-$C_6$ alkynyl, substituted or unsubstituted heterocyclyl, substituted or unsubstituted cycloalkyl or carboxamido substituted with one or two $C_1$-$C_6$ alkyl; or
$R^{106}$, when M is —NR$^{140}$—, can form a heterocyclic structure when taken together with the nitrogen of M and R$^{140}$;
L is —CR$^{150}$R$^{151}$—SO$_2$-M-,
wherein R$^{150}$ and R$^{151}$ are independently selected from the group consisting of hydrogen, linear $C_1$-$C_3$ alkyl and fluorine, wherein M is a bond or —NR$^{140}$—;
$R^{140}$ is selected from hydrogen, linear of branched substituted or unsubstituted $C_1$-$C_8$ alkyl, and substituted or unsubstituted $C_3$-$C_8$ cycloalkyl;
or, alternatively, -L-R$^{106}$, when taken together is selected from

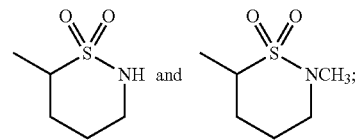

and/or tautomeric forms, N-oxide derivatives, prodrug derivatives, protected derivatives, individual isomers and mixtures of isomers thereof; and the pharmaceutically acceptable salts and solvates (e.g., hydrates) of such compounds.

DETAILED DESCRIPTION OF THE INVENTION

Definitions

The term "tautomer" as used herein includes all possible tautomeric forms of the structures used to show the compounds of the present invention, as well as their stereoisomeric, quaternary amine, N-oxide, salt, polymorph, solvate, and prodrug forms.

In certain embodiments, a compound of the invention, a salt form thereof, including a pharmaceutically acceptable salt, or a solvate form thereof, including a hydrate, is isolated. In certain embodiments, a compound of the invention, or a pharmaceutically acceptable salt thereof, is purified, e.g., to have a purity of at least 80%, preferably at least 90%, more preferably at least 95%, such as at least 97%, at least 98% or even at least 99%. Purity, as used herein, can refer to either absolute or relative purity. Absolute purity refers to the amount of compound of interest in relation to the total amount of a composition including such compound. Relative purity refers to the amount of a compound of interest in a composition relative to the amount of one or more other substances included in such composition, e.g. one or more impurities such as by-products, degradation products (e.g., metabolites, products of oxidation or hydrolysis, etc.) and/or compounds that degrade to form the compound of the invention (e.g., precursors or prodrugs). Such other substance(s) may, for example, be present in the product of a synthetic chemistry scheme for such compound of interest. Thus, absolute purity refers to the amount of the compound of interest relative to all others components of a composition including such compound, while relative purity is mainly used to describe purity with regard to closely related substances, and thus is unaffected by the addition of unrelated compounds, such as excipients, stabilizers, or other medicaments for conjoint administration. Purity can be assessed based upon weight, volume or molar ratios of one compound relative to others. Purity can be measured by a variety of analytical techniques, including elemental abundance, UV-visible spectrometry, HPLC, GC-MS, NMR, mass spectrometry, and thin layer chromatography, preferably by HPLC, GC-MS, or NMR.

In certain embodiments, a compound of the invention, or a salt thereof, is synthetically produced. The term "synthetically produced" refers to the generation of a compound using synthesis techniques well known to the skilled artisan with the aim of obtaining such compound.

In certain embodiments, a compound of the invention, a salt form thereof, including a pharmaceutically acceptable salt, or a solvate form thereof, including a hydrate, is in amorphous form.

In certain embodiments, a compound of the invention, a salt form thereof, including a pharmaceutically acceptable salt, or a solvate form thereof, including a hydrate, is in crystalline form.

The term "alkyl" refers to straight- or branched-chain saturated hydrocarbon groups. These groups may or may not be branched. Examples of alkyl include, but are not limited to, methyl, ethyl, n-propyl, i-propyl, n-butyl, s-butyl, t-butyl, n-pentyl, and s-pentyl. As disclosed herein, the terms "$C_{1-4}$ alkyl" "$C_1$-$C_4$ alkyl" are meant to refer to alkyl groups having 1 to 4 carbon atoms, such as methyl, ethyl, n-propyl, isopropyl, n-butyl, sec-butyl, isobutyl, tert-butyl. The terms "$C_{1-3}$ alkyl", "$C_{1-5}$ alkyl", "$C_{1-6}$ alkyl" and "$C_{1-8}$ alkyl" have similar meanings but have up to 3, 5, 6 and 8 carbon atoms, respectively. References to "$C_{0-4}$ alkyl" include both $C_{1-4}$ alkyl and hydrogen.

Unless otherwise specified, the term "substituted alkyl" refers to alkyl groups where one or more hydrogen atoms are replaced by one or more substituents such as, but not limited to, halogen, hydroxyl, carbonyl, alkoxy, ester, ether, cyano, phosphoryl, amino, imino, amido, sulfhydryl, alkylthio, thioester, sulfonyl, nitro, heterocyclo, aryl or heteroaryl.

It will also be understood by those skilled in the art that other moieties or groups can be substituted as well in the corresponding manner when appropriate (see, for example, in the sections describing "alkenyl", "alkynyl", "aryl", or "heteroaryl" below). It will furthermore be understood by those skilled in the art that the substituted moieties themselves can be substituted as well when appropriate.

The terms "alkenyl" and "alkynyl" herein refer to alkenyl and alkynyl groups, respectively. These groups may or may not be branched. At least one of the bonds of an alkenyl group is a double bond, other, additional, bonds may be single bonds or double bonds. At least one of the bonds of an alkynyl group is a triple bond, other, additional, bonds may be single bonds, double bonds or triple bonds. Examples of such alkenyl groups include ethenyl, 1-propenyl, 2-propenyl, 1-butenyl, 2-butenyl, 3-butenyl, 2-methyl-1-propenyl, 2-methyl-2-propenyl, and the like. Examples of such alkynyl groups include ethynyl, 1-propynyl, 2-propynyl, and so forth. The term "lower alkenyl" and "C2-6 alkenyl" refer to straight or branched chain alkene groups which have from 2 to 6 carbon atoms, such as, for example, vinyl, allyl, but-2-enyl, -but-3-enyl, or isopropenyl; the term "lower alkenyl" preferably represents allyl, -but-2-enyl, or -but-3-enyl. The terms "C3-4 alkenyl" and "C2-4 alkenyl" have similar meanings but include alkenyl groups with 3-4 and 2-4 carbon atoms, respectively.

Unless otherwise specified herein, the terms "substituted alkenyl" or "substituted alkynyl" refer to alkenyl groups or alkynyl groups, respectively, where one or more hydrogen atoms are replaced by one or more substituents such as, but not limited to, halogen, hydroxyl, carbonyl, alkoxy, ester, ether, cyano, phosphoryl, amino, imino, amido, sulfhydryl, alkylthio, thioester, sulfonyl, nitro, heterocyclo, aryl or heteroaryl. It will also be understood by those skilled in the art that the substituted moieties themselves can be substituted as well when appropriate.

As disclosed herein, the term "halo" is meant to include fluoro-, chloro-, bromo-, and iodo-.

The term C3-C8 cycloalkyl denotes the following cycloalkyls:

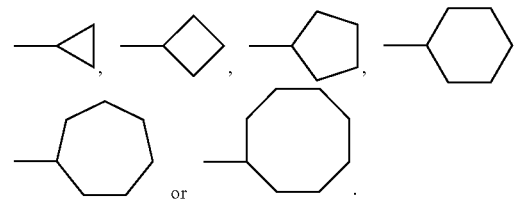

The term "aryl" is intended to mean any stable and optionally substituted monocyclic or polycyclic aromatic moiety, which may contain 3 to about 12 members per ring. This includes benzene rings or benzene ring systems fused to one or more benzene rings, to form, e.g., anthracene, phenanthrene, or naphthalene ring systems, or fused to heteroaryl rings. Wherever indicated, aryl moieties may be substituted with between 1 to about 10 substituents, and in certain embodiments greater than 10 substituents. Unless more specifically indicated herein, such substituents may be selected from a group consisting of $C_1$-$C_6$ alkyl, $C_1$-$C_6$ alkoxy, $C_1$-$C_6$ haloalkyl, $C_1$-$C_6$ haloalkoxy, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonylamino, alkylcarboxy, alkylcarboxamido, oxo, hydroxy, mercapto, amino (optionally substituted by alkyl, aryl, or heteroaryl), carboxy, tetrazolyl, carboxamido, carbamoyl (optionally substituted by alkyl, aryl, or heteroaryl), aminosulfonyl, acyl, aroyl, aroylamino, heteroaroyl, acyloxy, aroyloxy, heteroaroyloxy, alkoxycarbonyl, nitro, cyano, halo, heteroaryl, heterocyclyl, aryl, ureido, arylureido, alkylureido, cycloalkylureido, alkylthioureido, aryloxy, aralkoxy, or —O(CH$_2$)$_n$COOH, —(CH$_2$)$_n$COOH, —C(O)O (CH$_2$)$_n$R, —(CH$_2$)$_n$N(H)C(O)OR, or —N(R)S(O)$_2$R wherein n is 1-4 and R is —H, alkyl, aryl or heteroaryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, triazolyl, oxazolyl, isoxazolyl, oxadiazolyl, oxo-pyridyl, thiadiazolyl, isothiazolyl, pyridyl, pyridazyl, pyrazinyl, pyrimidyl, quinazolinyl, quinolinyl, isoquinolinyl, benzofuranyl, benzothiophenyl, indolyl, indazolyl, and substituted versions thereof. Examples of aryl groups include phenyl, p-tolyl, 4-methoxyphenyl, 4-tert-butoxyphenyl, 3-methylmethoxyphenyl, 4-fluorophenyl, 4-chlorophenyl, 3-nitrophenyl, 3-aminophenyl, 3-acetamidophenyl, 4-acetamidophenyl, 2-methyl acetamidophenyl, 2-methyl aminophenyl, 3-methyl aminophenyl, 2-amino methylphenyl, 2,4-dimethyl aminophenyl, 4-hydroxyphenyl, 3-methyl hydroxyphenyl, 1-naphthyl, 2-naphthyl, 3-amino-1-naphthyl, 2-methyl amino naphthyl, 6-amino naphthyl, 4,6-dimethoxy naphthyl and the like.

In particular embodiments of compounds of formula (III) (see below), the term aryl denotes an aromatic mono- or bicyclic 6 to 10 membered ring system such as phenyl, naphthyl, 3-chlorophenyl, 2,6-dibromophenyl, 2,4,6 tribromophenyl, 4,7-dichloronaphthyl, and preferably phenyl or naphthyl.

The terms heterocycloalkyl or heterocyclyl are meant to include a 5 to 10 membered mono- or bicyclic ring system, containing one to three heteroatoms independently selected from oxygen, sulfur or nitrogen and is preferably selected from the group comprising: aziridinyl, azetidinyl, pyrrolidinyl, tetrahydrofuranyl, tetrahydrothiophenyl, piperidinyl, piperadizinyl, piperazinyl, tetrahydropyranyl, tetrahydrothiopyranyl or morpholinyl.

The term heterocycloalkyl further comprises all heteroaryls as defined below, wherein all double bonds of the correspondent heteroaryls are replaced by single bonds.

As used herein, the term "heteroaryl" refers to any stable and optionally substituted mono- or polycyclic aromatic moiety containing one or more nitrogen, sulfur, and/or oxygen heteroatoms, where N-oxides and sulfur oxides and dioxides are permissible heteroatom substitutions. Heteroaryl moieties may contain 3 to about 12 members per ring. Wherever indicated, heteroaryl moieties may be substituted with between 1 to about 10 substituents, and in certain embodiments greater than 10 substituents. Unless more specifically indicated herein, such substituents may be selected from a group consisting of $C_1$-$C_6$ alkyl, $C_1$-$C_6$ alkoxy, $C_1$-$C_6$ haloalkyl, $C_1$-$C_6$ haloalkoxy, $C_1$-$C_6$ alkylsulfanyl, $C_1$-$C_6$ alkylsulfenyl, $C_1$-$C_6$ alkylsulfonyl, $C_1$-$C_6$ alkylsulfonylamino, arylsulfonoamino, alkylcarboxy, alkylcarboxyamido, oxo, hydroxy, mercapto, amino optionally substituted by alkyl, aryl, or heteroaryl, carboxy, tetrazolyl, carboxamido, carbamoyl optionally substituted by alkyl, aryl, or heteroaryl, aminosulfonyl, acyl, aroyl, aroylamino, heteroaroyl, acyloxy, aroyloxy, heteroaroyloxy, alkoxycarbonyl, nitro, cyano, halo, heteroaryl, heterocyclyl, aryl, ureido, arylureido, alkylureido, cycloalkylureido, alkylthioureido, aryloxy, aralkoxy, or —O(CH$_2$)$_n$COOH, —(CH$_2$)$_n$COOH, —C(O)O (CH$_2$)$_n$R, —(CH$_2$)$_n$N(H)C(O)OR, or —N(R')S(O)$_2$R wherein n is 1-4 and R is —H, alkyl, aryl or heteroaryl, multiple degrees of substitution being allowed. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl, quinazolinyl, quinolinyl, isoquinolinyl, benzofuranyl, benzothiophenyl, indolyl, indazolyl, and substituted versions thereof. In certain embodiments heteroaryl moieties are unsubstituted.

In particular embodiments of compounds of formula (III) (see below), the term heteroaryl denotes a partially or fully unsaturated 5 to 10 membered mono- or bicyclic ring system, containing one to three heteroatoms independently selected from oxygen, sulfur or nitrogen and is preferably selected from the group consisting of: pyrrolyl, furanyl, thiophenyl, thienyl, imidazolyl, pyrazolyl, thiazolyl, oxazolyl, isothiazolyl, isoxazolyl, pyridinyl, pyridyl, pyrimidinyl, pyrimidyl, pyrazinyl, pyrazyl, pyradizinyl, pyradizyl, 3-methylpyridyl, benzothienyl, 4-ethylbenzothienyl, 3,4-diethylfuranyl, pyrrolyl, tetrahydroquinolyl, quinolyl, tetrahydroisoquinolinyl, isoquinolinyl, benzoimidazolyl, benzothiazolyl, benzooxyzolyl, benzo[1,3]dioxolyl, indolyl, benzofuranyl, benzothiophenyl, indazolyl or chrom-2-onyl. It is to be understood, that in this context the term heteroaryl also comprises partially unsaturated 5 to 10 membered mono- or bicyclic ring system, wherein one up to 4 double bonds of the ring system are replaced by a single bond and wherein the ring system contains at least one double bond.

When any variable occurs more than once in general formulae (I) to (III)(including formula (IIIa)) (see below) or in any substituent, its definition on each occurrence is independent of its definition at every other occurrence. For example, when a compound comprises more than one $R^5$ and/or $R^6$ substituent, they can be the same or different.

Compounds of the Present Invention

In the context of the present invention, it is intended to include all stereoisomeric forms of the compounds of the present invention, as well as their quaternary amine, N-oxide, salt, polymorph, solvate, prodrug and derivative forms. The term "stereoisomer" as used herein includes all possible stereoisomeric forms, including all chiral, diastereomeric, racemic forms and all geometric isomeric forms of a structure, unless the specific stereochemistry or isomer form is specifically indicated. Where the compounds of the present invention contain one or more chiral centers, all possible enantiomeric and diastereomeric forms, as well as the racemate, are included. It is well known in the art how to prepare optically active forms, such as by resolution of racemic forms or by synthesis from optically active starting materials. All processes used to prepare compounds of the present invention and intermediates made therein are considered to be part of the present invention.

In certain embodiments, the compounds of formula (I) do not include protected derivatives, derivative forms, individual isomers other than stereoisomers, and mixtures of isomers thereof other than mixture of stereoisomers. In certain embodiments, the compounds of formula (I) do not include tautomeric forms.

One aspect of the present invention relates to compounds of formula (I)
wherein
$R^{101}$ is selected from the group comprising:
hydrogen, linear or branched $C_1$-$C_6$ substituted or unsubstituted alkyl, linear or branched $C_2$-$C_6$ alkenyl or linear or branched $C_2$-$C_6$ alkynyl;
$R^{102}$ and $R^{104}$ are independently selected from the group consisting of:
hydrogen, linear or branched substituted or unsubstituted $C_1$-$C_6$ alkyl, linear or branched $C_2$-$C_6$ alkenyl, linear or branched $C_2$-$C_6$ alkynyl, —F, —Cl, —Br, —I, —CN, —NH$_2$ or —NO$_2$;
$R^{103}$ and $R^{105}$ are independently selected from substituted or unsubstituted phenyl or pyridine, wherein each substituent is independently selected from the group consisting of linear or branched $C_1$-$C_6$ substituted or unsubstituted alkyl, linear or branched substituted or unsubstituted $C_1$-$C_6$ alkoxy, linear or branched $C_2$-$C_6$ alkenyl, linear or branched $C_2$-$C_6$ alkynyl, —F, —Cl, —Br, —I, —CN, —NH$_2$, —NO$_2$, —NR$^{20}$R$^{21}$, —CO—R$^{20}$ or —CO—NR$^{20}$R$^{21}$, wherein R$^{20}$ and R$^{21}$ are independently of each other selected from hydrogen, linear or branched substituted or unsubstituted $C_1$-$C_6$ alkyl, acetyl, or substituted or unsubstituted amino;

R$^{106}$ is selected from hydrogen, linear or branched substituted or unsubstituted C$_1$-C$_8$ alkyl, substituted or unsubstituted aryl, substituted or unsubstituted heteroaryl, substituted or unsubstituted heterocyclyl, substituted or unsubstituted C$_3$-C$_8$ cycloalkyl or —(CH$_2$)$_q$-A, wherein q is an integer selected from 0 to 5 and A is selected from hydrogen, —F, —Cl, —Br, —I, —CN, —NH$_2$, —NO$_2$, linear or branched substituted or unsubstituted C$_1$-C$_6$ alkyl, linear or branched substituted or unsubstituted C$_1$-C$_6$ alkoxy, linear or branched C$_2$-C$_6$ alkenyl, linear or branched C$_2$-C$_6$ alkynyl, substituted or unsubstituted heterocyclyl, substituted or unsubstituted cycloalkyl or carboxamido substituted with one or two C$_1$-C$_6$ alkyl; or R$^{106}$, when M is —NR$^{140}$—, can form a heterocyclic structure when taken together with the nitrogen of M and R$^{140}$; L is —CR$^{150}$R$^{151}$—SO$_2$-M-, wherein R$^{150}$ and R$^{151}$ are independently selected from the group consisting of hydrogen, linear C$_1$-C$_3$ alkyl and fluorine, wherein M is a bond or —NR$^{140}$—;

R$^{140}$ is selected from hydrogen, linear or branched substituted or unsubstituted C$_1$-C$_8$ alkyl, and substituted or unsubstituted C$_3$-C$_8$ cycloalkyl;

and/or tautomeric forms and/or pharmaceutically acceptable salts thereof.

In particular embodiments of this aspect of the invention, R$^{101}$ is selected from methyl and hydrogen. In more particular embodiments R$^{101}$ is hydrogen.

In particular embodiments R$^{102}$ and R$^{104}$ are independently selected from methyl, amino and hydrogen. In other particular embodiments R$^{102}$ is —NH$_2$ or hydrogen and R$^{104}$ is hydrogen. In other particular embodiments R$^{102}$ is hydrogen. In other particular embodiments R$^{104}$ is hydrogen. In even other particular embodiments R$^{102}$ and R$^{104}$ are both hydrogen.

In particular embodiments of the invention R$^{103}$ is substituted or unsubstituted phenyl. In other particular embodiments R$^{103}$ is substituted or unsubstituted pyridine. In certain embodiments R$^{103}$ is substituted with linear or branched C$_1$-C$_8$ alkoxy, particularly linear or branched C$_1$-C$_4$ alkoxy, more particularly methoxy. In certain particular embodiments R$^{103}$ is phenyl substituted with linear or branched C$_1$-C$_6$ alkoxy, particularly linear or branched C$_1$-C$_4$ alkoxy, more particularly methoxy. In other particular embodiments R$^{103}$ is pyridine substituted with linear or branched C$_1$-C$_6$ alkoxy, particularly linear or branched C$_1$-C$_4$ alkoxy, more particularly methoxy. In certain embodiments R$^{103}$ is substituted in the ortho-position. In certain particular embodiments R$^{103}$ is phenyl substituted in the ortho-position. In other particular embodiments R$^{103}$ is phenyl substituted with methoxy in the ortho-position.

Where R$^{103}$ is pyridine, the nitrogen atom of said pyridine may be in any position of the pyridine group. In particular embodiments R$^{103}$ is ortho-pyridine. In other embodiments R$^{103}$ is meta-pyridine. In yet other embodiments R$^{103}$ is para-pyridine.

In other particular embodiments R$^{103}$ is substituted with one or more residues R$^{141}$.

In particular embodiments R$^{105}$ is substituted or unsubstituted phenyl. In certain particular embodiments R$^{105}$ is substituted phenyl. In other particular embodiments R$^{105}$ is unsubstituted phenyl.

In other particular embodiments, R$^{105}$ is substituted or unsubstituted phenyl and L is linked to said phenyl group in meta-position to —NR$^{101}$—.

In other particular embodiments R$^{105}$ is substituted or unsubstituted pyridine. In certain particular embodiments R$^{105}$ is substituted pyridine. In other particular embodiments R$^{105}$ is unsubstituted pyridine. Where R$^{105}$ is pyridine, the nitrogen atom of said pyridine may be in any position of the pyridine group. In particular embodiments R$^{105}$ is pyrid-2-yl. In other embodiments R$^{105}$ is pyrid-3-yl. In yet other embodiments R$^{105}$ is pyrid-4-yl.

The optional substituents of R$^{105}$ are in addition to the residue -L-R$^{106}$ depicted in formula (I), which is compulsory. In particular embodiments the substituent of R$^{105}$ is selected from methyl, methoxy, trifluoromethyl, isopropyl, ethyl, ethoxy, —NMe$_2$, —NHAc, —NMeAc, —CO-Me, —CO—NH$_2$, —CO—NH-Me and —CO—NMe$_2$. In particular embodiments such optional substituent of R$^{105}$ is linear or branched substituted or unsubstituted C$_1$-C$_4$ alkyl. In yet other particular embodiments the substituent of R$^{105}$ is methyl, ethyl and isopropyl. In particular embodiments, R$^{105}$ is linear or branched C$_1$-C$_4$ alkoxy. In yet other particular embodiments R$^{105}$ is methoxy or ethoxy. Substituent on R$^{105}$ may be in ortho-, meta-, or para-position to —NR$_1$—. In particular embodiments R$^{105}$ is in ortho-position. In other particular embodiments R$^{105}$ is in meta-position. In yet other particular embodiments R$^{105}$ is in the para-position. In certain alternative embodiments, R$^{105}$ is unsubstituted.

In particular aspects of the invention, R$^{106}$ is selected from hydrogen, linear or branched substituted or unsubstituted C$_1$-C$_8$ alkyl, and —(CH$_2$)$_q$-A, wherein q is an integer selected from 0 to 105 and A is selected from linear or branched substituted or unsubstituted C$_1$-C$_6$ alkoxy, substituted or unsubstituted heterocyclyl, substituted or unsubstituted heteroaryl and carboxamido substituted with one or two C$_1$-C$_6$ alkyl. In certain particular aspects of the invention, R$^{106}$ is hydrogen. In other particular aspects of the invention R$^{106}$ is linear or branched unsubstituted C$_1$-C$_5$ alkyl. In certain particular aspects of the invention R$^{106}$ is methyl, isopropyl or 3-methyl-butyl. In some particular aspects of the invention R$^{106}$ is methyl.

In certain aspects of the invention R$^{106}$ is —(CH$_2$)$_q$-A, wherein q is an integer selected from 0 to 3 and A is linear, unsubstituted C$_1$-C$_6$ alkoxy. In certain particular aspects of the invention q is 2 and A is methoxy.

In other aspects of the invention R$^{106}$ is —(CH$_2$)$_q$-A, wherein q is an integer selected from 0 to 3 and A is carboxamido substituted with two C$_1$-C$_3$ alkyl groups. In certain particular aspects of the invention q is 2 and A is carboxamido substituted with two methyl groups. In other aspects of the invention R$^{106}$ is —(CH$_2$)$_q$-A, wherein q is an integer selected from 0 to 3 and A is substituted or unsubstituted heterocyclyl. In certain particular aspects of the invention said substituted or unsubstituted heterocyclyl is substituted or unsubstituted pyrrolidine or piperidine. In other aspects of the invention R$^{106}$ is (CH$_2$)$_q$-A, wherein q is 0 and A is unsubstituted heteroaryl. In certain particular aspects of the invention said unsubstituted heteroaryl is thiazole or oxazole.

In other particular aspects of the invention M is —NR$^{140}$— and R$^{106}$ is selected from

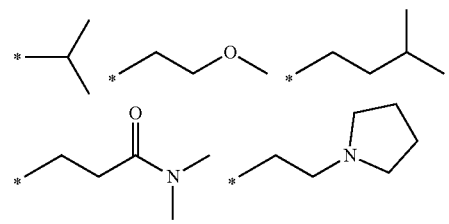

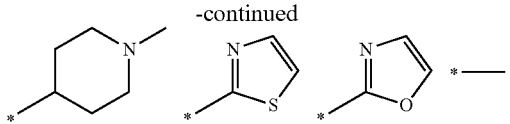

hydrogen

In certain aspects of the present invention M is —NR$^{140}$— and R$^{106}$ taken together with the nitrogen of M and R$^{140}$ forms a heterocyclic structure. In particular aspects of the invention said heterocyclic structure is selected from:

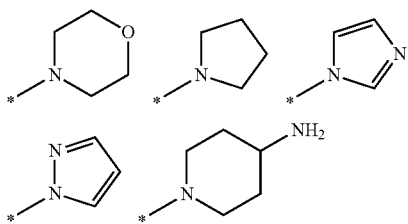

In particular embodiments R$^{140}$ is selected from hydrogen and linear C$_1$-C$_4$ alkyl or C$_3$-C$_4$ cycloalkyl. In particular embodiments R$^{140}$ is selected from hydrogen, methyl, ethyl and isopropyl. In certain particular embodiments wherein R$^{140}$ is hydrogen. In other particular embodiments R$^{140}$ is methyl.

L is —CR$^{150}$R$^{151}$—SO$_2$-M-,

Wherein R$^{150}$ and R$^{151}$ are independently selected from the group consisting of hydrogen, linear C$_1$-C$_3$ alkyl and fluorine, wherein M is a bond or —NR$^{140}$—.

For the avoidance of doubt it is noted that the —CR$^{150}$R$^{151}$ group of L, and not the -M-group of L, is linked to R$^{105}$ of a compound of formula (I) or the phenyl group of a compound of formula (II). L can be linked to R$^{105}$ of a compound of formula (I) or the phenyl group of a compound of formula (II) in ortho-, meta- or para-position. In particular embodiments L is linked to R$^{105}$ in meta-position.

In particular embodiments R$^{150}$ is hydrogen. In other particular embodiments R$^{151}$ is hydrogen. In other particular embodiments R$^{150}$ and R$^{151}$ are both hydrogen. In yet other embodiments R$^{150}$ and R$^{151}$ are independently selected from the group consisting of hydrogen, methyl and fluorine. In particular embodiments, both R$^{150}$ and R$^{151}$ are fluorine.

M is a bond or —NR$^{140}$—. In particular embodiments M is —NR$^{140}$—. In other embodiments R$^{150}$ and R$^{151}$ are both hydrogen and M is —NR$^{140}$—. In other particular embodiments of the invention M is a bond.

In a further aspect of the present invention, there is provided a compound of general formula (II),

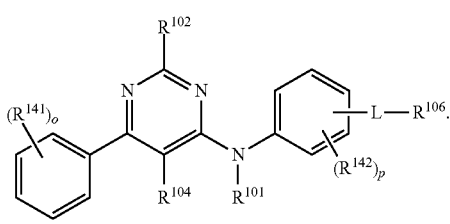

R$^{101}$ and R$^{104}$ are hydrogen;
R$^{102}$ is hydrogen or —NH$_2$.

R$^{106}$ is selected from hydrogen, linear or branched substituted or unsubstituted C$_1$-C$_8$ alkyl, substituted or unsubstituted aryl, substituted or unsubstituted heteroaryl, substituted or unsubstituted heterocyclyl, substituted or unsubstituted C$_3$-C$_8$ cycloalkyl and —(CH$_2$)$_q$-A, wherein q is an integer selected from 0 to 5 and A is selected from hydrogen, —F, —Cl, —Br, —I, —CN, —NH$_2$, —NO$_2$, linear or branched substituted or unsubstituted C$_1$-C$_6$ alkyl, linear or branched substituted or unsubstituted C$_1$-C$_6$ alkoxy, linear or branched C$_2$-C$_6$ alkenyl, linear or branched C$_2$-C$_6$ alkynyl, substituted or unsubstituted heterocyclyl, substituted or unsubstituted cycloalkyl or carboxamido substituted with one or two C$_1$-C$_6$ alkyl; or R$^{106}$, when M is —NR$^{140}$—, can form a heterocyclic structure when taken together with the nitrogen of M and R$^{140}$;

L is —CR$^{150}$R$^{151}$—SO$_2$-M-,
wherein R$^{150}$ and R$^{151}$ are independently selected from the group consisting of hydrogen, linear C$_1$-C$_3$ alkyl and fluorine, wherein M is a bond or —NR$^{140}$—;

R$^{140}$ is selected from hydrogen, linear or branched substituted or unsubstituted C$_1$-C$_8$ alkyl, and substituted or unsubstituted C$_3$-C$_8$ cycloalkyl;

o is an integer selected from 0 to 5;
p is an integer selected from 0 to 4;
each R$^{141}$ and R$^{142}$ is independently selected from the group consisting of linear or branched C$_1$-C$_6$ substituted or unsubstituted alkyl, linear or branched substituted or unsubstituted C$_1$-C$_6$ alkoxy, linear or branched C$_2$-C$_6$ alkenyl, linear or branched C$_2$-C$_6$ alkynyl, —F, —Cl, —Br, —I, —CN, —NH$_2$ or —NO$_2$;

and/or tautomeric forms and/or pharmaceutically acceptable salts thereof.

In particularly suitable compounds of general formula (II), R$^{102}$ is hydrogen.

In particular embodiments at least one R$^{141}$ is linear or branched C$_1$-C$_6$ alkoxy. In other particular embodiments at least one R$^{141}$ is linear C$_1$-C$_6$ alkoxy. In yet other particular embodiments at least one R$^{141}$ is methoxy. In particular embodiments the substitution of at least one residue R$^{141}$ is in the ortho-position. In other particular embodiments at least one residue R$^{141}$ is methoxy and the substitution of said methoxy residue is in the ortho-position.

In other particular embodiments, o is 1 or 2, but is most suitably 1.

In other particular embodiments, p is 0 or 1, but is most suitably 0.

In certain embodiments of the compounds of general formula (II), R$^{150}$ and R$^{151}$ are both fluorine.

In other embodiments, R$^{150}$ is hydrogen, in yet other embodiments, R$^{151}$ is hydrogen. In particular embodiments, R$^{150}$ and R$^{151}$ are both hydrogen In compounds of general formula (II), wherein M is —NR$^{140}$, R$^{140}$ is suitably selected from hydrogen, methyl, ethyl and isopropyl, especially hydrogen or methyl.

In suitable compounds of general formula (II), R$^{106}$ is selected from hydrogen, linear or branched substituted or unsubstituted C$_1$-C$_8$ alkyl, and —(CH$_2$)$_q$-A, wherein q is an integer selected from 0 to 5 and A is selected from linear or branched substituted or unsubstituted C$_1$-C$_6$ alkoxy, substituted or unsubstituted heterocyclyl, substituted or unsubstituted heteroaryl and carboxamido substituted with one or two C$_1$-C$_6$ alkyl.

In particularly suitable compounds of general formula (II) R$^{106}$ is hydrogen or linear or branched unsubstituted C$_{1-5}$ alkyl.

In particular embodiments of general formula (II) L is linked to the phenyl group of a compound of formula (II) in meta-position.

In other particular embodiments, L is —CH$_2$—SO$_2$—NR$^{140}$—, especially —CH$_2$—SO$_2$—NH—.

In an alternative aspect of the present invention, the inhibitor is selected among compounds according to the general Formula (III):

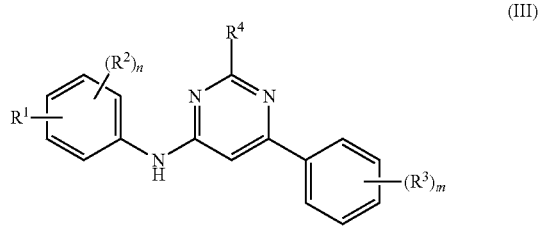

wherein

R$^1$ is —XSO$_2$NR$^5$R$^6$ or —XSO$_2$R$^8$; wherein

X is methylene;

R$^5$ and R$^6$ independently of each other are hydrogen, C$_{1-4}$alkyl, hydroxy-C$_{1-4}$alkyl or C$_{3-4}$alkenyl, C$_{3-8}$-cycloalkyl, C$_{3-8}$-cycloalkyl-C$_{1-4}$alkyl or C$_{4-7}$-heterocycloalkyl-C$_{0-4}$alkyl, C$_{4-7}$-aryl-C$_{0-4}$alkyl, C$_{4-7}$-heteroaryl-C$_{0-4}$alkyl or wherein R$^5$ and R$^6$ together with the N-atom to which they are bound also may form a 5- to 8-membered heterocycloalkyl, wherein said cycloalkyl, heterocycloalkyl, aryl, heteroaryl or alkyl is further optionally substituted by up to 2 radicals selected from the group consisting of halo, hydroxy, aminocarbonyl, C$_{1-4}$ alkyl, hydroxy-C$_{1-4}$ alkyl, C$_{1-4}$ alkyl —O—C$_{1-4}$ alkyl, C$_{1-4}$ alkyl —O— and —NR$^5$R$^6$;

or —XSO$_2$NR$^5$R$^6$ is:

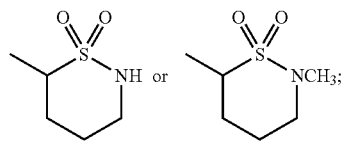

R$^8$ is C$_{1-4}$ alkyl, hydroxy-C$_{2-4}$alkyl or C$_{3-4}$alkenyl, C$_{3-8}$-cycloalkyl, C$_{3-8}$-cycloalkyl-C$_{1-4}$alkyl or C$_{4-7}$-heterocycloalkyl-C$_{0-4}$ alkyl;

wherein said cycloalkyl, heterocycloalkyl or alkyl is further optionally substituted by up to 2 radicals selected from the group consisting of halo, hydroxy, C$_{1-4}$ alkyl, hydroxy-C$_{1-4}$ alkyl, C$_{1-4}$ alkyl —O—C$_{1-4}$ alkyl, C$_{1-4}$ alkyl —O and —NR$^5$R$^6$;

n is selected from 0, 1 and 2;

R$^2$ is independently selected from halo;

m is selected from 0, 1, 2 and 3;

R$^3$ is independently selected from the group consisting of: halo, hydroxy, C$_{1-4}$alkyl, C$_{3-7}$cycloalkyl, C$_{1-4}$ alkyl -cycloalkyl, C$_{1-4}$ alkyl -heterocycloalkyl, —O-heterocycloalkyl, C$_{1-4}$alkoxy, C$_{2-4}$ alkenyloxy, —OCF$_3$, C$_{2-4}$ alkanoyl, C$_{1-4}$alkylsulfonyl, mono- and di-(C$_1$-C$_4$alkyl)sulfonamido, aminocarbonyl, mono- and di-(C$_1$-C$_4$alkyl)aminocarbonyl, aryl-C$_{1-4}$ alkoxy, heteroaryl-C$_{1-4}$ alkoxy, heterocycloalkyl-C$_{1-4}$ alkoxy, heterocycloalkyl-C$_{1-4}$ alkyl, heteroaryl-C$_{1-4}$-alkyl, C$_{1-4}$ alkyloxymethyl, hydroxy-C$_{1-4}$alkyloxymethyl, cyano, —COOH and C$_1$-C$_4$ alkoxycarbonyl, wherein the above mentioned substituents can be further substituted by radicals selected from the group of C$_{1-4}$-alkyl, hydroxyl-C$_{0-4}$-alkyl, C$_{1-4}$-alkoxy, aminocarbonyl, halo and NR$^5$R$^6$;

R$^4$ is hydrogen, C$_{1-4}$ alkyl or —NR'R'', wherein R' and R'' are each independently selected from hydrogen and C$_{1-4}$ alkyl;

and the N-oxide derivatives, prodrug derivatives, protected derivatives, individual isomers and mixtures of isomers thereof; and the pharmaceutically acceptable salts and solvates (e.g., hydrates) of such compounds.

In certain embodiments, the compounds of formula (III) do not include protected derivatives, individual isomers other than stereoisomers, and mixtures of isomers thereof other than mixture of stereoisomers.

In the compounds of general formula (III):

n is preferably 0;

m is preferably selected from 1, 2 and 3, wherein R$^3$ is preferably independently selected from the group consisting of halo, hydroxy, C$_{1-4}$alkyl, C$_{1-4}$ alkoxy, C$_{2-4}$ alkenyloxy, —OCF$_3$, C$_{2-4}$ alkanoyl, C$_{1-4}$alkylsulfonyl, mono- and di-(C$_1$-C$_4$alkyl)sulfonamido, aminocarbonyl, mono- and di-(C$_1$-C$_4$alkyl)aminocarbonyl, C$_{1-4}$ alkyloxymethyl, hydroxy-C$_{1-4}$alkyloxymethyl, cyano, —COOH and C$_1$-C$_4$ alkoxycarbonyl; or one substituent selected from C$_{3-7}$cycloalkyl, C$_{1-4}$ alkyl -cycloalkyl, C$_{1-4}$ alkyl -heterocycloalkyl, —O-heterocycloalkyl, aryl-C$_{1-4}$ alkoxy, heterocycloalkyl-C$_{1-4}$ alkoxy, heterocycloalkyl-C$_{1-4}$-alkyl, heteroaryl-C$_{1-4}$ alkoxy, heteroaryl-C$_{1-4}$-alkyl; wherein said substituents can be further substituted by one or more radicals selected from the group of C$_{1-4}$-alkyl, hydroxyl-C$_{0-4}$-alkyl, C$_{1-4}$-alkoxy, halo, aminocarbonyl, and NR$^5$R$^6$.

More preferably, m is selected from 1, 2 and 3, wherein R$^3$ is independently selected from the group consisting of methyl, ethyl, hydroxymethyl, hydroxy, methoxy, ethoxy, isopropoxy, benzyloxy, hydrogen, fluoro, chloro, trifluoromethyl, 2-methoxy-ethoxy, methoxymethyl, 2-methoxy-ethyl, tetrahydro-furan-3-yloxy, tetrahydro-furan-2-yl-methoxy, —N(CH$_3$)SO$_2$CH$_3$, piperidin-1-yl-methyl, 2-hydroxymethyl-piperidin-1-yl-methyl, 3-hydroxymethyl-piperidin-1-yl-methyl, 3-(2-hydroxy-ethyl)-piperidin-1-yl-methyl, 3-aminocarbonyl-piperidin-1-yl-methyl, dimethylaminomethyl, diethylaminomethyl, (ethyl-isopropyl-amino)-methyl, morpholin-4-ylmethyl, 4-methyl-piperazin-1-yl-methyl, [1,2,4]triazol-1-yl-methyl, pyridine-3-yl-methoxy or pyridine-4-yl-methoxy.

R$^3$ is most preferably methoxy or ethoxy.

R$^4$ is preferably hydrogen, C$_{1-4}$ alkyl or —NH$_2$, more preferably hydrogen.

R$^6$ is preferably hydrogen or methyl and R$^5$ is ethyl, 2-hydroxyethyl, isopropyl, cyclopropyl, cyclobutyl, cyclopentyl, cyclohexyl, n-propyl, tert-butyl, 3-methoxy-propyl, 2-dimethylaminoethyl, 3-dimethylaminopropyl, piperidinyl and especially 4-piperidinyl, pyridinyl and especially pyridine-3-yl or pyridin-4-yl, pyrrolidinyl and especially pyrrolidin-3-yl, tetrahydrofuranyl and especially tetrahydro-furan-3-yl, tetrahydro-furan-2-ylmethyl, 4-chloro-benzyl, thiophen-2-yl-methyl.

It is more preferred that $R^5$ and $R^6$ are both hydrogen, methyl or ethyl, or $R^5$ and $R^6$ together with the N-atom to which they are bound form morpholine, 4-aminocarbonyl-piperidine or azepane.

$R^5$ and $R^6$ are most preferably hydrogen.

$R^8$ is preferably $C_{1-4}$ alkyl or hydroxy-$C_{2-4}$-alkyl; $R^8$ is more preferably methyl or 2-hydroxyethyl.

A preferred group of compounds of formula (III) comprises those of general formula (IIIa):

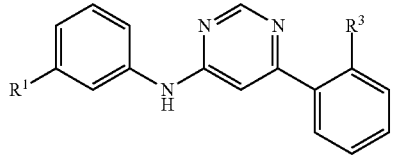

(IIIa)

wherein $R^1$ and $R^3$ have the same meaning as previously mentioned for general formula (III).

Particularly preferred compounds of the invention are those listed in Table 1.

TABLE 1

| Compound No. | Structure and IUPAC name | MS m/z | Melt Point (Celsius) |
|---|---|---|---|
| 1 | {3-[6-(2-Ethoxy-phenyl)-pyrimidin-4-ylamino]-phenyl}-methanesulfonamide | 385 (M + 1) | 236.3-238.6 |
| 2 | {3-[6-(2,3-Dimethoxy-phenyl)-pyrimidin-4-ylamino]-phenyl}-methanesulfonamide | 401 (M + 1) | 146.9-150.0 |
| 3 | {3-[6-(4-Fluoro-2-methoxy-phenyl)-pyrimidin-4-ylamino]-phenyl}-methanesulfonamide | 389 (M + 1) | 232.5-234.2 |
| 4 | {3-[6-(2-Ethoxy-5-fluoro-phenyl)-pyrimidin-4-ylamino]-phenyl}-methanesulfonamide | 403 (M + 1) | 237.9-240.4 |
| 5 | {3-[6-(2-Isopropoxy-phenyl)-pyrimidin-4-ylamino]-phenyl}-methanesulfonamide | 399 (M + 1) | 125.0-128.6 |
| 6 | {3-[6-(3-Fluoro-phenyl)-pyrimidin-4-ylamino]-phenyl}-methanesulfonamide | 359 (M + 1) | 258.8-263.1 |

TABLE 1-continued

| Compound No. | Structure and IUPAC name | MS m/z | Melt Point (Celsius) |
|---|---|---|---|
| 7 | 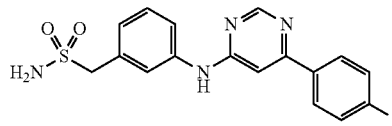<br>{3-[6-(4-Fluoro-phenyl)-pyrimidin-4-ylamino]-phenyl}-methanesulfonamide | 359 (M + 1) | 255.0-258.2 |
| 8 | 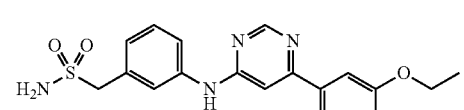<br>{3-[6-(3-Ethoxy-phenyl)-pyrimidin-4-ylamino]-phenyl}-methanesulfonamide | 385 (M + 1) | 249-252.3 |
| 9 | 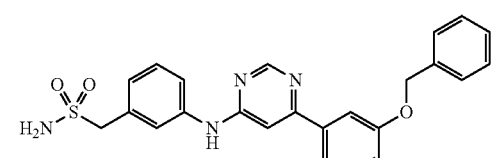<br>{3-[6-(3-Benzyloxy-phenyl)-pyrimidin-4-ylamino]-phenyl}-methanesulfonamide | 447 (M + 1) | 233.2-234.8 |
| 10 | 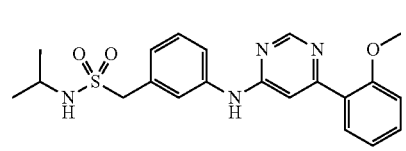 [SMILES: COc1ccccc1-c1cc(Nc2cccc(CS(=O)(=O)NC(C)C)c2)ncn1]<br>N-Isopropyl-C-{3-[6-(2-methoxy-phenyl)-pyrimidin-4-ylamino]-phenyl}-methanesulfonamide | 413 (M + 1) | 179.0-180.0 |
| 11 | 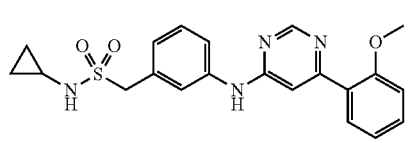 [SMILES: COc1ccccc1-c1cc(Nc2cccc(CS(=O)(=O)NC3CC3)c2)ncn1]<br>N-Cyclopropyl-C-{3-[6-(2-methoxy-phenyl)-pyrimidin-4-ylamino]-phenyl}-methanesulfonamide | 411 (M + 1) | 216.5-218.0 |
| 12 | 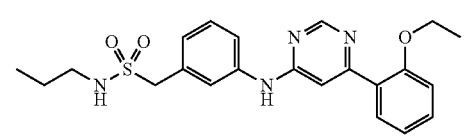 [SMILES: CCCNS(=O)(=O)Cc1cccc(Nc2cc(-c3ccccc3OCC)ncn2)c1]<br>C-{3-[6-(2-Ethoxy-phenyl)-pyrimidin-4-ylamino]-phenyl}-N-propyl-methanesulfonamide | 427 (M + 1) | 178.8-179.6 |
| 13 | 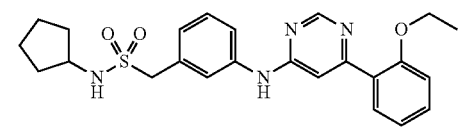 [SMILES: CCOc1ccccc1-c1cc(Nc2cccc(CS(=O)(=O)NC3CCCC3)c2)ncn1]<br>N-Cyclopentyl-C-{3-[6-(2-ethoxy-phenyl)-pyrimidin-4-ylamino]-phenyl}-methanesulfonamide | 453 (M + 1) | 178.5-179.1 |

TABLE 1-continued

| Compound No. | Structure and IUPAC name | MS m/z | Melt Point (Celsius) |
|---|---|---|---|
| 14 | 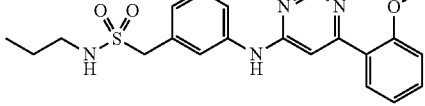<br>C-{3-[6-(2-Methoxy-phenyl)-pyrimidin-4-ylamino]-phenyl}-N-propyl-methanesulfonamide | 413 (M + 1) | 190.4-190.9 |
| 15 | 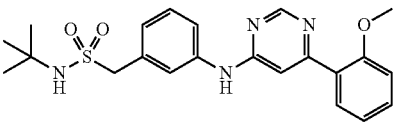 [SMILES: COc1ccccc1-c1cc(Nc2cccc(CS(=O)(=O)NC(C)(C)C)c2)ncn1]<br>N-tert-Butyl-C-{3-[6-(2-methoxy-phenyl)-pyrimidin-4-ylamino]-phenyl}-methanesulfonamide | 427 (M + 1) | 172.5-173.5 |
| 16 | 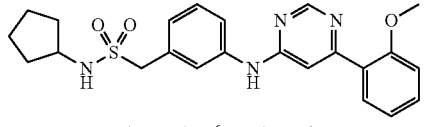<br>N-Cyclopentyl-C-{3-[6-(2-methoxy-phenyl)-pyrimidin-4-ylamino]-phenyl}-methanesulfonamide | 439 (M + 1) | 204.6-205.7 |
| 17 | 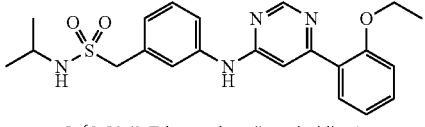<br>C-{3-[6-(2-Ethoxy-phenyl)-pyrimidin-4-ylamino]-phenyl}-N-isopropyl-methanesulfonamide | 427 (M + 1) | 142.5-143.3 |
| 18 | 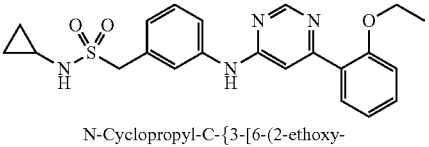<br>N-Cyclopropyl-C-{3-[6-(2-ethoxy-phenyl)-pyrimidin-4-ylamino]-phenyl}-methanesulfonamide | 425 (M + 1) | amorphous softening above 90° C. |
| 19 | 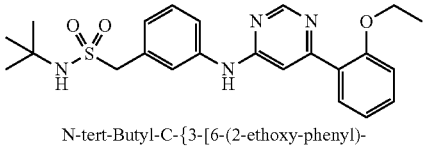<br>N-tert-Butyl-C-{3-[6-(2-ethoxy-phenyl)-pyrimidin-4-ylamino]-phenyl}-methanesulfonamide | 441 (M + 1) | 170.5-171.5 |
| 20 | 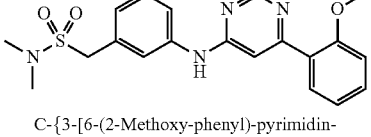<br>C-{3-[6-(2-Methoxy-phenyl)-pyrimidin-4-ylamino]-phenyl}-N,N-dimethyl-methanesulfonamide | 399 (M + 1) | 187.5-188.8 |
| 21 | <br>C-{3-[6-(2-Benzyloxy-phenyl)-pyrimidin-4-ylamino]-phenyl}-N-propyl-methanesylfonamide | 489 (M + 1) | 114.7-116.0 |

TABLE 1-continued

| Compound No. | Structure and IUPAC name | MS m/z | Melt Point (Celsius) |
|---|---|---|---|
| 22 | 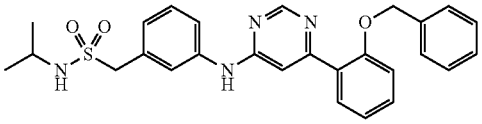 [SMILES: CC(C)NS(=O)(=O)Cc1cccc(Nc2cc(-c3ccccc3OCc3ccccc3)ncn2)c1]

C-{3-[6-(2-Benzyloxy-phenyl)-pyrimidin-4-ylamino]-phenyl}-N-isopropyl-methanesulfonamide | 489 (M + 1) | amorphous, softening above 80° C. |
| 23 | 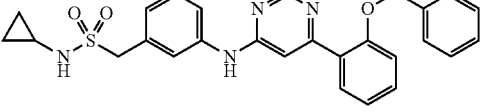

C-{3-[6-(2-Benzyloxy-phenyl)-pyrimidin-4-ylamino]-phenyl}-N-cyclopropyl-methanesulfonamide | 487 (M + 1) | 164.5-166.0 |
| 24 | 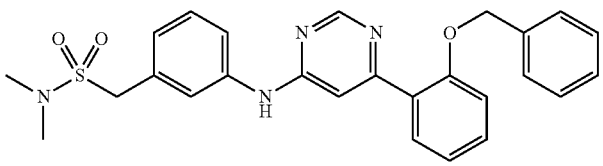 [SMILES: CN(C)S(=O)(=O)Cc1cccc(Nc2cc(-c3ccccc3OCc3ccccc3)ncn2)c1]

C-{3-[6-(2-Benzyloxy-phenyl)-pyrimidin-4-ylamino)-phenyl}-N,N-dimethyl-methanesulfonamide | 475 (M + 1) | amorphous, softening above 85° C. |
| 25 | 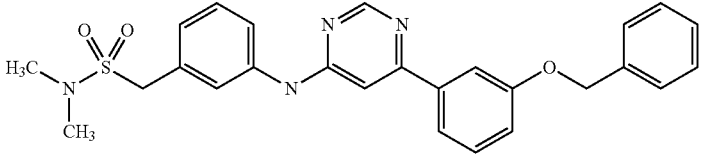 [SMILES: CN(C)S(=O)(=O)Cc1cccc(Nc2cc(-c3cccc(OCc4ccccc4)c3)ncn2)c1]

C-{3-[6-(3-Benzyloxy-phenyl)-pyrimidin-4-ylamino]-phenyl}-N,N-dimethyl-methanesulfonamide | 475 (M + 1) | 166.2-166.7 |
| 26 | 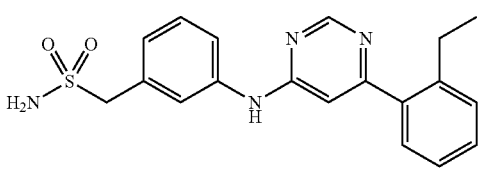 [SMILES: CCc1ccccc1-c1cc(Nc2cccc(CS(N)(=O)=O)c2)ncn1]

{3-[6-(2-Ethyl-phenyl)-pyrmidin-4-ylamino]-phenyl}-methanesulfonamide | 369 (M + 1) | amorphous, softening above 140° C. |
| 27 | 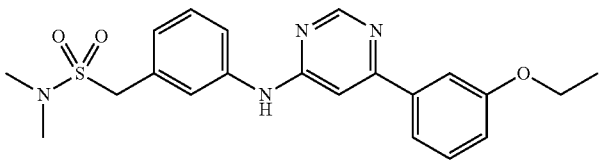 [SMILES: CCOc1cccc(-c2cc(Nc3cccc(CS(=O)(=O)N(C)C)c3)ncn2)c1]

C-{3-[6-(3-Ethoxy-phenyl)-pyrimidin-4-ylamino]-phenyl}-N,N-dimethyl-methanesulfonamide | 413 (M + 1) | 177.6-178.4 |
| 28 | 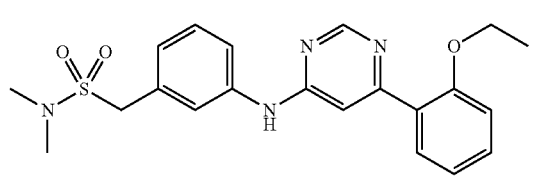 [SMILES: CCOc1ccccc1-c1cc(Nc2cccc(CS(=O)(=O)N(C)C)c2)ncn1]

C-{3-[6-(2-Ethoxy-phenyl)-pyrimidin-4-ylamino]-phenyl}-N,N-dimethyl-methanesulfonamide | 413 (M + 1) | 123.7-124.6 |

TABLE 1-continued

| Compound No. | Structure and IUPAC name | MS m/z | Melt Point (Celsius) |
|---|---|---|---|
| 29 | 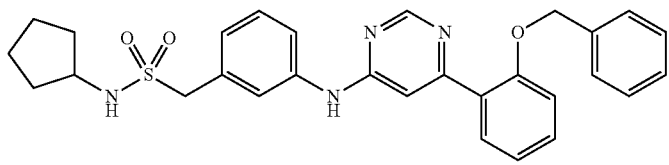 [SMILES: O=S(=O)(Cc1cccc(Nc2cc(-c3ccccc3OCc3ccccc3)ncn2)c1)NC1CCCC1]<br>C-{3-[6-(2-Benzyloxy-phenyl)-pyrimidin-4-ylamino]-phenyl}-N-cyclopentyl-methanesulfonamide | 515 (M + 1) | amorphous, softening above 75° C. |
| 30 | <br>C-{3-[6-(2-Benzyloxy-phenyl)-pyrimidin-4-ylamino]-phenyl}-N-tert-butyl-methanesulfonamide | 503 (M + 1) | amorphous, softening above 75° C. |
| 31 | 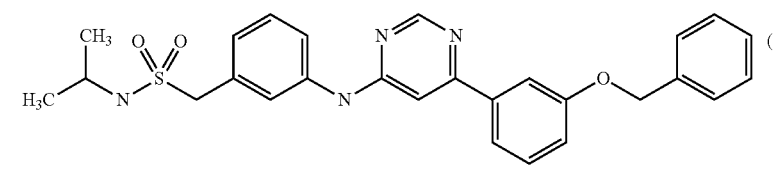<br>C-{3-[6-(3-Benzyloxy-phenyl)-pyrimidin-4-ylamino]-phenyl}-N-isopropyl-methanesulfonamide | 489 (M + 1) | 205.8-206.7 |
| 32 | 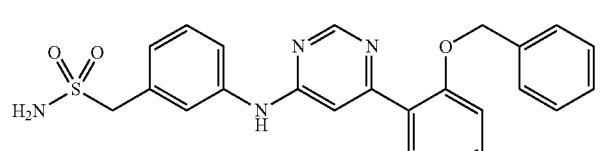<br>{3-[6-(2-Benzyloxy-phenyl)-pyrimidin-4-ylamino]-phenyl}-methanesulfonamide | 447 (M + 1) | amorphous, softening above 105° C. |
| 33 | 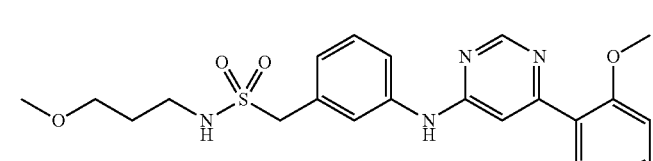<br>C-{3-[6-(2-Methoxy-phenyl)-pyrimidin-4-ylamino]-phenyl}-N-(3-methoxy-propyl)-methanesulfonamide | 443 (M + 1) | 149.2-150.8 |
| 34 | 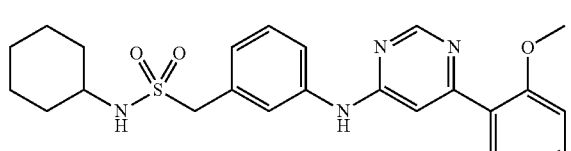<br>N-Cylcohexyl-C-{3-[6-(2-methoxy-phenyl)-pyrimidin-4-ylamino]-phenyl}-methanesulfonamide | 453 (M + 1) | 198.4-201.0 |

TABLE 1-continued

| Compound No. | Structure and IUPAC name | MS m/z | Melt Point (Celsius) |
|---|---|---|---|
| 35 | 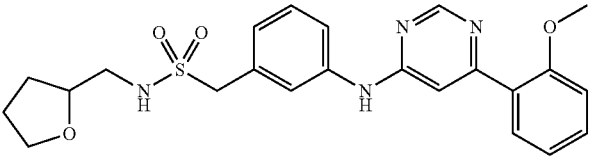 [SMILES: COc1ccccc1-c1cc(Nc2cccc(CS(=O)(=O)NCC3CCCO3)c2)ncn1]<br>C-{3-[6-(2-Methoxy-phenyl)-pyrimidin-4-ylamino]-phenyl}-N-(tetrahydro-furan-2-ylmethyl)-methanesulfonamide | 455 (M + 1) | 157.4-159.0 |
| 36 | 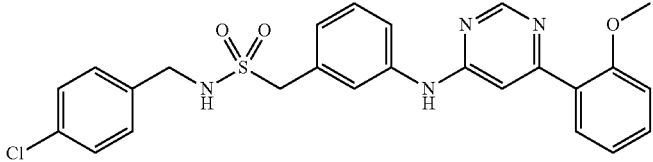 [SMILES: COc1ccccc1-c1cc(Nc2cccc(CS(=O)(=O)NCc3ccc(Cl)cc3)c2)ncn1]<br>N-(4-Chloro-benzyl)-C-{3-[6-(2-methoxy-phenyl)-pyrimidin-4-ylamino]-phenyl}-methanesulfonamide | 495 (M + 1) | 182.0-184.4 |
| 37 | 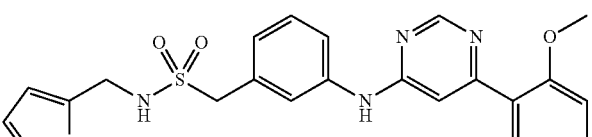<br>C-{3-[6-(2-Methoxy-phenyl)-pyrimidin-4-ylamino]-phenyl}-N-thiophen-2-ylmethyl-methanesulfonamide | 467 (M + 1) | 180.2-181.7 |
| 38 | 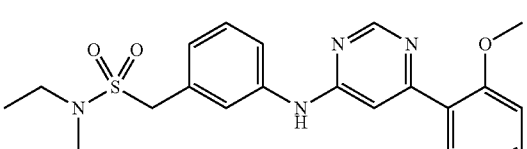<br>N,N-Diethyl-C-{3-[6-(2-methoxy-phenyl)-pyrimidin-4-ylamino]-phenyl}-methanesulfonamide | 427 (M + 1) | 107.7-110.5 |
| 39 | 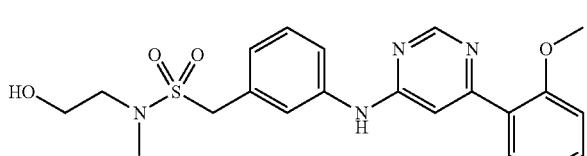<br>N-(2-Hydroxy-ethyl)-C-{3-[6-(2-methoxy-phenyl)-pyrimidin-4-ylamino]-phenyl}-N-methyl-methanesulfonamide | 429 (M + 1) | amorphous, softening above 60° C. |
| 40 | 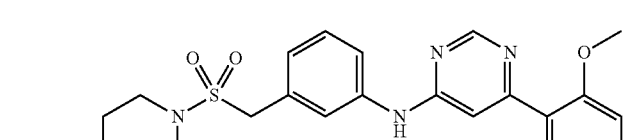<br>1-{3-[6-(2-Methoxy-phenyl)-pyrimidin-4-ylamino]-phenylmethanesulfonyl}-piperidine-4-carboxylic acid amide | 482 (M + 1) | 136.2-139.0 |

TABLE 1-continued

| Compound No. | Structure and IUPAC name | MS m/z | Melt Point (Celsius) |
|---|---|---|---|
| 41 | 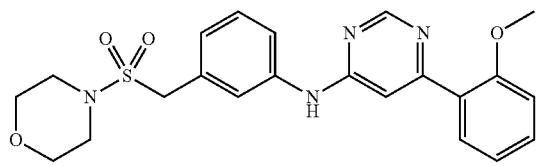 [SMILES: COc1ccccc1-c1cc(Nc2cccc(CS(=O)(=O)N3CCOCC3)c2)ncn1]<br>[6-(2-Methoxy-phenyl)-pyrimdin-4-yl]-[3-(morpholine-4-sulfonylmethyl)-phenyl]-amine | 441 (M + 1) | 145.2-147.0 |
| 42 | 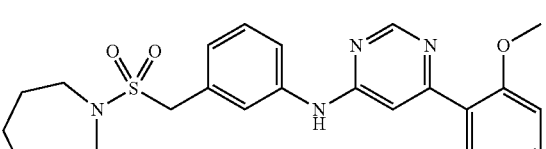<br>[3-(Azepane-1-sulfonylmethyl)-phenyl]-[6-(2-methoxy-phenyl)-pyrimidin-4-yl]-amine | 453 (M + 1) | 181.2-182.6 |
| 43 | 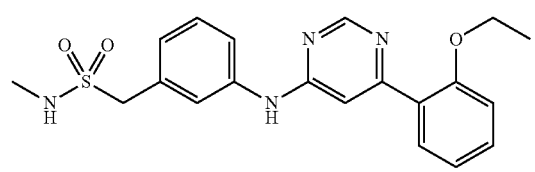<br>C-{3-[6-(2-Ethoxy-phenyl)-pyrimidin-4-ylamino]-phenyl}-N-methyl-methanesulfonamide | 399 (M + 1) | 155.9-156.5 |
| 44 | <br>C-{3-[6-(2-Benzyloxy-phenyl)-pyrimidin-4-ylamino]-phenyl}-N-methyl-methanesulfonamide | 461 (M + 1) | amorphous, softening above 80° C. |
| 45 | 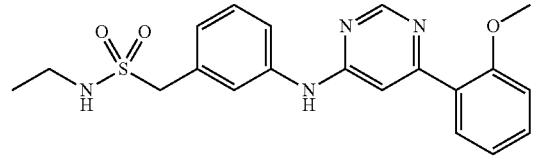 [SMILES: CCNS(=O)(=O)Cc1cccc(Nc2cc(-c3ccccc3OC)ncn2)c1]<br>N-Ethyl-C-{3-[6-(2-methoxy-phenyl)-pyrimidin-4-ylamino]-phenyl}-methanesulfonamide | 399 (M + 1) | 190.0-193.0 |
| 46 | 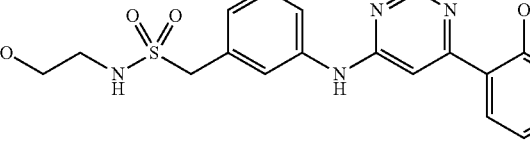<br>N-(2-Hydroxy-ethyl)-C-{3-[6-(2-methoxy-phenyl)-pyrimidin-4-ylamino]-phenyl}-methanesulfonamide | 415 (M + 1) | amorphous, softening above 70° C. |

TABLE 1-continued

| Compound No. | Structure and IUPAC name | MS m/z | Melt Point (Celsius) |
|---|---|---|---|
| 47 | C-{3-[6-(2-Benzyloxy-phenyl)-pyrimidin-4-ylamino]-phenyl}-N,N-diethyl-methanesulfonamide | 503 (M + 1) | 64.2-67.5 |
| 48 | C-{3-[6-(2-Benzyloxy-phenyl)-pyrimidin-4-ylamino]-phenyl}-N-(2-hydroxy-ethyl)-N-methyl-methanesulfonamide | 505 (M + 1) | amorphous, softening above 55° C. |
| 49 | C-{3-[6-(2-Methoxy-phenyl)-pyrimidin-4-ylamino]-phenyl}-N-methyl-methanesulfonamide | 385 (M + 1) | 213-214 |
| 50 | [3-(6-Phenyl-pyrimidin-4-ylamino)-phenyl]-methanesulfonamide | 341 (M + 1) | |
| 51 | {3-[6-(2-Chloro-phenyl)-pyrimidin-4-ylamino]-phenyl}-methanesulfonamide | 375, 377, 378 (M + 1) | |
| 52 | 2-[6-(3-Methanesulfonylmethyl-phenylamino)-pyrimidin-4-yl]-phenol | 356 (M + 1) | 200-202 |
| 53 | [6-(2-Benzyloxy-phenyl)-pyrimidin-4-yl]-(3-methanesulfonylmethyl-phenyl)-amine | 446 (M + 1) | 145.0-146.5 |

TABLE 1-continued

| Compound No. | Structure and IUPAC name | MS m/z | Melt Point (Celsius) |
|---|---|---|---|
| 54 | {3-[6-(2-Hydroxy-phenyl)-pyrimidin-4-ylamino]-phenyl}-methanesulfonamide | 357 (M + 1) | 226.0-227 |
| 55 | {3-[6-(2-Hydroxymethyl-phenyl)-pyrimidin-4-ylamino]-phenyl}-methanesulfonamide | 371 (M + 1) | 192-194 |
| 56 | {2-[6-(3-Methanesulfonylmethyl-phenylamino)-pyrimidin-4-yl]-phenyl}-methanol | 370 (M + 1) | 185.0-187.0 |
| 57 | (3-Methanesulfonylmethyl-phenyl)-{6-[2-(2-methoxy-ethoxy)-phenyl]-pyrimidin-4-yl}-amine | 414 (M + 1) | 141.0-142.9 |
| 58 | [6-(2-Benzyloxy-phenyl)-pyrimidin-4-yl]-(3-methanesulfonylmethyl-phenyl)-amine | 446 (M + 1) | |
| 59 | (3-Methanesulfonylmethyl-phenyl)-[6-(2-methoxy-phenyl)-pyrimidin-4-yl]-amine | 370 (M + 1) | |

TABLE 1-continued

| Compound No. | Structure and IUPAC name | MS m/z | Melt Point (Celsius) |
|---|---|---|---|
| 60 | 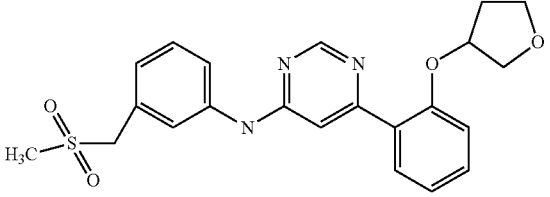 [SMILES: CS(=O)(=O)Cc1cccc(Nc2cc(-c3ccccc3OC3CCOC3)ncn2)c1] (3-Methanesulfonylmethyl-phenyl)-{6-[2-(tetrahydro-furan-3-yloxy)-phenyl]-pyrimidin-4-yl}-amine | 426 (M + 1) | |
| 61 | 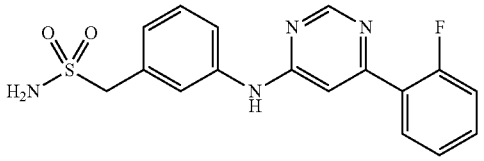 [SMILES: NS(=O)(=O)Cc1cccc(Nc2cc(-c3ccccc3F)ncn2)c1] {3-[6-(2-Fluoro-phenyl)-pyrimidin-4-ylamino]-phenyl}-methanesulfonamide | 359, 361 (M + 1) | |
| 62 | 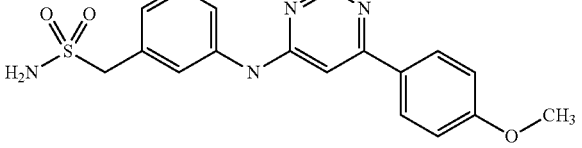 {3-[6-(4-Methoxy-phenyl)-pyrimidin-4-ylamino]-phenyl}-methanesulfonamide | 371 (M + 1) | 228-229 |
| 63 | 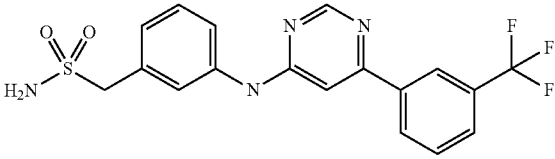 [SMILES: NS(=O)(=O)Cc1cccc(Nc2cc(-c3cccc(C(F)(F)F)c3)ncn2)c1] {3-[6-(3-Trifluoromethyl-phenyl)-pyrimidin-4-ylamino]-phenyl}-methanesulfonamide | 409 (M + 1) | 221.5-223 |
| 64 | 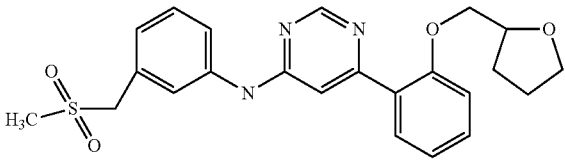 [SMILES: CS(=O)(=O)Cc1cccc(Nc2cc(-c3ccccc3OCC3CCCO3)ncn2)c1] (3-Methanesulfonylmethyl-phenyl)-{6-[2-(tetrahydro-furan-2-ylmethoxy)-phenyl]-pyrimidin-4-yl}-amine | 440 (M + 1) | 160.0-162.6 |
| 65 | 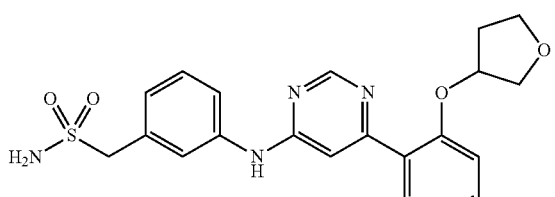 (3-{6-[2-(Tetrahydro-furan-3-yloxy)-phenyl]-pyrimidin-4-ylamino}-phenyl)-methanesulfonamide | 427 (M + 1) | |

TABLE 1-continued

| Compound No. | Structure and IUPAC name | MS m/z | Melt Point (Celsius) |
|---|---|---|---|
| 66 | 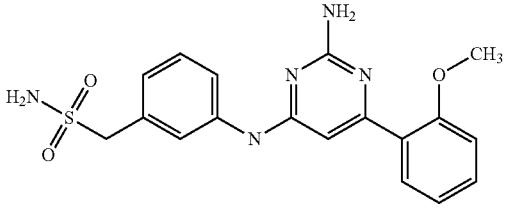 [SMILES: COc1ccccc1-c1cc(Nc2cccc(CS(N)(=O)=O)c2)nc(N)n1]<br>{3-[2-Amino-6-(2-methoxy-phenyl)-pyrimidin-4-ylamino]-phenyl}-methanesulfonamide | 386 (M + 1) | 211.7-213.1 |
| 67 | 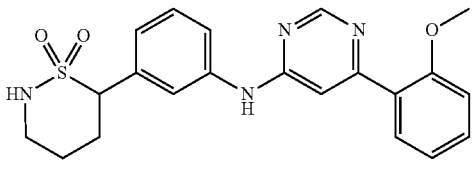 [SMILES: COc1ccccc1-c1cc(Nc2cccc(C3CCCNS3(=O)=O)c2)ncn1]<br>[3-(1,1-Dioxo-[1,2]thiazinan-6-yl)-phenyl]-[6-(2-methoxy-phenyl)-pyrimidin-4-yl]-amine | 410.9 (M + 1) | |
| 68 | 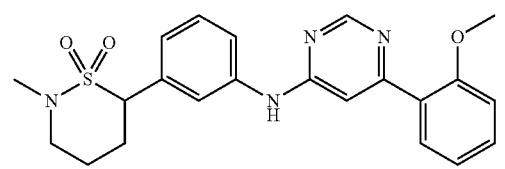<br>[6-(2-Methoxy-phenyl)-pyrimidin-4-yl]-[3-(2-methyl-1,1-dioxo-[1,2]thiazinan-6-yl)-phenyl]-amine | 425 (M + 1) | |
| 69 | 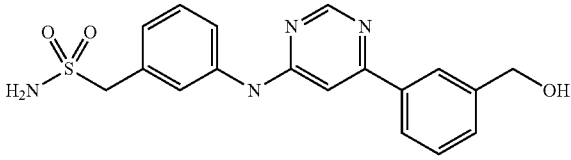 [SMILES: NS(=O)(=O)Cc1cccc(Nc2cc(-c3cccc(CO)c3)ncn2)c1]<br>{3-[6-(3-Hydroxymethyl-phenyl)-pyrimidin-4-ylamino]-phenyl}-methanesulfonamide | 371, 409 (M + 1) | |
| 70 | 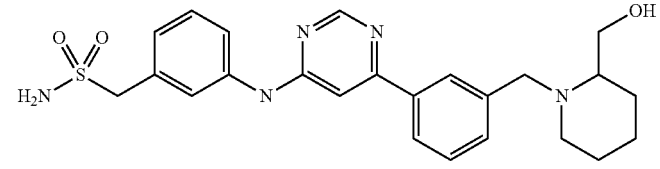 [SMILES: NS(=O)(=O)Cc1cccc(Nc2cc(-c3cccc(CN4CCCCC4CO)c3)ncn2)c1]<br>(3-{6-[3-(2-Hydroxymethyl-piperidin-1-ylmethyl)-phenyl]-pyrimidin-4-ylamino}-phenyl)-methanesulfonamide | 468 (M + 1) | |
| 71 | 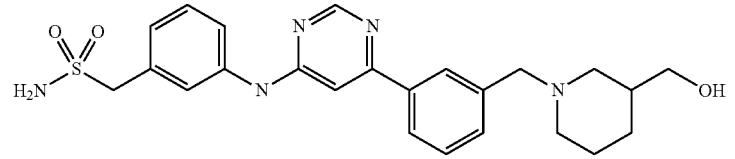 [SMILES: NS(=O)(=O)Cc1cccc(Nc2cc(-c3cccc(CN4CCCC(CO)C4)c3)ncn2)c1]<br>(3-{6-[3-(3-Hydroxymethyl-piperidin-1-ylmethyl)-phenyl]-pyrimidin-4-ylamino}-phenyl)-methanesulfonamide | 468 (M + 1) | |

TABLE 1-continued

| Compound No. | Structure and IUPAC name | MS m/z | Melt Point (Celsius) |
|---|---|---|---|
| 72 | [3-(6-{3-[3-(2-Hydroxy-ethyl)-piperidin-1-ylmethyl]-phenyl}-pyrimidin-4-ylamino)-phenyl]-methanesulfonamide | 425, 482 (M + 1) | |
| 73 | 1-{3-[6-(3-Sulfamoylmethyl-phenylamino)-pyrimidin-4-yl]-benzyl}-piperidine-3-carboxylic acid amide | 481, 503 (M + 1) | |
| 74 | {3-[6-(3-Dimethylaminomethyl-phenyl)-pyrimidin-4-ylamino]-phenyl}-methanesulfonamide | 398, 468, 609 (M + 1) | |
| 75 | {3-[6-(3-Diethylaminomethyl-phenyl)-pyrimidin-4-ylamino]-phenyl}-methanesulfonamide | 426 (M + 1) | |
| 76 | [3-(6-{3-[(Ethyl-isopropyl-amino)-methyl]-phenyl}-pyrimidin-4-ylamino)-phenyl]-methanesulfonamide | 440 (M + 1) | |
| 77 | {3-[6-(3-Morpholin-4-ylmethyl-phenyl)-pyrimidin-4-ylamino]-phenyl}-methanesulfonamide | 440 (M + 1) | |

TABLE 1-continued

| Compound No. | Structure and IUPAC name | MS m/z | Melt Point (Celsius) |
|---|---|---|---|
| 78 | 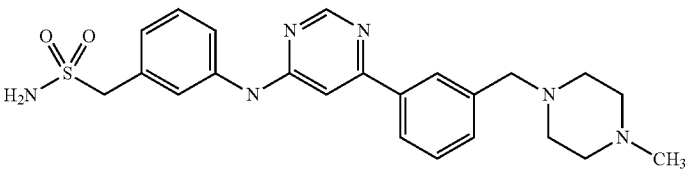 [SMILES: CN1CCN(Cc2cccc(-c3cc(Nc4cccc(CS(N)(=O)=O)c4)ncn3)c2)CC1]<br>(3-{6-[3-(4-Methyl-piperazin-1-ylmethyl)-phenyl]-pyrimidin-4-ylamino}-phenyl)-methanesulfonamide | 453 (M + 1) | |
| 79 | 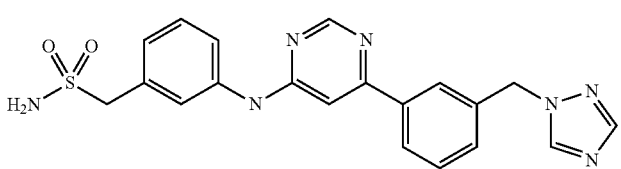 [SMILES: NS(=O)(=O)Cc1cccc(Nc2cc(-c3cccc(Cn4cncn4)c3)ncn2)c1]<br>{3-[6-(3-[1,2,4]Triazol-1-ylmethyl-phenyl)-pyrimidin-4-ylamino]-phenyl}-methanesulfonamide | 422 (M + 1) | |
| 80 | 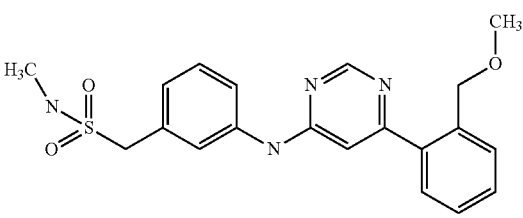<br>C-{3-[6-(2-Methoxymethyl-phenyl)-pyrimidin-4-ylamino]-phenyl}-N-methyl-methanesulfonamide | 399 (M + 1) | 171-172 |
| 81 | 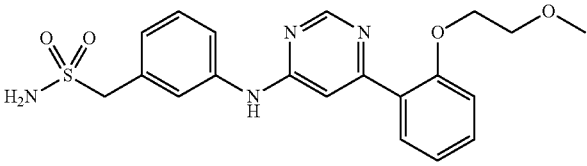 [SMILES: COCCOc1ccccc1-c1cc(Nc2cccc(CS(N)(=O)=O)c2)ncn1]<br>(3-{6-[2-(2-Methoxy-ethoxy)-phenyl]-pyrimidin-4-ylamino}-phenyl)-methanesulfonamide | 415 (M + 1) | 143.3-145.5 |
| 82 | 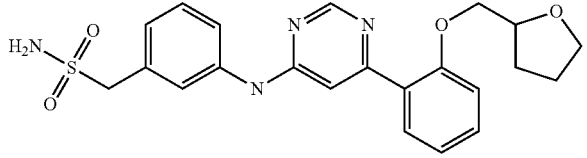 [SMILES: NS(=O)(=O)Cc1cccc(Nc2cc(-c3ccccc3OCC3CCCO3)ncn2)c1]<br>(3-{6-[2-(Tetrahydro-furan-2-ylmethoxy)-phenyl]-pyrimidin-4-ylamino}-phenyl)-methanesulfonamide | 441 (M + 1) | 168.4-169.4 |
| 83 | 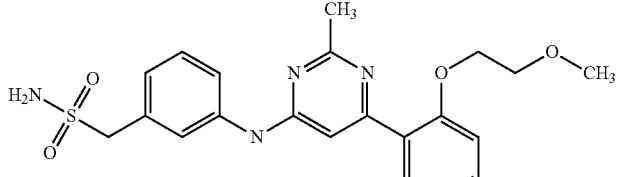<br>(3-{6-[2-(2-Methoxy-ethoxy)-phenyl]-2-methyl-pyrimidin-4-ylamino}-phenyl)-methanesulfonamide | 429 (M + 1) | 209.0-211.1 |

TABLE 1-continued

| Compound No. | Structure and IUPAC name | MS m/z | Melt Point (Celsius) |
|---|---|---|---|
| 84 | 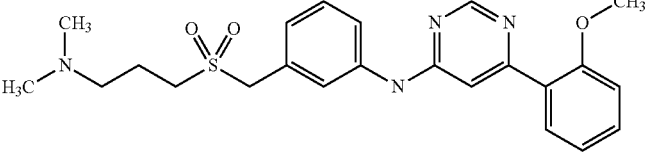<br>[3-(3-Dimethylamino-propane-1-sulfonylmethyl)-phenyl]-[6-(2-methoxy-phenyl)-pyrimidin-4-yl]-amine | 441 (M + 1) | 68-71 |
| 85 | 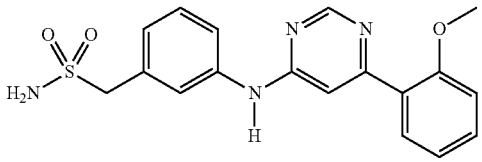 [SMILES: COc1ccccc1-c1cc(Nc2cccc(CS(N)(=O)=O)c2)ncn1]<br>C-{3-[6-(2-Methoxy-phenyl)-pyrimidin-4-ylamino]-phenyl}-methanesulfonamide | | |
| 86 | 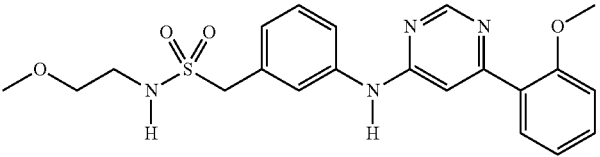 [SMILES: COCCNS(=O)(=O)Cc1cccc(Nc2cc(-c3ccccc3OC)ncn2)c1]<br>N-(2-Methoxy-ethyl)-C-{3-[6-(2-methoxy-phenyl)-pyrimidin-4-ylamino]-phenyl}-methanesulfonamide | | |

In a further embodiment, the invention provides the above mentioned compounds according to general formulae (I) to (III) (including formula (IIIa)), for medical use, in particular for use in the treatment of inflammatory disorders, immunological diseases, proliferative diseases, infectious diseases, cardiovascular diseases and neurodegenerative diseases and pain, including inflammatory pain, chronic pain, and/or neuropathic pain.

In a further embodiment, the invention provides pharmaceutical compositions containing a compound as outlined above, together with a pharmaceutically acceptable carrier.

In a further embodiment, the invention provides use of a compound as outlined above for preparing a pharmaceutical composition for treating inflammatory disorders, immunological diseases, proliferative diseases, infectious diseases, cardiovascular diseases and neurodegenerative diseases.

In a further embodiment, the invention provides use of a compound as outlined above for preparing a pharmaceutical composition for treating pain, including inflammatory pain, chronic pain, and/or neuropathic pain.

In a further embodiment, the invention provides a method for treating inflammatory disorders, immunological diseases, proliferative diseases, infectious diseases, cardiovascular diseases and neurodegenerative diseases comprising the administration of an effective amount of at least one of the compounds as mentioned above to a subject in need thereof.

In a further embodiment, the invention provides a method for treating pain, for example inflammatory pain, chronic pain and/or neuropathic pain comprising the administration of an effective amount of at least one of the compounds as mentioned above to a subject in need thereof.

In a preferred embodiment of this invention, the cyclin-dependent kinase inhibitor according to any one of Formulae (I) to (III) (including formula (IIIa)) inhibits a CDK selected from the group consisting of CDK1, CDK2, CDK3, CDK4, CDK5, CDK6, CDK7, CDK8, CDK9, CDK10, CDK11, CrkRS (Crk7, CDC2-related protein kinase 7), CDKL1 (cyclin-dependent kinase-like 1); KKIALRE, CDKL2 (cyclin-dependent kinase-like 2), KKIAMRE, CDKL3 (cyclin-dependent kinase-like 3), NKIAMRE, CDKL4, similar to cyclin-dependent kinase-like 1, CDC2L1 (cell division cycle 2-like 1), PITSLRE B, CDC2L1 (cell division cycle 2-like 1), PITSLRE A, CDC2L5 (cell division cycle 2-like 5), PCTK1 (PCTAIRE protein kinase 1), PCTK2 (PCTAIRE protein kinase 2), PCTK3 (PCTAIRE protein kinase 3) or PFTK1 (PFTAIRE protein kinase 1).

The inhibitor may also inhibit more than one cyclin-dependent kinase selected from the above-recited group.

In a particular preferred embodiment of this invention, the compounds according to general formulae (I) to (III) (including formula (IIIa)) inhibit CDK9.

In a further embodiment of this invention, the compounds according to general formulae (I) to (III) (including formula (IIIa)) selectively inhibit one or more CDKs without having a substantial inhibitory effect on other enzymes or proteins.

In a preferred embodiment, such inhibitory compounds display an increased selectivity for a particular CDK. "Increased selectivity" as used herein means that the inhibitory compound is at least 10-100× more selective for a particular CDK selected from the group of CDKs as recited herein, supra. In a preferred embodiment of the present invention, the inhibitory compound is 20-90× more selective for a particular CDK. In a particular preferred embodiment, the inhibitory compound is 30-80× more selective for a particular CDK.

In a particular preferred embodiment, the compounds according to general formulae (I) to (III) (including formula (IIIa)) display an increased selectivity for CDK9 than for other CDKs.

As used herein, the term "inhibiting" or "inhibition" refers to the ability of a compound to downregulate, decrease, reduce, suppress, inactivate, or inhibit at least partially the cellular function of a cyclin-dependent kinase, i.e. its activity or the expression of the cyclin-dependent kinase.

Furthermore, the term "cyclin-dependent kinase inhibitor" refers to any compound or group of compounds capable of downregulating, decreasing, suppressing or otherwise regulating the amount and/or activity of a cyclin-dependent kinase. Inhibition of said kinases can be achieved by any of a variety of mechanisms known in the art, including, but not limited to binding directly to the kinase polypeptide, denaturing or otherwise inactivating the kinase, or inhibiting the expression of the gene (e.g., transcription to mRNA, translation to a nascent polypeptide, and/or final polypeptide modifications to a mature protein), which encodes the kinase. Furthermore, a cyclin-dependent kinase inhibitor may also interfere with expression, modification, regulation or activation of a molecule acting downstream of a CDK in a CDK-dependent pathway. Generally, kinase inhibitors may be proteins, polypeptides, nucleic acids, small molecules, or other chemical moieties. Specifically, kinase inhibitors also include monoclonal or polyclonal antibodies directed against cyclin-dependent kinases.

In a preferred embodiment, the cyclin-dependent kinase inhibitor is selected from the compounds as represented by any one of Formulae (I) to (III) (including formula (IIIa)) as disclosed herein.

Therapeutic Use

The compounds of any one of Formulae (I) to (III) (including formula (IIIa)) are inhibitors of cyclin-dependent kinases. Thus, they are expected to have the ability to arrest, or to recover control of the cell cycle in abnormally dividing cells. Consequently, it is suggested that the compounds according to any one of Formulae (I) to (III) (including formula (IIIa)) will prove useful in treating and/or preventing proliferative disorders such as cancers.

It is known that CDKs play a role in apoptosis, proliferation, differentiation and transcription and therefore, the compounds according to any one of Formulae (I) to (III) (including formula (IIIa)) may also be useful in the treatment of diseases other than proliferative diseases, such as infectious diseases, immunological diseases, neurodegenerative diseases and cardiovascular diseases.

Furthermore, the compounds according to any one of Formulae (I) to (III) (including formula (IIIa)) also display an unexpected antinociceptive and anti-inflammatory effect.

Thus, in a preferred embodiment, the compounds of any one of Formulae (I) to (III) (including formula (IIIa)) may be used in methods and/or pharmaceutical compositions for the treatment of any type of pain, including chronic pain, neuropathic and/or inflammatory pain.

In a further preferred embodiment, the compounds of any one of Formulae (I) to (III) (including formula (IIIa)) may be used in methods and/or pharmaceutical compositions for the treatment of inflammatory disorders.

In a particular preferred embodiment, the compounds of any one of Formulae (I) to (III) (including formula (IIIa)) for use in the treatment of any type of pain or in the treatment of inflammatory disorders display an increased selectivity for CDK9 than for other CDKs.

Pain

It has turned out that administration of CDK inhibitors according to any one of Formulae (I) to (III) (including formula (IIIa)) to mice suffering from nerve lesion exerts a hypoalgesic effect, in particular in murine models of inflammatory and neuropathic pain.

The discovery that inhibition of a cyclin-dependent kinase is involved in mediating a hypoalgesic effect was unexpected.

Thus, in a preferred embodiment, this invention relates to a method of treating any type of pain comprising administering an effective amount of an inhibitor of cyclin-dependent kinase according to any one of Formulae (I) to (III) (including formula (IIIa)). Specifically, the compounds of Formula I may be used for the treatment of chronic, neuropathic and/or inflammatory pain. In a particular preferred embodiment, the compounds of any one of Formulae (I) to (III) (including formula (IIIa)) for use in the treatment of any type of pain display an increased selectivity for CDK9 than for other CDKs.

The role of CDK9 in the development of pain could be based on the following mechanism of action: Both cyclin T1 and CDK9 stimulate the basal promoter activity of TNFα. TNFα is a pro-inflammatory cytokine and pain mediator that controls expression of inflammatory genetic networks. For mediation of cellular TNF receptor responses, the nuclear factor-κB (NFκB) pathway is crucial. TNFα triggers its recruitment to cytokine genes while NfκB interacts with p-TEFb complex for stimulation of gene transcription (Barboric M et al., 2001).

Additionally, it has been shown that CDK9 is a binding partner of TRAF2, a member of the TNFα receptor complex (MacLachlan et al, 1998), while GP130, a subunit of the pro-inflammatory IL6 receptor complex has recently been identified as another potential binding partner of CDK9 (Falco et al, 2002). As a key player in TNFα and interleukin signaling as well as in NfκB mediated expression of several genes (e.g. cytokines as pain mediators), CDK9 can thus be considered as a central target for the treatment of any type of pain, such as inflammatory pain (see FIG. 2).

For the treatment of neuropathic pain, pharmacological action has to take place beyond the blood-brain-barrier (BBB) in the central nervous system (CNS). Microglial cells as the principal immune cells in the CNS, for example, release, upon activation, a variety of noxious factors such as cytokines (TNFα, IL1β, IL6) and other pro-inflammatory molecules (Huwe 2003). Microglia are activated by stimulation of TNFα receptor or Toll-like receptor and signal is mediated via Iκ kinase (IKK) and NfκB leading to transcriptional activation of the cytokines described above. Microglial contribution has been discussed as instrumental in chronic CNS diseases and may contribute to pain perception (Watkins et al, 2003).

Recently it has been shown that the transcription factor NfκB regulates expression of Cyclooxygenase-2 (COX-2) via Interleukin 1β (IL1β) in the spinal cord (Lee et al. 2004). As the major contributor to elevation of spinal prostaglandin E2, the pain mediator COX-2 is already known as a target for a variety of anti-nociceptive/anti-inflammatory drugs. NfκB inhibitors have proven their ability to significantly reduce COX-2 levels and mechanical allodynia as well as thermal hyperalgesia in animal models.

In contrast to COX-2, inhibition of CDK9 action would lead to suppression of a variety of pain mediators instead of just a single one. Thus, anti-nociceptive action of CDK9 inhibitors may be superior compared to e.g. COX-2 inhibitors.

Due to its relevance for NfκB mediated gene transcription, the inhibitory interaction with CDK9 may therefore be a reasonable approach not only for the treatment of acute inflammatory pain, but also for the treatment of chronic pain.

The term "pain" as used herein generally relates to any type of pain and broadly encompasses types of pain such as acute pain, chronic pain, inflammatory and neuropathic pain. In a preferred embodiment of the present invention, "pain" comprises neuropathic pain and associated conditions. The pain may be chronic, allodynia (the perception of pain from a normally innocuous stimulus), hyperalgesia (an exaggerated response to any given pain stimulus) and an expansion of the receptive field (i.e. the area that is "painful" when a stimulus is applied), phantom pain or inflammatory pain.

Acute pain types comprise, but are not limited to pain associated with tissue damage, postoperative pain, pain after trauma, pain caused by burns, pain caused by local or systemic infection, visceral pain associated with diseases comprising: pancreatits, intestinal cystitis, dysmenorrhea, Irritable Bowel syndrome, Crohn's disease, ureteral colic and myocardial infarction Furthermore, the term "pain" comprises pain associated with CNS disorders comprising: multiple sclerosis, spinal cord injury, traumatic brain injury, Parkinson's disease and stroke In a preferred embodiment, "pain" relates to chronic pain types comprising headache (for example migraine disorders, episodic and chronic tension-type headache, tension-type like headache, cluster headache, and chronic paroxysmal hemicrania), low back pain, cancer pain, osteoarthritis pain and neuropathic pain, but is not limited thereto.

Inflammatory pain (pain in response to tissue injury and the resulting inflammatory process) as defined herein relates to inflammatory pain associated with diseases comprising connective tissue diseases, rheumatoid arthritis, systemic lupus erythematosus, multiple sclerosis and arthritis, but is not limited thereto.

Neuropathic pain (pain resulting from damage to the peripheral nerves or to the central nervous system itself) includes conditions comprising, but not limited to metabolic neuropathies (e.g., diabetic neuropathy), post-herpetic neuralgia, trigeminal neuralgia, cranial neuralgia, post-stroke neuropathic pain, multiple sclerosis-associated neuropathic pain, HIV/AIDS-associated neuropathic pain, cancer-associated neuropathic pain, carpal tunnel-associated neuropathic pain, spinal cord injury-associated neuropathic pain, complex regional pain syndrome, fibromyalgia-associated neuropathic pain, reflex sympathetic dystrophy, phantom limb syndrome or peripheral nerve or spinal cord trauma, nerve transection including surgery, limb amputation and stump pain, pain caused by the side effects of anti-cancer and anti-AIDS therapies, post-surgical neuropathic pain, neuropathy-associated pain such as in idiopathic or post-traumatic neuropathy and mononeuritis, and neuropathic pain caused by connective tissue disease such as rheumatoid arthritis, Wallenberg's syndrome, systemic lupus erythematosus, multiple sclerosis, or polyarteritis nodosa. The neuropathy can be classified as radiculopathy, mononeuropathy, mononeuropathy multiplex, polyneuropathy or plexopathy.

The term "allodynia" denotes pain arising from stimuli which are not normally painful. Allodynic pain may occur other than in the area stimulated.

The term "hyperalgesia" denotes an increased sensitivity to a painful stimulus. The term "hypoalgesia" denotes a decreased sensitivity to a painful stimulus.

Inflammatory Diseases

Surprisingly, it could be shown that the CDK inhibiting compounds according to any one of Formulae (I) to (III) (including formula (IIIa)) as disclosed herein exert an anti-inflammatory effect in in vitro and in vivo inflammatory assays.

Thus, in a preferred embodiment, this invention relates to a method of treating inflammatory diseases comprising administering an effective amount of an inhibitor of cyclin-dependent kinase according to any one of Formulae (I) to (III) (including formula (IIIa)). In a particular preferred embodiment, the compounds of any one of Formulae (I) to (III) (including formula (IIIa)) for use in the treatment of inflammatory diseases display an increased selectivity for CDK9 than for other CDKs.

The role of CDK9 in the development of inflammatory diseases could be based on the following mechanism of action: inflammatory diseases such as rheumatoid arthritis (RA); atherosclerosis; asthma; inflammatory bowel disease, systemic lupus erythematosus and several other autoimmune diseases are mediated by tumor necrosis factor α (TNFα), a key regulator of inflammatory and tissue obstructive pathways in said diseases. It is known that the TNFα signal is mediated via several transducers such as IκB Kinase (IKK), which phosphorylates the IκB protein which dissociates from NfκB upon its phosphorylation. Dissociated NfκB, a positive regulator of cytokine transcription, translocates into the cell nucleus where it binds to its recognition sites.

Activated NfκB has been found in the synovium of RA patients [Han et al.; 2003, Autoimmunity, 28, 197-208]. It regulates pro-inflammatory genes such as TNFα, IL-6, IL-8, NOS and COX2. Targeting NfκB and its upstream signalling partner IKK has already proven to be an efficient therapeutic strategy in many animal models of arthritis [Firestein, 2003, Nature 423, 356-361].

Bound NfκB associates with a coactivator complex containing histone acetyltransferases (CBP, p300, p/CAF, SRC-1, and SRC-1-related proteins) that recruits and activates CDK9 which catalyzes the phosphorylation of the CTD of RNA Pol II [West et al.; 2001, Journal of Virology 75(18), 8524-8537]. Resulting hyperphosphorylation of the RNA Pol II CTD leads to transcriptional activation of pro-inflammatory cytokines such as IL-1β, IL-6 and IL-8 that are also known as being regulated by TNFα.

Several studies showed that TNFα is a 'master regulator' of an autologous signalling cascade that regulates pro-inflammatory cytokine expression. To interrupt this pro-inflammatory cascade, specific antibodies (Abs) can be used successfully to block the TNFα signal. Anti-TNFα treatment of RA with Abs has already proven its therapeutic efficacy in several clinical studies and FDA approved drugs such as Infliximab and Etanercept have entered the market [Feldmann and Maini, NatMed, 2003, 9 (10); 356-61]. However, disadvantages of Ab based therapies include their immunogenic potential, attendant loss of efficacy during progressive treatment and high treatment costs. Additionally, the Ab kinetics permits a more or less all-or-nothing reduction of circulating TNFα. As a result, physiologic functions of the immune response are also suppressed [Laufer et al., Inflammation and Rheumatic Diseases, 2003; Thieme, pp. 104-5].

Therapeutic interventions into the TNFα-mediated signalling cascade with kinase inhibitors aiming at targets such as p38 MAPK or IKK have shown severe adverse effects—in most cases due to a lack of specificity against the respective target.

In contrast thereto, CDK specific inhibitors according to any one of Formulae (I) to (III) (including formula (IIIa)) as presented herein may intervene at the very bottom end of the TNFα signalling pathways reducing the interaction with physiological functions. Additionally, said compounds will allow interruption of the autologous TNFα mediated inflammatory network by avoidance of adverse effects via superior specificity. Therefore, treatment of with CDK specific inhibitors of any one of Formulae (I) to (III) (including formula (IIIa)) constitutes a promising strategy for the treatment of inflammatory and autoimmune diseases.

Thus, the compounds according to any one of Formulae (I) to (III) (including formula (IIIa)) as presented herein may be used for the treatment and/or prevention of inflammatory diseases.

The term "inflammatory diseases" as used herein relates to diseases triggered by cellular or non-cellular mediators of the immune system or tissues causing the inflammation of body tissues and subsequently producing an acute or chronic inflammatory condition.

Examples for such inflammatory diseases are hypersensitivity reactions of type I-IV, for example but not limited to hypersensitivity diseases of the lung including asthma, atopic diseases, allergic rhinitis or conjunctivitis, angioedema of the lids, hereditary angioedema, antireceptor hypersensitivity reactions and autoimmune diseases, Hashimoto's thyroiditis, systemic lupus erythematosus, Goodpasture's syndrome, pemphigus, myasthenia gravis, Grave's and Raynaud's disease, type B insulin-resistant diabetes, rheumatoid arthritis, psoriasis, Crohn's disease, scleroderma, mixed connective tissue disease, polymyositis, sarcoidosis, Wegener's granulomatosis, glomerulonephritis, acute or chronic host versus graft reactions.

Furthermore, the term "inflammatory diseases" includes but is not limited to abdominal cavity inflammation, dermatitis, gastrointestinal inflammation (including inflammatory bowel disease, ulcerative colitis), fibrosis, ocular and orbital inflammation, dry eye disease and severe dry eye disease resulting from Sjörgen's syndrome, mastitis, otitis, mouth inflammation, musculoskeletal system inflammation (including gout, osteoarthritis), inflammatory diseases of the central nervous system (including multiple sclerosis, bacterial meningitis, meningitis), genitourinary tract inflammation (incl prostatitis, glomerulonephritis), cardiovascular inflammation (including atherosclerosis, heart failure), respiratory tract inflammation (including chronic bronchitis, chronic obstructive pulmonary disease), thyroiditis, diabetes mellitus, osteitis, myositis, multiple organ failure (including. sepsis), polymyositis and psoriatic arthritis.

Immunological Diseases

The compounds according to any one of Formulae (I) to (III) (including formula (IIIa)) are also envisaged to be useful in the treatment and/or prevention of immunological diseases, such as, for example, autoimmune diseases.

Accordingly, the present invention provides a method for the treatment and/or prevention of immunological diseases comprising the administration of an effective amount of at least one CDK inhibitor according to any one of Formulae (I) to (III) (including formula (IIIa)) to a subject in need thereof.

The term "immunological diseases" as used herein relates to diseases including but not limited to allergy, asthma, graft-versus-host disease, immune deficiencies and autoimmune diseases.

Specifically, immunological diseases include diabetes, rheumatic diseases, AIDS, chronic granulomatosis disease, rejection of transplanted organs and tissues, rhinitis, chronic obstructive pulmonary diseases, osteoporosis, ulcerative colitis, Crohn's disease, sinusitis, lupus erythematosus, psoriasis, multiple sclerosis, myasthenia gravis, alopecia, recurrent infections, atopic dermatitis, eczema and severe anaphylactic reactions, but are not limited thereto. Furthermore, "immunological diseases" also include allergies such as contact allergies, food allergies or drug allergies.

Proliferative Diseases

The compounds of any one of Formulae (I) to (III) (including formula (IIIa)) are inhibitors of cyclin-dependent kinases, which represent key molecules involved in regulation of the cell cycle. Cell-cycle disregulation is one of the cardinal characteristics of neoplastic cells. Thus, said compounds are expected to prove useful in arresting or recovering control of the cell cycle in abnormally dividing cells. It is thus expected that the compounds according to any one of Formulae (I) to (III) (including formula (IIIa)) are useful in the treatment and/or prevention of proliferative diseases such as cancer.

Accordingly, the invention provides a method for the treatment and/or prevention of proliferative diseases comprising administering an effective amount of at least one inhibitor of a cyclin-dependent kinase according to any one of Formulae (I) to (III) (including formula (IIIa)).

As used herein, the term "proliferative disease" relates to cancer disorders, including, but not limited to benign neoplasms, dysplasias, hyperplasias as well as neoplasms showing metastatic growth or any other transformations.

The term "cancer" includes but is not limited to benign and malign neoplasia like carcinoma, sarcoma, carcinosarcoma, cancers of the blood-forming tissues, tumors of nerve tissues including the brain and cancer of skin cells.

Examples of cancers which may be treated include, but are not limited to, a carcinoma, for example a carcinoma of the bladder, breast, colon (e.g. colorectal carcinomas such as colon adenocarcinoma and colon adenoma), kidney, epidermal, liver, lung, for example adenocarcinoma, small cell lung cancer and non-small cell lung carcinomas, oesophagus, gall bladder, ovary, pancreas e.g. exocrine pancreatic carcinoma, stomach, cervix, thyroid, prostate, or skin, for example squamous cell carcinoma; a hematopoietic tumour of lymphoid lineage, for example leukemia, acute lymphocytic leukemia, B-cell lymphoma, T-cell lymphoma, Hodgkin's lymphoma, non-Hodgkin's lymphoma, hairy cell lymphoma, or Burkett's lymphoma; a hematopoietic tumor of myeloid lineage, for example acute and chronicmyelogenous leukemias, myelodysplastic syndrome, or promyelocytic leukemia; thyroid follicular cancer; a tumour of mesenchymal origin, for example fibrosarcoma or habdomyosarcoma; a tumor of the central or peripheral nervous system, for example astrocytoma, neuroblastoma, glioma or schwannoma; melanoma; seminoma; teratocarcinoma; osteosarcoma; xenoderoma pigmentoum; keratoctanthoma; thyroid follicular cancer; Kaposi's sarcoma, astrocytoma, basal cell carcinoma, small intestine cancer, small intestinal tumors, gastrointestinal tumors, glioblastomas, liposarcoma, germ cell tumor, head and neck tumors (tumors of the ear, nose and throat area), cancer of the mouth, throat, larynx, and the esophagus, cancer of the bone and its supportive and connective tissues like malignant or benign bone tumour, e.g. malignant osteogenic sarcoma, benign osteoma, cartilage tumors; like malignant chondrosarcoma or benign chondroma, osteosarcomas; tumors of the urinary bladder and the internal and external organs and structures of the urogenital system of male and female, soft tissue tumors, soft tissue sarcoma, Wilm's tumor or cancers of the endocrine and exocrine glands like e.g. thyroid, parathyroid, pituitary, adrenal glands, salivary glands.

Infectious Diseases

Furthermore, the invention relates to a method of treating and/or preventing infectious diseases comprising administering an effective amount of at least one inhibitor of a cyclin-dependent kinase according to any one of Formulae (I) to (III) (including formula (IIIa)).

It is known that certain host cell CDKs are involved in viral replication, i.e. CDK2, CDK7, CDK8 and CDK9 (J. Virol. 2001; 75: 7266-7279). Specifically, the role of CDK9 kinase activity in regulation of HIV-1 transcription elongation and histone methylation has been described (J. Virol 2004, 78(24):13522-13533.

In a preferred embodiment, the invention thus relates to a method of treating and/or preventing infectious diseases comprising administering an effective amount of at least one inhibitor of a cyclin-dependent kinase according to any one of Formulae (I) to (III) (including formula (IIIa)), wherein said compound displays an increased selectivity for CDK9 than for other CDKs.

The term "infectious diseases" as used herein comprises infections caused by pathogens such as viruses, bacteria, fungi and/or parasites.

Virus-induced infectious diseases include diseases caused by infection with retroviruses, human endogenous retroviruses, hepadnaviruses, herpesviruses, flaviviruses, adenoviruses, togaviruses and poxviruses. Specifically, infectious diseases are caused by viruses comprising, but not limited to viruses such as HIV-1, HIV-2, HTLV-I and HTLV-II, hepadnaviruses such as HBV, herpesviruses such as Herpes simplex virus I (HSV I), herpes simplex virus 11 (HSV II), Epstein-Barr virus (EBV), varicella zoster virus (VZV), human cytomegalovirus (HCMV) or human herpesvirus 8 (HHV-8), flaviviruses such as HCV, West nile or Yellow Fever virus, human papilloma virus, poxviruses, Sindbis virus or adenoviruses.

Examples of infectious diseases include, but are not limited to AIDS, borreliosis, botulism, diarrhea, BSE (Bovine Spongiform Encephalopathy), chikungunya, cholera, CJD (Creutzfeldt-Jakob Disease), conjunctivitis, cytomegalovirus infection, dengue/dengue Fever, encephalitis, eastern equine encephalitis, western equine encephalitis, Epstein-Barr Virus Infection, *Escherichia coli* Infection, foodborne infection, foot and mouth disease, fungal dermatitis, gastroenteritis, *Helicobacter pylori* Infection, Hepatitis (HCV, HBV), Herpes Zoster (Shingles), HIV Infection, Influenza, malaria, measles, meningitis, meningoencephalitis, molluscum contagiosum, mosquito-borne Diseases, Parvovirus Infection, plague, PCP (*Pneumocystis carinii* Pneumonia), polio, primary gastroenteritis, Q Fever, Rabies, Respiratory Syncytial Virus (RSV) Infection, rheumatic fever, rhinitis, Rift Valley Fever, Rotavirus Infection, salmonellosis, *salmonella enteritidis*, scabies, shigellosis, smallpox, streptococcal infection, tetanus, Toxic Shock Syndrome, tuberculosis, ulcers (peptic ulcer disease), hemorrhagic fever, variola, warts, West Nile Virus Infection (West Nile Encephalitis), whooping cough, yellow fever.

Cardiovascular Diseases

Furthermore, the invention relates to the treatment and/or prevention of cardiovascular diseases comprising administering an effective amount of at least one inhibitor of a cyclin-dependent kinase according to any one of Formulae (I) to (III) (including formula (IIIa)).

It has been reported that the field of cardiovascular diseases constitutes a possible clinical application for CDK inhibitors (Pharmacol Ther 1999, 82(2-3):279-284). Furthermore, it is known that inhibition of the cyclin T/CDK9 complex and more specifically, inhibition of CDK9 may play a beneficial role in the treatment of cardiovascular diseases such as heart failure (WO2005/027902).

Thus, in a preferred embodiment, the invention relates to a method of treating and/or preventing cardiovascular diseases comprising administering an effective amount of at least one inhibitor of a cyclin-dependent kinase according to any one of Formulae (I) to (III) (including formula (IIIa)), wherein said compound displays an increased selectivity for CDK9 than for other CDKs.

The term "cardiovascular diseases" includes but is not limited to disorders of the heart and the vascular system like congestive heart failure, myocardial infarction, ischemic diseases of the heart, such as stable angina, unstable angina and asymptomatic ischemia, all kinds of atrial and ventricular arrhythmias, hypertensive vascular diseases, peripheral vascular diseases, coronary heart disease and atherosclerosis. Furthermore, as used herein, the term includes, but is not limited to adult congenital heart disease, aneurysm, angina pectoris, angioneurotic edema, aortic valve stenosis, aortic aneurysm, aortic regurgitation, arrhythmogenic right ventricular dysplasia, arteriovenous malformations, atrial fibrillation, Behcet syndrome, bradycardia, cardiomegaly, cardiomyopathies such as congestive, hypertrophic and restrictive cardiomyopathy, carotid stenosis, cerebral hemorrhage, Churg-Strauss syndrome, cholesterol embolism, bacterial endocarditis, fibromuscular dysplasia, congestive heart failure, heart valve diseases such as incompetent valves or stenosed valves, heart attack, epidural or subdural hematoma, von Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, mitral valve prolapse, long QT syndrome mitral valve prolapse, myocardial ischemia, myocarditis, disorders of the pericardium, pericarditis, peripheral vascular diseases, phlebitis, polyarteritis nodosa, pulmonary atresia, Raynaud disease, restenosis, rheumatic heart disease, Sneddon syndrome, stenosis, superior vena cava syndrome, syndrome X, tachycardia, hereditary hemorrhagic telangiectasia, telangiectasis, temporal arteritis, thromboangiitis obliterans, thrombosis, thromboembolism, varicose veins, vascular diseases, vasculitis, vasospasm, ventricular fibrillation, Williams syndrome, peripheral vascular disease, varicose veins and leg ulcers, deep vein thrombosis and Wolff-Parkinson-White syndrome.

Furthermore, the term cardiovascular diseases includes diseases resulting from congenital defects, genetic defects, environmental influences (i.e., dietary influences, lifestyle, stress, etc.), and other defects or influences.

Neurodegenerative Diseases

CDK inhibitors have been described to exert neuroprotective effects. Specifically, it has been reported that CDK inhibitors prevent neuronal death in neurodegenerative diseases such as Alzheimer's disease (Biochem Biophys Res Commun 2002 (297):1154-1158; Trends Pharmacol Sci 2002 (23):417-425; Pharmacol Ther 1999, 82(2-3):279-284).

Thus, the compounds according to any one of Formulae (I) to (III) (including formula (IIIa)), which are CDK inhibitors, are expected to provide beneficial effects in the therapeutic management of neurodegenerative diseases.

Accordingly, the invention relates a method of treating and/or preventing neurodegenerative diseases comprising administering an effective amount of at least one inhibitor of a cyclin-dependent kinase according to any one of Formulae (I) to (III) (including formula (IIIa)).

The term "neurodegenerative diseases" as used herein includes disorders of the central nervous system as well as disorders of the peripheral nervous system, including, but not limited to brain injuries, cerebrovascular diseases and their consequences, Parkinson's disease, corticobasal degeneration, motor neuron disease, dementia, including ALS, multiple sclerosis, traumatic brain injury, stroke, post-stroke, post-traumatic brain injury, and small-vessel cerebrovascular disease, dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld-Jakob dementia, HIV dementia, schizophrenia with dementia, Korsakoff's psychosis and AIDS-related dementia.

Similarly, cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities are also considered to be neurodegenerative disorders.

Specifically, the present invention relates to a method for treating the above-referenced types of pain and associated conditions and inflammatory disorders, immunological diseases, proliferative diseases, infectious diseases, cardiovascular diseases and neurodegenerative diseases, wherein the term "treating" comprises the prevention, amelioration or treating of pain and associated conditions and inflammatory disorders, immunological diseases, proliferative diseases, infectious diseases, cardiovascular diseases and neurodegenerative diseases Pharmaceutical Compositions Preferred embodiments of the present invention include the administration of compositions comprising at least one cyclin-dependent kinase inhibitor according to any one of Formulae (I) to (III) (including formula (IIIa)) as an active ingredient together with at least one pharmaceutically acceptable (i.e. non-toxic) carrier, excipient and/or diluent.

Preferably, the composition comprises at least one cyclin-dependent kinase inhibitor according to any one of Formulae (I) to (III) (including formula (IIIa)) as an active ingredient, wherein said at least one cyclin-dependent kinase inhibitor has an increased selectivity for CDK9 than for other CDKs.

Furthermore, the invention also comprises compositions combining at least two inhibitors of CDK and/or pharmaceutically acceptable salts thereof. Said at least two inhibitors may inhibit the same cyclin-dependent kinase or may also inhibit different types of cyclin-dependent kinases, e.g. one inhibitor in the composition may inhibit CDK9 while the other inhibitor is capable of inhibiting CDK2, for example.

Having regard to pain treatment, an individual pain medication often provides only partially effective pain alleviation because it interferes with just one pain-transducing pathway out of many. Thus, it is also intended to administer CDK inhibitors according to any one of Formulae (I) to (III) (including formula (IIIa)) in combination with a pain-reducing (analgesic) agent that acts at a different point in the pain perception process.

An "analgesic agent" comprises a molecule or combination of molecules that causes a reduction in pain perception. An analgesic agent employs a mechanism of action other than inhibition of CDK.

One class of analgesics, such as nonsteroidal anti-inflammatory drugs (NSAIDs), down-regulates the chemical messengers of the stimuli that are detected by the nociceptors and another class of drugs, such as opioids, alters the processing of nociceptive information in the CNS. Other analgesics are local anesthetics, anticonvulsants and antidepressants such as tricyclic antidepressants. Administering one or more classes of drug in addition to CDK inhibitors can provide more effective amelioration of pain.

Preferred NSAIDs for use in the methods and compositions of the present invention are aspirin, acetaminophen, ibuprofen, and indomethacin. Furthermore, cyclooxygenase-2 (COX-2) inhibitors, such as specific COX-2 inhibitors (e.g. celecoxib, COX189, and rofecoxib) may also be used as an analgesic agent in the methods or compositions of the present invention.

Preferred tricyclic antidepressants are selected from the group consisting of Clomipramine, Amoxapine, Nortriptyline, Amitriptyline, Imipramine, Desipramine, Doxepin, Trimipramine, Protriptylin, and Imipramine pamoate.

Furthermore, the use of anticonvulsants (e.g. gabapentin), GABAB agonists (e.g. L-baclofen), opioids, vanniloid receptor antagonists and cannabinoid (CB) receptor agonists, e.g. CB1 receptor agonists as analgesic is also preferred in the methods and compositions in the present invention.

In preparing cyclin-dependent kinase inhibitor compositions of this invention, one can follow the standard recommendations of well-known pharmaceutical sources such as Remington: The Science and Practice of Pharmacy, $19^{th}$ ed. (Mack Publishing, 1995).

The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, wherein said preparations in addition to typical vehicles and/or diluents contain at least one inhibitor according to the present invention and/or a pharmaceutical acceptable salt thereof as active ingredient.

The pharmaceutical compositions according to the present invention containing at least one inhibitor according to the present invention and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like.

Moreover, suitable binders, lubricants, disintegrating agents and coloring agents may also be incorporated into the tablet or capsule. Powders and tablets may contain about 5 to about 95% by weight of a cyclin-dependent kinase inhibitor according to the any one of Formulae (I) to (III) (including formula (IIIa)) as recited herein or analogues thereof or the respective pharmaceutical active salt as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like.

Suitable disintegrants include starch, methylcellulose, guar gum, and the like.

Sweetening and flavoring agents as well as preservatives may also be included, where appropriate. The disintegrants, diluents, lubricants, binders etc. are discussed in more detail below.

Moreover, the pharmaceutical compositions of the present invention may be formulated in sustained release form to provide the rate controlled release of any one or more of the components or active ingredients to optimise the therapeutic effect (s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration.

Aerosol preparations suitable for inhalation may include solutions and solids in powder form, which may be present in combination with a pharmaceutically acceptable carrier such as an inert, compressed gas, e.g. nitrogen.

For preparing suppositories, a low melting wax, such as a mixture of fatty acid glycerides like cocoa butter is melted first, and the active ingredient is then dispersed homogeneously therein e.g. by stirring. The molten, homogeneous mixture is then poured into conveniently sized moulds, allowed to cool, and thereby solidified.

Also included are solid form preparations, which are intended to be converted, shortly before use, to liquid form preparations for either oral or parenteral administration. Such liquid forms include solutions, suspensions, and emulsions.

The compounds according to the present invention may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methylcellulose, polyvinyl alcohols, or denatured gelatins or starch for holding or containing compositions comprising the active ingredient(s). Capsules with hard shells are typically made of blended or relatively high gel strength gelatins from bones or pork skin. The capsule itself may contain small amounts of dyes, opaquing agents, plasticisers and/or preservatives. Under tablet a compressed or moulded solid dosage form is understood which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix.

Powders for constitution refers to powder blends containing the active ingredients and suitable diluents which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75% by weight, and more preferably from about 30 to about 60% by weight.

The term disintegrants refers to materials added to the composition to support disintegration and release of the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium-croscaramellose, alginates such as alginic acid and sodium alginate, clays such as bentonites, and effervescent mixtures. The amount of disintegrant in the composition may range from about 2 to about 20% by weight of the composition, more preferably from about 5 to about 10% by weight.

Binders are substances which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20% by weight of the composition, preferably from about 3 to about 10% by weight, and more preferably from about 3 to about 6% by weight.

Lubricants refer to a class of substances which are added to the dosage form to enable the tablet granules etc. after being compressed to release from the mould or die by reducing friction or wear. Suitable lubricants include metallic stearates such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5% by weight of the composition, preferably from about 0.5 to about 2% by weight, and more preferably from about 0.3 to about 1.5% by weight of the composition.

Glidents are materials that prevent baking of the components of the pharmaceutical composition together and improve the flow characteristics of granulate so that flow is smooth and uniform. Suitable glidents include silicon dioxide and talc.

The amount of glident in the composition may range from about 0.1 to about 5% by weight of the final composition, preferably from about 0.5 to about 2% by weight.

Coloring agents are excipients that provide coloration to the composition or the dosage form. Such excipients can include food grade dyes adsorbed onto a suitable adsorbent such as clay or aluminum oxide. The amount of the coloring agent may vary from about 0.1 to about 5% by weight of the composition, preferably from about 0.1 to about 1% by weight.

The present invention relates to the administration of compositions containing as active ingredient a cyclin-dependent kinase inhibitor to a subject in need thereof for the treatment of any type of pain, inflammatory disorders, immunological diseases, proliferative diseases, cardiovascular diseases or neurodegenerative diseases.

"A subject in need thereof "comprises an animal, preferably a mammal, and most preferably a human, expected to experience any type of pain, inflammatory disorders, immunological diseases, proliferative diseases, cardiovascular diseases or neurodegenerative diseases in the near future or which has ongoing experience of said conditions. For example, such animal or human may have an ongoing condition that is causing pain currently and is likely to continue to cause pain, or the animal or human has been, is or will be enduring a procedure or event that usually has painful consequences. Chronic painful conditions such as diabetic neuropathic hyperalgesia and collagen vascular diseases are examples of the first type; dental work, particularly in an area of inflammation or nerve damage, and toxin exposure (including exposure to chemotherapeutic agents) are examples of the latter type.

In order to achieve the desired therapeutic effect, the respective cyclin-dependent kinase inhibitor has to be administered in a therapeutically effective amount.

The term "therapeutically effective amount" is used to indicate an amount of an active compound, or pharmaceutical agent, that elicits the biological or medicinal response indicated. This response may occur in a tissue, system, animal or human that is being sought by a researcher, veterinarian, medical doctor or other clinician, and includes alleviation of the symptoms of the disease being treated. In the context of the present invention, a therapeutically effective amount comprises, e.g., an amount that reduces pain, in particular inflammatory or neuropathic pain. Specifically, a therapeutically effective amount denotes an amount which exerts a hypoalgesic effect in the subject to be treated.

Such effective amount will vary from subject to subject depending on the subject's normal sensitivity to, e.g., pain, its height, weight, age, and health, the source of the pain, the mode of administering the inhibitor of CDKs, the particular inhibitor administered, and other factors. As a result, it is advisable to empirically determine an effective amount for a particular subject under a particular set of circumstances.

Alternative Applications of the Compounds of the Present Invention

In a further aspect of the present invention, the compounds of the present invention are used as pharmaceutically active agents.

Further aspects of the present invention relate to the use of the compounds of the present invention for the preparation of a pharmaceutical composition useful for prophylaxis and/or treatment of a disease selected from: cell proliferative disease, such as cancer; pain, such as inflammatory pain and neuropathic pain; inflammation; cardiovascular diseases, such as cardiac hypertrophy; and infectious disease, such as viral infections including HIV.

Other aspects of the present invention relate to methods for the prophylaxis and/or treatment of a disease selected from: cell proliferative disease, such as cancer; pain, such as inflammatory pain and neuropathic pain; inflammation; cardiovascular disease, such as cardiac hypertrophy; and infectious disease, such as viral infections including HIV; comprising administering to an individual a compound according to the present invention.

In certain embodiments of these aspects of the invention, the disease for prophylaxis and/or treatment can be found in an individual, such as a patient in need of such prophylaxis and/or treatment. An "individual" means a multi-cellular organism, for example an animal such as a mammal, including a primate. In addition to primates, such as humans, a variety of other mammals can be treated according to a method that utilizes one or more compounds of the present invention. For example, other mammals including, but not limited to, cows, sheep, goats, horses, dogs, cats, guinea pigs, rabbits, rats, mice or other bovine, ovine, equine, canine, feline, or rodent species can be used. In one particular such embodiment of these aspects, the individual is a human.

Infectious Diseases Including Opportunistic Infections

In yet another aspect of the present invention, the compounds of the present invention can be used for the preparation of a pharmaceutical composition for the prophylaxis and/or treatment of infectious disease, including opportunistic diseases and opportunistic infections. The term infectious disease comprises infections caused by viruses, bacteria, prions, fungi, and/or parasites.

Virally induced infectious diseases, including opportunistic diseases are addressed in particular aspects of the invention. In a particular embodiment of this aspect, the virally induced infectious diseases, including opportunistic diseases, are caused by retroviruses, human endogenous retroviruses (HERVs), hepadnaviruses, herpesviruses, flaviviridae, and/or adenoviruses. In certain embodiments, the retroviruses are selected from lentiviruses or oncoretroviruses, wherein the lentivirus can be selected from the group comprising: HIV-1, HIV-2, feline immunodeficiency virus (FIV), bovine immunodeficiency virus (BIV), sivian immunodeficiency viruses (SIVs), chimeras of HIV and SIV (SHIV), caprine arthritis encephalitis virus (CAEV), visna/maedi virus (VMV) or equine infectious anemia virus (EIAV), preferably HIV-1 and HIV-2, and the oncoretrovirus is preferably selected from HTLV-I, HTLV-II or bovine leukemia virus (BLV), preferably HTLV-I and HTLV-II. In particular embodiments, the hepadnavirus is selected from HBV, ground squirrel hepatitis virus (GSHV) or woodchuck hepatitis virus (WHV), and in certain embodiments the hepadnavirus is HBV. In other particular embodiments, the herpesvirus is selected from the group comprising: Herpes simplex virus I (HSV I), herpes simplex virus II (HSV II), Epstein-Barr virus (EBV), varicella zoster virus (VZV), human cytomegalovirus (HCMV) or human herpesvirus 8 (HHV-8), and in certain embodiments the herpesvirus is HCMV. In other particular embodiments, the flaviviridae is selected from HCV, West Nile or Yellow Fever.

Hence, in a further aspect of the present invention, a method for preventing and/or treating infectious disease, including opportunistic disease, in a mammal, including a human, is provided, which method comprises administering to the mammal an amount of at least one compound of the present invention, effective to prevent and/or treat said infectious disease, including a opportunistic disease. In a particular embodiment of this method, the infectious disease, including opportunistic disease, includes virally induced infectious diseases. The virally induced infectious diseases, including opportunistic diseases, are caused by retroviruses, hepadnaviruses, herpesviruses, flaviviridae, and/or adenoviruses. In a further particular embodiment of this method, the retroviruses are selected from lentiviruses or oncoretroviruses, wherein the lentivirus is selected from the group comprising: HIV-1, HIV-2, FIV, BIV, SIVs, SHIV, CAEV, VMV or EIAV, including certain embodiments where the lentivirus is HIV-1 or HIV-2, or wherein the oncoretrovirus is selected from the group consisting of: HTLV-I, HTLV-II or BLV. In a further particular embodiment of this method, the hepadnavirus is selected from HBV, GSHV or WHV, including certain embodiments where the hepadnavirus is HBV, or wherein the herpesvirus is selected from the group comprising: HSV I, HSV II, EBV, VZV, HCMV or HHV 8, including certain embodiments where the herpesivirus is HCMV, or wherein the flaviviridae is selected from HCV, West Nile or Yellow Fever.

Cell Proliferative Disease

As used herein, a "cell proliferative disease" includes a disease or disorder that affects a cellular growth, differentiation, or proliferation process. As used herein, a "cellular growth, differentiation or proliferation process" is a process by which a cell increases in number, size or content, by which a cell develops a specialized set of characteristics which differ from that of other cells, or by which a cell moves closer to or further from a particular location or stimulus. A cellular growth, differentiation, or proliferation process includes amino acid transport and degradation and other metabolic processes of a cell. A cellular proliferation disorder may be characterized by aberrantly regulated cellular growth, proliferation, differentiation, or migration. Cellular proliferation disorders include tumorigenic diseases or disorders. As used herein, a "tumorigenic disease or disorder" includes a disease or disorder characterized by aberrantly regulated cellular growth, proliferation, differentiation, adhesion, or migration, which may result in the production of or tendency to produce tumors. As used herein, a "tumor" includes a benign or malignant mass of tissue. Examples of cellular growth or proliferation disorders include, but are not limited to tumors, cancer, autoimmune diseases, viral diseases, fungal diseases, neurodegenerative disorders and cardiovascular diseases.

In certain embodiments, tumors may be solid tumors, which are cancer of body tissues other than blood, bone marrow, or the lymphatic system. In other embodiments tumors may be hematological tumors, such as leukemia and lymphomas. Leukemia is a collective term for malignant diseases characterized by a proliferation of malignantly changed white blood cells. Diseases arising from lymphatic tissue are called lymphomas.

Solid tumors may be selected from: liver cancer, stomach cancer, colon cancer, breast cancer, pancreas cancer, prostate cancer, skin cancer, renal cancer, bone cancer, thyroid cancer, skin cancer, including squamous cell carcinoma, esophagus cancer, kidney cancer, bladder cancer, gall cancer, cervical cancer, ovarian cancer, lung cancer, bronchial, small and non-small-cell lung cancer, gastric, and head and neck cancer.

Hematological tumors may be leukemia, such as Acute Myelogenous Leukemia (AML), Acute Lymphoblastic Leukemia (ALL), Acute Lymphocytic Leukemia, Acute Leukemia, Acute Promyelocytic Leukemia, Chronic Granulocytic Leukemia (CGL), Chronic Leukemia, Chronic Lymphocytic Leukemia (CLL), Chronic Myelogenous Leukemia (CML), Chronic Myelomonocytic Leukemia, Common-type Acute Lymphoblastic Leukemia, Eosinophilic Leukemia, Erythroleukemia, Extranodal Lymphoma, Follicular Lymphoma, Hairy Cell Leukemia, Monocytic Leukemia, Prolymphocytic Leukemia.

Hematological tumors may also be lymphoma, such as B Cell Lymphomas, Burkitt Lymphoma, Cutaneous T Cell Lymphoma, High-Grade Lymphoma, Hodgkin Lymphoma, Non-Hodgkin Lymphoma, Low-grade Lymphoma, Lymphoblastic Lymphoma, Mantle Cell Lymphoma, Marginal Zone Lymphoma, Mucosa-Associated Lymphoid Tissue (MALT) Lymphomas, T Cell Lymphomas, peripheral T cell lymphoma, multiple myeloma, Essential Thrombocythemia, Hairy Cell Lymphoma, Extramedullary myeloma, Granulocytic Sarcomae.

Hematological tumors may also be tumors of myeloid lineage, including acute and chronic myelogenous leukemias, myelodysplastic syndrome, and promyelocytic leukaemia.

Tumors may also be of mesenchymal origin, such as fibrosarcoma and rhabdomyosarcoma. Furthermore, tumors may be tumors of the central and peripheral nervous system, such as astrocytoma, neuroblastoma, glioma, and schwannomas; and tumors may be other tumors, such as melanoma, seminoma, teratocarcinoma, osteosarcoma, xenoderoma pigmentosum, keratoctanthoma, thyroid follicular cancer, and Kaposi's sarcoma.

Compounds of the present invention may induce or inhibit apoptosis. The apoptotic response is aberrant in a variety of human diseases. Compounds described herein, as modulators of apoptosis, will be useful in the treatment of cancer (including but not limited to those types mentioned hereinabove), viral infections (including but not limited to herpesvirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

As described above, in certain embodiments of the invention, the compounds of the present invention are pharmaceutically active agents for prophylaxis and/or treatment of cell proliferative disease, including cancer. Thus, these compounds can be used for the manufacture of a pharmaceutical formulation for prophylaxis and/or treatment of cell proliferative disease, including such disease in a mammal such as a human.

Compounds of the present invention may also be useful in the chemoprevention of cancer. Chemoprevention is defined as inhibiting the development of invasive cancer by either blocking the initiating mutagenic event or by blocking the progression of pre-malignant cells, such as by blocking growth of the tumor, that have already suffered an insult or inhibiting tumor relapse.

Compounds disclosed herein may also be useful in inhibiting tumor angiogenesis and metastasis.

Inflammation

As described above, in certain embodiments of the invention, the compounds of the present invention are pharmaceutically active agents for prophylaxis and/or treatment of inflammatory diseases. Thus, these compounds can be used for the manufacture of a pharmaceutical formulation for prophylaxis and/or treatment of inflammation and inflammatory disease in mammals, including humans.

In yet another particular embodiment, said inflammation is mediated preferably by the cytokines TNF-α, IL-1β, GM-CSF, IL-6 and/or IL-8.

Inflammatory diseases can emanate from infectious and non-infectious inflammatory conditions which may result from infection by an invading organism or from irritative, traumatic, metabolic, allergic, autoimmune, or idiopathic causes as shown in the following list.

I. Acute Infections

| | | |
|---|---|---|
| A. | | Viral |
| B. | | Bacterial |

II. Noninfectious Causes
III. Chronic (Granulomatous) Diseases

| | | |
|---|---|---|
| A. | | Bacterial |
| B. | | Spirochetal |
| C. | | Mycotic (Fungal) |
| D. | | Idiopathic |

IV. Allergic, immune, and Idiopathic Disorders
   A. Hypersensitivity reactions
   B. Immune and idiopathic disorders
V. Miscellaneous Inflammatory Conditions
   A. Parasitic infections
   B. Inhalation causes: Acute (thermal) injury
     Pollution and inhalant allergy
     Carcinogens
   C. Radiation injury: Radionecrosis Thus, the compounds of the present invention can be used for prophylaxis and/or treatment of inflammation caused by invading organisms such as viruses, bacteria, prions, and parasites as well as for prophylaxis and/or treatment of inflammation caused by irritative, traumatic, metabolic, allergic, autoimmune, or idiopathic reasons.

Consequently, the compounds of the present invention can be used for prophylaxis and/or treatment of inflammatory disease which is initiated or caused by viruses, parasites, and bacteria which are connected to or involved in inflammations.

The following bacteria are known to cause inflammatory diseases: mycoplasma pulmonis (causes e.g. chronic lung diseases (CLD), murine chronic respiratory disease), *ureaplasma urealyticum* (causes pneumonia in newborns), *mycoplasma pneumoniae* and *chlamydia pneumoniae* (cause chronic asthma), *C. pneumoniae* (causes atherosclerosis, pharyngitis to pneumonia with empyema, human coronary heart disease), *Helicobacter pylori* (human coronary heart disease, stomach ulcers).

The following viruses are known to cause inflammatory diseases: herpesviruses especially cytomegalovirus (causes human coronary heart disease).

The compounds of the present invention can be used for prophylaxis and/or treatment of inflammatory disease caused and/or induced and/or initiated and/or enhanced by any of the afore-mentioned bacteria or viruses.

Furthermore, the compounds of the present invention can be used for prophylaxis and/or treatment of a disease selected from: inflammatory disease of the central nervous system (CNS), inflammatory rheumatic disease, inflammatory disease of blood vessels, inflammatory disease of the middle ear, inflammatory bowel disease, inflammatory disease of the skin, inflammatory disease uveitis, inflammatory disease of the larynx, including such disease in a mammal, such as a human.

Examples for inflammatory diseases of the central nervous system (CNS) are algal disorders, protothecosis, bacterial disorders, abscessation, bacterial meningitis, idiopathic inflammatory disorders, eosinophilic meningoencephalitis, feline polioencephalomyelitis, granulomatous meningoencephalomyelitis, meningitis, steroid responsive meningitis-arteritis, miscellaneous meningitis/meningoencephalitis, meningoencephalitis in greyhounds, necrotizing encephalitis, pug dog encephalitis, pyogranulomatous meningoencephalomyelitis, shaker dog disease, mycotic diseases of the CNS, parasitic encephalomyelitis, prion protein induced diseases, feline spongiform encephalopathy, protozoal encephalitis-encephalomyelitis, toxoplasmosis, neosporosis, sarcocystosis, encephalitozoonosis, trypanosomiasis, acanthamebiasis, babesiosis, leishmaniasis, rickettsial disorders, rocky mountain spotted fever, canine ehrlichiosis, salmon poisoning, viral disorders, aujeszky's disease, borna disease, canine herpes virus encephalomyelitis, canine distemper encephalomyelitis, canine distemper encephalomyelitis in immature animals, multifocal distemper encephalomyelitis in mature animals, old dog encephalitis, chronic relapsing encephalomyelitis, post-vaccinal canine distemper encephalitis, feline immunodeficiency virus, feline infectious peritonitis, feline leukemia virus, infectious canine hepatitis, La Crosse virus encephalitis, parvovirus encephalitis, rabies, post-vaccinal rabies, tick-borne encephalitis in dogs.

Examples for inflammatory rheumatic diseases are rheumatoid arthritis, scleroderma, lupus, polymyositis, dermatomyositis, psoriatic arthritis, ankylosing spondylitis, Reiters's syndrome, juvenile rheumatoid arthritis, bursitis, tendinitis (tendonitis), and fibromyositis.

Examples for inflammatory diseases of blood vessels are vasculitis, autoantibodies in vasculitis, microscopic polyangiitis, giant cell arteritis, Takayasu's arteritis, vasculitis of the central nervous system, thromboangiitis obliterans (Buerger's Disease), vasculitis secondary to bacterial, fungal, and parasitic infection, vasculitis and rheumatoid arthritis, vasculitis in systemic lupus erythematosus, vasculitis in the idiopathic inflammatory myopathies, relapsing polychondritis, systemic vasculitis in sarcoidosis, vasculitis and malignancy, and drug-induced vasculitis.

Examples for inflammatory diseases of the middle ear are acute suppurative otitis media, bullous myringitis, granular myringitis, and chronic suppurative otitis media, which can manifest as mucosal disease, cholesteatoma, or both.

Examples for inflammatory bowel diseases are ulcerative colitis, Crohn's disease.

Examples for inflammatory diseases of the skin are acute inflammatory dermatoses, urticaria (hives), spongiotic dermatitis, allergic contact dermatitis, irritant contact dermatitis, atopic dermatitis, erythemal multiforme (EM minor), Stevens-Johnson syndrome (SJS, EM major), toxic epidermal necrolysis (TEN), chronic inflammatory dermatoses, psoriasis, lichen planus, discoid lupus erythematosus, and acne vulgaris Uveitis is an inflammation located in and/or on the eye and may be associated with inflammation elsewhere in the body. In most circumstances, patients who have uveitis as part of a disease elsewhere in the body are aware of that illness. The majority of patients with uveitis do not have an apparent associated systemic illness. Causes of uveitis can be infectious causes, masquerade syndromes, suspected immune-mediated diseases, and/or syndromes confined primarily to the eye.

The following viruses are associated with inflammations: human immunodeficiency virus-I, herpes simplex virus, herpes zoster virus, and cytomegalovirus.

Bacterial or spirochetal caused, induced, initiated and/or enhanced inflammations are tuberculosis, leprosy, proprionobacterium, syphilis, Whipple's disease, leptospirosis, brucellosis, and lyme disease.

Parasitic (protozoan or helminthic) caused, induced, initiated and/or enhanced inflammations are toxoplasmosis, acanthameba, toxocariasis, cysticercosis, onchocerciasis.

Examples of inflammatory diseases caused, induced, initiated and/or enhanced by fungi are histoplasmosis, coccidioidomycosis, candidiasis, aspergillosis, sporotrichosis, blastomycosis, and cryptococcosis.

Masquerade syndromes are, for instance, leukemia, lymphoma, retinitis pigmentosa, and retinoblastoma.

Suspected immune-mediated diseases can be selected from the group comprising ankylosing spondylitis, Behcet's disease, Crohn's disease, drug or hypersensitivity reaction, interstitial nephritis, juvenile rheumatoid arthritis, Kawasaki's disease, multiple sclerosis, psoriatic arthritis, Reiter's syndrome, relapsing polychondritis, sarcoidosis, Sjogren's syndrome, systemic lupus erythematosus, ulcerative colitis, vasculitis, vitiligo, Vogt Koyanagi Harada syndrome.

Syndromes confined primarily to the eye are, for instance, acute multifocal placoid pigmentary epitheliopathy, acute retinal necrosis, birdshot choroidopathy, Fuch's heterochromic cyclitis, glaucomatocyclitic crisis, lens-induced uveitis, multifocal choroiditis, pars planitis, serpiginous choroiditis, sympathetic ophthalmia, and trauma.

Examples for inflammatory diseases of the larynx are gastroesophageal (laryngopharyngeal) reflux disease, pediatric laryngitis, acute laryngeal infections of adults, chronic (granulomatous) diseases, allergic, immune, and idiopathic disorders and miscellaneous inflammatory conditions.

Pediatric laryngitis is known as acute (viral or bacterial) infection such as laryngotracheitis (croup), supraglottitis (epiglottitis), diphtheria, and noninfectious causes are for example spasmodic croup and traumatic laryngitis.

Acute laryngeal infections of adults are, for instance, viral laryngitis, common upper respiratory infection, laryngotracheitis, herpes simplex, bacterial laryngitis, supraglottitis, laryngeal abscess, and gonorrhea.

Chronic (granulomatous) diseases can be selected from the group comprising bacterial diseases, tuberculosis, leprosy, scleroma, actinomycosis, tularemia, glanders, spirochetal (syphilis) diseases, mycotic (fungal) diseases, candidiasis, blastomycosis, histoplasmosis, coccidiomycosis, aspergillosis, idiopathic diseases, sarcoidosis, and Wegener's granulomatosis.

Allergic, immune, and idiopathic disorders are, for example, hypersensitivity reactions, angioedema, Stevens-Johnson syndrome, immune and idiopathic disorders, infections of the immunocompromised host, rheumatoid arthritis, systemic lupus erythematosus, cicatricial pemphigoid, relapsing polychondritis, Sjogren's syndrome, and amyloidosis.

Miscellaneous inflammatory conditions are, for instance, parasitic infections, trichinosis, leishmaniasis, schistosomiasis, syngamus laryngeus, inhalation laryngitis, acute (thermal) injury, pollution and inhalant allergy, carcinogens, radiation injury, radiation laryngitis, radionecrosis, vocal abuse, vocal-cord hemorrhage, muscle tension dysphonias, and contact ulcer and granuloma.

Cardiovascular Diseases

As described above, in certain embodiments of the invention, the compounds of the present invention can be used for prophylaxis and/or treatment of cardiovascular disease such as a cardiovascular diseases selected from: adult congenital heart disease, aneurysm, stable angina, unstable angina, angina pectoris, angioneurotic edema, aortic valve stenosis, aortic aneurysm, arrhythmia, arrhythmogenic right ventricular dysplasia, arteriosclerosis, arteriovenous malformations, atrial fibrillation, Behcet syndrome, bradycardia, cardiac tamponade, cardiomegaly, congestive cardiomyopathy, hypertrophic cardiomyopathy, restrictive cardiomyopathy, cardiovascular disease prevention, carotid stenosis, cerebral hemorrhage, Churg-Strauss syndrome, diabetes, Ebstein's Anomaly, Eisenmenger complex, cholesterol embolism, bacterial endocarditis, fibromuscular dysplasia, congenital heart defects, heart diseases, congestive heart failure, heart valve diseases, heart attack, epidural hematoma, hematoma, subdural, Hippel-Lindau disease, hyperemia, hypertension, pulmonary hypertension, hypertrophic growth, left ventricular hypertrophy, right ventricular hypertrophy, hypoplastic left heart syndrome, hypotension, intermittent claudication, ischemic heart disease, Klippel-Trenaunay-Weber syndrome, lateral medullary syndrome, long QT syndrome mitral valve prolapse, moyamoya disease, mucocutaneous lymph node syndrome, myocardial infarction, myocardial ischemia, myocarditis, pericarditis, peripheral vascular diseases, phlebitis, polyarteritis nodosa, pulmonary atresia, Raynaud disease, restenosis, Sneddon syndrome, stenosis, superior vena cava syndrome, syndrome X, tachycardia, Takayasu's arteritis, hereditary hemorrhagic telangiectasia, telangiectasis, temporal arteritis, tetralogy of fallot, thromboangiitis obliterans, thrombosis, thromboembolism, tricuspid atresia, varicose veins, vascular diseases, vasculitis, vasospasm, ventricular fibrillation, Williams syndrome, peripheral vascular disease, varicose veins and leg ulcers, deep vein thrombosis, Wolff-Parkinson-White syndrome, including such disease in a mammal, such as a human.

In particular embodiments the compounds of the present invention can be used for prophylaxis and/or treatment of a cardiovascular disease selected from: adult congenital heart disease, aneurysms, angina, angina pectoris, arrhythmias, cardiovascular disease prevention, cardiomyopathies, congestive heart failure, myocardial infarction, pulmonary hypertension, hypertrophic growth, restenosis, stenosis, thrombosis and arteriosclerosis, including such disease in a mammal, such as a human.

In other particular embodiments the compounds of the present invention can be used for prophylaxis and/or treatment of cardiac hypertrophy, including such disease in a mammal, such as a human.

Cardiac hypertrophy is the heart's response to a variety of extrinsic and intrinsic stimuli that impose increased biomechanical stress. While hypertrophy can eventually normalize wall tension, it is associated with an unfavorable outcome and threatens affected patients with sudden death or progression to overt heart failure. Accumulating evidence from studies in human patients and animal models suggests that in most instances hypertrophy is not a compensatory response to the change in mechanical load, but rather is a maladaptive process. Cardiac hypertrophy, or thickening, of the heart muscle (myocardium) occurs in response to increased stress on the heart. It typically involves one of the bottom chambers of the heart, which are known as the ventricles. The right ventricle pumps blood to the lungs and the left ventricle pumps blood to the body. The most common causes of hypertrophy are related to increased blood pressure in either the lungs or the body. The extra work of pumping blood against the increased pressure causes the ventricle to thicken over time, the same way a body muscle increases in mass in response to weight-lifting.

High blood pressure, or hypertension, is the most frequent cause of left ventricular hypertrophy (LVH). Stenosis of the aortic valve—a condition in which, for a variety of reasons, this heart valve cannot open fully—is another common cause of LVH. Hypertrophic cardiomyopathy (a disease previously known as idiopathic hypertrophic subaortic stenosis or IHSS), and the ongoing use of cocaine round out the list of most common causes of LVH. Hypertrophic cardiomyopathy is a genetic disease related to weakness of the individual muscle fibers of the heart. These fibers need to work harder to pump blood and become thickened over time. Hypertrophic cardiomyopathy occurs in 1 in 500 people and is the most common cardiac cause of sudden death in young athletes.

The most common causes of right ventricle hypertrophy (RVH) are diseases that damage the lung like emphysema and cystic fibrosis. These diseases destroy blood vessels in the lung, causing increased pressure in the remaining vessels. Conditions that decrease oxygen levels, such as chronic bronchitis and sleep apnea, also lead to RVH. Stenosis of the pulmonic heart valve, repeated blood clots to the lungs (chronic pulmonary embolism), and primary pulmonary hypertension are a few of the remaining causes of RVH.

CDK9 is known to be involved in cardiac hypertrophy (reviewed in Sano & Schneider, Circulation Research, 2004, 95, 867). Activation of CDK9 to pathophysiological levels leads to mitochondrial dysfunction, apoptosis, and heart failure via suppression of PGC-1, an essential co-activator for the transcription of nuclear and mitochondrial genes that encode mitochondrial proteins (Sano et al., EMBO J., 2004, 23, 3559-3569), and hence blockade of Cdk9 activity is an accepted strategy expected to aid in the treatment of cardiac hypertrophy.

Pain

As described above, in certain embodiments of the invention, the compounds of the present invention may also be used to treat one or more of any type of pain, including those referenced herein, including such pain in a mammal, such as a human. In particular such embodiments said pain comprises inflammatory pain and/or neuropathic pain.

Debilitating acute or chronic pain is a constant backdrop to daily life for many people. Current estimates suggest that 1 in 10 adults suffer from chronic pain at some point in their lives. In terms of both lost productivity and treatment, the cost to society in the US alone surpasses 100 billion dollars annually. Unfortunately, current treatments for pain are only partially effective, and many also cause debilitating or dangerous side effects. For example, many of the traditional analgesics used to treat severe pain induce debilitating side effects such as nausea, dizziness, constipation, respiratory depression, and cognitive dysfunction (Brower, New paths to pain relief, Nat Biotechnol, 2000, 18(4), 387-39).

Although there is already a broad panel of approved pain medications like non-narcotic analgesics, opioid analgesics, calcium channel blockers, muscle relaxants, and systemic corticosteroids available, said treatments remain merely empirical and, while they may relieve the symptoms of pain, they do not lead to complete relief in most cases. This is also due to fact that the mechanisms underlying the development of the different types of pain are still only poorly understood. Researchers are only just beginning to appreciate the complexity and diversity of the signaling systems used to relay nerve impulses for each type of pain.

Generally, pain is defined as an unpleasant sensory and emotional experience associated with actual or potential tissue damage, or described in terms of such damage, according to the International Association for the Study of Pain (IASP). Specifically, pain may occur as acute or chronic pain.

Acute pain occurs for brief periods of time, typically less than 1 month and is associated with temporary disorders. It is a natural body response to let the host be aware of physiological or biochemical alteration that could result in further damage within a short period of time. It is felt when noxious stimuli activate high threshold mechanical and/or thermal nociceptors in peripheral nerve endings and the evoked action potentials in thinly myelinated (AS) and/or unmyelinated (C) afferent fibres reach a conscious brain.

Said noxious stimuli may be provided by injury, surgery, illness, trauma or painful medical procedures. Acute pain usually disappears when the underlying cause has been treated or has healed. Unrelieved acute pain, however, may lead to chronic pain problems that may result in long hospital stays, rehospitalizations, visits to outpatient clinics and emergency departments, and increased health care costs.

In contrast to acute pain, chronic pain persists long after the initial injury has healed and often spreads to other parts of the body, with diverse pathological and psychiatric consequences. Chronic somatic pain results from inflammatory responses to trauma in peripheral tissues (e.g., nerve entrapment, surgical procedures, cancer, or arthritis), which leads to oversensitization of nociceptors and intense searing pain responses to normally non-noxious stimuli (hyperalgesia). Chronic pain is continuous and recurrent and its intensity will vary from mild to severe disabling pain that may significantly reduce quality of life. Chronic pain is currently treated with conventional analgesics such as Non steroidal anti-inflammatory drugs (NSAIDs such as Ibuprofen, Naproxen), Cox-2 inhibitors (Celecoxib, Valdecoxib, Rofecoxib) and opiates (codeine, morphine, thebaine, papaverine, noscapine). For a significant number of patients however, these drugs provide insufficient pain relief.

Another subtype of pain, inflammatory pain, can occur as acute as well as chronic pain. Resulting injuries of tissue and neurons must not but may develop into long-lasting chronic neuropathic pain effects in succession to such inflammatory events.

Inflammatory pain is mediated by noxious stimuli like e.g. inflammatory mediators (e.g. cytokines, such as TNF, prostaglandins, substance P, bradykinin, purines, histamine, and serotonine), which are released following tissue injury, disease, or inflammation and other noxious stimuli (e.g. thermal, mechanical, or chemical stimuli). In addition, cytokines and growth factors can influence neuronal phenotype and function (Besson J. M., The neurobiology of pain, Lancet, 1999, 353(9164), 1610-1615). These mediators are detected by nociceptors (sensory receptors) that are distributed throughout the periphery of the tissue. Said nociceptors are sensitive to noxious stimuli (e.g. mechanical, thermal, or chemical), which would damage tissue if prolonged (Koltzenburg M, Neural mechanisms of cutaneous nociceptive pain, Clin J Pain, 2000, 16(3 Suppl), 131-138). A particular class of so called C-nociceptors represent a class of "silent" nociceptors that do not respond to any level of mechanical or thermal stimuli but are activated in presence of inflammation only.

Current approaches for the treatment of especially inflammatory pain aim at cytokine inhibition (e.g. 1L1) and suppression of pro-inflammatory TNF. Current approved anticytokine/antiTNF treatments are based on chimeric antibodies such as Infliximab and Etanercept which reduce TNF circulation in the bloodstream. TNF is one of the most important inflammatory mediators which induces synthesis of important enzymes such as COX-2, MMP, iNOS, cPLa2 and others. The main drawbacks of "biologicals" such as chimeric antibodies, however, reside in their immunogenic potential with attendant loss of efficacy and their kinetics, leading to a more or less digital all-or-nothing reduction of circulating TNF. The latter can result in severe immune suppressive side effects.

A distinct form of chronic pain, neuropathic (or neurogenic) pain, arises as a result of peripheral or central nerve dysfunction and includes a variety of conditions that differ in aetiology as well as location. Generally, the causes of neuropathic pain are diverse, but share the common symptom of damage to the peripheral nerves or components of central pathways. Without being bound by theory, the causative factors of neuropathic pain may be metabolic, viral or a mechanical nerve lesion. Neuropathic pain is believed to be sustained by aberrant somatosensory processes in the peripheral nervous system, the CNS, or both. Neuropathic pain is not directly linked to stimulation of nociceptors, but instead, is thought to arise e.g. from oversensitization of glutamate receptors on postsynaptic neurons in the gray matter (dorsal horn) of the spinal cord. Neuropathic pain is associated with conditions such as nerve degeneration in diabetes and postherpetic neuralgia (shingles). Neuropathic pain conditions are the consequence of a number of diseases and conditions, including diabetes, AIDS, multiple sclerosis, stump and phantom pain after amputation, cancer-related neuropathy, post-herpetic neuralgia, traumatic nerve injury, ischemic neuropathy, nerve compression, stroke and spinal cord injury.

Management of neuropathic pain remains a major clinical challenge, partly due to an inadequate understanding of the mechanisms involved in the development and maintenance of neuropathic pain. Many existing analgesics are ineffective in treating neuropathic pain and most of current narcotic and non-narcotic drugs do not provide control of neuropathic pain. Current clinical practice includes the use of a number of drug classes for the management of neuropathic pain, for example anticonvulsants, tricyclic antidepressants, and systemic local anaesthetics. However, the usual outcome of such treatment is merely partial or unsatisfactory pain relief, and in some cases the adverse effects of these drugs outweigh their clinical usefulness. Classic analgesics are widely believed to be poorly effective or ineffective in the treatment of neuropathic pain. Few clinical studies on the use of non steroidal anti-inflammatory drugs (NSAIDs) or opiates in the treatment of neuropathic pain have been conducted, but in those which have, the results appear to indicate that NSAIDs are poorly effective or ineffective and opiates only work at high doses. A review analysing the controlled clinical data for peripheral neuropathic pain (PNP) (Pain 1997 73(2), 123-39) reported that NSAIDs were probably ineffective as analgesics for PNP and that there was no long-term data supporting the analgesic effectiveness of any drug.

Summarizing, available analgesic drugs often only produce insufficient pain relief. Although tricyclic antidepressants and some antiepileptic drugs, for example gabapentine, lamotrigine and carbamazepine, are efficient in some patients, there remains a large unmet need for efficient drugs for the treatment of these conditions. In conclusion, there is a high unmet need for safe and effective methods of treating one or more of any type of pain, in particular chronic inflammatory and/or neuropathic pain.

One aspect of the invention relates to methods and compositions for treating one or more of any type of pain, including those referenced herein, comprising administering an effective amount of at least one compound according to the present invention to a subject in need thereof, including where such subject is a mammal such as a human.

The term "pain" as used herein generally relates to any type of pain and broadly encompasses types of pain such as acute pain, chronic pain, inflammatory and neuropathic pain.

One aspect of the present invention relates to a pharmaceutical composition comprising at least one compound according to the present invention as an active ingredient, together with at least one pharmaceutically acceptable carrier, excipient and/or diluent, in combination with an analgesic agent, wherein said analgesic agent has a mechanism of action other than inhibition of a CDK.

In a particular embodiment of the present invention, pain comprises neuropathic pain and associated conditions. The pain may be chronic, allodynia (the perception of pain from a normally innocuous stimulus), hyperalgesia (an exaggerated response to any given pain stimulus) and an expansion of the receptive field (i.e. the area that is "painful" when a stimulus is applied), phantom pain or inflammatory pain.

Acute pain types comprise, but are not limited to pain associated with tissue damage, postoperative pain, pain after trauma, pain caused by burns, pain caused by local or systemic infection, visceral pain associated with diseases comprising: pancreatitis, intestinal cystitis, dysmenorrhea, Irritable Bowel syndrome, Crohn's disease, ureteral colic and myocardial infarction.

Furthermore, the term "pain" comprises pain associated with CNS disorders comprising: multiple sclerosis, spinal cord injury, traumatic brain injury, Parkinson's disease and stroke.

In a particular embodiment, "pain" relates to chronic pain types comprising headache (for example migraine disorders, episodic and chronic tension-type headache, tension-type like headache, cluster headache, and chronic paroxysmal hemicrania), low back pain, cancer pain, osteoarthritis pain and neuropathic pain, but is not limited thereto.

Inflammatory pain (pain in response to tissue injury and the resulting inflammatory process) as defined herein relates to inflammatory pain associated with diseases comprising connective tissue diseases, rheumatoid arthritis, systemic lupus erythematosus, multiple sclerosis and arthritis, but is not limited thereto.

Neuropathic pain (pain resulting from damage to the peripheral nerves or to the central nervous system itself) may comprise painful diabetic peripheral neuropathy, post-herpetic neuralgia, trigeminal neuralgia, cranial neuralgia, post-stroke neuropathic pain, multiple sclerosis-associated neuropathic pain, post-surgical neuropathic pain, neuropathy-associated pain such as in idiopathic or post-traumatic neuropathy and mononeuritis, HIV/AIDS-associated neuropathic pain, cancer-associated neuropathic pain, carpal tunnel-associated neuropathic pain, spinal cord injury-associated pain, complex regional pain syndrome, fibromyalgia-associated neuropathic pain, lumbar and cervical pain, reflex sympathic dystrophy, phantom limb syndrome or peripheral nerve or spinal cord trauma, entrapment neuropathy, nerve transection including surgery, Lissauer tract section, limb amputation and stump pain, neuroma/tumour compression, arteriovenous malformation, Vitamin B12 deficiency, diabetic neuropathy, alcoholic neuropathy, pain caused by the side effects of anti-cancer and anti-AIDS therapies, pain associated with inflammation or infection of a tooth (toothache), visceral pain, pain caused by chemical burns, pain caused by local or systemic infection, or pain caused by connective tissue disease. The connective tissue disease may be one of: rheumatoid arthritis, Wallenberg's syndrome, systemic lupus erythematosus, multiple sclerosis, or polyarteritis nodosa. The neuropathy can be classified as radiculopathy, mononeuropathy, mononeuropathy multiplex, polyneuropathy or plexopathy. Diseases in this class can be caused by a variety of nerve-damaging conditions or procedures, including, without limitation, trauma, stroke, demyelinating diseases, abscess, surgery, amputation, inflammatory diseases of the nerves, causalgia, diabetes, collagen vascular diseases, trigeminal neuralgia, rheumatoid arthritis, toxins, cancer, chronic alcoholism, herpes infection, AIDS and chemotherapy. Nerve damage causing hyperalgesia can be in peripheral or CNS nerves.

The term "allodynia" denotes pain arising from stimuli which are normally not painful. Allodynic pain may occur other than in the area stimulated. The terms "hyperalgesia"/"hyperalgesic" denote an increased sensitivity to a painful stimulus.

The terms "hypoalgesia"/"hypoalgesic" denote a decreased sensitivity to a painful stimulus.

One aspect of the present invention relates to a method for treating one or more of any type of pain, such as the types of pain referenced herein, and associated conditions, wherein the term "treating" comprises the prevention, amelioration or treatment of any type of pain and associated conditions. Specifically, the one aspect of the invention relates to a method for the treatment of neuropathic and/or inflammatory pain, comprising administering an effective amount of at least one compound according to the present invention to a subject in need thereof, including where such subject is a mammal such as a human.

Without being bound by theory, the role of CDK9 in the development of pain could be based on the following mechanism of action: Both cyclin T1 and CDK9 stimulate the basal promoter activity of TNF. TNF is a pro-inflammatory cytokine and pain mediator that controls expression of inflammatory genetic networks. For mediation of cellular TNF receptor responses, the nuclear factor-KB (NF B) pathway is crucial. TNF triggers its recruitment to cytokine genes while NF B interacts with the p-TEFb complex for stimulation of gene transcription (Barboric M. et al., NF B Binds p-TEFb to Stimulate Transcriptional Elongation by RNA Polymerase II. Molecular Cell, 2001, Vol. 8, 327-337).

Additionally, it has been shown that CDK9 is a binding partner of TRAF2, a member of the TNF receptor complex (MacLachlan T. K. et al., Binding of CDK9 to TRAF2. J Cell Biochem, 1998, 71(4), 467-478), while GP130, a subunit of the pro-inflammatory IL6 receptor complex has recently been identified as another potential binding partner of CDK9 (Falco G. D. et al., CDK9, a member of the cdc2-like family of kinases, binds to gp130, the receptor of the IL-6 family of cytokines. Oncogene, 2002, 21(49), 7464-7470). As a key player in TNF and interleukin signaling as well as NF B mediated expression of several genes (e.g. cytokines as pain mediators), CDK9 can thus be considered as a central target for the treatment of inflammatory pain.

One aspect of the present invention relates to methods to down-regulate NF B by administering a compound according to the present invention to a patient in need thereof, including where such patient is a mammal such as a human.

For the treatment of neuropathic pain, pharmacological action has to take place beyond blood-brain-barrier (BBB) in the central nervous system (CNS). Microglial cells as the principal immune cells in the CNS, release, if activated, a variety of noxious factors such as cytokines (TNF, IL1, IL6) and other pro-inflammatory molecules (Huwe et al., Small molecules as inhibitors of cyclin-dependent kinases. Angew Chem Int Ed Engl, 2003, 42(19), 2122-2138). Microglia is activated by stimulation of TNF receptor or Toll-like receptor and signal is mediated via I kinase (IKK) and NF B leading to transcriptional activation of the cytokines described above. Microglial contribution has been discussed as instrumental in chronic CNS diseases and may contribute to pain perception (Watkins L. R. et al., Glial proinflammatory cytokines mediate exaggerated pain states: implications for clinical pain. Adv Exp Med. Biol., 2003, 521, 1-21).

Recently it has been shown that NF B regulates expression of Cyclooxygenase-2 (COX-2) via Interleukin 1 (IL1) in the spinal cord (Lee K. M. et al., Spinal NF B activation induces COX-2 upregulation and contributes to inflammatory pain hypersensitivity. European Journal of Neuroscience, 2004, Vol. 19, 3375-3381). As the major contributor to elevation of spinal prostaglandin E2, the pain mediator COX-2 is already known as a target for a variety of anti-nociceptive/anti-inflammatory drugs. NF B inhibitors have proven their ability to reduce COX-2 levels and mechanical allodynia as well as thermal hyperalgesia in animal models significantly.

In contrast to inhibition of Cox-2, inhibition of CDK9 action could lead to suppression of a variety of pain mediators instead of just a single one. Thereby, anti-nociceptive action of CDK9 inhibitors might be improved in comparison to e.g. COX-2 inhibitors.

Due to its relevance for NF B mediated gene transcription, inhibition of CDK9 may therefore be a reasonable approach not only for the treatment of acute inflammatory pain, but also for the treatment of chronic pain.

The present invention is also directed to pharmaceutical compositions comprising at least one compound according to the present invention as an active ingredient together with at least one pharmaceutically acceptable (i.e. non-toxic) carrier, excipient and/or diluent for administration to a subject in need thereof, including where such subject is a mammal such as a human.

Furthermore, the invention also comprises compositions combining at least two inhibitors of CDK, wherein at least one of said inhibitors of said CDK is a compound according to the present invention, and/or pharmaceutically acceptable salts thereof. Said at least two inhibitors may inhibit the same cyclin-dependent kinase or may also inhibit different types of cyclin-dependent kinases, e.g. one inhibitor in the composition may inhibit CDK9 while the other inhibitor is capable of inhibiting CDK2, for example.

In a further particular embodiment, the invention is directed to compositions comprising at least one compound according to the present invention in combination with one or more additional pain-reducing agents and to a method of administering such a composition.

An individual pain medication often provides only partially effective pain alleviation because it interferes with just one pain-transducing pathway out of many. Thus, it is also intended to administer a compound according to the present invention in combination with a pain-reducing (analgesic) agent that acts at a different point in the pain perception process.

An "analgesic agent" comprises a molecule or combination of molecules that causes a reduction in pain. An analgesic agent employs a mechanism of action other than inhibition of CDK.

One class of analgesics, such as nonsteroidal anti-inflammatory drugs (NSAIDs), down-regulates the chemical messengers of the stimuli that are detected by the nociceptors and another class of drugs, such as opioids, alters the processing of nociceptive information in the CNS. Other analgesics are local anesthetics, anticonvulsants and antidepressants such as tricyclic antidepressants. Administering one or more classes of drug in addition to CDK inhibitors can provide even more effective amelioration of pain. Particular NSAIDs for use in the methods and compositions of the present invention include aspirin, acetaminophen, ibuprofen, and indomethacine. Furthermore, cyclooxygenase-2 (COX-2) inhibitors, such as specific COX-2 inhibitors (e.g. celecoxib, COX189, and rofecoxib) may also be used as an analgesic agent in the methods or compositions of the present invention. Particular tricyclic antidepressants are selected from the group consisting of Clomipramine, Amoxapine, Nortriptyline, Amitriptyline, Imipramine, Desipramine, Doxepine, Trimipramine, Protriptyline, and Imipramine pamoate. Furthermore, the use of anticonvulsants (e.g. gabapentine), GABAB agonists (e.g. L-baclofen), opioids, vanniloid receptor antagonists and cannabinoid (CB) receptor agonists, e.g. CB1 receptor agonists as analgesic is also preferred in the methods and compositions in the present invention.

Other Uses

In another aspect of the present invention, the compounds of the present invention or pharmaceutically acceptable salts thereof can be used as an inhibitor for a protein kinase, preferably as an inhibitor for a cellular protein kinase.

In a particular embodiment of these aspects said cellular protein kinase is a cyclin-dependent protein kinase (CDK). The cyclin-dependent protein kinase can be selected from the group comprising: CDK1, CDK2, CDK3, CDK4, CDK5, CDK6, CDK7, CDK8, CDK9, CDK10, CDK11, CDK12, CDK13, CrkRS (Crk7, CDC2-related protein kinase 7), CDKL1 (cyclin-dependent kinase-like 1); KKIALRE, CDKL2 (cyclin-dependent kinase-like 2), KKIAMRE, CDKL3 (cyclin-dependent kinase-like 3), NKIAMRE, CDKL4, similar to cyclin-dependent kinase-like 1, CDC2L1 (cell division cycle 2-like 1), PITSLRE B, CDC2L1 (cell division cycle 2-like 1), PITSLRE A, CDC2L5 (cell division cycle 2-like 5), PCTK1 (PCTAIRE protein kinase 1), PCTK2 (PCTAIRE protein kinase 2), PCTK3 (PCTAIRE protein kinase 3) or PFTK1 (PFTAIRE protein kinase 1). In particular such embodiments, said cyclin-dependent protein kinase is CDK9.

In other aspects the present invention provides a method to inhibit a cyclin-dependent protein kinase, including a cyclin-dependent protein kinase in a cell, such as a cell in a patient in need thereof, including where patient is a mammal such as a human. In certain such aspects the present invention provides a method to inhibit CDK9, including in a patient in need thereof.

In a further aspect the present invention provides methods for prophylaxis and/or treatment of a disease selected from: cell proliferative disease, such as cancer; pain, such as inflammatory pain or neuropathic pain; inflammation; cardiovascular disease, such as cardiac hypertrophy; and infectious diseases, such as viral infections including HIV, comprising administering to an individual, such as a mammal an amount of at least one compound according to the present invention and/or pharmaceutically acceptable salts thereof, effective to prevent and/or treat such disease. In certain such aspects of the invention, said mammal is a human.

Formulations, Dosages, Packages and Applications

The compositions of this invention can be formulated and administered to treat individuals in need by any means that produces contact of the active ingredient with the agent's site of action in the body of a mammal. They can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice.

Pharmaceutical compositions for use in accordance with the present invention may be formulated in conventional manner using one or more physiologically acceptable carriers or excipients. The pharmaceutical compositions of the invention can be formulated for a variety of routes of administration, including systemic and topical or localized administration. Techniques and formulations generally may be found in Remington's Pharmaceutical Sciences, Meade Publishing Co., Easton, Pa. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. In certain embodiments, the pharmaceutical preparations may be non-pyrogenic, i.e., do not elevate the body temperature of a patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of inhibitor which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

For systemic administration, injection is preferred, including intramuscular, intravenous, intraperitoneal, and subcutaneous (i.m., i.v., i.p., and i.c. respectively). The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

For injection, the pharmaceutical compositions of the invention can be formulated in liquid solutions, preferably in physiologically compatible buffers such as Hank's solution or Ringer's solution. In addition, the pharmaceutical compositions may be formulated in solid form and redissolved or suspended immediately prior to use. Lyophilized forms are also included.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. An inhibitor of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract. Solid compositions of a similar type are also employed as fillers in soft and hard-filled gelatin capsules; preferred materials in this connection also include lactose or milk sugar as well as high molecular weight polyethylene glycols. A particular formulation is a solution or suspension in an oil, for example olive oil, Miglyol, or Capmul, in a soft gelatin capsule. Antioxidants may be added to prevent long-term degradation as appropriate.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered inhibitor moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulations so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active inhibitor(s) of the present invention, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

For buccal administration the therapeutic compositions may take the form of tablets or lozenges formulated in a conventional manner.

For administration by inhalation, the compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the therapeutic agents and a suitable powder base such as lactose or starch.

The pharmaceutical compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

Pharmaceutical compositions of this invention suitable for parenteral administration comprise one or more inhibitors of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In addition to the formulations described previously, the pharmaceutical compositions may also be formulated as a depot preparation. Such long acting formulations may be administered by implantation (for example subcutaneously or intramuscularly) or by intramuscular injection. Thus, for example, the therapeutic compositions may be formulated with suitable polymeric or hydrophobic materials (for example as an emulsion in an acceptable oil) or ion exchange resins, or as sparingly soluble derivatives, for example, as a sparingly soluble salt.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the compositions of the invention are formulated into ointments, salves, gels, or creams as generally known in the art. A wash solution can be used locally to treat an injury or inflammation to accelerate healing.

In some cases, in order to prolong the therapeutic effect of an inhibitor, it is desirable to slow the absorption of the inhibitor from subcutaneous or intramuscular injection. This may be accomplished by the use of a liquid suspension of crystalline or amorphous material having poor water solubility. The rate of absorption of the inhibitor then depends upon its rate of dissolution which, in turn, may depend upon crystal size and crystalline form. Alternatively, delayed absorption of a parenterally administered inhibitor form is accomplished by dissolving or suspending the inhibitor in an oil vehicle.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active inhibitor.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to a compound of the invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing an inhibitor of the present invention in the proper medium. Absorption enhancers can also be used to increase the flux of the drug across the skin. The rate of such flux can be controlled by either providing a rate controlling membrane or dispersing the compound of the present invention in a polymer matrix or gel.

Ophthalmic formulations, eye ointments, powders, solutions and the like, are also contemplated as being within the scope of this invention.

The pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. In other embodiments, the pack or dispenser may be further packaged in an outer carton.

A pharmaceutical composition of the present invention can also be formulated as a sustained and/or timed release formulation. Such sustained and/or timed release formulations may be made by sustained release means or delivery devices that are well known to those of ordinary skill in the art, such as those described in U.S. Pat. Nos. 3,845,770; 3,916,899; 3,536,809; 3,598,123; 4,008,719; 4,710,384; 5,674,533; 5,059,595; 5,591,767; 5,120,548; 5,073,543; 5,639,476; 5,354,556; and 5,733,566, the disclosures of which are each incorporated herein by reference. The pharmaceutical compositions of the present invention can be used to provide slow or sustained release of one or more of the active ingredients using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable sustained release formulations known to those of ordinary skill in the art, including those described herein, may be readily selected for use with the pharmaceutical compositions of the invention. Thus, single unit dosage forms suitable for oral administration, such as, but not limited to, tablets, capsules, gelcaps, caplets, powders, and the like, that are adapted for sustained release are encompassed by the present invention.

Injectable depot forms are made by forming microencapsuled matrices of the subject inhibitors in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to individuals, such as humans and animals, they can be given per se or as a pharmaceutical composition containing, for example, 0.1 to 99.5% (in certain embodiments, 0.5 to 90%) of active ingredient in combination with a pharmaceutically acceptable carrier.

The present invention provides new methods of treating proliferative, degenerative and other disorders or diseases, including cancer, by administering a therapeutically effective amount of at least one of the compounds disclosed herein or an isomeric, prodrug, tautomeric, pharmaceutically acceptable salt, N-oxide or stereoisomeric form thereof. The present invention further provides methods of treating proliferative, degenerative or other disorders or diseases, including cancer, by administering a therapeutically effective combination of at least one of these compounds and another anti-cancer or anti-proliferative agent.

The term "prodrug", as used herein, refers to an agent which is converted into a pharmacologically active parent drug in vivo, such as a compound as defined herein. The term "prodrug" includes any covalently bonded carriers which release an active parent drug of the present invention in vivo when such prodrug is administered to an individual. Since prodrugs are known to enhance numerous desirable qualities of pharmaceuticals (i.e., solubility, bioavailability, manufacturing, transport, pharmacodynamics etc.) the compounds of the present invention may be delivered in prodrug form. Prodrugs, for instance, may be bioavailable by oral administration whereas the parent drug is not. Thus, the present invention is intended to cover prodrugs of the presently claimed compounds, methods of delivering the same, and compositions containing the same. Prodrugs of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

Generally speaking, prodrugs are derivatives of per se drugs, which after administration undergo conversion to the physiologically active species. The conversion may be spontaneous, such as hydrolysis in the physiological environment, or may be enzyme catalyzed. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, and/or dephosphorylated to produce the active compound.

From among the voluminous scientific literature devoted to prodrugs in general, the foregoing examples are cited: Gangwar et al., "Prodrug, molecular structure and percutaneous delivery", Des. Biopharm. Prop. Prodrugs Analogs, [Symp.] Meeting Date 1976, 409-21. (1977); Nathwani and Wood, "Penicillins: a current review of their clinical pharmacology and therapeutic use", Drugs 45(6): 866-94 (1993); Sinhababu and Thakker, "Prodrugs of anticancer agents", Adv. Drug Delivery Rev. 19(2): 241-273 (1996); Stella et al., "Prodrugs. Do they have advantages in clinical practice?", Drugs 29(5): 455-73 (1985); Tan et al. "Development and optimization of anti-HIV nucleoside analogs and prodrugs: A review of their cellular pharmacology, structure-activity relationships and pharmacokinetics", Adv. Drug Delivery Rev. 39(1-3): 117-151 (1999); Design of Prodrugs (Bundgaard H. ed.) 1985 Elsevier Science Publishers B. V. (Biomedical Division), Chapter 1; Design of Prodrugs: Bioreversible derivatives for various functional groups and chemical entities (Hans Bundgaard); Bundgaard et al. Int. J. of Pharmaceutics 22 (1984) 45-56 (Elsevier); Bundgaard et al. Int. J. of Pharmaceutics 29 (1986) 19-28 (Elsevier); Bundgaard et al. J. Med. Chem. 32 (1989) 2503-2507 Chem. Abstracts 93, 137935y (Bundgaard et al.); Chem. Abstracts 95, 138493f (Bundgaard et al.); Chem. Abstracts 95, 138592n (Bundgaard et al.); Chem. Abstracts 110, 57664p (Alminger et al.); Chem. Abstracts 115, 64029s (Buur et al.); Chem. Abstracts 115, 189582y (Hansen et al.); Chem. Abstracts 117, 14347q (Bundgaard et al.); Chem. Abstracts 117, 55790x (Jensen et al.); and Chem. Abstracts 123, 17593b (Thomsen et al.).

An active compound may be administered as a salt or prodrug that, upon administration to the individual, is capable of providing directly or indirectly the parent compound, such as a compound as defined herein, or that exhibits activity itself. Nonlimiting examples include a pharmaceutically-acceptable salt, alternatively referred to as a "physiologically acceptable salt". In addition, modifications made to a compound can affect its biologic activity, in some cases increasing the activity over the parent compound. This activity can be assessed by preparing a salt or prodrug form of the compound, and testing its activity by using methods described herein or other methods known to those of skill in the art.

As will be apparent to a person skilled in the art, through the use of a prodrug of a given subject compound, an individual treated with such prodrug will be exposed to, and hence indirectly administered with, the subject compound.

Such a procedure may expose those cells associated with a disease, such as a proliferative disease or disorder including cancer, to the subject compound.

The present invention is intended to include all isotopes of atoms occurring on the present compounds. Isotopes include those atoms having the same atomic number but different mass numbers. By way of general example and without limitation, isotopes of hydrogen include tritium and deuterium. Isotopes of carbon include $^{12}C$ and $^{14}C$.

The term "metabolite", as used herein, refers to any substance produced by the metabolism or by a metabolic process. Metabolism, as used herein, refers to the various physical/chemical/biochemical/pharmacological reactions involved in the transformation of molecules or chemical compounds occurring in the cell, tissue, system, body, animal, individual, patient or human therein.

Another aspect of the invention relates to a packaged pharmaceutical comprising a pharmaceutical composition of a compound according to the present invention and/or stereoisomeric form and/or pharmaceutically acceptable salts thereof wherein said packaged pharmaceutical further comprises instructions to administer an effective amount of the pharmaceutical composition to an individual suffering from a disease selected from a cell proliferative diseases, such as cancer, pain, inflammation, a cardiovascular diseases, such as cardiac hypertrophy, and a infectious diseases, especially viral infections such as HIV.

Another aspect of the invention relates to a method to treat a disease amenable to the inhibition of CDK9 by administering a compound according to the present invention to a patient suffering from said disease.

Another aspect of the invention relates to a method to inhibit CDK9 with a compound according to the present invention. Said inhibition of CDK9 may be in vivo or in vitro. Inhibition of CDK9 in vivo includes inhibition of CDK9 in a patient suffering from a disease amenable to the inhibition of CDK9.

Thus, one aspect of the present invention relates to the use of at least one compound of the present invention for the preparation of a pharmaceutical composition for the prophylaxis and/or treatment of a disease selected from: cell proliferative disease, pain, inflammation, cardiovascular disease and infectious disease.

In particular embodiments, said disease is a cell proliferative disease.

In particular embodiments, said cell proliferative disease is cancer.

In particular embodiments, said disease is an infectious disease.

In particular embodiments, said infectious disease is a viral infection.

In particular embodiments, said viral infection is an infection with HIV.

In particular embodiments, said disease is a cardiovascular disease.

In particular embodiments, said cardiovascular disease is cardiac hypertrophy.

In particular embodiments, said disease is inflammation.

In particular embodiments, said disease is pain.

In particular embodiments, said pain comprises inflammatory pain and/or neuropathic pain.

In particular embodiments, said pharmaceutical composition is for administration to a human.

Another aspect of the present invention relates to pharmaceutical composition comprising at least one compound of the present invention as an active ingredient, together with at least one pharmaceutically acceptable carrier, excipient and/or diluent.

In particular embodiments, said pharmaceutical composition is for use in combination with an analgesic agent, wherein said analgesic agent has a mechanism of action other than inhibition of a CDK.

In particular embodiments, said pharmaceutical composition further comprises an analgesic agent, wherein said analgesic agent has a mechanism of action other than inhibition of a CDK.

Figure 1:
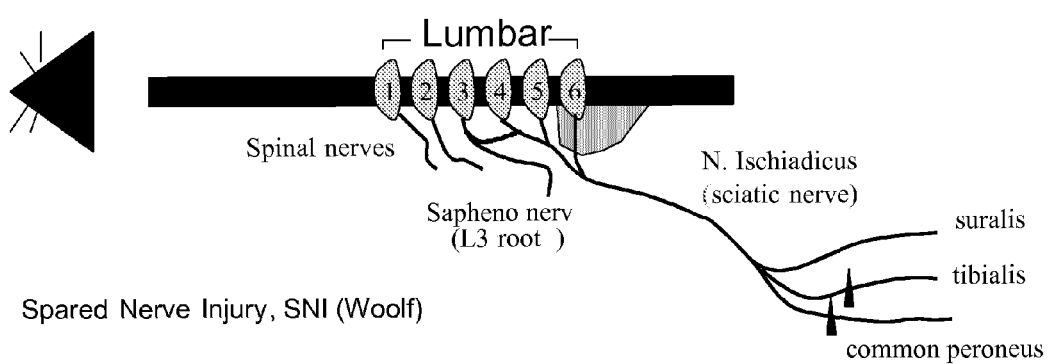
FIG. 1 schematically depicts the spared nerve injury model (SNI model, as developed by Decosterd and Woolf (2000), which is characterized by ligation and section of two branches of the sciatic nerve (namely tibial and common peroneal nerves) leaving the sural nerve intact.

The invention is further illustrated by the following non-limiting examples.

EXAMPLES

All reagents were purchased from ACROS Organics, Aldrich, Lancaster, Maybridge and Boron Molecular.

The LC/MS analyses for the compounds were done at Surveyor MSQ (Thermo Finnigan, USA) with APCI ionization.

The $^1$H NMR spectra were recorded on <<MERCURY plus 400 MHz>> spectrometer (Varian). Chemical shift values are given in ppm relative to tetramethylsilane (TMS), with the residual solvent proton resonance as internal standard.

Melting points were determined on Sanyo Gallenkamp apparatus.

Example 1

Synthesis of {3-[6-(2-Ethoxy-phenyl)-pyrimidin-4-ylamino]-phenyl}-methanesulfonamide (Compound 1)

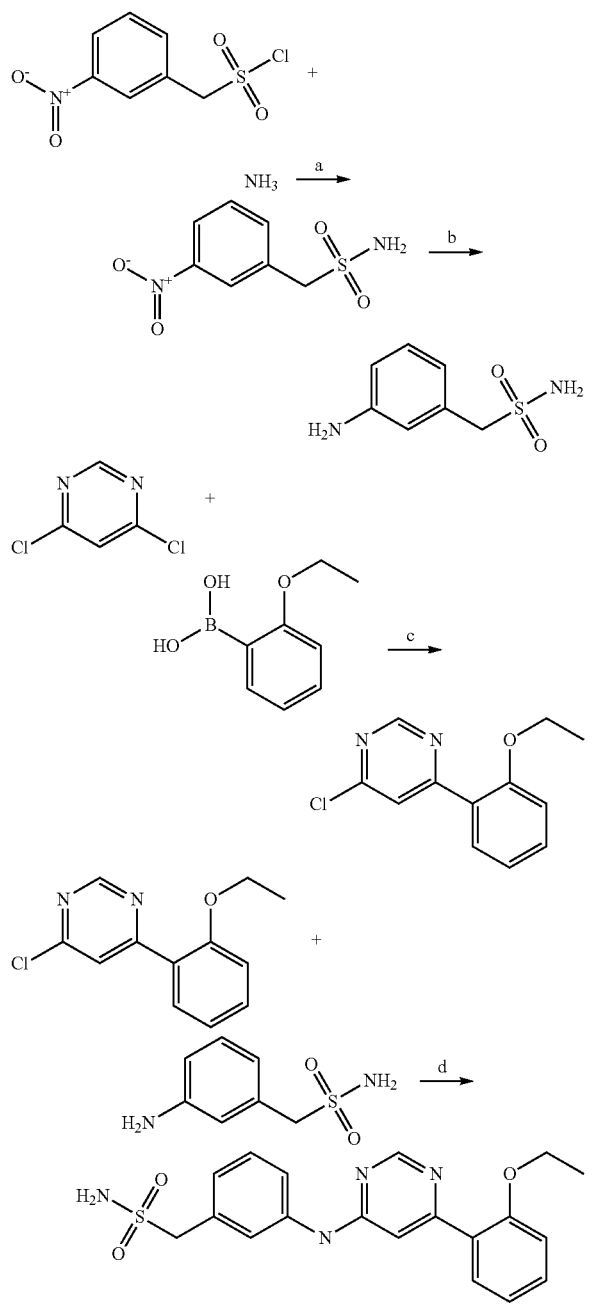

a. Synthesis of (3-nitrophenyl)methanesulfonyl amide (3-Nitrophenyl)methanesulfonyl chloride (4.71 g, 20 mmol) was dissolved in acetonitrile (20 mL), then to this solution was added concentrated aqueous ammonia (20 mL) saturated with ammonium carbonate and the reaction mixture was vigorously stirred for 1 h at room temperature. Then acetonitrile was evaporated, the residue was diluted with cold water (20 mL), which led to a precipitate formation. The precipitated was filtered off and washed with water (2×5 mL) and ether and dried under reduced pressure. Yield of (3-nitrophenyl)methanesulfonyl amide 3.5 g (80%)

b. Synthesis of (3-aminophenyl)methanesulfonyl amide (3-nitrophenyl)methanesulfonyl amide (3.5 g, 16 mmol) was hydrogenated over Raney nickel (0.5 g) in methanol at 50° C. and 70 psi for 4 h, then the catalyst was filtered off, washed with warm methanol, the combined filtrates were evaporated to give 2.83 g (95%) of (3-aminophenyl)methanesulfonyl amide.

c. Synthesis of 4-chloro-6-(2-ethoxyphenyl)-pyrimidine

To a solution of 4,6-dichloropyrimidine (6.0 g, 0.04 mol) and 2-ethoxyphenylboronic acid (4.81 g, 0.029 mol) in mixture of dimethoxyethane (120 mL) and water (18 mL) were added $NaHCO_3$ (6.72 g, 0.08 mol) and $(PPh_3)_2PdCl_2$ (0.84 g) and the reaction mixture was allowed to reflux for 8 h, then it was concentrated under reduced pressure. The residue was dissolved in $CH_2Cl_2$ (100 mL), the resulting solution was washed with water (20 mL), dried over anhydrous $K_2CO_3$, filtered and the solvent removed under reduced pressure. The crude product was purified by flash chromatography on silica (eluent $CH_2Cl_2$) and recrystallized from hexanes. Yield of 4-chloro-6-(2-ethoxyphenyl)-pyrimidine 4.97 g (73%).

d. Synthesis of {3-[6-(2-Ethoxy-phenyl)-pyrimidin-4-ylamino]-phenyl}-methanesulfonamide (Compound 1)

A mixture of (3-aminophenyl)-methanesulfonyl amide (0.112 g, 0.60 mmol) and 4-chloro-6-(2-ethoxyphenyl)-pyrimidine (0.141 g, 0.60 mmol) in DMFA (3 mL) was stirred at 80° C. to the completion of the reaction (TLC control), then evaporated in vacuo. The residue was recrystallized from isopropanol to give {3-[6-(2-Ethoxy-phenyl)-pyrimidin-4-ylamino]-phenyl}-methanesulfonamide (Compound 1)

Yield: 0.180 g (78%).
Melting point 236.3-238.6° C.
$^1$H-NMR (400 MHz, DMSO-$d_6$); δ (ppm) 1.37 (3H, t), 4.18 (2H, q), 4.32 (2H, s), 6.82 (2H, br. s), 7.15 (1H, t), 7.25 (2H, d), 7.45 (2H, t), 7.58 (1H, t), 7.66 (1H, s), 7.68 (1H, d), 7.76 (1H, d), 8.88 (1H, s), 11.41 (1H, br. s).
Cl MS m/z 385 (MH+)

Example 2

Synthesis of (3-[6-(2,3-dimethoxyphenyl)-4-pyrimidinyl-aminophenyl)-methanesulfonamide (Compound 2)

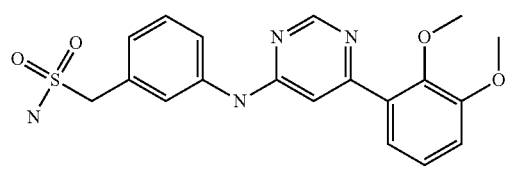 [SMILES: COc1cccc(-c2cc(Nc3cccc(CS(N)(=O)=O)c3)ncn2)c1OC]

83 a. Synthesis of (3-nitrophenyl)methanesulfonamide

The same procedure as for Compound 1.

b. Synthesis of (3-aminophenyl)methanesulfonamide

The same procedure as for Compound 1.

c. Synthesis of 4-chloro-6-(2,3-dimethoxyphenyl)-pyrimidine

The same procedure as for Compound 1.

d. Synthesis of (3-[6-(2,3-dimethoxyphenyl)-4-pyrimidinyl]aminophenyl)methanesulfonamide (Compound 2)

The same procedure as for Compound 1.
Yield: 0.100 g (55%).
Melting point 146.9-150.0° C.
$^1$H-NMR (400 MHz, DMSO-d$_6$); δ (ppm) 3.75 (3H, s), 3.87 (3H, s), 4.28 (2H, s), 676 (2H, br. s), 7.05 (1H, d), 7.19 (2H, d), 7.35 (3H, m), 7.42 (1H, t), 7.66 (1H, s), 7.80 (1H, d), 8.68 (1H, s), 9.67 (1H, br. s).
Cl MS m/z 401 (MH+)

Example 3

Synthesis of (3-[6-(2-methoxy-4-fluorophenyl)-4-pyrimidinyl]-aminophenyl)-methanesulfonamide (Compound 3)

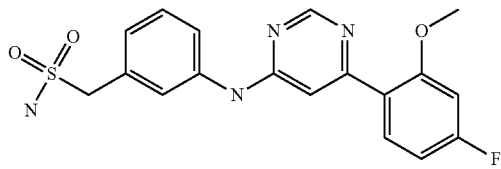 [SMILES: COc1cc(F)ccc1-c1cc(Nc2cccc(CS(N)(=O)=O)c2)ncn1]

a. Synthesis of (3-nitrophenyl)methanesulfonamide

The same procedure as for Compound 1.

b. Synthesis of (3-aminophenyl)methanesulfonamide

The same procedure as for Compound 1.

c. Synthesis of 4-chloro-6-(2-methoxy-4-fluorophenyl)-pyrimidine

The same procedure as for Compound 1.

d. Synthesis of (3-[6-(2-methoxy-4-fluorophenyl)-4-pyrimidinyl]-aminophenyl)-methanesulfonamide (Compound 3)

The same procedure as for Compound 1.
Yield: 0.15 g (76%).
Melting point 232.5-234.2° C.
$^1$H-NMR (400 MHz, DMSO-d$_6$); δ (ppm) 3.92 (3H, s), 4.30 (2H, s), 6.85 (2H, br. s), 7.10 (1H, t), 7.16-7.26 (2H, m), 7.38-7.48 (2H, m), 7.65 (1H, s), 7.71-7.83 (2H, m), 8.87 (1H, s), 11.6 (1H, br. s).
Cl MS m/z 389 (MH+)

84

Example 4

Synthesis of (3-[6-(2-ethoxy-5-fluorophenyl)-4-pyrimidinyl]-aminophenyl)-methanesulfonamide (Compound 4)

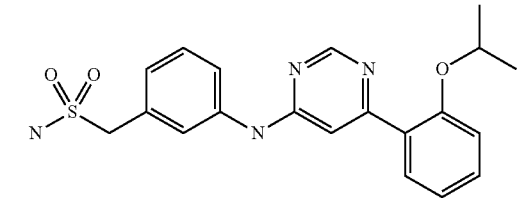 [SMILES: CC(C)Oc1ccccc1-c1cc(Nc2cccc(CS(N)(=O)=O)c2)ncn1]

a. Synthesis of (3-nitrophenyl)methanesulfonamide

The same procedure as for Compound 1.

b. Synthesis of (3-aminophenyl)methanesulfonamide

The same procedure as for Compound 1.

c. Synthesis of 4-chloro-6-(2-ethoxy-5-fluorophenyl)-pyrimidine

The same procedure as for Compound 1.

d. Synthesis of (3-[6-(2-ethoxy-5-fluorophenyl)-4-pyrimidinyl]-aminophenyl)-methanesulfonamide (Compound 4)

The same procedure as for Compound 1.
Yield: 0.12 g (74%).
Melting point 237.9-240.4° C.
$^1$H-NMR (400 MHz, DMSO-d$_6$); δ (ppm) 1.33 (3H, t), 4.15 (2H, q), 4.31 (2H, s), 6.82 (2H, br. s), 7.18-7.30 (2H, m), 7.35-7.52 (3H, m), 7.58-7.66 (1H, m), 7.64 (1H, s), 7.72-7.80 (1H, d), 8.86 (1H, s), 11.25 (1H, br. s)
Cl MS m/z 403 (MH+)

Example 5

Synthesis of (3-[6-(2-isopropoxyphenyl)-4-pyrimidinyl]aminophenyl)methanesulfonamide (Compound 5)

a. Synthesis of (3-nitrophenyl)methanesulfonamide

The same procedure as for Compound 1.

b. Synthesis of (3-aminophenyl)methanesulfonamide

The same procedure as for Compound 1.

c. Synthesis of 4-chloro-6-(2-isopropoxyphenyl)-pyrimidine

To a solution of 4,6-dichloropyrimidine (0.207 g, 1.38 mmol) and 2-isopropoxyphenylboronic acid (0.18 g, 1.0 mmol) in mixture of dimethoxyethane (4 mL) and water (0.6 mL) were added $NaHCO_3$ (0.231 g, 2.76 mmol) and $(PPh_3)_2PdCl_2$ (0.029 g) and the reaction mixture was refluxed for 8 h, then was evaporated. The residue was dissolved in $CH_2Cl_2$ (10 mL) and washed with water, dried over anhydrous $K_2CO_3$ and evaporated. The crude product was isolated by column chromatography on silica (eluent $CH_2Cl_2$) as oil. Yield of 4-chloro-6-(2-isopropoxyphenyl)-pyrimidine 0.18 g (72%).

d. Synthesis of (3-[6-(2-isopropoxyphenyl)-4-pyrimidinyl]aminophenyl)methanesulfonamide (Compound 5)

The same procedure as for Compound 1.
Yield: 0.075 g (32%).
Melting point 125.0-128.6° C.
$^1$H-NMR (400 MHz, DMSO-$d_6$); δ (ppm) 1.31 (6H, d), 4.29 (2H, s), 6.80 (2H, br. s), 7.04-7.24 (3H, m), 7.33-7.52 (3H, m), 7.62 (1H, s), 7.79 (2H, t), 8.76 (1H, s), 10.30 (1H, br. s).
Cl MS m/z 399 (MH+)

Example 6

Synthesis of (3-[6-(3-fluorophenyl)-4-pyrimidinyl]aminophenyl)methanesulfonamide (Compound 6)

a. Synthesis of (3-nitrophenyl)methanesulfonamide

The same procedure as for Compound 1.

b. Synthesis of (3-aminophenyl)methanesulfonamide

The same procedure as for Compound 1.

c. Synthesis of 4-chloro-6-(3-fluorophenyl)-pyrimidine

The same procedure as for Compound 1.

d. Synthesis of (3-[6-(3-fluorophenyl)-4-pyrimidinyl]aminophenyl)methanesulfonamide (Compound 6)

The same procedure as for Compound 1.
Yield: 0.11 g (84%).
Melting point 258.8-263.1° C.

$^1$H-NMR (400 MHz, DMSO-$d_6$); δ (ppm) 4.30 (2H, s), 6.80 (2H, br. s), 7.15 (1H, d), 7.37-7.45 (3H, m), 7.58-7.66 (1H, m), 7.66 (1H, s), 7.73 (1H, d), 7.79-7.87 (2H, m), 8.80 (1H, s), 10.50 (1H, br. s).
Cl MS m/z 359 (MH+)

Example 7

Synthesis of (3-[6-(4-fluorophenyl)-4-pyrimidinyl]aminophenyl)methanesulfonamide (Compound 7)

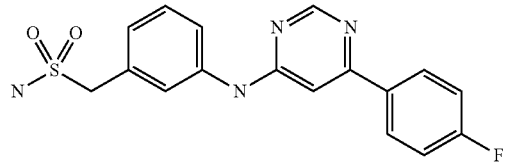 [SMILES: NS(=O)(=O)Cc1cccc(Nc2cc(-c3ccc(F)cc3)ncn2)c1]

a. Synthesis of (3-nitrophenyl)methanesulfonamide

The same procedure as for Compound 1.

b. Synthesis of (3-aminophenyl)methanesulfonamide

The same procedure as for Compound 1.

c. Synthesis of 4-chloro-6-(4-fluorophenyl)-pyrimidine

The same procedure as for Compound 1.

d. Synthesis of (3-[6-(4-fluorophenyl)-4-pyrimidinyl]aminophenyl)methanesulfonamide (Compound 7)

The same procedure as for Compound 1.
Yield: 0.11 g (67%).
Melting point 255.0-258.2° C.
$^1$H-NMR (400 MHz, DMSO-$d_6$); δ (ppm) 4.30 (2H, s), 6.82 (2H, br. s), 7.19 (1H, t), 7.35-7.48 (5H, m), 7.66 (1H, s), 7.73 (1H, d), 8.03-8.12 (2H, t), 8.82 (1H, s), 10.80 (1H, br. s).
Cl MS m/z 359 (MH+)

Example 8

Synthesis of (3-[6-(3-ethoxyphenyl)-4-pyrimidinyl]aminophenyl)methanesulfonamide (Compound 8)

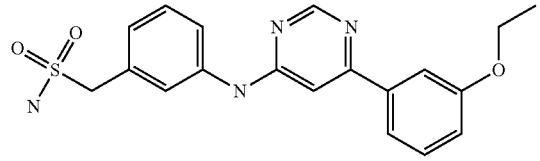 [SMILES: CCOc1cccc(-c2cc(Nc3cccc(CS(N)(=O)=O)c3)ncn2)c1]

a. Synthesis of (3-nitrophenyl)methanesulfonamide

The same procedure as for Compound 1.

b. Synthesis of (3-aminophenyl)methanesulfonamide

The same procedure as for Compound 1.

c. Synthesis of 4-chloro-6-(3-ethoxyphenyl)-pyrimidine

The same procedure as for Compound 1.

d. Synthesis of (3-[6-(3-ethoxyphenyl)-4-pyrimidinyl]aminophenyl)methanesulfonamide (Compound 8)

The same procedure as for Compound 1.
Yield: 0.10 g (65%).
Melting point 249-252.3° C.
$^1$H-NMR (400 MHz, DMSO-d$_6$); δ (ppm) 1.36 (3H, t), 4.15 (2H, q), 4.31 (2H, s), 6.83 (2H, br. s), 7.14-7.24 (2H, m), 7.38-7.47 (2H, m), 7.47-7.57 (3H, m), 7.67 (1H, s), 7.74 (1H, d), 8.83 (1H, s), 11.00 (1H, br. s).
Cl MS m/z 385 (MH+)

Example 9

Synthesis of (3-[6-(3-benzyloxyphenyl)-4-pyrimidinyl]aminophenyl)methanesulfonamide (Compound 9)

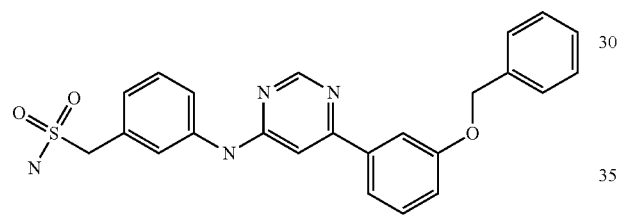

a. Synthesis of (3-nitrophenyl)methanesulfonamide

The same procedure as for Compound 1.

b. Synthesis of (3-aminophenyl)methanesulfonamide

The same procedure as for Compound 1.

c. Synthesis of 4-chloro-6-(3-benzyloxyphenyl)-pyrimidine

The same procedure as for Compound 1.

d. Synthesis of (3-[6-(3-benzyloxyphenyl)-4-pyrimidinyl]aminophenyl)methanesulfonamide (Compound 9)

The same procedure as for Compound 1.
Yield: 0.10 g (69%).
Melting point 233.2-234.8° C.
$^1$H-NMR (400 MHz, DMSO-d$_6$); δ (ppm) 4.30 (2H, s), 5.22 (2H, s), 6.82 (2H, br. s), 7.20 (1H, d), 7.27 (1H, d), 7.31-7.58 (10H, m), 7.66 (1H, s), 7.73 (1H, d), 8.84 (1H, s), 10.90 (1H, br. s).
Cl MS m/z 447 (MH+)

Example 10

Synthesis of (3-[6-(2-methoxyphenyl)-4-pyrimidinyl]aminophenyl)-N-isopropylmethanesulfonamide (Compound 10)

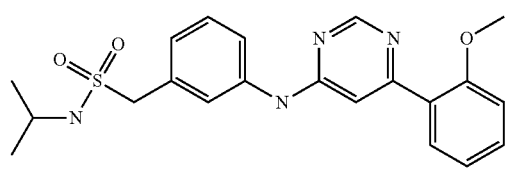 [SMILES: COc1ccccc1-c1cc(Nc2cccc(CS(=O)(=O)NC(C)C)c2)ncn1]

a. Synthesis of (3-nitrophenyl)-N-isopropylmethanesulfonamide

The same procedure as for Compound 14.

b. Synthesis of (3-aminophenyl)-N-isopropylmethanesulfonamide

The same procedure as for Compound 1.

c. Synthesis of 4-chloro-6-(2-methoxyphenyl)-pyrimidine

The same procedure as for Compound 1.

d. Synthesis of (3-[6-(2-methoxyphenyl)-4-pyrimidinyl]aminophenyl)-N-isopropylmethanesulfonamide (Compound 10)

The same procedure as for Compound 14.
Yield: 0.102 g (50%).
Melting point 179.0-180.0° C.
$^1$H-NMR (400 MHz, DMSO-d$_6$); δ (ppm) 1.15 (6H, d), 3.89 (3H, s), 4.30 (2H, s), 7.07 (1H, t), 7.13 (1H, d), 7.17 (1H, d), 7.28 (1H, s), 7.36 (1H, t), 7.43 (1H, t), 7.61 (1H, d), 7.72 (1H, d), 7.77 (1H, s) 8.60 (1H, s).
Cl MS m/z 413 (MH+)

Example 11

Synthesis of (3-[6-(2-methoxyphenyl)-4-pyrimidinyl]aminophenyl)-N-cyclopropylmethanesulfonamide (Compound 11)

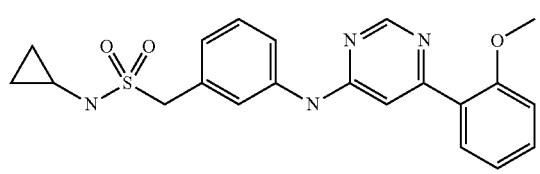 [SMILES: COc1ccccc1-c1cc(Nc2cccc(CS(=O)(=O)NC3CC3)c2)ncn1]

a. Synthesis of (3-nitrophenyl)-N-cyclopropylmethanesulfonamide

The same procedure as for Compound 14.

b. Synthesis of (3-aminophenyl)-N-cyclopropylmethanesulfonamide

The same procedure as for Compound 1.

c. Synthesis of 4-chloro-6-(2-methoxyphenyl)-pyrimidine

The same procedure as for Compound 1.

d. Synthesis of (3-[6-(2-methoxyphenyl)-4-pyrimidinyl]aminophenyl)-N-cyclopropylmethanesulfonamide (Compound 11)

The same procedure as for Compound 14.
Yield: 0.050 g (25%).
Melting point 216.5-218.0° C.
$^1$H-NMR (400 MHz, DMSO-d$_6$); δ (ppm) 0.63 (4H, m), 2.55 (1H, m), 3.90 (3H, s), 4.40 (2H, s), 7.07 (1H, t), 7.13 (1H, d), 7.17 (1H, d), 7.28 (1H, s), 7.36 (1H, t), 7.43 (1H, t), 7.61 (1H, d), 7.72 (1H, d), 7.77 (1H, s) 8.61 (1H, s).
CI MS m/z 411 (MH+)

Example 12

Synthesis of (3-[6-(2-ethoxyphenyl)-4-pyrimidinyl]aminophenyl)-N-propylmethanesulfonamide (Compound 12)

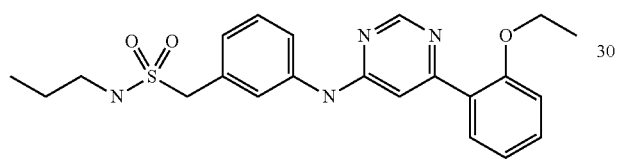

a. Synthesis of (3-nitrophenyl)-N-propylmethanesulfonamide

The same procedure as for Compound 14.

b. Synthesis of (3-aminophenyl)-N-propylmethanesulfonamide

The same procedure as for Compound 1.

c. Synthesis of 4-chloro-6-(2-ethoxyphenyl)-pyrimidine

The same procedure as for Compound 1.

d. Synthesis of (3-[6-(2-ethoxyphenyl)-4-pyrimidinyl]aminophenyl)-N-propylmethanesulfonamide (Compound 12)

The same procedure as for Compound 14.
Yield: 0.117 g (55%).
Melting point 178.8-179.6° C.
$^1$H-NMR (400 MHz, DMSO-d$_6$); δ (ppm) 0.88 (3H, t), 1.37 (3H, t), 1.50 (2H, dt), 2.95 (2H, t), 4.13 (2H, q), 4.32 (2H, s), 7.05 (1H, t), 7.10 (1H, d), 7.17 (1H, d), 7.29 (1H, s), 7.36 (1H, t), 7.40 (1H, t), 7.59 (1H, d), 7.69 (1H, d), 7.73 (1H, s) 8.61 (1H, s).
CI MS m/z 427 (MH+)

Example 13

Synthesis of (3-[6-(2-ethoxyphenyl)-4-pyrimidinyl]aminophenyl)-N-cyclopentylmethanesulfonamide (Compound 13)

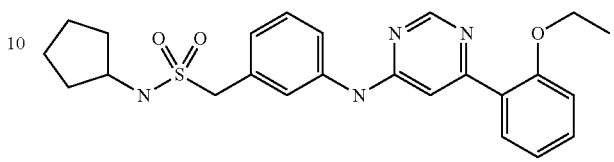

a. Synthesis of (3-nitrophenyl)-N-cyclopentylmethanesulfonamide

The same procedure as for Compound 14.

b. Synthesis of (3-aminophenyl)-N-cyclopentylmethanesulfonamide

The same procedure as for Compound 1.

c. Synthesis of 4-chloro-6-(2-ethoxyphenyl)-pyrimidine

The same procedure as for Compound 1.

d. Synthesis of (3-[6-(2-ethoxyphenyl)-4-pyrimidinyl]aminophenyl)-N-cyclopentylmethanesulfonamide (Compound 13)

The same procedure as for Compound 14.
Yield: 0.105 g (46%).
Melting point 178.5-179.1° C.
$^1$H-NMR (400 MHz, DMSO-d$_6$); δ (ppm) 1.37 (3H, t), 1.40-1.95 (8H, m), 3.55-3.66 (1H, m), 4.13 (2H, q), 4.32 (2H, s), 7.05 (1H, t), 7.09 (1H, d), 7.18 (1H, d), 7.29 (1H, s), 7.36 (1H, t), 7.40 (1H, t), 7.58 (1H, d), 7.70 (1H, d), 7.73 (1H, s) 8.61 (1H, s).
CI MS m/z 453 (MH+)

Example 14

Synthesis of Synthesis of (3-[6-(2-methoxyphenyl)-4-pyrimidinyl]aminophenyl)-N-propylmethanesulfonamide (Compound 14)

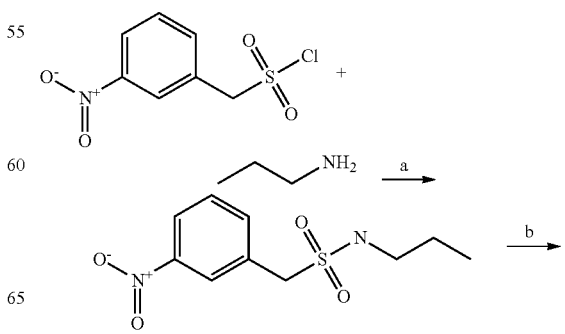

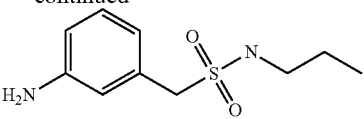

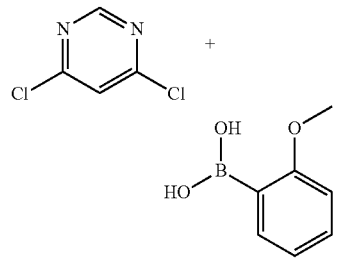

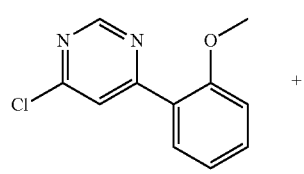

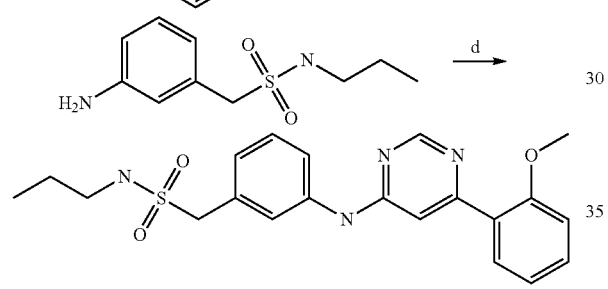

a. Synthesis of (3-nitrophenyl)-N-propylmethanesulfonamide (3-Nitrophenyl)methanesulfonyl chloride (0.6 g, 2.55 mmol) was dissolved in acetonitrile (10 mL), then to this solution was added propylamine (0.247 mL, 3 mmol) and triethylamine (1 mL). The reaction mixture was allowed to vigorously stir for 3 h at room temperature, then the diluted with cold water (30 ml), leading to a precipitate formation. The precipitate was filtered off, washed with water (2×10 mL) and dried under reduced pressure. Yield of (3-nitrophenyl)-N-propylmethanesulfonamide 0.63 g (95%).

b. Synthesis of (3-aminophenyl)-N-propylmethanesulfonamide

The same procedure as for Compound 1.

c. Synthesis of 4-chloro-6-(2-methoxyphenyl)-pyrimidine

The same procedure as for Compound 1.

d. Synthesis of (3-[6-(2-methoxyphenyl)-4-pyrimidinyl]aminophenyl)-N-propylmethanesulfonamide (Compound 14)

A mixture of (3-nitrophenyl)-N-propylmethanesulfonamide (0.114 g, 0.5 mmol) and 4-chloro-6-(2-methoxyphenyl)-pyrimidine (0.110 g, 0.5 mmol) in DMFA (3 mL) was stirred at 80° C. till the end of the reaction (TLC control) and then concentrated under reduced pressure. The resulting residue was purified by column chromatography on silica to afford the (3-[6-(2-methoxyphenyl)-4-pyrimidinyl]aminophenyl)-N-propylmethanesulfonamide.

Yield: 0.130 g (63%).

Melting point 190.4-190.9° C.

$^1$H-NMR (400 MHz, DMSO-$d_6$); δ (ppm) 0.90 (3H, t), 1.45-1.55 (2H, m), 3.90 (3H, s), 4.32 (2H, s), 7.06 (1H, t), 7.13 (1H, d), 7.16 (1H, d), 7.27 (1H, s), 7.36 (1H, t), 7.43 (1H, t), 7.61 (1H, d), 7.72 (1H, d), 7.75 (1H, s) 8.60 (1H, s).

Cl MS m/z 413 (MH+)

Example 15

Synthesis of (3-[6-(2-methoxyphenyl)-4-pyrimidinyl]aminophenyl)-N-(tert-butyl)methanesulfonamide (Compound 15)

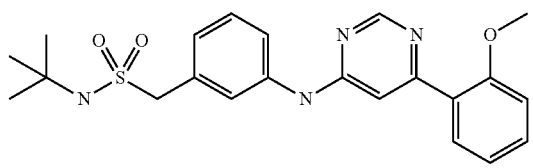 [SMILES: COc1ccccc1-c1cc(Nc2cccc(CS(=O)(=O)NC(C)(C)C)c2)ncn1]

a. Synthesis of (3-nitrophenyl)-N-(tert-butyl)methanesulfonamide

The same procedure as for Compound 14.

b. Synthesis of (3-aminophenyl)-N-(tert-butyl)methanesulfonamide

The same procedure as for Compound 1.

c. Synthesis of 4-chloro-6-(2-methoxyphenyl)-pyrimidine

The same procedure as for Compound 1.

d. Synthesis of (3-[6-(2-methoxyphenyl)-4-pyrimidinyl]aminophenyl)-N-(tert-butyl)methanesulfonamide (Compound 15)

The same procedure as for Compound 14.

Yield: 0.054 g (25%).

Melting point 172.5-173.5° C.

$^1$H-NMR (400 MHz, DMSO-$d_6$); δ (ppm) 1.35 (9H, s), 3.89 (3H, s), 4.30 (2H, s), 7.06 (1H, t), 7.12 (1H, d), 7.15 (1H, d), 7.27 (1H, s), 7.35 (1H, t), 7.43 (1H, t), 7.58 (1H, d), 7.72 (1H, d), 7.77 (1H, s) 8.60 (1H, s).

Cl MS m/z 427 (MH+)

Example 16

Synthesis of (3-[6-(2-methoxyphenyl)-4-pyrimidinyl]aminophenyl)-N-cyclopentylmethanesulfonamide (Compound 16)

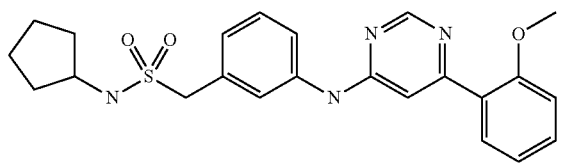 [SMILES: COc1ccccc1-c1cc(Nc2cccc(CS(=O)(=O)NC3CCCC3)c2)ncn1]

a. Synthesis of (3-nitrophenyl)-N-cyclopentylmethanesulfonamide

The same procedure as for Compound 14.

b. Synthesis of (3-aminophenyl)-N-cyclopentylmethanesulfonamide

The same procedure as for Compound 1.

c. Synthesis of 4-chloro-6-(2-methoxyphenyl)-pyrimidine

The same procedure as for Compound 1.

d. Synthesis of (3-[6-(2-methoxyphenyl)-4-pyrimidinyl]aminophenyl)-N-cyclopentylmethanesulfonamide (Compound 16)

The same procedure as for Compound 14.
Yield: 0.61 g (28%).
Melting point 204.6-205.7° C.
$^1$H-NMR (400 MHz, DMSO-d$_6$); δ (ppm) 1.40-1.95 (8H, m), 3.60 (1H, m), 3.89 (3H, s), 4.30 (2H, s), 7.07 (1H, t), 7.13 (1H, d), 7.17 (1H, d), 7.28 (1H, s), 7.36 (1H, t), 7.43 (1H, t), 7.59 (1H, d), 7.72 (1H, d), 7.76 (1H, s) 8.60 (1H, s).
Cl MS m/z 439 (MH+)

Example 17

Synthesis of (3-[6-(2-ethoxyphenyl)-4-pyrimidinyl]aminophenyl)-N-isopropylmethanesulfonamide (Compound 17)

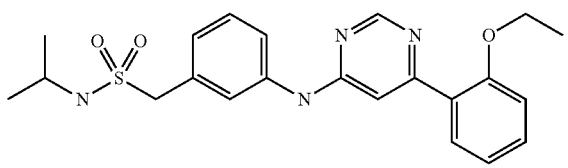 [SMILES: CCOc1ccccc1-c1cc(Nc2cccc(CS(=O)(=O)NC(C)C)c2)ncn1]

a. Synthesis of (3-nitrophenyl)-N-isopropylmethanesulfonamide

The same procedure as for Compound 14.

b. Synthesis of (3-aminophenyl)-N-isopropylmethanesulfonamide

The same procedure as for Compound 1.

c. Synthesis of 4-chloro-6-(2-ethoxyphenyl)-pyrimidine

The same procedure as for Compound 1.

d. Synthesis of (3-[6-(2-ethoxyphenyl)-4-pyrimidinyl]aminophenyl)-N-isopropylmethanesulfonamide (Compound 17)

The same procedure as for Compound 14.
Yield: 0.137 g (64%).
Melting point 142.5-143.3° C.
$^1$H-NMR (400 MHz, DMSO-d$_6$); δ (ppm) 1.16 (6H, d), 1.37 (3H, t), 1.50 (2H, dt), 3.40-3.50 (1H, m), 4.13 (2H, q), 4.30 (2H, s), 7.05 (1H, t), 7.09 (1H, d), 7.18 (1H, d), 7.29 (1H, s), 7.36 (1H, t), 7.40 (1H, t), 7.59 (1H, d), 7.70 (1H, d), 7.73 (1H, s) 8.61 (1H, s).
Cl MS m/z 427 (MH+)

Example 18

Synthesis of (3-[6-(2-ethoxyphenyl)-4-pyrimidinyl]aminophenyl)-N-cyclopropylmethanesulfonamide (Compound 18)

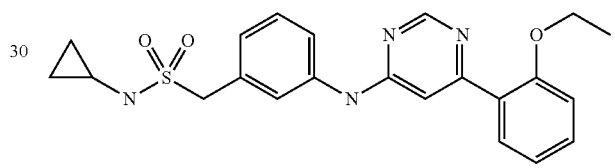

a. Synthesis of (3-nitrophenyl)-N-cyclopropylmethanesulfonamide

The same procedure as for Compound 14.

b. Synthesis of (3-aminophenyl)-N-cyclopropylmethanesulfonamide

The same procedure as for Compound 1.

c. Synthesis of 4-chloro-6-(2-ethoxyphenyl)-pyrimidine

The same procedure as for Compound 1.

d. Synthesis of (3-[6-(2-ethoxyphenyl)-4-pyrimidinyl]aminophenyl)-N-cyclopropylmethanesulfonamide (Compound 18)

The same procedure as for Compound 14.
Yield: 0.122 g (57%).
Has no melting point: substance softens and melts above 90° C.
$^1$H-NMR (400 MHz, DMSO-d$_6$); δ (ppm) 0.58-0.70 (4H, m), 1.37 (3H, t), 2.50-2.60 (1H, m), 4.13 (2H, q), 4.29 (2H, s), 7.05 (1H, t), 7.09 (1H, d), 7.19 (1H, d), 7.30 (1H, s), 7.37 (1H, t), 7.41 (1H, t), 7.59 (1H, d), 7.71 (1H, d), 7.74 (1H, s), 8.61 (1H, s).
Cl MS m/z 425 (MH+)

Example 19

Synthesis of (3-[6-(2-ethoxyphenyl)-4-pyrimidinyl]aminophenyl)-N-(tert-butyl)methanesulfonamide (Compound 19)

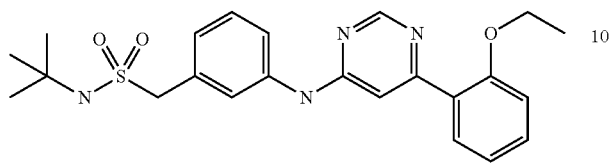

a. Synthesis of (3-nitrophenyl)-N-(tert-butyl)methanesulfonamide

The same procedure as for Compound 14.

b. Synthesis of (3-aminophenyl)-N-(tert-butyl)methanesulfonamide

The same procedure as for Compound 1.

c. Synthesis of 4-chloro-6-(2-ethoxyphenyl)-pyrimidine

The same procedure as for Compound 1.

d. Synthesis of (3-[6-(2-ethoxyphenyl)-4-pyrimidinyl]aminophenyl)-N-(tert-butyl)methanesulfonamide (Compound 19)

The same procedure as for Compound 14.
Yield: 0.108 g (49%).
Melting point 170.5-171.5° C.
$^1$H-NMR (400 MHz, DMSO-$d_6$); δ (ppm) 1.34 (9H, s), 1.37 (3H, t), 4.13 (2H, q), 4.30 (2H, s), 7.04 (1H, t), 7.09 (1H, d), 7.17 (1H, d), 7.29 (1H, s), 7.36 (1H, t), 7.40 (1H, t), 7.58 (1H, d), 7.70 (1H, d), 7.74 (1H, s), 8.61 (1H, s).
Cl MS m/z 441 (MH+)

TABLE 2-continued

Examples 1-19: Yields of the intermediates

| (3-nitrophenyl)methanesulfonamide | Yield % | (3-aminophenyl)methanesulfonamide | Yield % | 4-chloro-6-aryl-pyrimidine | Yield % |
|---|---|---|---|---|---|
| | | | | 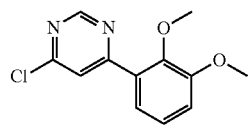 [SMILES: COc1cccc(-c2cc(Cl)ncn2)c1OC] | 66 |
| | | | | 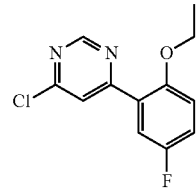 [SMILES: CCOc1ccc(F)cc1-c1cc(Cl)ncn1] | 44 |
| | | | | 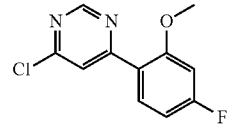 [SMILES: COc1cc(F)ccc1-c1cc(Cl)ncn1] | 55 |

Example 20

Synthesis of C-{3-[6-(2-methoxy-phenyl)-pyrimidin-4-ylamino]-phenyl}-N,N-dimethyl-methanesulfonamide (Compound 20)

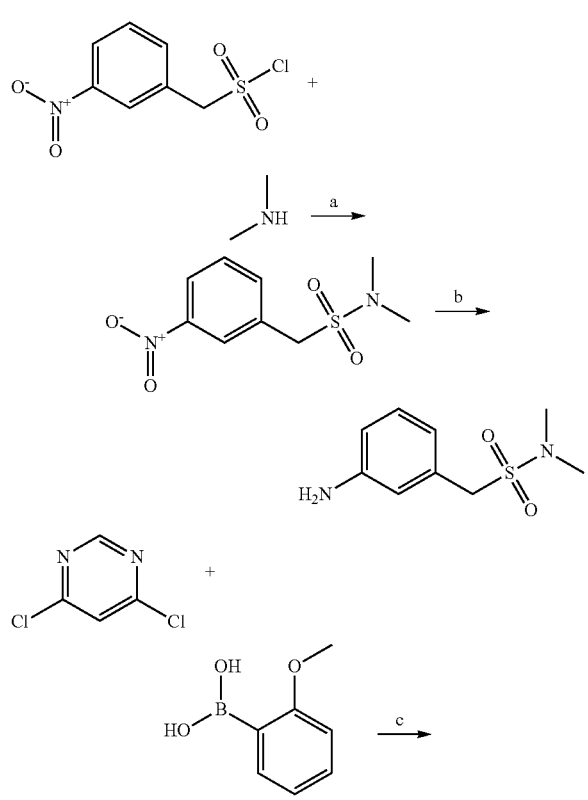

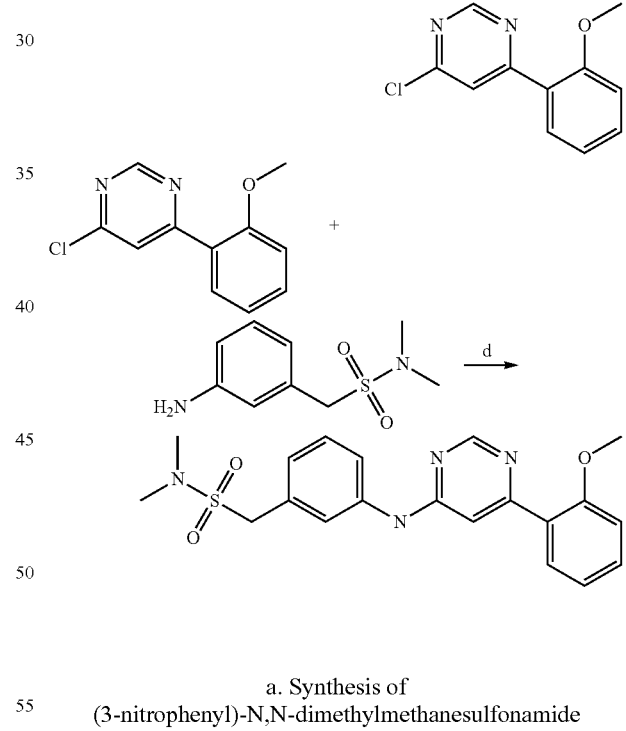

a. Synthesis of (3-nitrophenyl)-N,N-dimethylmethanesulfonamide (3-Nitrophenyl)methanesulfonyl chloride (2.36 g, 10 mmol) was dissolved in benzene (30 mL), then to this solution was added 40% aqueous dimethylamine (12.6 mL, 0.1 mol) and the reaction mixture was vigorously stirred for 2 h at room temperature. The benzene layer was separated and the aqueous layer extracted with $CH_2Cl_2$ (2×25 mL). The recombined organic layers were washed with saturated aqueous $NaHCO_3$ (30 mL), water (30 mL) and the solvent removed under reduced pressure to give 2.32 g (95%) of (3-nitrophenyl)-N,N-dimethylmethanesulfonamide as crystals.

b. Synthesis of (3-aminophenyl)-N,N-dimethylmethanesulfonamide (3-nitrophenyl)-N,N-dimethylmethanesulfonamide (2.32 g, 9.5 mmol) was hydrogenated over Raney nickel (0.5 g) in methanol at 50° C. and 70 psi for 4 h, then catalyst was filtered off, washed with warm methanol, combined filtrates were evaporated to give 1.95 g (96%) of (3-aminophenyl)-N,N-dimethylmethanesulfonamide.

c. Synthesis of 4-chloro-6-(2-methoxyphenyl)-pyrimidine

To a solution of 4,6-dichloropyrimidine (6.0 g, 40 mmol) and 2-methoxyphenylboronic acid (4.41 g, 29 mmol) in mixture of dimethoxyethane (120 mL) and water (18 mL) were added NaHCO₃ (6.72 g, 80 mmol) and (PPh₃)₂PdCl₂ (0.84 g) and the reaction mixture was refluxed for 8 h, and concentrated under reduced pressure. The resulting residue was taken up in CH₂Cl₂ (100 mL) and the solution washed with water, dried over anhydrous K₂CO₃, filtered and the solvent removed under reduced pressure. The obtained crude product was purified by flash chropatography on silica (eluent CH₂Cl₂) and recrystallized from hexanes. Yield of 4-chloro-6-(2-ethoxyphenyl)-pyrimidine 4.78 g (75%).

d. Synthesis of C-{3-[6-(2-methoxy-phenyl)-pyrimidin-4-ylamino]-phenyl}-N,N-dimethyl-methanesulfonamide (Compound 20)

A mixture of (3-aminophenyl)-N,N-dimethylmethanesulfonamide (0.107 g, 0.50 mmol) and 4-chloro-6-(2-ethoxyphenyl)-pyrimidine (0.110 g, 0.10 mmol) in DMFA (3 mL) was stirred at 80° C. till the reaction completion (TLC control), then concentrated in vacuo and the residue was recrystallized from isopropanol to give C-{3-[6-(2-methoxy-phenyl)-pyrimidin-4-ylamino]-phenyl}-N,N-dimethyl-methanesulfonamide (Compound 20)

Yield: 0.101 g (51%).

Melting point 187.5-188.8° C.

1H-NMR (400 MHz, DMSO-d₆); δ (ppm) 2.76 (6H, s), 3.90 (3H, s), 4.40 (2H, s), 7.05-7.12 (2H, m), 7.18 (1H, d), 7.35 (1H, d), 7.42-7.49 (7H, m), 7.72 (1H, s), 7.77 (1H, d), 7.95 (1H, d), 8.70 (1H, s), 9.63 (1H, br. s).

Cl MS m/z 399 (MH+)

Example 21

Synthesis of C-{3-[6-(2-benzyloxy-phenyl)-pyrimidin-4-ylamino]-phenyl}-N-propyl-methanesulfonamide (Compound 21)

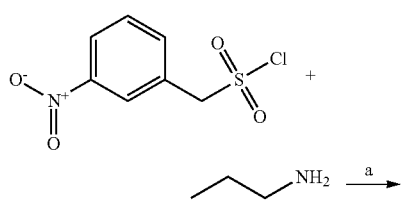

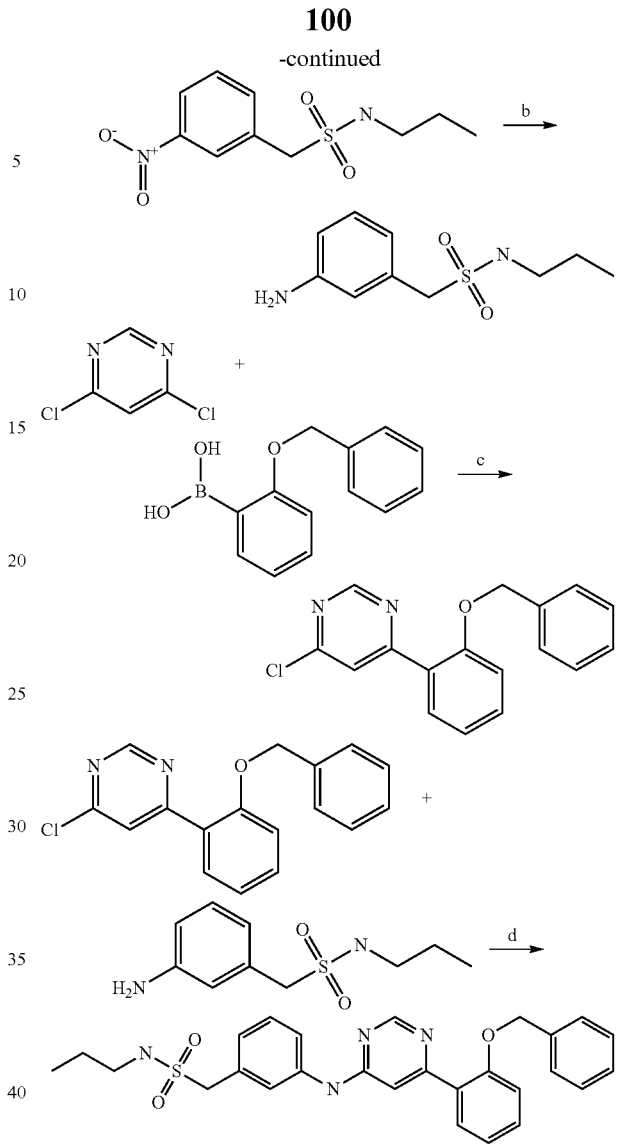

a. Synthesis of (3-nitrophenyl)-N-propylmethanesulfonamide (3-Nitrophenyl)methanesulfonyl chloride (0.6 g, 2.55 mmol) was dissolved in acetonitrile (10 mL), then to this solution was added propylamine (0.247 ml, 3 mmol) and triethylamine (1 mL) and the reaction mixture was vigorously stirred for 3 h at room temperature. The obtained mixture was diluted with cold water (30 ml), which led to the formation of a precipitate that was filtered off, washed with water (2×10 mL) and dried. Yield of (3-nitrophenyl)-N-propylmethanesulfonamide 0.63 g (95%).

b. Synthesis of (3-aminophenyl)-N-propylmethanesulfonamide

The same procedure as for Compound 20.

c. Synthesis of 4-chloro-6-(2-benzyloxyphenyl)-pyrimidine

The same procedure as for Compound 20.

d. Synthesis of C-{3-[6-(2-benzyloxy-phenyl)-pyrimidin-4-ylamino]-phenyl}-N-propyl-methanesulfonamide (Compound 21)

The same procedure as for Compound 20.
Yield: 0.193 g (79%).
Melting point 114.7-116.0° C.
1H-NMR (400 MHz, CDCl$_3$); δ (ppm) 0.90 (3H, t), 1.45-1.60 (2H, m), 3.01 (2H, q), 4.15 (2H, s), 5.15 (2H, s), 6.81 (1H, br. s), 7.03-7.46 (14H, m), 8.00 (1H, d), 8.79 (1H, s).
Cl MS m/z 489 (MH+)

Example 22

Synthesis of C-{3-[6-(2-benzyloxy-phenyl)-pyrimidin-4-ylamino]-phenyl}-N-isopropyl-methanesulfonamide (Compound 22)

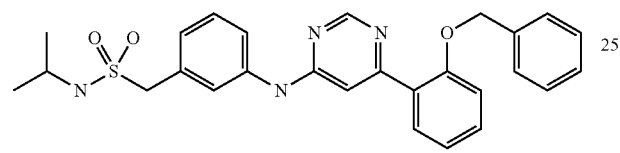

a. Synthesis of (3-nitrophenyl)-N-isopropylmethanesulfonamide

The same procedure as for Compound 21.

b. Synthesis of (3-aminophenyl)-N-isopropylmethanesulfonamide

The same procedure as for Compound 20.

c. Synthesis of 4-chloro-6-(2-benzyloxyphenyl)-pyrimidine

The same procedure as for Compound 20.

d. Synthesis of C-{3-[6-(2-benzyloxy-phenyl)-pyrimidin-4-ylamino]-phenyl}-N-isopropyl-methanesulfonamide (Compound 22)

The same procedure as for Compound 20.
Yield: 0.176 g (72%).
Melting point: sample resulted to be amorphous, softening above 80° C.
1H-NMR (400 MHz, CDCl$_3$); δ (ppm) 1.18 (6H, d), 3.45-3.60 (1H, m), 4.16 (2H, s), 5.16 (2H, s), 6.81 (1H, br. s), 7.03-7.47 (14H, m), 8.00 (1H, d), 8.79 (1H, s).
Cl MS m/z 489 (MH+)

Example 23

Synthesis of C-{3-[6-(2-benzyloxy-phenyl)-pyrimidin-4-ylamino]-phenyl}-N-cyclopropyl-methanesulfonamide (Compound 23)

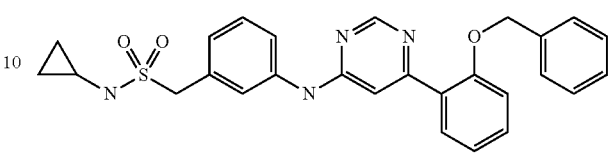

a. Synthesis of (3-nitrophenyl)-N-cyclopropylmethanesulfonamide

The same procedure as for Compound 21.

b. Synthesis of (3-aminophenyl)-N-cyclopropylmethanesulfonamide

The same procedure as for Compound 20.

c. Synthesis of 4-chloro-6-(2-benzyloxyphenyl)-pyrimidine

The same procedure as for Compound 20.

d. Synthesis of C-{3-[6-(2-benzyloxy-phenyl)-pyrimidin-4-ylamino]-phenyl}-N-cyclopropyl-methanesulfonamide (Compound 23)

The same procedure as for Compound 20.
Yield: 0.160 g (66%).
Melting point 164.5-166.0° C.
1H-NMR (400 MHz, CDCl$_3$); δ (ppm) 0.70 (4H, m), 2.56 (1H, m), 4.22 (2H, s), 5.12 (2H, s), 6.89 (1H, br. s), 7.02-7.47 (14H, m), 7.99 (1H, d), 8.75 (1H, s).
Cl MS m/z 487 (MH+)

Example 24

Synthesis of C-{3-[6-(2-benzyloxy-phenyl)-pyrimidin-4-ylamino]-phenyl}-N,N-dimethyl-methanesulfonamide (Compound 24)

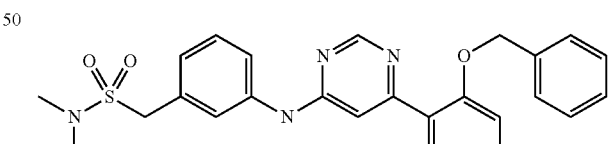

a. Synthesis of (3-nitrophenyl)-N,N-dimethylmethanesulfonamide

The same procedure as for Compound 20.

b. Synthesis of (3-aminophenyl)-N,N-dimethylmethanesulfonamide

The same procedure as for Compound 20.

c. Synthesis of 4-chloro-6-(2-benzyloxyphenyl)-pyrimidine

The same procedure as for Compound 20.

d. Synthesis of C-{3-[6-(2-benzyloxy-phenyl)-pyrimidin-4-ylamino]-phenyl}-N,N-dimethyl-methanesulfonamide (Compound 24)

The same procedure as for Compound 20.
Yield: 0.097 g (41%).
Melting point: sample was amorphous, softening above 85° C.
1H-NMR (400 MHz, DMSO-d$_6$); δ (ppm) 2.75 (6H, s), 4.38 (2H, s), 4.26 (2H, s), 7.03-7.12 (2H, m), 7.19 (1H, d), 7.23-7.48 (8H, m), 7.66 (1H, s), 7.70 (1H, d), 7.84 (1H, d), 8.70 (1H, s), 9.60 (1H, br. s).
Cl MS m/z 475 (MH+)

Example 25

Synthesis of {3-[6-(2-ethyl-phenyl)-pyrimidin-4-ylamino]-phenyl}-methanesulfonamide (Compound 26)

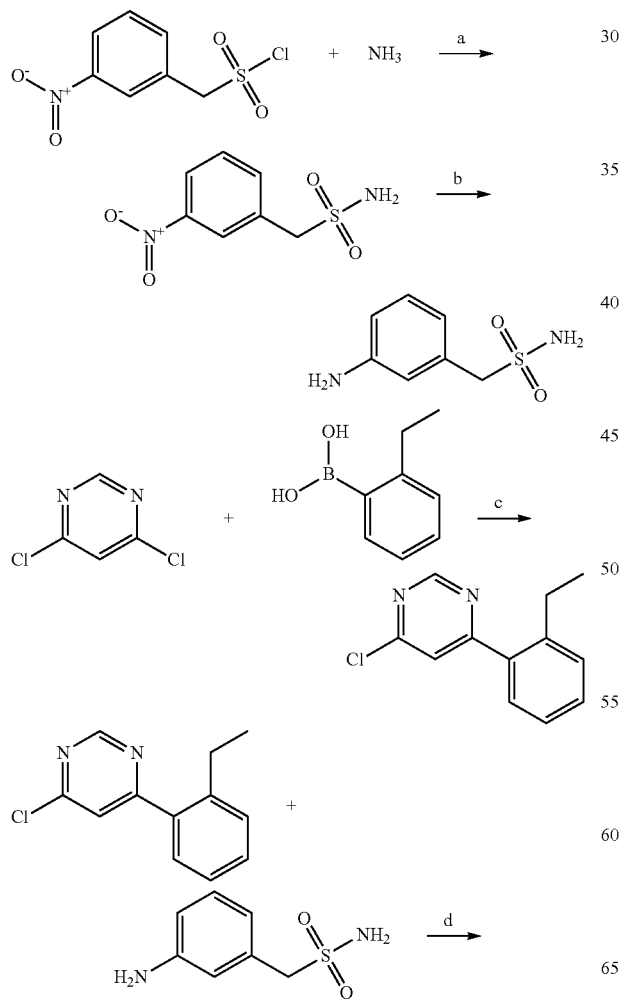

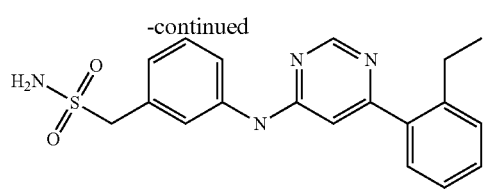

a. Synthesis of (3-nitrophenyl)methanesulfonyl amide (3-Nitrophenyl)methanesulfonyl chloride (4.71 g, 20 mmol) was dissolved in acetonitrile (20 mL), then to this solution was added concentrated aqueous ammonia (20 mL) saturated with ammonium carbonate and the reaction mixture was vigorously stirred for 1 h at room temperature. Then acetonitrile was removed under reduced pressure and the residue was diluted with cold water (20 mL), which led to the formation of a precipitate that was filtered off and washed with water (2×5 mL) and ether. Yield of (3-nitrophenyl)methanesulfonyl amide 3.5 g (80%)

b. Synthesis of (3-aminophenyl)methanesulfonyl amide

The same procedure as for Compound 20.

c. Synthesis of 4-chloro-6-(2-ethylphenyl)-pyrimidine

The same procedure as for Compound 20.

d. Synthesis of {3-[6-(2-ethyl-phenyl)-pyrimidin-4-ylamino]-phenyl}-methanesulfonamide (Compound 26)

A mixture of (3-aminophenyl)methanesulfonyl amide (0.112 g, 0.60 mmol) and 4-chloro-6-(2-ethylphenyl)-pyrimidine (0.131 g, 0.60 mmol) in DMFA (3 mL) was stirred at 80° C. till the reaction completion (TLC control), then concentrated in vacuo, and the residue was recrystallized from isopropanol to give {3-[6-(2-ethyl-phenyl)-pyrimidin-4-ylamino]-phenyl}-methanesulfonamide (Compound 26)
Yield: 0.133 g (60%).
Melting point: sample was amorphous, softening above 140° C.
1H-NMR (400 MHz, DMSO-d$_6$); δ (ppm) 1.11 (3H, t), 2.70 (2H, q), 4.29 (2H, s), 6.81 (2H, br. s), 6.98 (1H, s), 7.13 (1H, d), 7.30-7.48 (5H, m), 7.64 (1H, s), 7.77 (1H, d), 8.77 (1H, s), 10.52 (1H, br. s).
Cl MS m/z 369 (MH+)

Example 26

Synthesis of C-{3-[6-(3-ethoxy-phenyl)-pyrimidin-4-ylamino]-phenyl}-N,N-dimethyl-methanesulfonamide (Compound 27)

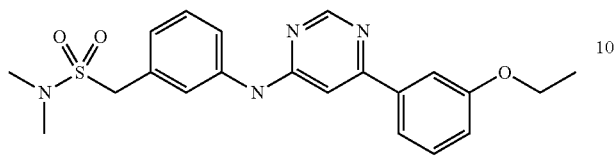

a. Synthesis of (3-nitrophenyl)-N,N-dimethylmethanesulfonamide

The same procedure as for Compound 20.

b. Synthesis of (3-aminophenyl)-N,N-dimethylmethanesulfonamide

The same procedure as for Compound 20.

c. Synthesis of 4-chloro-6-(3-ethoxyphenyl)-pyrimidine

The same procedure as for Compound 20.

d. Synthesis of C-{3-[6-(3-ethoxy-phenyl)-pyrimidin-4-ylamino]-phenyl}-N,N-dimethyl-methanesulfonamide (Compound 27)

The same procedure as for Compound 20.
Yield: 0.136 g (66%).
Melting point 177.6-178.4° C.
1H-NMR (400 MHz, DMSO-d$_6$); δ (ppm) 1.36 (3H, t), 2.77 (6H, s), 4.12 (2H, q), 4.41 (2H, s), 7.07 (1H, d), 7.09 (1H, d), 7.26 (1H, s), 7.36 (1H, t), 7.43 (1H, t), 7.57 (1H, d), 7.58 (1H, s), 7.72 (1H, s), 7.74 (1H, d), 8.70 (1H, s), 9.67 (1H, br. s).
Cl MS m/z 413 (MH+)

Example 27

Synthesis of C-{3-[6-(2-ethoxy-phenyl)-pyrimidin-4-ylamino]-phenyl}-N,N-dimethyl-methanesulfonamide (Compound 28)

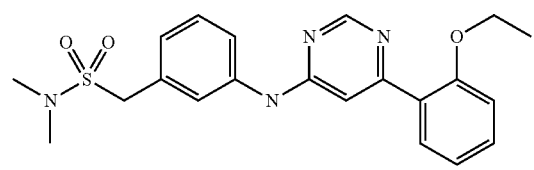 [SMILES: CCOc1ccccc1-c1cc(Nc2cccc(CS(=O)(=O)N(C)C)c2)ncn1]

a. Synthesis of (3-nitrophenyl)-N,N-dimethylmethanesulfonamide

The same procedure as for Compound 20.

b. Synthesis of (3-aminophenyl)-N,N-dimethylmethanesulfonamide

The same procedure as for Compound 20.

c. Synthesis of 4-chloro-6-(2-ethoxyphenyl)-pyrimidine

The same procedure as for Compound 20.

d. Synthesis of C-{3-[6-(2-ethoxy-phenyl)-pyrimidin-4-ylamino]-phenyl}-N,N-dimethyl-methanesulfonamide (Compound 28)

The same procedure as for Compound 20.
Yield: 0.140 g (68%).
Melting point 123.7-124.6° C.
1H-NMR (400 MHz, DMSO-d$_6$); δ (ppm) 1.37 (3H, t), 2.77 (6H, s), 4.16 (2H, q), 4.40 (2H, s), 7.07 (1H, t), 7.09 (1H, d), 7.15 (1H, d), 7.36 (1H, t), 7.43 (1H, t), 7.48 (1H, s), 7.68 (1H, s), 7.76 (1H, d), 7.44 (1H, d), 8.70 (1H, s), 9.60 (1H, br. s).
Cl MS m/z 413 (MH+)

Example 28

Synthesis of C-{3-[6-(2-benzyloxy-phenyl)-pyrimidin-4-ylamino]-phenyl}-N-cyclopentyl-methanesulfonamide (Compound 29)

a. Synthesis of (3-nitrophenyl)-N-cyclopentylmethanesulfonamide

The same procedure as for Compound 21.

b. Synthesis of (3-aminophenyl)-N-cyclopentylmethanesulfonamide

The same procedure as for Compound 20.

c. Synthesis of 4-chloro-6-(2-benzyloxyphenyl)-pyrimidine

The same procedure as for Compound 20.

d. Synthesis of C-{3-[6-(2-benzyloxy-phenyl)-pyrimidin-4-ylamino]-phenyl}-N-cyclopentyl-methanesulfonamide (Compound 29)

The same procedure as for Compound 20.
Yield: 0.163 g (63%).
Melting point: sample was amorphous, softening above 75° C.
1H-NMR (400 MHz, CDCl$_3$); δ (ppm) 1.35-2.00 (8H, m), 3.70 (1H, m), 4.17 (2H, s), 5.15 (2H, s), 6.85 (1H, br. s), 7.02-7.47 (14H, m), 7.99 (1H, d), 8.77 (1H, s).
Cl MS m/z 515 (MH+)

Example 29

Synthesis of C-{3-[6-(2-benzyloxy-phenyl)-pyrimidin-4-ylamino]-phenyl}-N-(tert-butyl)-methanesulfonamide (Compound 30)

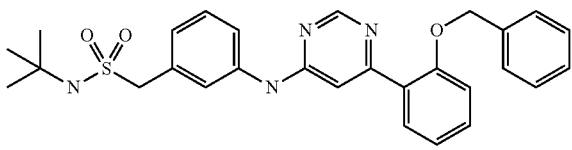 [SMILES: CC(C)(C)NS(=O)(=O)Cc1cccc(Nc2cc(-c3ccccc3OCc3ccccc3)ncn2)c1]

a. Synthesis of (3-nitrophenyl)-N-(tert-butyl)methanesulfonamide

The same procedure as for Compound 21.

b. Synthesis of (3-aminophenyl)-N-(tert-butyl)methanesulfonamide

The same procedure as for Compound 20.

c. Synthesis of 4-chloro-6-(2-benzyloxyphenyl)-pyrimidine

The same procedure as for Compound 20.

d. Synthesis of C-{3-[6-(2-benzyloxy-phenyl)-pyrimidin-4-ylamino]-phenyl}-N-(tert-butyl)-methanesulfonamide (Compound 30)

The same procedure as for Compound 20.
Yield: 0.205 g (82%).
Melting point: sample was amorphous, softening above 75° C.
1H-NMR (400 MHz, CDCl$_3$); δ (ppm) 1.37 (9H, s), 4.17 (2H, s), 5.15 (2H, s), 6.84 (1H, br. s), 7.06 (1H, d), 7.12 (2H, t), 7.21 (1H, t), 7.25-7.60 (10H, m), 7.99 (1H, d), 8.79 (1H, s).
Cl MS m/z 503 (MH+)

Example 30

Synthesis of C-{3-[6-(3-benzyloxy-phenyl)-pyrimidin-4-ylamino]-phenyl}-N-isopropyl-methanesulfonamide (Compound 31)

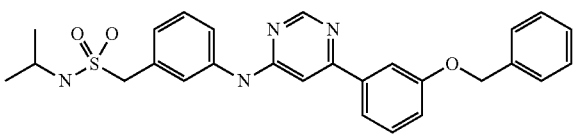

a. Synthesis of (3-nitrophenyl)-N-isopropylmethanesulfonamide

The same procedure as for Compound 21.a b. Synthesis of (3-aminophenyl)-N-isopropylmethanesulfonamide

The same procedure as for Compound 20.

c. Synthesis of 4-chloro-6-(3-benzyloxyphenyl)-pyrimidine

The same procedure as for Compound 20.

d. Synthesis of C-{3-[6-(3-benzyloxy-phenyl)-pyrimidin-4-ylamino]-phenyl}-N-isopropyl-methanesulfonamide (Compound 31)

The same procedure as for Compound 20.
Yield: 0.070 g (39%).
Melting point 205.8-206.7° C.
1H-NMR (400 MHz, CDCl$_3$); δ (ppm) 1.20 (6H, d), 3.50-3.65 (1H, m), 4.28 (2H, s), 5.19 (2H, s), 6.86 (1H, br. s), 7.10 (1H, d), 7.15 (1H, s), 7.17-7.52 (10H, m), 7.58 (1H, s), 7.62 (1H, d), 7.72 (1H, d), 8.79 (1H, s).
Cl MS m/z 489 (MH+)

Example 31

Synthesis of {3-[6-(2-benzyloxy-phenyl)-pyrimidin-4-ylamino]-phenyl}-methanesulfonamide (Compound 32)

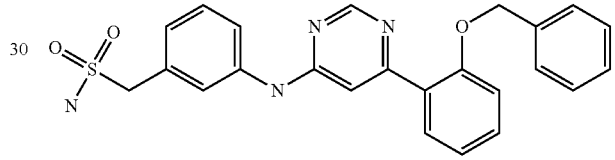

a. Synthesis of (3-nitrophenyl)methanesulfonyl amide

The same procedure as for (Compound 26).

b. Synthesis of (3-aminophenyl)methanesulfonyl amide

The same procedure as for (Compound 20).

c. Synthesis of 4-chloro-6-(2-benzyloxyphenyl)-pyrimidine

The same procedure as for (Compound 20).

d. Synthesis of {3-[6-(2-benzyloxy-phenyl)-pyrimidin-4-ylamino]-phenyl}-methanesulfonamide (Compound 32)

The same procedure as for (Compound 26).
Yield: 0.117 g (44%).
Melting point: sample was amorphous, softening above 105° C.
1H-NMR (400 MHz, DMSO-d$_6$); δ (ppm) 4.25 (2H, s), 5.26 (2H, s), 6.77 (2H, br. s), 7.07 (2H, dt), 7.20 (1H, d), 7.25-7.48 (8H, m), 7.59 (1H, s), 7.73 (1H, d), 7.82 (1H, d), 8.71 (1H, s), 9.71 (1H, br. s).
Cl MS m/z 447 (MH+)

TABLE 3
Yields of the intermediates
| (3-nitrophenyl) methanesulfonamide | Yield % | (3-aminophenyl) methanesulfonamide | Yield % | 4-chloro-6-aryl-pyrimidine | Yield % |
|---|---|---|---|---|---|
| | 80 | | 95 | | 70 |
| | 95 | | 95 | | 73 |
| | 95 | | 95 | | 43 |
| | 95 | | 95 | | 40 |
| | 95 | | 95 | | 42 |
| | 95 | | 95 | | 60 |
Example 32
Synthesis of C-{3-[6-(2-methoxy-phenyl)-pyrimidin-4-ylamino]-phenyl}-N-(3-methoxy-propyl)-methanesulfonamide (Compound 33)
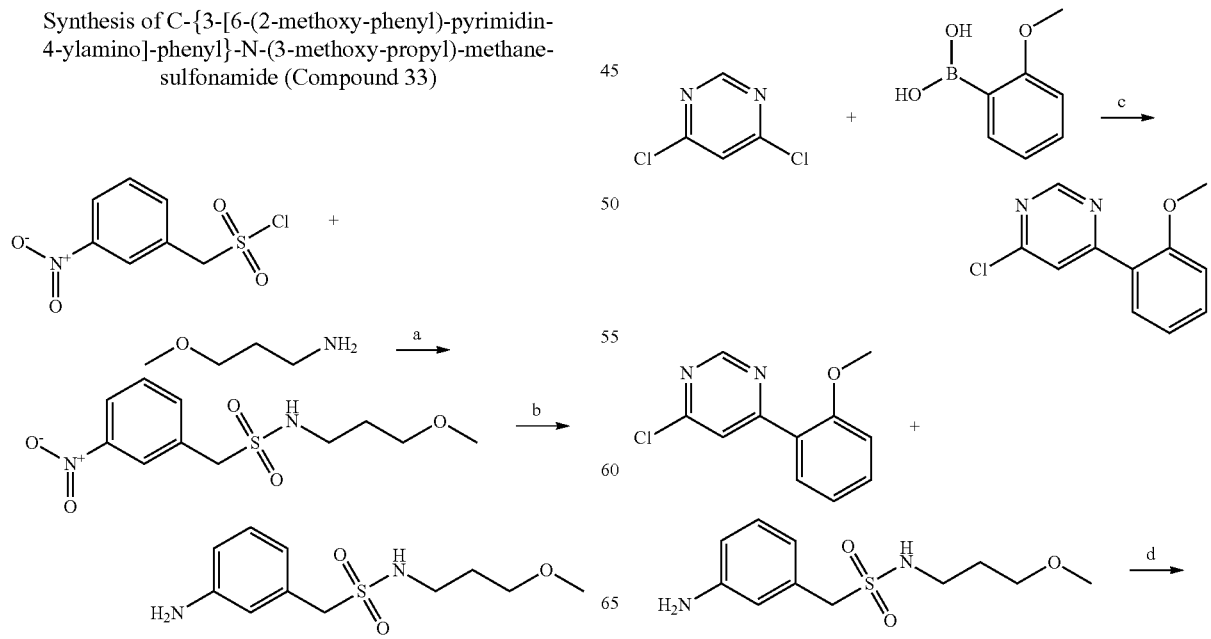

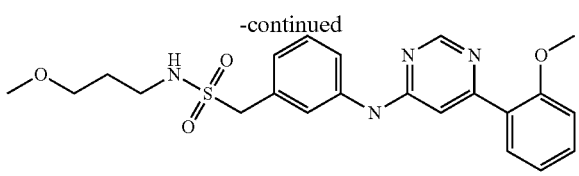

a. Synthesis of N-(3-methoxy-propyl)-C-(3-nitro-phenyl)-methanesulfonamide 3-metoxypropylamine (0.184 mL, 1.80 mmol) and triethylamine (0.3 mL) were added to a solution of (3-Nitrophenyl) methanesulfonyl chloride (0.35 g, 1.50 mmol) in acetonitrile (10 mL). The resulting solution was vigorously stirred for 3 h at room temperature and then diluted with cold water (30 ml), which lead to the formation of a precipitate. The precipitate was filtered off, washed with water (2×10 mL) and dried. Yield of N-(3-methoxy-propyl)-C-(3-nitro-phenyl)-methanesulfonamide 0.31 g (72%).

b. Synthesis of C-(3-amino-phenyl)-N-(3-methoxy-propyl)-methanesulfonamide

N-(3-Methoxy-propyl)-C-(3-nitro-phenyl)-methanesulfonamide (0.31 g, 1.08 mmol) was hydrogenated over Raney nickel (0.05 g) in methanol at 50° C. and 70 psi for 4 h. Then, the catalyst was filtered off, washed with warm methanol, and the combined filtrates were evaporated to give 0.14 g (50%) of C-(3-amino-phenyl)-N-(3-methoxy-propyl)-methanesulfonamide.

c. Synthesis of 4-chloro-6-(2-methoxyphenyl)-pyrimidine 4,6-dichloropyrimidine (6.0 g, 40 mmol) and 2-methoxyphenylboronic acid (4.41 g, 29 mmol) were added to a solution of dimethoxyethane (120 mL) and water (18 mL), followed by the addition of $NaHCO_3$ (6.72 g, 80 mmol) and $(PPh_3)_2PdCl_2$ (0.84 g). to this end the reaction mixture was allowed to reflux for 8 h, and then the solvent removed under reduced pressure. The residue was taken up in $CH_2Cl_2$ (100 mL), and the resulting solution washed with water, dried over anhydrous $K_2CO_3$, filtered and the solvent removed under reduced pressure. The crude product was purified by flash chropatography on silica gel (eluent $CH_2Cl_2$) and recrystallized from hexanes yielding 4-chloro-6-(2-methoxyphenyl)-pyrimidine (4.78 g; 75%).

d. Synthesis of C-{3-[6-(2-methoxy-phenyl)-pyrimidin-4-ylamino]-phenyl}-N-(3-methoxy-propyl)-methanesulfonamide (Compound 33)

A mixture of C-(3-amino-phenyl)-N-(3-methoxy-propyl)-methanesulfonamide (0.129 g, 0.50 mmol) and 4-chloro-6-(2-methoxyphenyl)-pyrimidine (0.110 g, 0.10 mmol) in DMFA (3 mL) was stirred at 80° C. till the reaction completion (TLC control), then evaporated in vacuo. The resulting residue was purified by column chromatography on silica gel yielding C-{3-[6-(2-methoxy-phenyl)-pyrimidin-4-ylamino]-phenyl}-N-(3-methoxy-propyl)-methanesulfonamide Yield: 0.140 g (63%).
Melting point: 149.2-150.8° C.
$^1$H-NMR (400 MHz, DMSO-$d_6$); δ (ppm) 1.63 (2H, quint), 2.96 (2H, dt), 3.18 (3H, s), 3.33 (2H, t), 3.89 (3H, s), 4.28 (2H, s), 6.95-7.10 (3H, m), 7.17 (1H, d), 7.33 (1H, t), 7.40-7.48 (2H, m), 7.67 (1H, s), 7.77 (1H, d), 7.94 (1H, d), 8.67 (1H, s), 9.61 (1H, br. s).
Cl MS m/z 443 (MH+)

Example 33

Synthesis of C-{3-[6-(2-methoxy-phenyl)-pyrimidin-4-ylamino]-phenyl}-N-cyclohexylmethanesulfonamide (Compound 34)

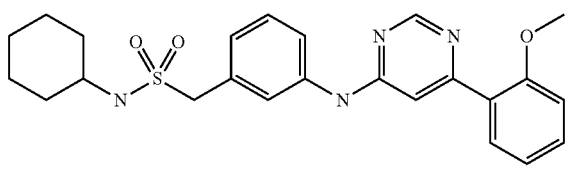 [SMILES: COc1ccccc1-c1cc(Nc2cccc(CS(=O)(=O)NC3CCCCC3)c2)ncn1]

a. Synthesis of C-(3-nitrophenyl)-N-cyclohexylmethanesulfonamide

The same procedure as for (Compound 33).

b. Synthesis of C-(3-aminophenyl)-N-cyclohexylmethanesulfonamide

The same procedure as for (Compound 33).

c. Synthesis of 4-chloro-6-(2-methoxyphenyl)-pyrimidine

The same procedure as for (Compound 33).

d. Synthesis of C-{3-[6-(2-methoxy-phenyl)-pyrimidin-4-ylamino]-phenyl}-N-cyclohexylmethanesulfonamide (Compound 34)

The same procedure as for (Compound 33).
Yield: 0.150 g (71%).
Melting point: 198.4-201.0° C.
$^1$H-NMR (400 MHz, DMSO-$d_6$); δ (ppm) 0.97-1.30 (5H, m), 1.43-1.55 (1H, m), 1.57-1.72 (2H, m), 1.75-1.92 (2H, m), 2.96-3.10 (1H, m), 3.89 (3H, s), 4.28 (2H, s), 6.96 (1H, d), 7.16 (2H, dd), 7.18 (1H, d), 7.33 (1H, t), 7.40-7.50 (2H, m), 7.71 (1H, s), 7.76 (1H, d), 7.95 (1H, d), 8.67 (1H, s), 9.61 (1H, br. s).
Cl MS m/z 453 (MH+)

Example 34

Synthesis of C-{3-[6-(2-methoxy-phenyl)-pyrimidin-4-ylamino]-phenyl}-N-(tetrahydrofuran-2-ylmethyl)-methanesulfonamide (Compound 35)

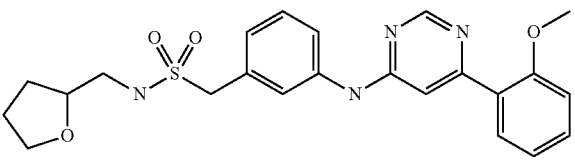 [SMILES: COc1ccccc1-c1cc(Nc2cccc(CS(=O)(=O)NCC3CCCO3)c2)ncn1]

a. Synthesis of C-(3-nitrophenyl)-N-(tetrahydrofuran-2-ylmethyl)-methanesulfonamide The same procedure as for (Compound 33).

b. Synthesis of C-(3-aminophenyl)-N-(tetrahydrofuran-2-ylmethyl)-methanesulfonamide The same procedure as for (Compound 33).

c. Synthesis of 4-chloro-6-(2-methoxyphenyl)-pyrimidine

The same procedure as for (Compound 33).

d. Synthesis of C-{3-[6-(2-methoxy-phenyl)-pyrimidin-4-ylamino]-phenyl}-N-(tetrahydrofuran-2-ylmethyl)-methanesulfonamide (Compound 35)

The same procedure as for (Compound 33).
Yield: 0.120 g (53%).
Melting point: 157.4-159.0° C.
$^1$H-NMR (400 MHz, DMSO-d$_6$); δ (ppm) 1.48-1.60 (1H, m), 1.70-1.93 (3H, m), 2.95 (2H, m), 3.60 (1H, m), 3.73 (1H, m), 3.82 (1H, m), 3.89 (3H, s), 4.31 (2H, s), 7.00-7.12 (3H, m), 7.16 (1H, d), 7.33 (1H, t), 7.40-7.50 (2H, m), 7.67 (1H, s), 7.78 (1H, d), 7.94 (1H, d), 8.68 (1H, s), 9.61 (1H, br. s).
Cl MS m/z 455 (MH+)

Example 35

Synthesis of N-(4-chloro-benzyl)-C-{3-[6-(2-methoxy-phenyl)-pyrimidin-4-ylamino]-phenyl}-methanesulfonamide (Compound 36)

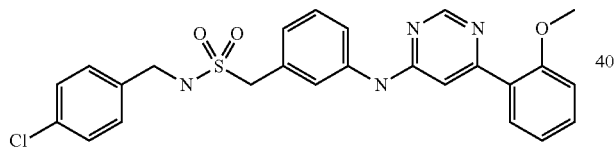

a. Synthesis of C-(3-nitro-phenyl)-N-(4-chloro-benzyl)-methanesulfonamide

The same procedure as for (Compound 33).

b. Synthesis of C-(3-amino-phenyl)-N-(4-chloro-benzyl)-methanesulfonamide

The same procedure as for (Compound 33).

c. Synthesis of 4-chloro-6-(2-methoxyphenyl)-pyrimidine

The same procedure as for (Compound 33).

d. Synthesis of N-(4-chloro-benzyl)-C-{3-[6-(2-methoxy-phenyl)-pyrimidin-4-ylamino]-phenyl}-methanesulfonamide (Compound 36)

The same procedure as for (Compound 33).
Yield: 0.230 g (93%).
Melting point: 182.0-184.4° C.
$^1$H-NMR (400 MHz, DMSO-d$_6$); δ (ppm) 3.87 (3H, s), 4.10 (2H, d), 4.31 (2H, s), 6.95-7.10 (2H, m), 7.16 (1H, d), 7.27-7.38 (5H, m), 7.39-7.47 (2H, m), 7.61 (1H, t), 7.66 (1H, s), 7.77 (1H, d), 7.93 (1H, d), 8.67 (1H, s), 9.60 (1H, br. s).
Cl MS m/z 495 (MH+)

Example 36

Synthesis of C-{3-[6-(2-methoxy-phenyl)-pyrimidin-4-ylamino]-phenyl}-N-thiophen-2-ylmethyl-methanesulfonamide (Compound 37)

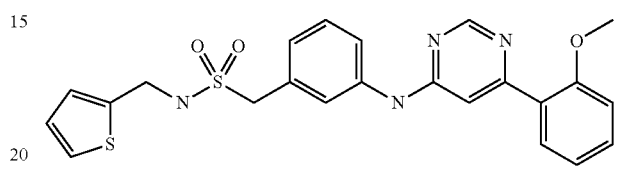

a. Synthesis of C-(3-nitro-phenyl)-N-thiophen-2-ylmethyl-methanesulfonamide

The same procedure as for (Compound 33).

b. Synthesis of C-(3-amino-phenyl)-N-thiophen-2-ylmethyl-methanesulfonamide

The same procedure as for (Compound 33).

c. Synthesis of 4-chloro-6-(2-methoxyphenyl)-pyrimidine

The same procedure as for (Compound 33).

d. Synthesis of C-{3-[6-(2-methoxy-phenyl)-pyrimidin-4-ylamino]-phenyl}-N-thiophen-2-ylmethyl-methanesulfonamide (Compound 37)

The same procedure as for (Compound 33).
Yield: 0.150 g (65%).
Melting point: 180.2-181.7° C.
$^1$H-NMR (400 MHz, DMSO-d$_6$); δ (ppm) 3.87 (3H, s), 4.30 (4H, s), 6.90-7.02 (3H, m), 7.07 (1H, t), 7.17 (1H, d), 7.33 (1H, t), 7.38-7.50 (3H, m), 7.65 (1H, s), 7.71 (1H, br. s), 7.78 (1H, d), 7.94 (1H, d), 8.68 (1H, s), 9.61 (1H, br. s).
Cl MS m/z 467 (MH+)

Example 37

Synthesis of N,N-diethyl-C-{3-[6-(2-methoxy-phenyl)-pyrimidin-4-ylamino]-phenyl}-methanesulfonamide (Compound 38)

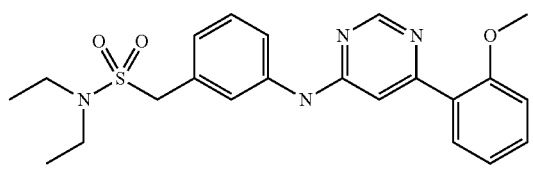 [SMILES: CCN(CC)S(=O)(=O)Cc1cccc(Nc2cc(-c3ccccc3OC)ncn2)c1]

a. Synthesis of C-(3-nitro-phenyl)-N,N-diethyl-methanesulfonamide

The same procedure as for (Compound 33).

b. Synthesis of C-(3-amino-phenyl)-N,N-diethyl-methanesulfonamide

The same procedure as for (Compound 33).

c. Synthesis of 4-chloro-6-(2-methoxyphenyl)-pyrimidine

The same procedure as for (Compound 33).

d. Synthesis of N,N-diethyl-C-{3-[6-(2-methoxy-phenyl)-pyrimidin-4-ylamino]-phenyl}-methane-sulfonamide (Compound 38)

The same procedure as for (Compound 33).
Yield: 0.100 g (47%).
Melting point: 107.7-110.5° C.
$^1$H-NMR (400 MHz, DMSO-d$_6$); δ (ppm) 1.02 (6H, t), 3.08 (4H, quart), 3.87 (3H, s), 4.32 (2H, s), 7.05 (2H, dd), 7.16 (1H, d), 7.31 (1H, t), 7.38-7.46 (2H, m), 7.68 (1H, s), 7.73 (1H, d), 7.92 (1H, d), 8.67 (1H, s), 9.59 (1H, br. s).
Cl MS m/z 427 (MH+)

Example 38

Synthesis of N-(2-hydroxy-ethyl)-C-{3-[6-(2-methoxy-phenyl)-pyrimidin-4-ylamino]-phenyl}-N-methyl-methanesulfonamide (Compound 39)

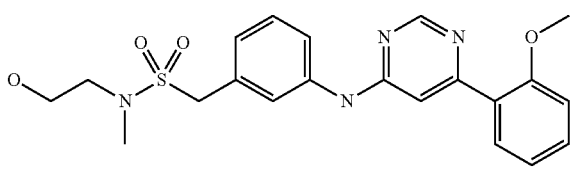 [SMILES: COc1ccccc1-c1cc(Nc2cccc(CS(=O)(=O)N(C)CCO)c2)ncn1]

a. Synthesis of C-(3-nitro-phenyl)-N-(2-hydroxy-ethyl)-N-methyl-methanesulfonamide The same procedure as for (Compound 33).

b. Synthesis of C-(3-amino-phenyl)-N-(2-hydroxy-ethyl)-N-methyl-methanesulfonamide The same procedure as for (Compound 33).

c. Synthesis of 4-chloro-6-(2-methoxyphenyl)-pyrimidine

The same procedure as for (Compound 33).

d. Synthesis of N-(2-hydroxy-ethyl)-C-{3-[6-(2-methoxy-phenyl)-pyrimidin-4-ylamino]-phenyl}-N-methyl-methanesulfonamide (Compound 39)

The same procedure as for (Compound 33).
Yield: 0.207 g (70%).
Melting point: amorphous behavior, softening above 60° C.
$^1$H-NMR (400 MHz, DMSO-d$_6$); δ (ppm) 2.79 (3H, s), 3.08 (2H, t), 3.47 (2H, dt), 3.87 (3H, s), 4.39 (2H, s), 4.67 (1H, t), 7.06 (2H, dd), 7.16 (1H, d), 7.32 (1H, t), 7.39-7.47 (2H, m), 7.70 (1H, s), 7.73 (1H, d), 7.93 (1H, d), 8.68 (1H, s), 9.60 (1H, br. s).
Cl MS m/z 429 (MH+)

Example 39

Synthesis of 1-{3-[6-(2-methoxy-phenyl)-pyrimidin-4-ylamino]-phenylmethanesulfonyl}-piperidine-4-carboxylic acid amide (Compound 40)

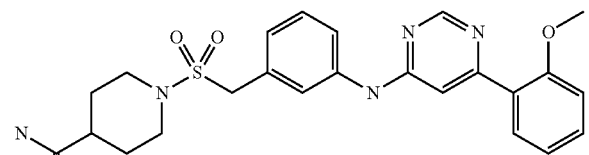

a. Synthesis of 1-(3-nitro-phenylmethanesulfonyl)-piperidine-4-carboxylic acid amide The same procedure as for (Compound 33).

b. Synthesis of 1-(3-amino-phenylmethanesulfonyl)-piperidine-4-carboxylic acid amide The same procedure as for (Compound 33).

c. Synthesis of 4-chloro-6-(2-methoxyphenyl)-pyrimidine

The same procedure as for (Compound 33).

d. Synthesis of 1-{3-[6-(2-methoxy-phenyl)-pyrimidin-4-ylamino]-phenylmethanesulfonyl}-piperidine-4-carboxylic acid amide (Compound 40)

The same procedure as for (Compound 33).
Yield: 0.155 g (65%).
Melting point 136.2-139.0° C.
1H-NMR (400 MHz, DMSO-d$_6$); δ (ppm) 1.47 (2H, dt), 1.72 (2H, d), 2.16 (1H, quint), 2.76 (2H, dt), 3.56 (2H, d), 3.89 (3H, s), 4.37 (2H, s), 6.70 (1H, br. s), 7.02-7.10 (2H, m), 7.13-7.22 (2H, m), 7.33 (1H, t), 7.40-7.47 (2H, m), 7.71 (1H, s), 7.76 (1H, d), 7.94 (1H, d), 8.68 (1H, s), 9.64 (1H, br. s).
Cl MS m/z 482 (MH+)

Example 40

Synthesis of [6-(2-methoxy-phenyl)-pyrimidin-4-yl]-[3-(morpholine-4-sulfonylmethyl)-phenyl]-amine (Compound 41)

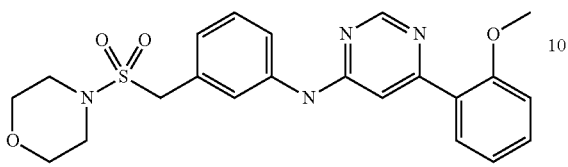

a. Synthesis of 4-(3-nitro-phenylmethanesulfonyl)-morpholine

The same procedure as for (Compound 33).

b. Synthesis of 3-(morpholine-4-sulfonylmethyl)-phenylamine

The same procedure as for (Compound 33).

c. Synthesis of 4-chloro-6-(2-methoxyphenyl)-pyrimidine

The same procedure as for (Compound 33).

d. Synthesis of [6-(2-methoxy-phenyl)-pyrimidin-4-yl]-[3-(morpholine-4-sulfonylmethyl)-phenyl]-amine (Compound 41)

The same procedure as for (Compound 33).
Yield: 0.200 g (90%).
Melting point 145.2-147.0° C.
1H-NMR (400 MHz, DMSO-$d_6$); δ (ppm) 3.15 (4H, s), 3.60 (4H, s), 3.89 (3H, s), 4.42 (2H, s), 7.02-7.12 (3H, m), 7.18 (1H, d), 7.33 (1H, t), 7.40-7.50 (2H, m), 7.75 (1H, s), 7.77 (1H, d), 7.95 (1H, d), 8.68 (1H, s), 9.62 (1H, br. s).
Cl MS m/z 441 (MH+)

Example 41

Synthesis of [3-(azepane-1-sulfonylmethyl)-phenyl]-[6-(2-methoxy-phenyl)-pyrimidin-4-yl]-amine (Compound 42)

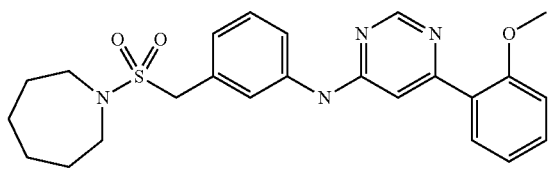 [SMILES: COc1ccccc1-c1cc(Nc2cccc(CS(=O)(=O)N3CCCCCC3)c2)ncn1]

a. Synthesis of 1-(3-nitro-phenylmethanesulfonyl)-azepane

The same procedure as for (Compound 33).

b. Synthesis of 3-(azepane-1-sulfonylmethyl)-phenylamine

The same procedure as for (Compound 33).

c. Synthesis of 4-chloro-6-(2-methoxyphenyl)-pyrimidine

The same procedure as for (Compound 33).

d. Synthesis of [3-(azepane-1-sulfonylmethyl)-phenyl]-[6-(2-methoxy-phenyl)-pyrimidin-4-yl]-amine (Compound 42)

The same procedure as for (Compound 33).
Yield: 0.110 g (49%).
Melting point: 181.2-182.6° C.
$^1$H-NMR (400 MHz, DMSO-$d_6$); δ (ppm) 1.40-1.70 (8H, m), 3.15 (4H, m), 3.89 (3H, s), 4.37 (2H, s), 7.00-7.12 (2H, m), 7.17 (1H, d), 7.33 (1H, t), 7.40-7.47 (2H, m), 7.71 (1H, s), 7.73 (1H, d), 7.94 (1H, d), 8.68 (1H, s), 9.62 (1H, br. s).
Cl MS m/z 453 (MH+)

Example 42

Synthesis of C-{3-[6-(2-ethoxy-phenyl)-pyrimidin-4-ylamino]-phenyl}-N-methyl-methanesulfonamide (Compound 43)

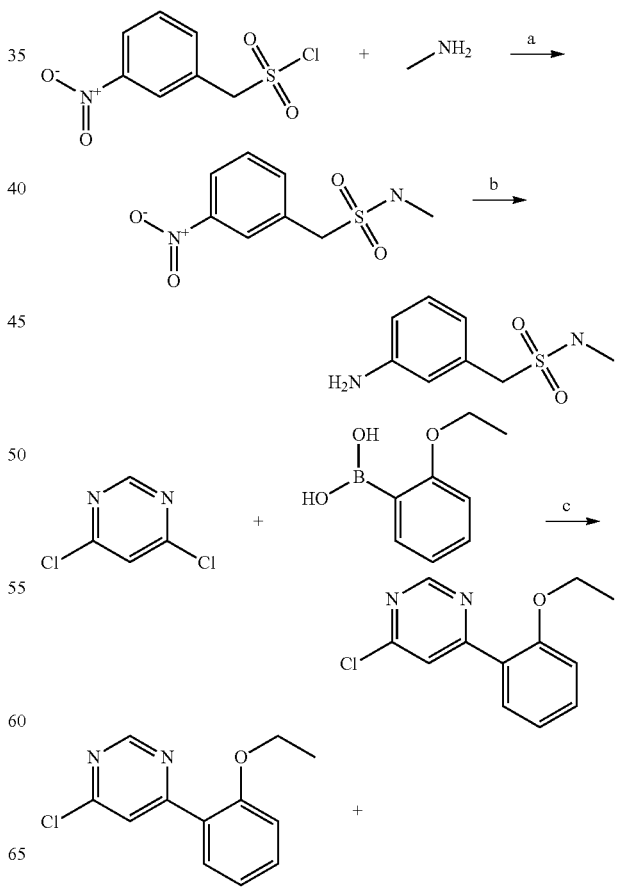

-continued

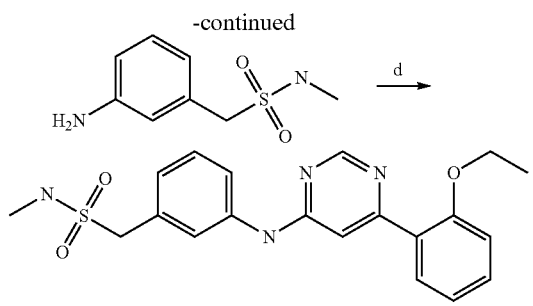

a. Synthesis of (3-nitrophenyl)-N-methylmethanesulfonamide

40% aqueous methylamine (10 mL, 0.1 mol) was added to a vigorously stirred solution of (3-Nitrophenyl)methanesulfonyl chloride (2.36 g, 10 mmol) in benzene (30 mL) and allowed to stir for 2 h at room temperature. To this end, the benzene layer was separated, and the aqueous layer extracted with $CH_2Cl_2$ (2×25 mL). The combined organic layers were washed with saturated aqueous $NaHCO_3$ (30 mL), water (30 mL), filtered over anhydrous $Na_2SO_4$, filtered and the solvent removed under reduced pressure to give 2.07 g (90%) of (3-nitrophenyl)-N-methylmethanesulfonamide as crystals.

b. Synthesis of (3-aminophenyl)-N-methylmethanesulfonamide

The same procedure as for (Compound 33).

c. Synthesis of 4-chloro-6-(2-ethoxyphenyl)-pyrimidine

The same procedure as for (Compound 33).

d. Synthesis of C-{3-[6-(2-ethoxy-phenyl)-pyrimidin-4-ylamino]phenyl}-N-methyl-methanesulfonamide (Compound 43)

The same procedure as for (Compound 33).
Yield: 0.209 g (76%).
Melting point: 155.9-156.5° C.
$^1$H-NMR (400 MHz, DMSO-$d_6$); δ (ppm) 1.37 (3H, t), 2.58 (3H, d), 4.12 (2H, quart), 4.28 (2H, s), 6.83 (1H, br, quart), 7.04 (2H, t), 7.12 (1H, d), 7.32 (1H, t), 7.39 (1H, t), 7.46 (1H, s), 7.60 (1H, s), 7.77 (1H, d), 7.92 (1H, d), 8.67 (1H, s), 9.56 (1H, br. s).
Cl MS m/z 399 (MH+)

Example 43

Synthesis of C-{3-[6-(2-benzyloxy-phenyl)-pyrimidin-4-ylamino]-phenyl}-N-methyl-methanesulfonamide (Compound 44)

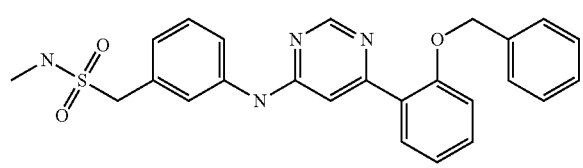 [SMILES: CNS(=O)(=O)Cc1cccc(Nc2cc(-c3ccccc3OCc3ccccc3)ncn2)c1]

a. Synthesis of (3-nitrophenyl)-N-methylmethanesulfonamide

The same procedure as for (Compound 43).

b. Synthesis of (3-aminophenyl)-N-methylmethanesulfonamide

The same procedure as for (Compound 33).

c. Synthesis of 4-chloro-6-(2-benzyloxyphenyl)-pyrimidine

The same procedure as for (Compound 33).

d. Synthesis of C-{3-[6-(2-benzyloxy-phenyl)-pyrimidin-4-ylamino]-phenyl}-N-methyl-methanesulfonamide (Compound 44)

The same procedure as for (Compound 33).
Yield: 0.110 g (49%).
Melting point: amorphous behavior, softening above 80° C.
$^1$H-NMR (400 MHz, DMSO-$d_6$); δ (ppm) 2.58 (3H, d), 4.28 (2H, s), 5.24 (2H, s), 6.82 (1H, br, quart), 6.99-7.09 (2H, m), 7.18 (1H, d), 7.23-7.46 (7H, m), 7.60 (1H, s), 7.72 (1H, d), 7.82 (1H, d), 8.68 (1H, s), 9.57 (1H, br. s).
Cl MS m/z 461 (MH+)

Example 44

Synthesis of N-ethyl-C-{3-[6-(2-methoxy-phenyl)-pyrimidin-4-ylamino]-phenyl}-methanesulfonamide (Compound 45)

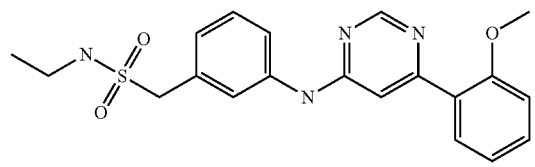 [SMILES: CCNS(=O)(=O)Cc1cccc(Nc2cc(-c3ccccc3OC)ncn2)c1]

a. Synthesis of (3-nitrophenyl)-N-ethylmethanesulfonamide

The same procedure as for (Compound 43).

b. Synthesis of (3-aminophenyl)-N-ethylmethanesulfonamide

The same procedure as for (Compound 33).

c. Synthesis of 4-chloro-6-(2-methoxyphenyl)-pyrimidine

The same procedure as for (Compound 33).

d. Synthesis of N-ethyl-C-{3-[6-(2-methoxy-phenyl)-pyrimidin-4-ylamino]-phenyl}-methanesulfonamide (Compound 45)

The same procedure as for (Compound 33).
Yield: 0.140 g (70%).
Melting point 190.0-193.0° C.

1H-NMR (400 MHz, DMSO-d$_6$); δ (ppm) 1.05 (3H, t), 2.94 (2H, d quart), 3.88 (3H, s), 4.28 (2H, s), 6.96 (1H, t), 7.01 (1H, d), 7.06 (1H, t), 7.16 (1H, d), 7.32 (1H, t), 7.38-7.47 (2H, m), 7.65 (1H, s), 7.77 (1H, d), 7.93 (1H, d), 8.68 (1H, s), 9.60 (1H, br. s).

Cl MS m/z 399 (MH+)

Example 45

Synthesis of N-(2-hydroxy-ethyl)-C-{3-[6-(2-methoxy-phenyl)-pyrimidin-4-ylamino]-phenyl}-methanesulfonamide (Compound 46)

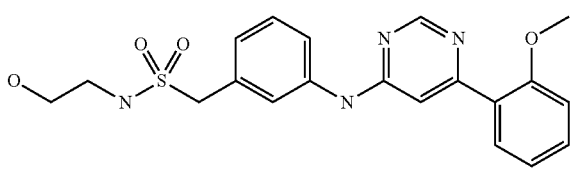 [SMILES: COc1ccccc1-c1cc(Nc2cccc(CS(=O)(=O)NCCO)c2)ncn1]

a. Synthesis of C-(3-nitro-phenyl)-N-(2-hydroxy-ethyl)-methanesulfonamide

The same procedure as for (Compound 33).

b. Synthesis of C-(3-amino-phenyl)-N-(2-hydroxy-ethyl)-methanesulfonamide

The same procedure as for (Compound 33).

c. Synthesis of 4-chloro-6-(2-methoxyphenyl)-pyrimidine

The same procedure as for (Compound 33).

d. Synthesis of N-(2-hydroxy-ethyl)-C-{3-[6-(2-methoxy-phenyl)-pyrimidin-4-ylamino]-phenyl}-methanesulfonamide (Compound 46)

The same procedure as for (Compound 33).
Yield: 0.172 g (61%).
Melting point: amorphous behavior, softening above 70° C.

$^1$H-NMR (400 MHz, DMSO-d$_6$); δ (ppm) 2.97 (2H, t), 3.41 (2H, dt), 3.88 (3H, s), 4.30 (2H, s), 4.59 (1H, t), 6.93 (1H, t), 7.05 (2H, dd), 7.16 (1H, d), 7.32 (1H, t), 7.39-7.47 (2H, m), 7.65 (1H, s), 7.76 (1H, d), 7.93 (1H, d), 8.68 (1H, s), 9.60 (1H, br. s).

Cl MS m/z 415 (MH+)

Example 46

Synthesis of N,N-diethyl-C-{3-[6-(2-benzyloxy-phenyl)-pyrimidin-4-ylamino]-phenyl}-methanesulfonamide (Compound 47)

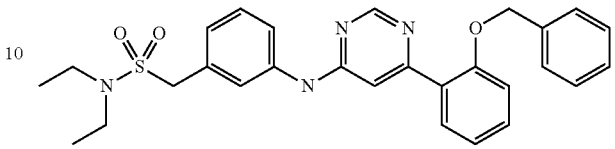

a. Synthesis of C-(3-nitro-phenyl)-N,N-diethyl-methanesulfonamide

The same procedure as for (Compound 33).

b. Synthesis of C-(3-amino-phenyl)-N,N-diethyl-methanesulfonamide

The same procedure as for (Compound 33).

c. Synthesis of 4-chloro-6-(2-benzyloxyphenyl)-pyrimidine

The same procedure as for (Compound 33).

d. Synthesis of N,N-diethyl-C-{3-[6-(2-benzyloxy-phenyl)-pyrimidin-4-ylamino]-phenyl}-methanesulfonamide (Compound 47)

The same procedure as for Compound 33
Yield: 0.100 g (40%).
Melting point: 64.2-67.5° C.
$^1$H-NMR (400 MHz, DMSO-d$_6$); δ (ppm) 1.02 (6H, t), 3.09 (4H, quart), 4.32 (2H, s), 5.24 (2H, s), 7.06 (2H, dd), 7.19 (1H, d), 7.23-7.47 (8H, m), 7.64 (1H, s), 7.69 (1H, d), 7.83 (1H, d), 8.69 (1H, s), 9.59 (1H, br. s).

Cl MS m/z 503 (MH+)

Example 47

Synthesis of N-(2-hydroxy-ethyl)-C-{3-[6-(2-benzyloxy-phenyl)-pyrimidin-4-ylamino]-phenyl}-N-methyl-methanesulfonamide (Compound 48)

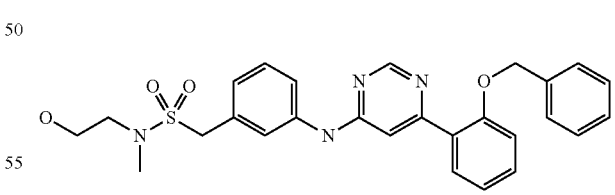

a. Synthesis of C-(3-nitro-phenyl)-N-(2-hydroxy-ethyl)-N-methyl-methanesulfonamide The same procedure as for (Compound 33).

b. Synthesis of C-(3-amino-phenyl)-N-(2-hydroxy-ethyl)-N-methyl-methanesulfonamide The same procedure as for (Compound 33).

c. Synthesis of 4-chloro-6-(2-benzyloxyphenyl)-pyrimidine

The same procedure as for (Compound 33).

d. Synthesis of N-(2-hydroxy-ethyl)-C-{3-[6-(2-benzyloxy-phenyl)-pyrimidin-4-ylamino]-phenyl}-N-methyl-methanesulfonamide (Compound 48)

The same procedure as for (Compound 33).
Yield: 0.196 g (57%).
Melting point: amorphous behavior softening above 55° C.
$^1$H-NMR (400 MHz, DMSO-$d_6$); δ (ppm) 2.79 (3H, s), 3.08 (2H, t), 3.47 (2H, dt), 4.37 (2H, s), 4.67 (1H, t), 5.23 (2H, s), 7.06 (2H, dd), 7.18 (1H, d), 7.22-7.46 (8H, m), 7.66 (1H, s), 7.78 (1H, d), 7.83 (1H, d), 8.69 (1H, s), 9.58 (1H, br. s).
Cl MS m/z 505 (MH+)

Example 48

Synthesis of C-{3-[6-(2-methoxy-phenyl)-pyrimidin-4-ylamino]-phenyl}-N-methyl-methanesulfonamide (Compound 49)

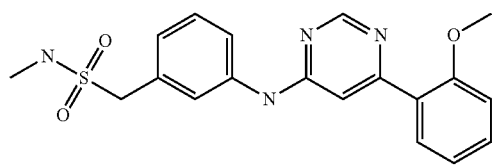

a. Synthesis of (3-nitrophenyl)-N-methylmethanesulfonamide

The same procedure as for (Compound 43).

b. Synthesis of (3-aminophenyl)-N-methylmethanesulfonamide

The same procedure as for (Compound 33).

c. Synthesis of 4-chloro-6-(2-methoxyphenyl)-pyrimidine

The same procedure as for (Compound 33).

d. Synthesis of C-{3-[6-(2-methoxy-phenyl)-pyrimidin-4-ylamino]-phenyl}-N-methyl-methanesulfonamide (Compound 49)

The same procedure as for (Compound 33).
Yield: 0.163 g (60%).
Melting point 213-214° C.
$^1$H-NMR (400 MHz, DMSO-$d_6$); δ (ppm) 2.58 (3H, d), 3.89 (3H, s), 4.27 (2H, s), 6.83 (1H, br, quart), 7.02 (1H, d), 7.06 (1H, t), 7.16 (1H, d), 7.32 (1H, t), 7.38-7.47 (2H, m), 7.63 (1H, s), 7.78 (1H, d), 7.93 (1H, d), 8.67 (1H, s), 9.60 (1H, br. s).
Cl MS m/z 385 (MH+)

TABLE 4

Examples 32-48: Yields of the intermediates

| (nitrophenyl) methanesulfonamide | Yield % | (aminophenyl) methanesulfonamide | Yield % | 4-chloro-6-aryl-pyrimidine | Yield % |
|---|---|---|---|---|---|
| 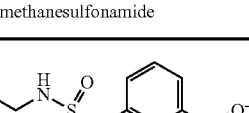 | 72 | 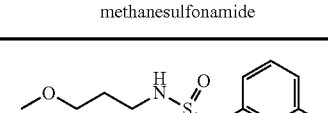 | 50 | 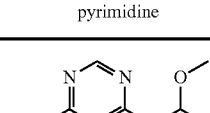 | 70 |
| 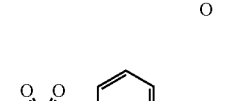 | 72 |  | 44 | 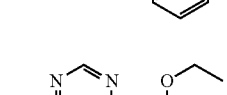 | 73 |
|  | 77 |  | 66 | 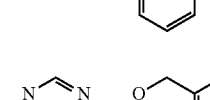 | 42 |
|  | 75 |  | 87 | 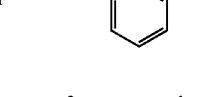 | 60 |

TABLE 4-continued

Examples 32-48: Yields of the intermediates

| (nitrophenyl) methanesulfonamide | Yield % | (aminophenyl) methanesulfonamide | Yield % | 4-chloro-6-aryl-pyrimidine | Yield % |
|---|---|---|---|---|---|
| [thiophen-2-ylmethyl sulfonamide, 3-nitrobenzyl] | 81 | [thiophen-2-ylmethyl sulfonamide, 3-aminobenzyl] | 87 | | |
| [N,N-diethyl sulfonamide, 3-nitrobenzyl] | 90 | [N,N-diethyl sulfonamide, 3-aminobenzyl] | 63 | | |
| [N-(2-methoxyethyl)-N-methyl sulfonamide, 3-nitrobenzyl] | 85 | [N-(2-methoxyethyl)-N-methyl sulfonamide, 3-aminobenzyl] | 80 | | |
| [piperidine-4-carboxamide sulfonamide, 3-nitrobenzyl] | 86 | [piperidine-4-carboxamide sulfonamide, 3-aminobenzyl] | 53 | | |
| [morpholine sulfonamide, 3-nitrobenzyl] | 86 | [morpholine sulfonamide, 3-aminobenzyl] | 78 | | |
| [azepane sulfonamide, 3-nitrobenzyl] | 67 | [azepane sulfonamide, 3-aminobenzyl] | 50 | | |
| [N-methyl sulfonamide, 3-nitrobenzyl] | 90 | [N-methyl sulfonamide, 3-aminobenzyl] | 95 | | |
| [N-ethyl sulfonamide, 3-nitrobenzyl] | 46 | [N-ethyl sulfonamide, 3-aminobenzyl] | 65 | | |
| [N-(2-methoxyethyl) sulfonamide, 3-nitrobenzyl] | 80 | [N-(2-methoxyethyl) sulfonamide, 3-aminobenzyl] | 89 | | |

Reference Example 49 (not According to the Present Invention)

Synthesis of 2-[6-(3-methanesulfonyl-phenylamino)-pyrimidin-4-yl]-phenol

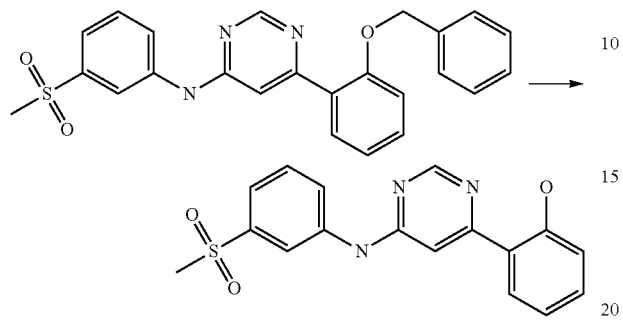

A mixture of [6-(2-benzyloxy-phenyl)-pyrimidin-4-yl]-(3-methanesulfonyl-phenyl)-amine (7.90 g, 18.3 mmol) and trifluoroacetic acid (100 mL) was refluxed to completion of the reaction. All the volatiles were evaporated in vacuo, the residue was re-crystallized from ethanol to give 2-[6-(3-methanesulfonyl-phenylamino)-pyrimidin-4-yl]-phenol as white powder.

Yield: 4.92 g (79%).
Melting point: 214.0-216.1° C.
$^1$H-NMR (400 MHz, DMSO-d$_6$); δ (ppm) 3.20 (3H, s), 6.92-7.00 (2H, m), 7.36 (1H, t), 7.42 (1H, s), 7.55-7.66 (2H, m), 7.83 (1H, d), 8.04 (1H, d), 8.34 (1H, s), 8.78 (1H, s), 10.15 (1H, s), 13.20 (1H, s).
Cl MS m/z 342 (MH+)

Example 50

Synthesis of 2-[6-(3-methanesulfonyl-phenylamino)-pyrimidin-4-yl]-phenol (Compound 52)

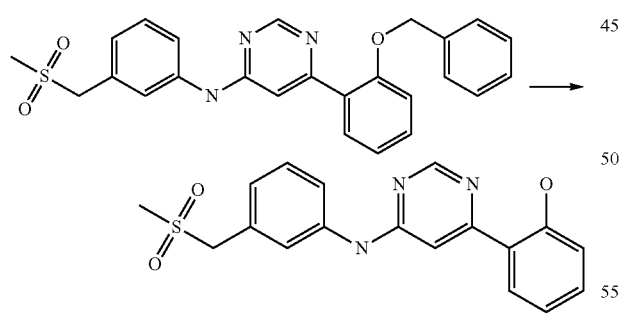

The same procedure as for 2-[6-(3-methanesulfonyl-phenylamino)-pyrimidin-4-yl]-phenol (reference example 49). Colorless solid.

Yield: 1.80 g (75%).
Melting point: 200.0-202.0° C.
$^1$H-NMR (400 MHz, DMSO-d$_6$); δ (ppm) 2.93 (3H, s), 4.48 (2H, s), 6.88-6.97 (2H, m), 7.12 (1H, s), 7.30-7.43 (3H, m), 7.67 (1H, s), 7.73 (1H, d), 7.80 (1H, d), 8.70 (1H, s), 9.87 (1H, s), 13.48 (1H, s).
Cl MS m/z 356 (MH+)

Reference Example 51 (not According to the Present Invention)

Synthesis of [6-(2-benzyloxy-phenyl)-pyrimidin-4-yl]-(3-methanesulfonyl-phenyl)-amine a. Synthesis of 4-(2-benzyloxy-phenyl)-6-chloro-pyrimidine 4,6-dichloropyrimidine (6.0 g, 40 mmol) and 2-benzyloxyphenylboronic acid (6.61 g, 29 mmol) were added to a solution of dimethoxyethane (120 mL) and water (18 mL), followed by the addition of NaHCO$_3$ (6.72 g, 80 mmol) and (PPh$_3$)$_2$PdCl$_2$ (0.84 g). To this end the reaction mixture was allowed to reflux for 8 h, and the solvent removed under reduced pressure. The residue was taken up in CH$_2$Cl$_2$ (100 mL), and the resulting solution washed with water, dried over anhydrous K$_2$CO$_3$, filtered and the solvent removed under reduced pressure. The crude product was purified by flash chromatography on silica gel (eluent CH$_2$Cl$_2$) and recrystalized from hexanes yielding 4-chloro-6-(2-benzyloxyphenyl)-pyrimidine (6.88 g; 80%) as white powder.
Cl MS m/z 297 (MH+)

b. Synthesis of [6-(2-benzyloxy-phenyl)-pyrimidin-4-yl]-(3-methanesulfonyl-phenyl)-amine A mixture of 3-methanesulfonyl-phenylamine hydrochloride (4.98 g, 24 mmol) and 4-chloro-6-(2-benzyloxyphenyl)- pyrimidine (6.88 g, 23.2 mmol) in DMFA (50 mL) was stirred at 80° C. till the reaction completion (TLC control). The reaction mixture was diluted with water (200 mL), treated with NaHCO$_3$ (4.2 g, 50 mmol). The resulting precipitate was filtered out, washed with water (2×200 mL), dried and purified by column chromatography on silica (eluent chloroform-ethanol 20:1) to yield [6-(2-benzyloxy-phenyl)-pyrimidin-4-yl]-(3-methanesulfonyl-phenyl)-amine as colorless solid.

Yield: 8.10 g (81%).

Melting point: 199.0-205.0° C.

$^1$H-NMR (400 MHz, DMSO-d$_6$); δ (ppm) 3.22 (3H, s), 5.28 (2H, s), 7.08 (1H, t), 7.21 (1H, d), 7.24-7.48 (6H, m), 7.48-7.63 (3H, m), 7.87 (1H, d), 8.06 (1H, d), 8.31 (1H, s), 8.78 (1H, s), 9.92 (1H, s).

Cl MS m/z 432 (MH+)

Example 52

Synthesis of [6-(2-benzyloxy-phenyl)-pyrimidin-4-yl]-(3-methanesulfonylmethyl-phenyl)-amine (Compound 53)

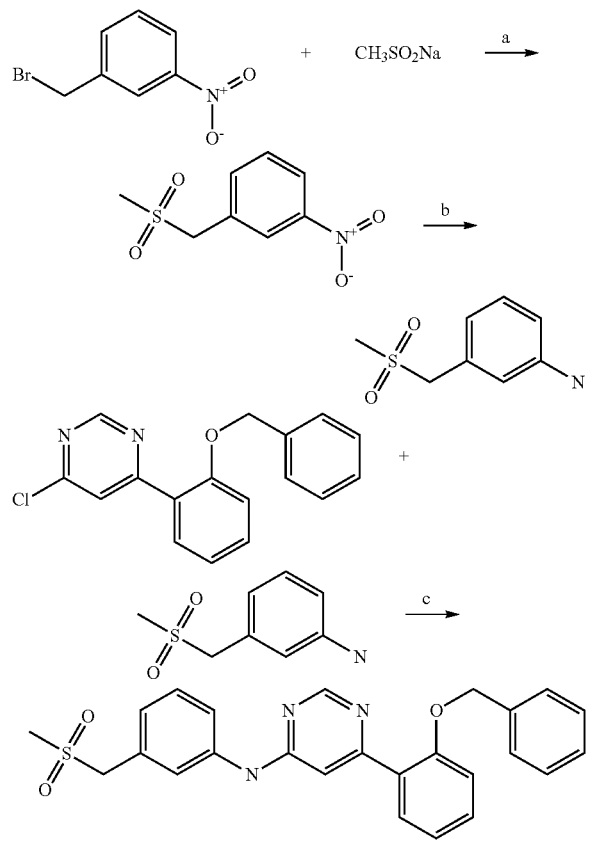

a. Synthesis of 1-methanesulfonylmethyl-3-nitro-benzene

To a solution of 1-bromomethyl-3-nitro-benzene (5.0 g, 23 mmol) in ethanol (50 mL) was added solution of sodium methanesulfinate (3.06 g, 30 mmol) in ethanol (30 mL) and the mixture was stirred for 4 h at room temperature, then was concentrated in vacuo to volume about 20 mL and diluted with water (200 mL). Formed precipitate was filtered out, washed with water (2×100 mL) and dried to give 1-methanesulfonylmethyl-3-nitro-benzene (4.3 g; 87%) as yellowish crystalline powder.

Cl MS m/z 216 (MH+)

b. Synthesis of 3-methanesulfonylmethyl-phenylamine

1-Methanesulfonylmethyl-3-nitro-benzene (4.3 g; 20 mmol) was hydrogenated over Raney nickel (0.5 g) in methanol at 50° C. and 70 psi for 4 h. The catalyst was filtered out, washed with warm methanol, and the combined filtrates were evaporated to give 3.33 g (90%) of 3-methanesulfonylmethyl-phenylamine as colorless solid.

Cl MS m/z 186 (MH+)

c. Synthesis of [6-(2-benzyloxy-phenyl)-pyrimidin-4-yl]-(3-methanesulfonylmethyl-phenyl)-amine (Compound 53)

The same procedure as for [6-(2-benzyloxy-phenyl)-pyrimidin-4-yl]-(3-methanesulfonyl-phenyl)-amine (reference example 51). Colorless solid.

Yield: 3.17 g (71%).

Melting point: 145.0-146.5° C.

$^1$H-NMR (400 MHz, DMSO-d$_6$); δ (ppm) 2.90 (3H, s), 4.43 (2H, s), 5.53 (2H, s), 7.02-7.10 (2H, m), 7.18 (1H, d), 7.22-7.43 (6H, m), 7.46 (1H, s), 7.63 (1H, s), 7.71 (1H, d), 7.83 (1H, d), 8.27 (1H, s), 8.68 (1H, s), 9.58 (1H, s).

Cl MS m/z 446 (MH+)

Reference Example 53 (not According to the Present Invention)

Synthesis of 3-[6-(2-benzyloxy-phenyl)-pyrimidin-4-ylamino]-benzenesulfonamide

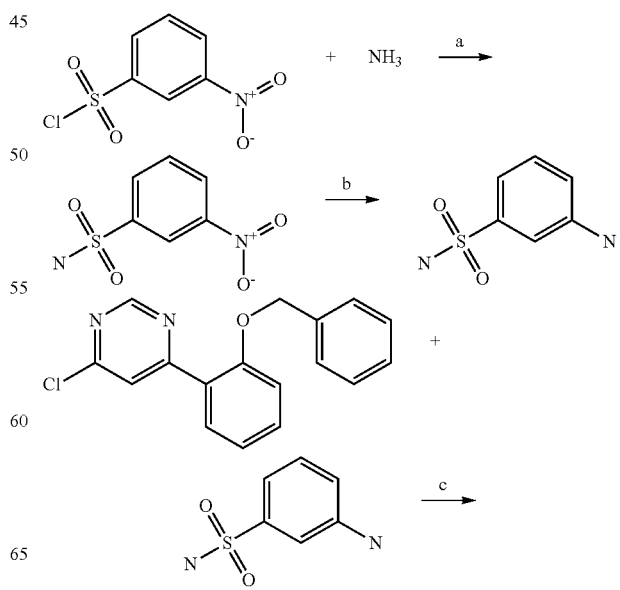

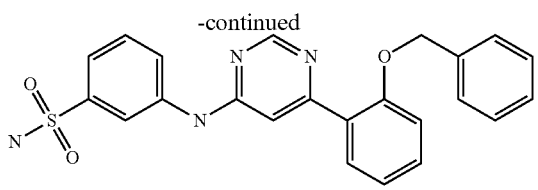

a. Synthesis of 3-Nitro-benzenesulfonamide

3-Nitro-benzenesulfonyl chloride (2.0 g, 9.0 mmol) was dissolved in acetonitrile (20 mL). To this solution was added concentrated aqueous ammonia (20 mL) saturated with ammonium carbonate and the reaction mixture was vigorously stirred for 1 h at room temperature. Then acetonitrile was removed under reduced pressure and the residue diluted with cold water (30 mL) leading to a precipitate formation. The precipitate was filtered out and washed with water (2×15 mL), ether and dried. Yield of 3-nitro-benzenesulfonamide 1.46 g (80%). Beige powder.
Cl MS m/z 203 (MH+)

b. Synthesis of 3-amino-benzenesulfonamide

3-Nitro-benzenesulfonamide (1.46 g, 7.2 mmol) was hydrogenated over Raney nickel (0.3 g) in methanol at 50° C. and 70 psi for 4 h, then catalyst was filtered out, washed with warm methanol, combined filtrates were evaporated to give 1.15 g (93%) of 3-amino-benzenesulfonamide as colorless solid.
Cl MS m/z 173 (MH+)

c. Synthesis of 3-[6-(2-benzyloxy-phenyl)-pyrimidin-4-ylamino]-benzenesulfonamide The same procedure as for [6-(2-benzyloxy-phenyl)-pyrimidin-4-yl]-(3-methanesulfonyl-phenyl)-amine (b) (reference example 51). Colorless solid.
Yield: 1.75 g (70%).
Melting point: 210.0-211.5° C.
$^1$H-NMR (400 MHz, DMSO-$d_6$); δ (ppm) 5.26 (2H, s), 7.07 (1H, t), 7.19 (1H, d), 7.22-7.53 (9H, m), 7.85 (1H, d), 7.92 (1H, d), 8.19 (1H, s), 8.74 (1H, s), 9.81 (1H, s).
Cl MS m/z 433 (MH+)

Example 54

Synthesis of {3-[6-(2-hydroxy-phenyl)-pyrimidin-4-ylamino]-phenyl}-methanesulfonamide (Compound 54)

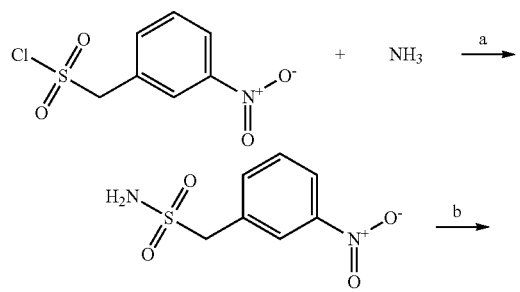

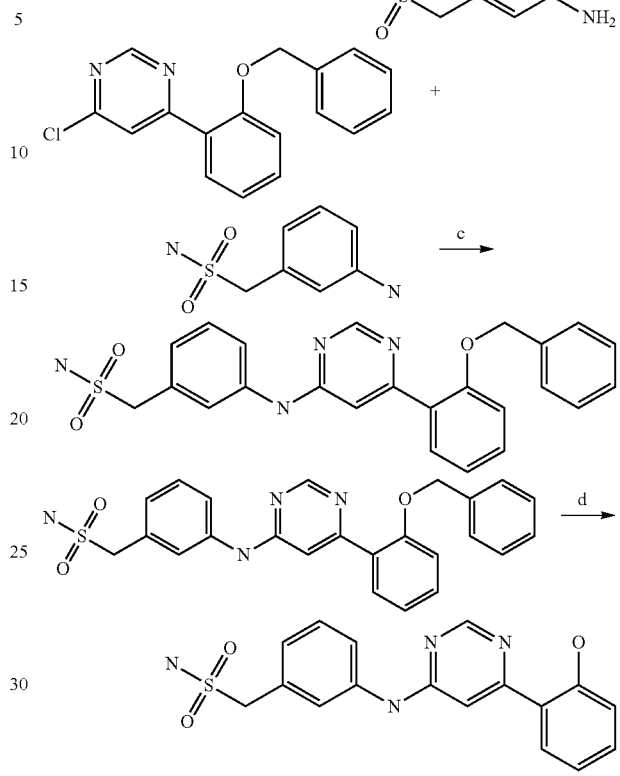

a. Synthesis of (3-nitro-phenyl)-methanesulfonamide

The same procedure as for 3-[6-(2-benzyloxy-phenyl)-pyrimidin-4-ylamino]-benzenesulfonamide (a) (reference example 53). Yield 3.5 g (82%). Beige powder.
Cl MS m/z 217 (MH+)

b. Synthesis of (3-amino-phenyl)-methanesulfonamide

The same procedure as for 3-[6-(2-benzyloxy-phenyl)-pyrimidin-4-ylamino]-benzenesulfonamide (b) (reference example 53). Yield 2.8 g (93%). Colorless solid.
Cl MS m/z 187 (MH+)

c. Synthesis of {3-[6-(2-benzyloxy-phenyl)-pyrimidin-4-ylamino]-phenyl}-methanesulfonamide The same procedure as for [6-(2-benzyloxy-phenyl)-pyrimidin-4-yl]-(3-methanesulfonyl-phenyl)-amine (b) (reference example 51). Yield: 1.0 g (72%). Colorless solid.
Cl MS m/z 447 (MH+)

d. Synthesis of {3-[6-(2-hydroxy-phenyl)-pyrimidin-4-ylamino]-phenyl}-methanesulfonamide (Compound 54)

The same procedure as for 2-[6-(3-methanesulfonyl-phenylamino)-pyrimidin-4-yl]-phenol (reference example 49). White powder.
Yield: 0.25 g (79%).

Melting point: 226.0-227.2° C.

¹H-NMR (400 MHz, DMSO-d₆); δ (ppm) 4.29 (2H, s), 6.81 (2H, s), 6.89-6.98 (2H, m), 7.10 (1H, d), 7.32-7.42 (3H, m), 7.63 (1H, s), 7.72 (1H, d), 7.82 (1H, d), 8.70 (1H, s), 9.86 (1H, s).

Cl MS m/z 357 (MH+)

Example 55

Synthesis of {3-[6-(2-hydroxymethyl-phenyl)-pyrimidin-4-ylamino]-phenyl}-methanesulfonamide (Compound 55)

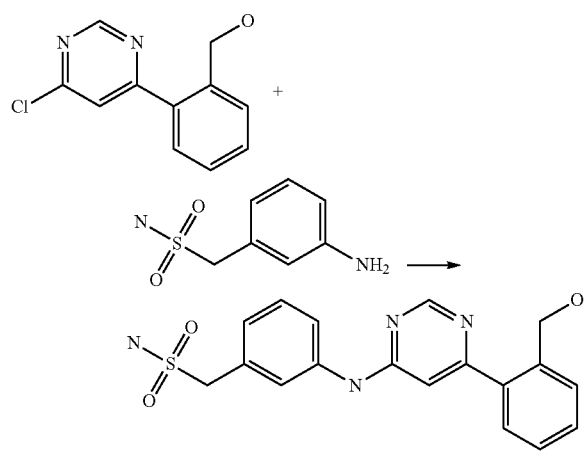

The same procedure as for reference example 51 (b). Colorless solid.

Yield: 0.035 g (16.5%).

Melting point: 192.0-194.0° C.

¹H-NMR (400 MHz, DMSO-d₆); δ (ppm) 4.26 (2H, s), 4.57 (2H, s), 5.20 (1H, br. s), 6.80 (2H, br. s), 6.97 (1H, s), 7.05 (2H, d), 7.26-7.41 (2H, m), 7.41-7.50 (2H, m), 7.58 (1H, d), 7.62 (1H, s), 7.74 (1H, d), 8.67 (1H, s), 9.60 (1H, br. s).

Cl MS m/z 371 (MH+)

Example 56

Synthesis of {2-[6-(3-Methanesulfonylmethyl-phenylamino)-pyrimidin-4-yl]-phenyl}-methanol (Compound 56)

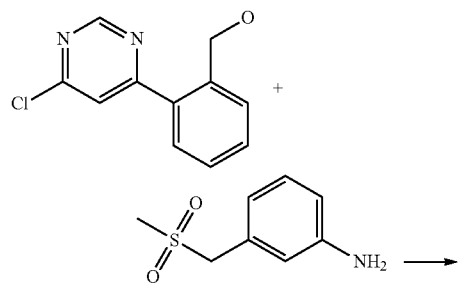

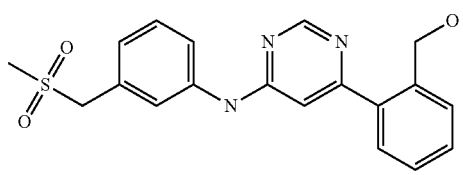

The same procedure as for reference example 51 (b). Colorless solid.

Melting point: 185.0-187.0° C.

Yield: 0.015 g (7.1%).

¹H-NMR (400 MHz, CDCl₃); δ (ppm) 2.83 (3H, s), 4.28 (2H, s), 4.52 (2H, s), 5.93 (1H, br. s), 6.97 (1H, s), 7.18 (1H, d), 7.34-7.56 (7H, m), 7.60 (1H, s), 8.72 (1H, s).

Cl MS m/z 370 (MH+)

Reference Example 57 (not According to the Present Invention)

Synthesis of (3-methanesulfonyl-phenyl)-{6-[2-(2-methoxy-ethoxy)-phenyl]-pyrimidin-4-yl}-amine

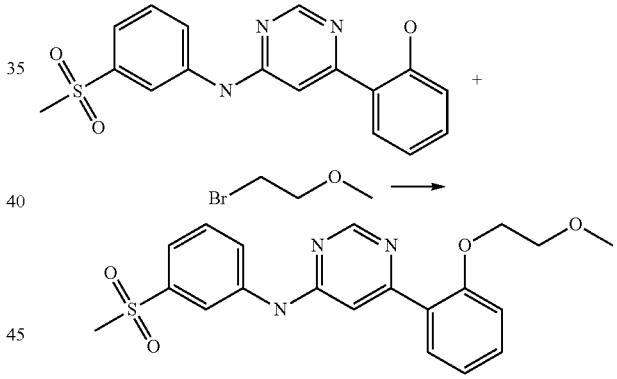

A mixture of 2-[6-(3-methanesulfonyl-phenylamino)-pyrimidin-4-yl]-phenol (reference example 49) (0.31 g, 0.94 mmol), 1-bromo-2-methoxy-ethane (0.516 g, 3.75 mmol), potassium carbonate (1.03 g, 7.5 mmol) and acetonitrile (15 mL) was refluxed for 8 h. Then the reaction mixture was evaporated, the residue was washed with water and purified by column chromatography on silica (eluent chloroform-ethanol 20:1) to give (3-methanesulfonyl-phenyl)-{6-[2-(2-methoxy-ethoxy)-phenyl]-pyrimidin-4-yl}-amine as colorless solid.

Yield: 0.030 g (7.9%).

Melting point: 153.0-154.4° C.

¹H-NMR (400 MHz, DMSO-d₆); δ (ppm) 3.15 (3H, s), 3.35 (3H, s), 3.73 (2H, t), 4.22 (2H, t), 7.08 (1H, t), 7.14 (1H, d), 7.36 (1H, s), 7.42 (1H, t), 7.54-7.65 (2H, m), 7.75 (1H, d), 7.98 (1H, d), 8.41 (1H, s), 8.71 (1H, s).

Cl MS m/z 400 (MH+)

Example 58

Synthesis of (3-methanesulfonylmethyl-phenyl)-{6-[2-(2-methoxy-ethoxy)-phenyl]-pyrimidin-4-yl}-amine (Compound 57)

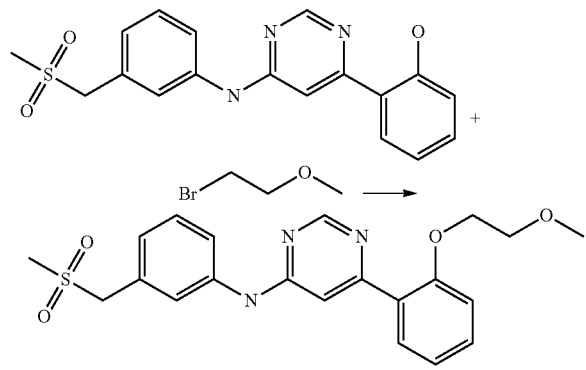

The same procedure as for reference example 57. Colorless solid.

Yield: 0.11 g (31%).

Melting point: 141.0-142.9° C.

$^1$H-NMR (400 MHz, DMSO-$d_6$); δ (ppm) 2.92 (3H, s), 3.68 (2H, t), 4.19 (2H, t), 4.46 (2H, s), 7.03-7.11 (2H, m), 7.17 (1H, d), 7.37 (1H, t), 7.42 (1H, t), 7.46 (1H, s), 7.64 (1H, s), 7.74 (1H, d), 7.90 (1H, d), 8.68 (1H, s), 9.58 (1H, s).

Cl MS m/z 414 (MH+)

Example 59

Synthesis of {3-[6-(4-methoxy-phenyl)-pyrimidin-4-ylamino]-phenyl}-methanesulfonamide (Compound 62)

-continued

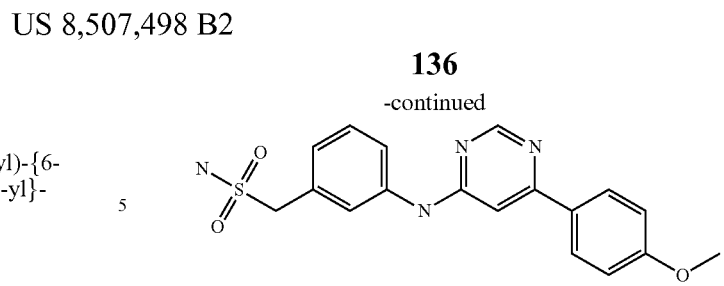

a. Synthesis of 4-chloro-6-(4-methoxy-phenyl)-pyrimidine

The same procedure as for reference example 51 (a). Yield 0.32 g (80%) as colorless powder.

Cl MS m/z 221 (MH+)

b. Synthesis of {3-[6-(4-methoxy-phenyl)-pyrimidin-4-ylamino]-phenyl}-methanesulfonamide)

The same procedure as for reference example 51 (b). Colorless powder.

Yield: 0.25 g (78%).

Melting point: 228.0-229.0° C.

$^1$H-NMR (400 MHz, DMSO-$d_6$); δ (ppm) 3.81 (3H, s), 4.26 (2H, s), 6.79 (2H, s), 7.00-7.10 (3H, m), 7.21 (1H, s), 7.33 (1H, t), 7.62 (1H, s), 7.73 (1H, d), 7.99 (2H, d) 8.65 (1H, s), 9.58 (1H, s).

Cl MS m/z 371 (MH+)

Example 60

Synthesis of {3-[6-(3-trifluoromethyl-phenyl)-pyrimidin-4-ylamino]-phenyl}-methanesulfonamide (Compound 63)

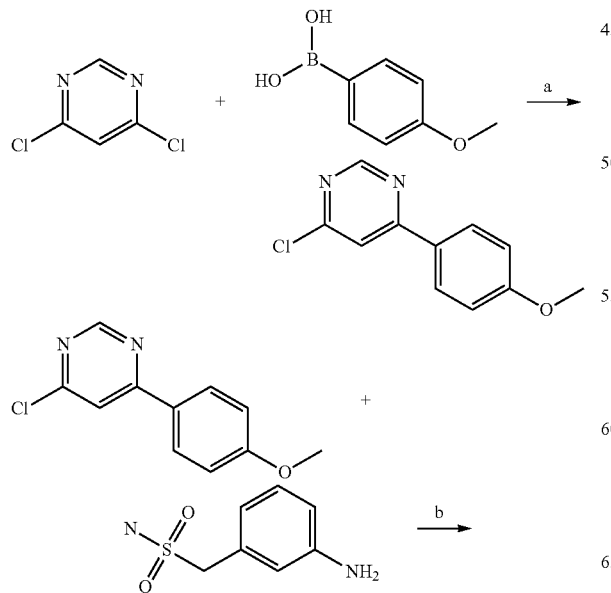

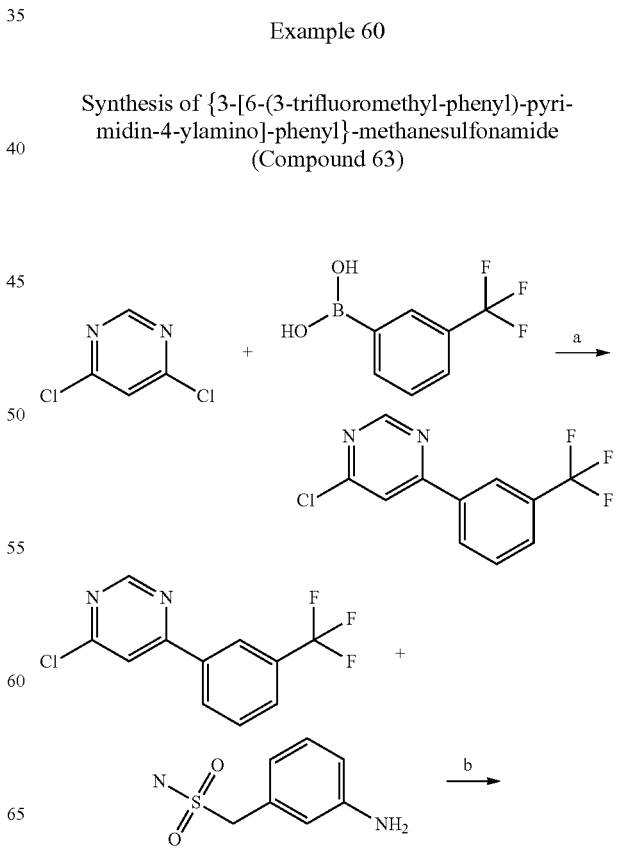

-continued

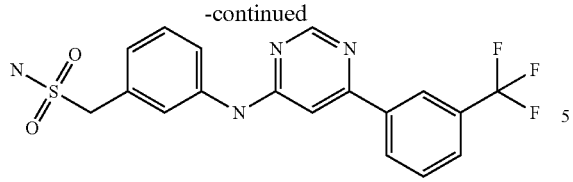

a. Synthesis of 4-chloro-6-(3-trifluoromethyl-phenyl)-pyrimidine

The same procedure as for reference example 51 (a). Yield 0.30 g (75%) as colorless oil.
Cl MS m/z 259 (MH+)

b. Synthesis of {3-[6-(3-trifluoromethyl-phenyl)-pyrimidin-4-ylamino]-phenyl}-methanesulfonamide (Compound 63)

The same procedure as for reference example 51 (b). Colorless powder.
Yield: 0.24 g (72%).
Melting point: 221.5-223.0° C.
$^1$H-NMR (400 MHz, DMSO-$d_6$); δ (ppm) 4.27 (2H, s), 6.79 (2H, s), 7.06 (1H, d), 7.31-7.40 (2H, m), 7.64 (1H, s), 7.70-7.81 (2H, m), 7.87 (1H, d), 8.30 (1H, d), 8.35 (1H, s), 8.74 (1H, s), 9.75 (1H, s).
Cl MS m/z 409 (MH+)

Example 61

Synthesis of (3-methanesulfonylmethyl-phenyl)-{6-[2-(tetrahydro-furan-2-ylmethoxy)-phenyl]-pyrimidin-4-yl}-amine (Compound 64)

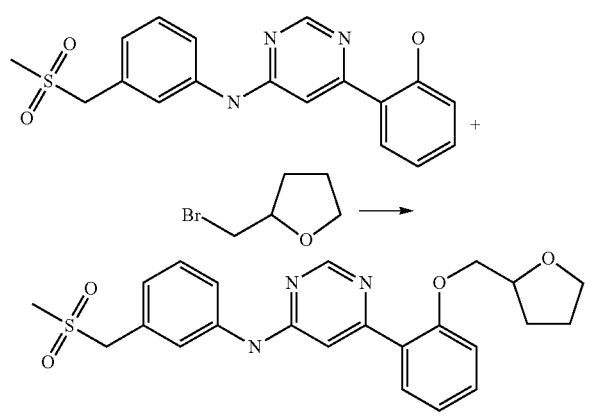

The same procedure as for reference example 57. Colorless solid.
Yield: 0.040 g (14.7%).
Melting point: 160.0-162.6° C.
$^1$H-NMR (400 MHz, DMSO-$d_6$); δ (ppm) 1.65-2.05 (4H, m), 2.89 (3H, s), 3.68-3.82 (2H, m), 4.03 (2H, d), 4.15-4.25 (1H, m), 4.40 (2H, s), 7.03-7.14 (2H, m), 7.18 (1H, d), 7.29 (1H, s), 7.35-7.44 (2H, m), 7.64 (1H, d), 7.69 (1H, d), 7.73 (1H, s), 8.62 (1H, s).
Cl MS m/z 440 (MH+)

Example 62

Synthesis of {3-[2-amino-6-(2-methoxy-phenyl)-pyrimidin-4-ylamino]-phenyl}-methanesulfonamide (Compound 66)

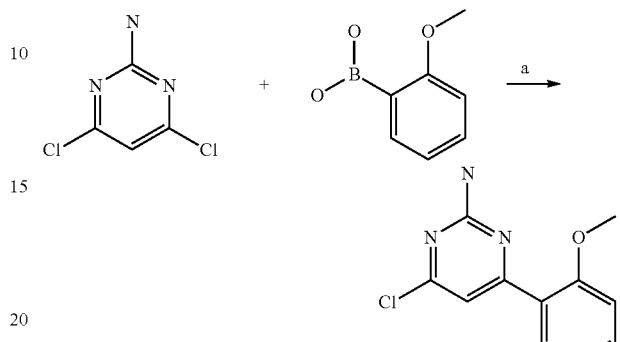

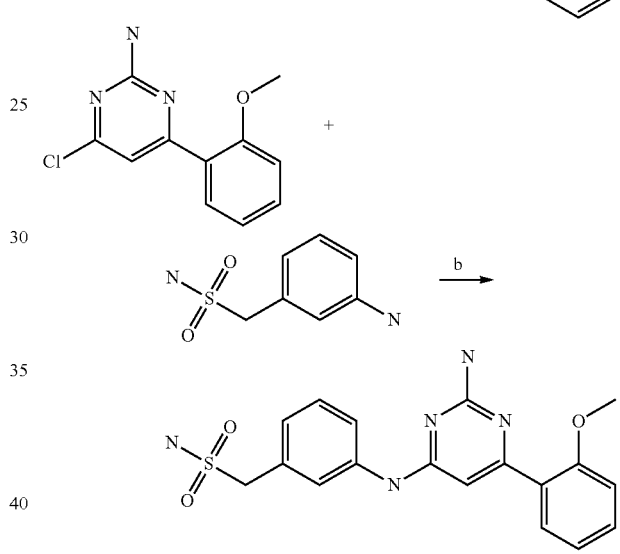

a. Synthesis of 4-chloro-6-(2-methoxy-phenyl)pyrimidin-2-ylamine 4,6-dichloropyrimidin-2-ylamine (1.0 g, 6.13 mmol) and 2-methoxyphenylboronic acid (0.775 g, 5.1 mmol) were added to a solution of dimethoxyethane (20 mL) and water (3 mL), followed by the addition of NaHCO$_3$ (1.03 g, 12.26 mmol) and (PPh$_3$)$_2$PdCl$_2$ (0.2 g) to this and the reaction mixture was allowed to reflux for 4 h, and then the solvent removed under reduced pressure. The residue was taken up in ethyl acetate (50 mL), and the resulting solution washed with water, dried over anhydrous K$_2$CO$_3$, filtered and the solvent removed under reduced pressure. The crude product was purified by flash chropatography on silica gel (eluent CH$_2$Cl$_2$) and recrystallized from hexanes yielding 4-chloro-6-(2-methoxyphenyl)-pyrimidin-2-ylamine (0.76 g; 63%) as light yellow powder.
Cl MS m/z 236 (MH+)

b. Synthesis of {3-[2-amino-6-(2-methoxy-phenyl)-pyrimidin-4-ylamino]-phenyl}-methanesulfonamide A mixture of (3-amino-phenyl)-methanesulfonamide (0.16 g, 0.85 mmol) and 4-chloro-6-(2-methoxyphenyl)-pyrimidin-2-ylamine (0.2 g, 0.85 mmol) in DMF (5 mL) was stirred at 80-90° C. till the reaction completion (TLC control), then evaporated in vacuo. The resulting residue was purified by column chromatography on silica gel yielding {3-[2-amino-6-(2-methoxy-phenyl)-pyrimidin-4-ylamino]-phenyl}-methanesulfonamide (Compound 66) as beige powder.
Yield: 0.25 g (65%).
Melting point: 211.7-213.1° C.
$^1$H-NMR (400 MHz, DMSO-$d_6$); δ (ppm) 3.82 (3H, s), 4.22 (2H, s), 6.07 (2H, s), 6.65 (1H, s), 6.75 (2H, s), 6.92-7.05 (2H, m), 7.10 (1H, d), 7.27 (1H, t), 7.38 (1H, t), 7.68 (1H, s), 7.80 (2H, t), 9.12 (1H, s).
Cl MS m/z 386 (MH+)

Reference Example 63

Synthesis of propane-1-sulfonic acid {2-methyl-5-[6-(3-nitro-phenyl)-pyrimidin-4-ylamino]-phenyl}-amide

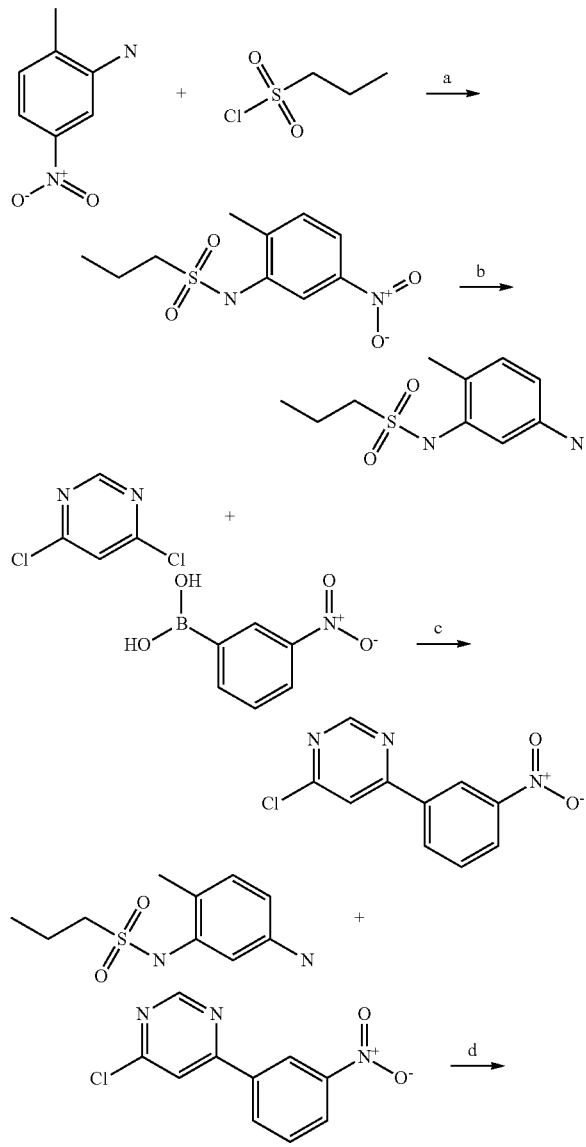

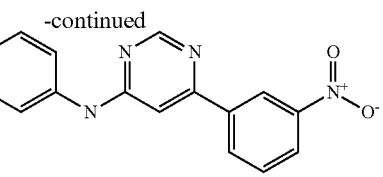

a. Synthesis of propane-1-sulfonic acid (2-methyl-5-nitro-phenyl)-amide

Propane-1-sulfonyl chloride (5.63 mL, 50 mmol) was added to a solution of 2-methyl-5-nitro-phenylamine (7.61 g, 50 mmol) and triethylamine (7 mL) in acetonitrile (100 mL). The resulting solution was vigorously stirred for 3 h at room temperature and diluted with cold water (500 mL), which lead to the formation of a precipitate. The precipitate was filtered out, washed with 1N HCl (100 mL), water (2×200 mL) and dried to give 10.2 g (79%) of propane-1-sulfonic acid (2-methyl-5-nitro-phenyl)-amide as colorless solid.
Cl MS m/z 259 (MH+)

b. Synthesis of propane-1-sulfonic acid (5-amino-2-methyl-phenyl)-amide

Propane-1-sulfonic acid (2-methyl-5-nitro-phenyl)-amide (10 g, 39 mmol) was hydrogenated over Raney nickel (1.0 g) in methanol at 50° C. and 70 psi for 4 h. Then, the catalyst was filtered out, washed with warm methanol, and the combined filtrates were evaporated to give 8.0 g (90%) of propane-1-sulfonic acid (5-amino-2-methyl-phenyl)-amide as colorless solid.
Cl MS m/z 229 (MH+)

c. Synthesis of 4-chloro-6-(3-nitro-phenyl)-pyrimidine 4,6-Dichloropyrimidine (5.58 g, 37.4 mmol) and 3-nitrophenylboronic acid (5.00 g, 27.2 mmol) were added to a stirred mixture of dimethoxyethane (112 mL) and water (17 mL), followed by the addition of NaHCO$_3$ (6.28 g, 75 mmol) and (PPh$_3$)$_2$PdCl$_2$ (0.787 g, 1.12 mmol) herein, and the reaction mixture was refluxed for 8 h. The solvent was removed under reduced pressure. The residue was taken up in CH$_2$Cl$_2$ (100 mL), and the resulting solution washed with water, dried over anhydrous K$_2$CO$_3$, filtered and the solvent removed under reduced pressure. The crude product was purified by column chropatography on silica (eluent CH$_2$Cl$_2$) to yield 4-chloro-6-(3-nitro-phenyl)-pyrimidine (5.52 g; 86%) as yellowish solid.
Cl MS m/z 236 (MH+)

d. Synthesis of propane-1-sulfonic acid {2-methyl-5-[6-(3-nitro-phenyl)-pyrimidin-4-ylamino]-phenyl}-amide)

A mixture of propane-1-sulfonic acid (5-amino-2-methyl-phenyl)-amide (5.5 g, 24 mmol) and 4-chloro-6-(3-nitro-phenyl)-pyrimidine (5.52 g, 23.4 mmol) in DMFA (50 mL) was stirred at 80° C. till the reaction completion (TLC control), the reaction mixture was diluted with water (200 mL), treated with NaHCO$_3$ (4.2 g, 50 mmol). The formed precipitate was filtered out, washed with water (2×200 mL), dried, washed with chloroform (2×50 ml), dried to yield propane-1-sulfonic acid {2-methyl-5-[6-(3-nitro-phenyl)-pyrimidin-4-ylamino]-phenyl}-amide as yellow powder.

Yield: 9.0 g (89%).

Melting point: 202.0-203.5° C.

$^1$H-NMR (400 MHz, DMSO-d$_6$); δ (ppm) 0.99 (3H, t), 1.67-1.83 (2H, m), 2.27 (3H, s), 3.09 (2H, t), 7.19 (1H, d), 7.37 (1H, s), 7.49 (1H, d), 7.62 (1H, s), 7.82 (1H, t), 8.34 (1H, d), 8.41 (1H, d), 8.73 (1H, s), 8.79 (1H, s), 8.97 (1H, s), 9.96 (1H, s).

Cl MS m/z 428 (MH+)

Example 64

Synthesis of C-{3-[6-(2-methoxymethyl-phenyl)-pyrimidin-4-ylamino]-phenyl}-N-methyl-methanesulfonamide (Compound 80)

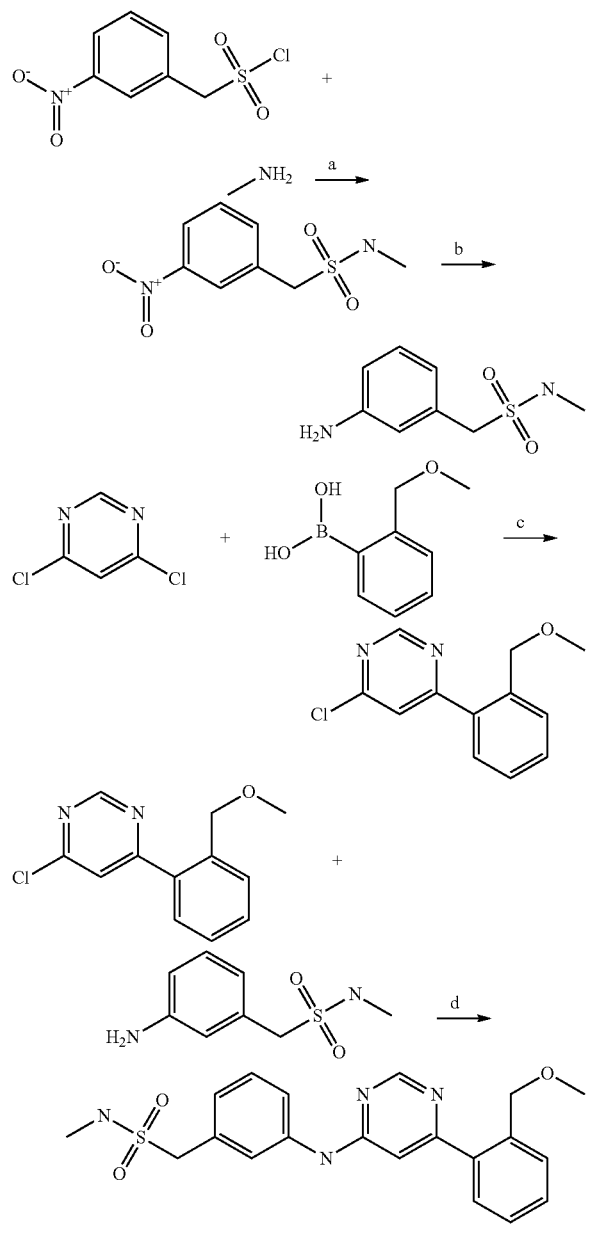

a. Synthesis of (3-nitrophenyl)-N-methylmethanesulfonamide

40% aqueous methylamine (10 mL, 0.1 mol) was added to a vigorously stirred solution of (3-Nitrophenyl)methanesulfonyl chloride (1.18 g, 5 mmol) in benzene (30 mL) and allowed to stir for 2 h at room temperature. To this end, the benzene layer was separated, and the aqueous layer extracted with CH$_2$Cl$_2$ (2×25 mL). The combined organic layers were washed with saturated aqueous NaHCO$_3$ (30 mL), water (30 mL), filtered over anhydrous Na$_2$SO$_4$, filtered and the solvent removed under reduced pressure to give 1.01 g (87%) of (3-nitrophenyl)-N-methylmethanesulfonamide as colorless crystals.

Cl MS m/z 231 (MH+)

b. Synthesis of (3-aminophenyl)-N-methylmethanesulfonamide

The same procedure as for reference example 63 (b). Yield 0.83 g (95%). White solid.

Cl MS m/z 201 (MH+)

c. Synthesis of 4-chloro-6-(2-methoxymethyl-phenyl)-pyrimidine

The same procedure as for reference example 51 (a). Yield 0.51 g (69%). Colorless solid.

Cl MS m/z 235 (MH+)

d. Synthesis of C-{3-[6-(2-methoxymethyl-phenyl)-pyrimidin-4-ylamino]-phenyl}-N-methyl-methanesulfonamide (Compound 80)

The same procedure as for reference example 51 (b). White powder.

Yield: 0.220 g (74%).

Melting point: 171.0-172.0° C.

$^1$H-NMR (400 MHz, DMSO-d$_6$); δ (ppm) 2.55 (3H, d), 4.29 (2H, s), 4.55 (2H, s), 6.82 (1H, q), 6.92 (1H, s), 7.04 (1H, d), 7.33 (1H, t), 7.36-7.50 (3H, m), 7.52 (1H, d), 7.62 (1H, s), 7.74 (1H, d), 8.67 (1H, s), 9.64 (1H, s).

Cl MS m/z 399 (MH+)

Example 65

Synthesis of {3-[6-(2-methoxy-ethoxy)-phenyl]-pyrimidin-4-ylamino]-phenyl}-methanesulfonamide (Compound 81)

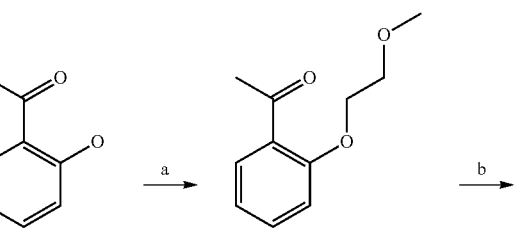

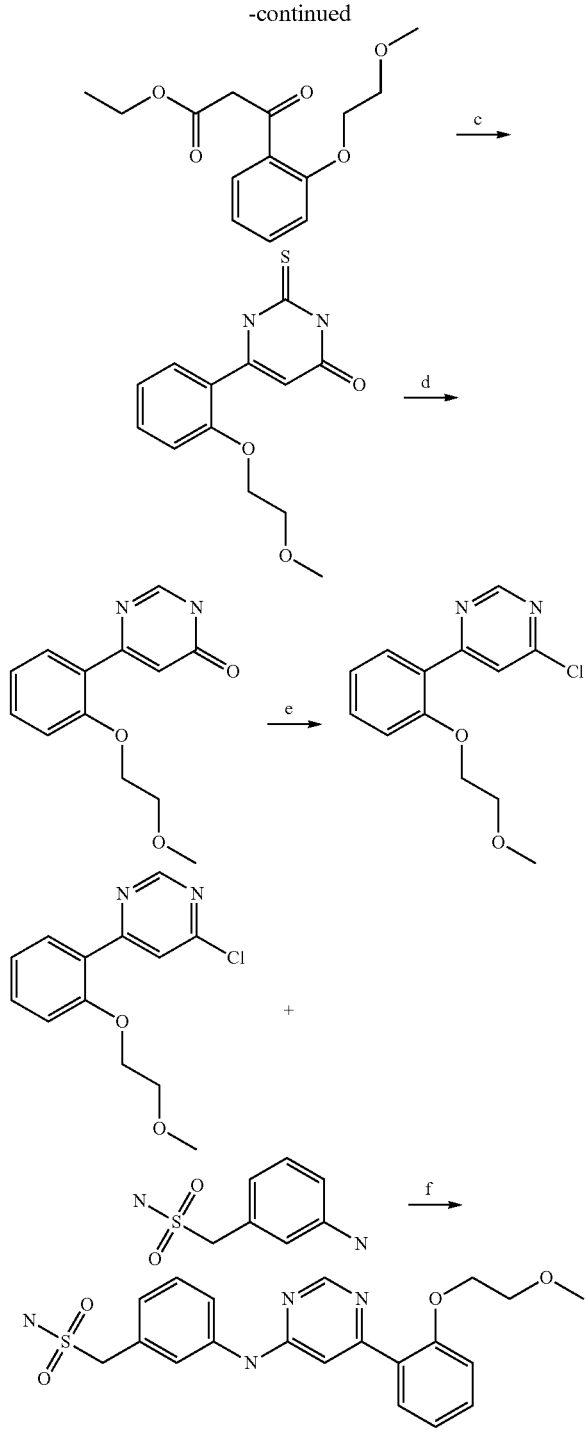

sure. The crude product was purified by flash chropatography on silica gel (eluent EtOAc-hexane, 1:5) to give 1-[2-2-methoxy-ethoxy)-phenyl]-ethanone (6.69 g; 94%) as a light yellow oil.

$^1$H-NMR (400 MHz, DMSO-$d_6$); δ (ppm) 2.48 (3H, s), 3.33 (3H, s), 3.72 (2H, t), 4.23 (2H, t), 6.98-7.05 (1H, m), 7.15 (1H, d), 7.47-7.60 (2H, m).

b. Synthesis of 3-[2-(2-methoxy-ethoxy)-phenyl]-3-oxo-propionic acid ethyl ester A mixture of 1-[2-2-methoxy-ethoxy)-phenyl]-ethanone (4.7 g, 0.024 mol) and diethylcarbonat (12.8 g, 0.11 mol) in anhydrous toluene (20 mL) was added dropwise to a suspension NaH (1.87 g, 0.047 mol) in anhydrous toluene (30 mL). After addition, the mixture refluxed for 1 h, cooled and poured slowly into a solution AcOH (3 mL) and water (70 mL). After separated the organic layer, the aqueous layer was extracted with ethyl acetate (2×70 mL). Organic layers were combined, washed with water (20 mL), then dried over anhydrous sodium sulfate and concentrated. The residue was purified by flash chropatography on silica gel (eluent hexane-CHCl$_3$, 1:1) to obtain 3.5 g (55%) 3-[2-(2-methoxy-ethoxy)-phenyl]-3-oxo-propionic acid ethyl ester as pale yellow oil.

$^1$H-NMR (400 MHz, CDCl$_3$); δ (ppm) 1.18-1.33 (m), 3.45 (3H, s), 3.78 (2H, t), 4.07 (2H, s), 4.16-4.30 (4H, m), 6.96 (1H, d), 7.08 (1H, t), 7.50 (1H, t), 7.86 (1H, d).

c. Synthesis of 6-[2-(2-methoxy-ethoxy)-phenyl]-2-thioxo-2,3-dihydro-1H-pyrimidin-4-one To a solution of 3-[2-(2-methoxy-ethoxy)-phenyl]-3-oxopropionic acid ethyl ester (0.5 g, 1.88 mmol) in 2-methoxyethanol (5 mL) was added thiourea (0.22 g, 2.8 mmol) and K$_2$CO$_3$ (0.28 g, 2 mmol). The reaction mixture refluxed 3 h. After cooling, a mixture poured into water (10 mL) and adjusted to pH 3 with concentrated HCl. A precipitate formed that was filtered and washed with water and diethyl ether to obtained 0.315 g (60%) 6-[2-(2-methoxy-ethoxy)-phenyl]-2-thioxo-2,3-dihydro-1H-pyrimidin-4-one as a cream solid.

$^1$H-NMR (400 MHz, DMSO-$d_6$); δ (ppm) 3.29 (3H, s), 3.65 (2H, t), 4.18 (2H, t), 5.90 (1H, s), 7.21 (1H, t), 7.13 (1H, d), 7.38-7.49 (2H, m), 11.98 (1H, s), 12.33 (1H, s).

d. Synthesis of 6-[2-(2-methoxy-ethoxy)-phenyl]-3H-pyrimidin-4-one

6-[2-(2-methoxy-ethoxy)-phenyl]-2-thioxo-2,3-dihydro-1H-pyrimidin-4-one (0.3 g, 1.08 mmol) is dissolved in EtOH (10 mL) and aqueous solution of ammonia (25%, 3 mL). After addition of Raney-Nickel (0.3 g) the reaction mixture is stirred under reflux for 1 h, filtered from the solid material, which is washed with a mixture of ammonia and EtOH. The combined solutions were evaporated, dissolved in water (5 mL), neutralized with 10% HCl and extracted with ethyl acetate (3×10 mL). Organic layers were combined, washed with water (5 mL) then dried over anhydrous sodium sulfate and concentrated. The residue was triturated with diethyl ether yielding 0.2 g (75%) 6-[2-(2-methoxy-ethoxy)-phenyl]-3H-pyrimidin-4-one as white powder.

Cl MS m/z 247 (MH+)

e. Synthesis of 4-chloro-6-[2-(2-methoxy-ethoxy)-phenyl]-pyrimidine

A stirred suspension of 6-[2-(2-methoxy-ethoxy)-phenyl]-3H-pyrimidin-4-one (0.2 g, 0.81 mmol) in POCl$_3$ (2 mL) was a. Synthesis of 1-[2-2-methoxy-ethoxy)-phenyl]-ethanone Cs$_2$CO$_3$ (12 g, 0.037 mol) was added to a solution of 2-hydroxy-acetophenone (5 g, 0.037 mol) and 1-bromo-2-methoxy-ethane (10 g, 0.072 mol) in DMF (20 mL). The resulting mixture was vigorously stirred for 5-7 h at 90-100° C., cooled and then diluted with water (100 mL), extracted with EtOAc (3×50 mL). The combined organic layers were washed with water (2×30 mL), filtered over anhydrous Na$_2$SO$_4$, filtered and the solvent removed under reduced presheated at reflux for 1 h. The reaction mixture was cooled to about 5° C. and poured cautiously into 10 ml ice-water, ammonia (10 mL) was added and extracted with ethyl acetate (2×10 mL), organic layers were combined, washed with water (5 mL) then dried over anhydrous sodium sulfate and concentrated. The residue was triturated with hexane yielding 0.18 g (84%) 4-chloro-6-[2-(2-methoxy-ethoxy)-phenyl]-pyrimidine as white powder.

f. Synthesis of {3-[6-(2-methoxy-ethoxy)-phenyl]-pyrimidin-4-ylamino]-phenyl}-methanesulfonamide (Compound 81)

A mixture of (3-amino-phenyl)-methanesulfonamide (0.06 g, 0.34 mmol) and 4-chloro-6-[2-(2-methoxy-ethoxy)-phenyl]-pyrimidine (0.09 g, 0.34 mmol) in DMF (3 mL) was stirred at 80° C. till the reaction completion (TLC control), then evaporated in vacuo. The resulting residue was purified by column chromatography on silica gel yielding {3-[6-(2-methoxy-ethoxy)-phenyl]-pyrimidin-4-ylamino]-phenyl}-methanesulfonamide (Compound 81) as cream solid.

Yield: 0.09 g (64%).
Melting point: 143.3-145.5° C.
$^1$H-NMR (400 MHz, DMSO-d$_6$); δ (ppm) 3.22 (3H, s), 3.70 (2H, t), 4.19 (2H, t), 4.24 (2H, s), 6.78 (2H, s), 7.00-7.11 (2H, m), 7.16 (1H, d), 7.38 (1H, t), 7.42 (1H, t), 7.46 (1H, s), 7.60 (1H, s), 7.75 (1H, d), 7.90 (1H, s), 8.67 (1H, s), 9.56 (1H, s).
Cl MS m/z 415 (MH+)

Example 66

Synthesis of (3-{6-[2-(tetrahydro-furan-2-yl-methoxy)-phenyl]-pyrimidin-4-ylamino}-phenyl)-methanesulfonamide (Compound 82)

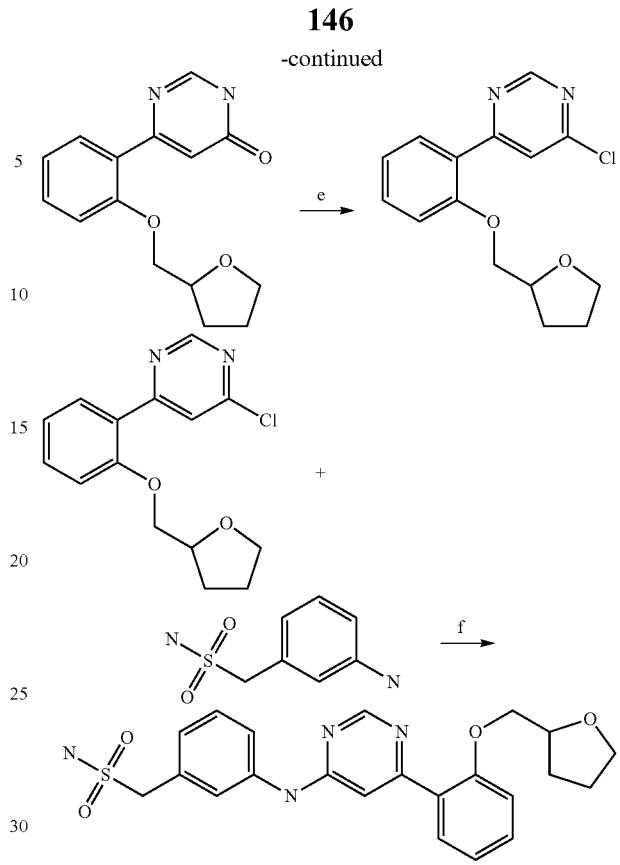

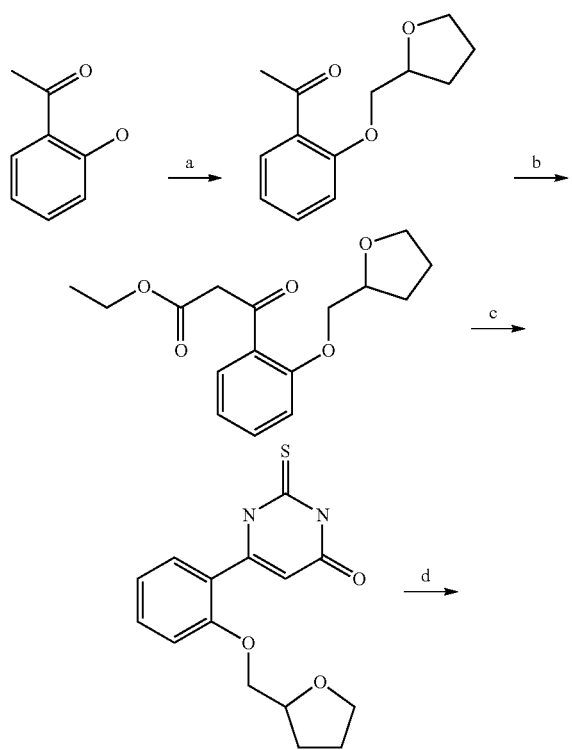

a. Synthesis of 1-[2-(tetrahydro-furan-2-ylmethoxy)-phenyl]-ethanone

K$_2$CO$_3$ (4.5 g, 0.032 mol) was added to a solution of 2-hydroxy-acetophenone (4 g, 0.03 mol) and 2-bromomethyl-tetrahydro-furan (10 g, 0.06 mol) in DMF (20 mL). The resulting mixture was vigorously stirred for 16 h at 110° C., cooled and then diluted with water (100 mL), extracted with EtOAc (3×50 mL). The combined organic layers were washed with water (2×30 mL), filtered over anhydrous Na$_2$SO$_4$, filtered and the solvent removed under reduced pressure. The crude product was purified by flash chropatography on silica gel (eluent EtOAc-hexane, 1:5) to give 1-[2-(tetrahydro-furan-2-ylmethoxy)-phenyl]-ethanone (2.22 g; 34%) as brown oil.

b. Synthesis of 3-oxo-3-[2-(tetrahydro-furan-2-yl-methoxy)-phenyl]-propionic acid ethyl ester A mixture of 1-[2-(tetrahydro-furan-2-ylmethoxy)-phenyl]-ethanone (2.22 g, 0.01 mol) and diethylcarbonat (10 mL, 0.083 mol) in anhydrous toluene (20 mL) was added dropwise to a suspension NaH (1.0 g, 0.025 mol) in anhydrous toluene (20 mL). After addition, the mixture refluxed for 2 h, cooled and poured slowly into a solution AcOH (3 mL) and water (50 mL). After separated the organic layer, the aqueous layer was extracted with ethyl acetate (2×50 mL). Organic layers were combined, washed with water (20 mL), then dried over anhydrous sodium sulfate and concentrated. The residue was purified by flash chromatography on silica gel (eluent hexane-ethylacetate, 1:5) to obtain 1.85 g (64%) 3-oxo-3-[2-(tetrahydro-furan-2-ylmethoxy)-phenyl]-propionic acid ethyl ester as yellow oil.

c. Synthesis of 6-[2-(tetrahydro-furan-2-ylmethoxy)-phenyl]-2-thioxo-2,3-dihydro-1H-pyrimidin-4-one To a solution of 3-oxo-3-[2-(tetrahydro-furan-2-ylmethoxy)-phenyl]-propionic acid ethyl ester (0.9 g, 3.08 mmol) in 2-methoxyethanol (5 mL) was added thiourea (0.31 g, 4.08 mmol) and $K_2CO_3$ (0.56 g, 4 mmol). The reaction mixture refluxed 5-6 h. After cooling, a mixture poured into water (10 mL), adjusted to pH 3 with 10% HCl and extracted with ethyl acetate (2×10 mL). Organic layers were combined, washed with water (10 mL), then dried over anhydrous sodium sulfate, concentrated and triturated with diethyl ether to obtained 0.6 g (64%) 6-[2-(tetrahydro-furan-2-ylmethoxy)-phenyl]-2-thioxo-2,3-dihydro-1H-pyrimidin-4-one as a beige solid.

d. Synthesis of 6-[2-(tetrahydro-furan-2-ylmethoxy)-phenyl]-3H-pyrimidin-4-one 6-[2-(2-methoxy-ethoxy)-phenyl]-2-thioxo-2,3-dihydro-1H-pyrimidin-4-one (0.6 g, 1.97 mmol) is dissolved in EtOH (12 mL) and aqueous solution of ammonia (25%, 4 mL). After addition of Raney-Nickel (0.5 g) the reaction mixture is stirred under reflux for 1 h, filtered from the solid material, which is washed with a mixture of ammonia and EtOH. The combined solutions were evaporated, dissolved in water (10 mL), neutralized with 10% HCl and extracted with ethyl acetate (3×15 mL). Organic layers were combined, washed with water (7 mL) then dried over anhydrous sodium sulfate and concentrated. The residue was triturated with diethyl ether yielding 0.47 g (87%) 6-[2-(tetrahydro-furan-2-ylmethoxy)-phenyl]-3H-pyrimidin-4-one as cream powder.
Cl MS m/z 273 (MH+)

e. Synthesis of 4-chloro-6-[2-(tetrahydro-furan-2-ylmethoxy)-phenyl]-pyrimidine To a stirred suspension of 6-[2-(tetrahydro-furan-2-ylmethoxy)-phenyl]-3H-pyrimidin-4-one (0.375 g, 1.37 mmol) in dichloromethane (5 mL) and dioxane (5 mL) was added DMF (0.05 mL) followed by a solution of oxalyl chloride (0.5 mL, 4 mmol). After stirring for 1 h, the mixture was concentrated under vacuum. The residue was partitioned between ethyl acetate (25 mL) and saturated aqueous sodium bicarbonate solution (10 mL). The organic phase was dried over anhydrous sodium sulfate and concentrated under vacuum to give 0.4 g (99%) 4-chloro-6-[2-(tetrahydro-furan-2-ylmethoxy)-phenyl]-pyrimidine as colorless oil.
Cl MS m/z 291 (MH+)

f. Synthesis of (3-{6-[2-(tetrahydro-furan-2-ylmethoxy)-phenyl]-pyrimidin-4-ylamino}-phenyl)-methanesulfonamide (Compound 82)

A mixture of (3-amino-phenyl)-methanesulfonamide (0.18 g, 0.62 mmol) and 4-chloro-6-[2-(tetrahydro-furan-2-ylmethoxy)-phenyl]-pyrimidine (0.115 g, 0.62 mmol) in DMF (3 mL) was stirred at 80-90° C. till the reaction completion (TLC control), then evaporated in vacuo. The resulting residue was purified by column chromatography on silica gel yielding (3-{6-[2-(tetrahydro-furan-2-ylmethoxy)-phenyl]-pyrimidin-4-ylamino}-phenyl)-methanesulfonamide (Compound 82) as white solid.
Yield: 0.18 g (66%).
Melting point: 168.4-169.4° C.

$^1$H-NMR (400 MHz, DMSO-$d_6$); δ (ppm) 1.60-2.00 (4H, m), 3.52-3.70 (2H, m), 4.03 (2H, m), 4.18 (1H, m), 4.22 (2H, s), 6.78 (2H, s), 7.05 (2H, m), 7.16 (1H, d), 7.28-7.44 (3H, m), 7.57 (1H, s), 7.74 (1H, d), 7.83 (1H, d), 8.66 (1H, s), 9.55 (1H, s).

Cl MS m/z 441 (MH+)

Example 67

Synthesis of (3-{6-[2-(2-methoxy-ethoxy)-phenyl]-2-methyl-pyrimidin-4-ylamino}-phenyl)-methanesulfonamide (Compound 83)

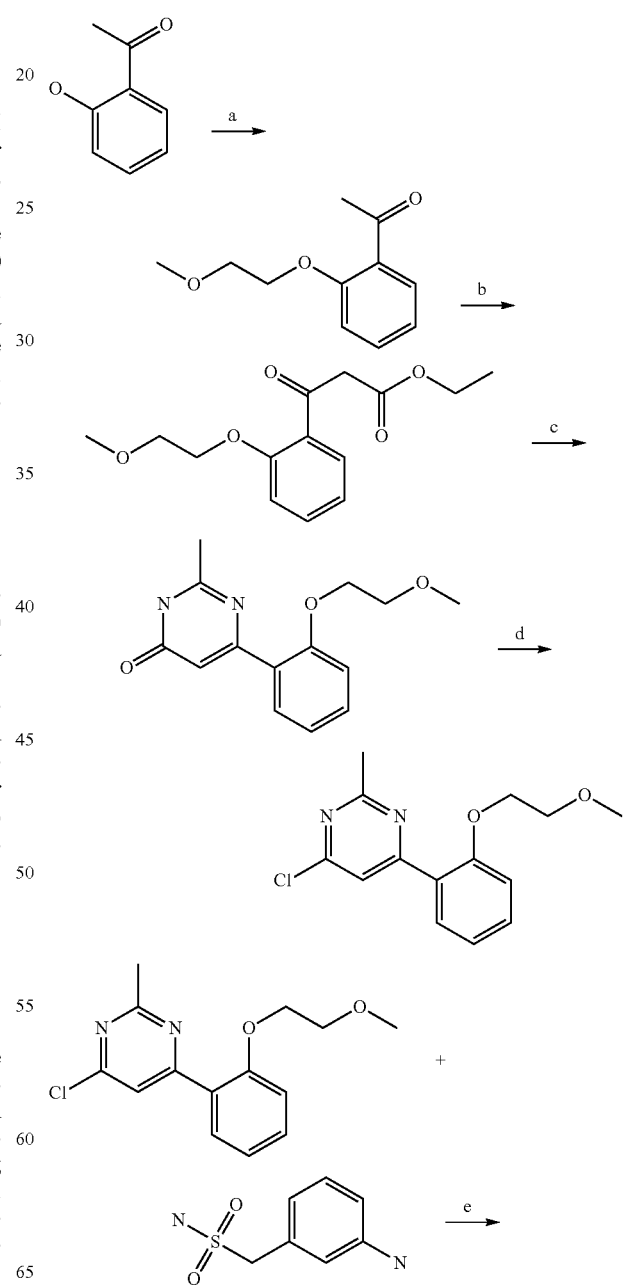

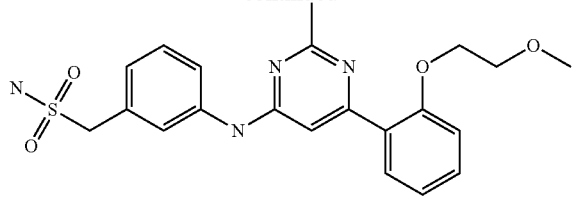

a. Synthesis of 1-[2-2-methoxy-ethoxy)-phenyl]-ethanone

The same procedure as for example 65 (a).

b. Synthesis of 3-[2-(2-methoxy-ethoxy)-phenyl]-3-oxo-propionic acid ethyl ester The same procedure as for example 65 (b).

c. Synthesis of 6-[2-(2-methoxy-ethoxy)-phenyl]-2-methyl-3H-pyrimidin-4-one

To a solution of 3-[2-(2-methoxy-ethoxy)-phenyl]-3-oxo-propionic acid ethyl ester (0.26 g, 0.98 mmol) in absolute ethanol (10 mL) was added acetamidine hydrochloride (0.3 g, 3.19 mmol) and tBuOK (0.5 g, 4.46 mmol). The reaction mixture refluxed 12 h. After cooling, a mixture poured into water (10 mL), adjusted to pH 3 with 10% HCl and extracted with CHCl$_3$ (3×20 mL). Organic layers were combined, washed with water (10 mL), then dried over anhydrous sodium sulfate, concentrated and triturated with hexane to obtained 0.17 g (67%) 6-[2-(2-methoxy-ethoxy)-phenyl]-2-methyl-3H-pyrimidin-4-one as a white powder.

d. Synthesis of 4-chloro-6-[2-(2-methoxy-ethoxy)-phenyl]-2-methyl-pyrimidine

A stirred suspension of 6-[2-(2-methoxy-ethoxy)-phenyl]-2-methyl-3H-pyrimidin-4-one (0.17 g, 0.66 mmol) in POCl$_3$ (2 mL) was heated at reflux for 1 h. The reaction mixture was cooled to about 5° C. and poured cautiously into 10 ml ice-water, ammonia (10 mL) was added and extracted with ethyl acetate (2×10 mL), organic layers were combined, washed with water (5 mL) then dried over anhydrous sodium sulfate and concentrated. The residue was purified by column chromatography on silica gel (eluent CHCl$_3$-EtOAc, 10:1), yielding 0.16 g (87%) 4-chloro-6-[2-(2-methoxy-ethoxy)-phenyl]-2-methyl-pyrimidine as colorless solid.

e. Synthesis of (3-{6-[2-(2-methoxy-ethoxy)-phenyl]-2-methyl-pyrimidin-4-ylamino}-phenyl)-methanesulfonamide (Compound 83)

A mixture of (3-amino-phenyl)-methanesulfonamide (0.1 g, 0.54 mmol) and 4-chloro-6-[2-(2-methoxy-ethoxy)-phenyl]-2-methyl-pyrimidine (0.16 g, 0.0.57 mmol) in DMF (3 mL) was stirred at 90° C. till the reaction completion (TLC control), then evaporated in vacuo. The resulting residue was purified by column chromatography on silica gel yielding (3-{6-[2-(2-methoxy-ethoxy)-phenyl]-2-methyl-pyrimidin-4-ylamino}-phenyl)-methanesulfonamide (Compound 83) as beige powder.

Yield: 0.2 g (87%).

Melting point: 209.0-211.1° C.

$^1$H-NMR (400 MHz, DMSO-d$_6$); δ (ppm) 2.62 (3H, s), 3.66 (2H, s), 4.20 (2H, s), 4.30 (2H, s) 6.81 (2H, s), 7.13-7.30 (4H, m), 7.43 (1H, t), 7.56-7.64 (2H, m), 7.71 (2H, br. s), 11.55 (1H, br. s).

Cl MS m/z 429 (MH+)

TABLE 5

| (3-nitrophenyl)methanesulfonamide | Yield % | (3-aminophenyl)methanesulfonamide | Yield % | 4-chloro-6-aryl-pyrimidine | Yield % |
|---|---|---|---|---|---|
| | 79 | | 90 | | 86 |
| | 87 | | 90 | | 80 |
| | 80 | | 93 | | 45 |
| | 82 | | 93 | | 69 |

TABLE 5-continued

Yields of the intermediates

| (3-nitrophenyl)methanesulfonamide | Yield % | (3-aminophenyl)methanesulfonamide | Yield % | 4-chloro-6-aryl-pyrimidine | Yield % |
|---|---|---|---|---|---|
| [3-nitrophenyl methanesulfonamide, N-methyl] | 87 | [3-aminophenyl methanesulfonamide, N-methyl] | 95 | [4-chloro-6-(4-methoxyphenyl)pyrimidine] | 80 |
| | | | | [4-chloro-6-(3-trifluoromethylphenyl)pyrimidine] | 75 |
| | | | | [4-chloro-6-(2-(2-methoxyethoxy)phenyl)pyrimidine] | 20 |
| | | | | [4-chloro-6-(2-((tetrahydrofuran-2-yl)methoxy)phenyl)pyrimidine] | 12 |
| | | | | [4-chloro-6-(2-methoxyphenyl)-2-aminopyrimidine] | 63 |
| | | | | [4-chloro-6-(2-(2-methoxyethoxy)phenyl)-2-methylpyrimidine] | 30 |

Example 68

Alternative Synthesis of C-{3-[6-(2-methoxy-phenyl)-pyrimidin-4-ylamino]-phenyl}-N,N-dimethyl-methanesulfonamide (Compound 20)

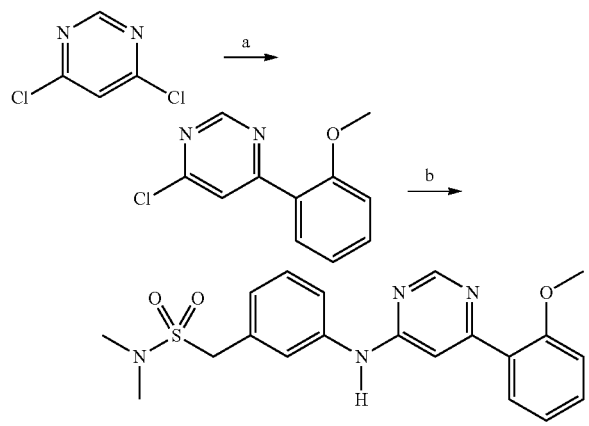

a) ArBr(OH)₂, PdCl₂(dppf), DME, 85° C., 16 hours
b) ArNH₂, PrOH, HCl, 85° C., 16 hours

Step a) 4-Chloro-6-(2-methoxy-phenyl)-pyrimidine

A mixture of 4,6-dichloropyrimdine (0.98 g), 2-methoxy-benzeneboronic acid (1.0 g), [1,1'-bis(diphenylphosphino)ferrocene]dichloropalladium (11) (0.54 g), 1,2-dimethoxy-ethane (60 ml), sodium hydrogen carbonate (1.1 g) and water (20 ml) were heated together at 85° C. for 16 hours. The mixture was cooled to room temperature, diluted with ethyl acetate and the organic phase separated, dried over magnesium sulphate, filtered, evaporated, then purified by column chromatography (silica gel, ethyl acetate/petroleum ether), to give 4-Chloro-6-(2-methoxy-phenyl)-pyrimidine, 1.18 g ¹H NMR CDCl₃, 3.94 (3H, s, CH₃), 7.04 (1H, d, ArH), 7.14 (1H, m, ArH), 7.47 (1H, m, ArH), 8.06 (2H, s, ArH), 9.05 (1H, s, ArH)

Step b) C-{3-[6-(2-methoxy-phenyl)-pyrimidin-4-ylamino]-phenyl}-N,N-dimethyl-methanesulfonamide (Compound 20)

A solution of 4-Chloro-6-(2-methoxy-phenyl)-pyrimidine (0.1 g), (3-Amino-phenyl)-N,N-dimethyl-methanesulfonamide (0.1 g) concentrated hydrochloric acid (3 drops) in propan-2-ol (10 ml) were heated together at 85° C. for 16 hours, then cooled and evaporated. The residue was dissolved in ethyl acetate and sodium hydrogen carbonate solution. The organic phases separated, over magnesium sulphate, filtered, evaporated, and then purified by column chromatography (silica gel, ethyl acetate/petroleum ether), to give C-{3-[6-(2-methoxy-phenyl)-pyrimidin-4-ylamino]-phenyl}-N,N-dimethyl-methanesulfonamide (Compound #1), 0.12 g, ¹H NMR DMSO-d6 2.79 (6H, s, 2×NCH₃), 3.94 (3H, s, OCH₃), 4.50 (ZH, s, CH₂), 7.21 (1H, t, ArH), 7.31 (2H, m, ArH), 7.39 (1H, s, ArH), 7.49 (1H, t, ArH), 7.65 (1H, t, ArH), 7.75 (2H, m, ArH), 7.80 (1H, m, ArH), 8.94 (1H, s, ArH), 11.21 (1H, br s, NH)

LCMS (ammonium bicarbonate) R$_T$=3.17 mins, 100%, MH⁺399

Example 69

Synthesis of C-{3-[6-(2-methoxy-phenyl)-pyrimidin-4-ylamino]-phenyl}-methanesulfonamide (Compound 85)

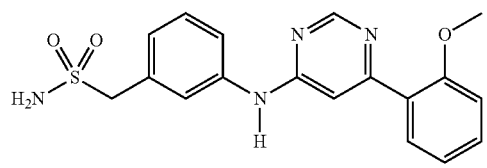 [SMILES: COc1ccccc1-c1cc(Nc2cccc(CS(N)(=O)=O)c2)ncn1]

C-{3-[6-(2-Methoxy-phenyl)-pyrimidin-4-ylamino]-phenyl}-methanesulfonamide was prepared in a similar manner to that used in Example 68 but using appropriate starting materials:

¹H NMR DMSO-d6, 3.94 (3H, s, OCH₃), 4.35 (2H, s, CH₂), 6.95 (2H, t, NH₂), 7.22 (2H, m, ArH), 7.31 (1H, d, ArH), 7.39 (1H, s, ArH), 7.49 (1H, t, ArH), 7.64 (2H, m, ArH), 7.73 (1H; d; ArH); 7.79 (1H, m, ArH), 8.93 (1H, s, ArH), 11.15 (1H, br s, NH)

LCMS (ammonium bicarbonate) R$_T$=2.75 mins, 100%, MH⁺371

Example 70

Alternative Synthesis of C-{3-[6-(2-methoxy-phenyl)-pyrimidin-4-ylamino]-phenyl}-N-methyl-methanesulfonamide (Compound 49)

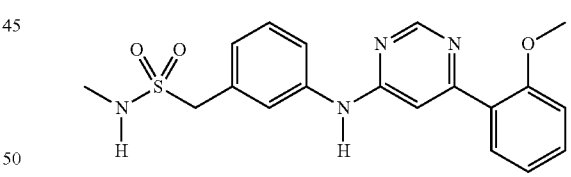

C-{3-[6-(2-Methoxy-phenyl)-pyrimidin-4-ylamino]-phenyl}-N-methyl-methanesulfonamide was prepared in a similar manner to that used in Example 68 but using appropriate starting materials:

¹H NMR DMSO-d6, 2.62 (3H, d, NCH₃), 3.94 (3H, s, OCH₃), 4.41 (2H, s, CH₂), 7.03 (1H, m, NH), 7.22 (2H, m, ArH), 7.31 (1H, d, ArH), 7.41 (1H, s, ArH), 7.49 (1H, t, ArH), 7.67 (2H, m, ArH), 7.73 (1H, d, ArH), 7.80 (1H, m, ArH), 8.94 (1H, s, ArH), 11.25 (1H, br s, NH)

LCMS (ammonium bicarbonate) R$_T$ 2.94 mins, 100%, MH⁺385

Example 71

Synthesis of N-(2-methoxy-ethyl)-C-{3-[6-(2-methoxy-phenyl)-pyrimidin-4-ylamino]-phenyl}-methanesulfonamide (Compound 86)

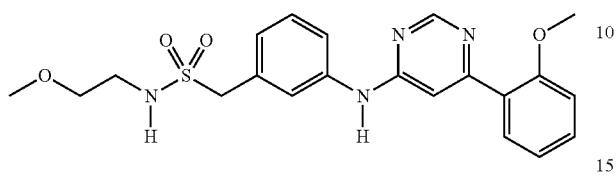

N-(2-Methoxy-ethyl)-C-{3-[6-(2-methoxy-phenyl)-pyrimidin-4-ylamino]-phenyl}-methanesulfonamide was prepared in a similar manner to that used in Example 68 but using appropriate starting materials:

$^1$H NMR DMSO-d6, 3.11 (2H, q, CH$_2$), 3.29 (3H, s, OCH$_3$), 3.40 (2H, m, CH$_2$), 3.94 (3H, s, CH$_3$), 4.42 (2H, s, CH$_2$), 7.50 (4H, m, ArH), 7.40 (1H, s, ArH), 7.70 (4H, m, NH+ArH), 8.93 (1H, s, ArH), 11.22 (1H, br s, NH)

LCMS (ammonium bicarbonate) R$_T$=3.00 mins, 97.66%, MH$^+$429

Preparation of Intermediates for Examples 68-71

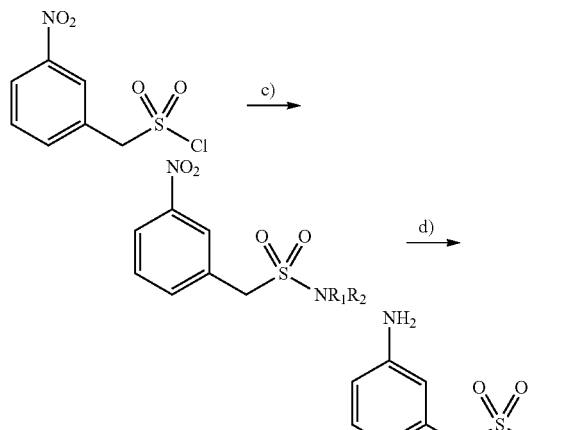

c) Amine, DCM
d) Fe, EtOH, HCl, 80° C. 2 hours

Intermediates of Step c)

N,N-Dimethyl-C-(3-nitro-phenyl)-methanesulfonamide

To a solution of (3-Nitrophenyl)methanesulfonyl chloride (1.0 g, 0.0042 mol) in dry dichloromethane (25 mls) at room temperature dimethylamine (2M in THF, 5.3 ml, 0.105 mol) was added dropwise. The mixture was stirred for 3 hours then filtered through silica, then evaporated to give N,N-Dimethyl-C-(3-nitro-phenyl)-methanesulfonamide, 1.0 g, $^1$H NMR CDCl$_3$ 2.84 (6H, s, 2×CH$_3$), 4.29 (2H, s, CH$_2$), 7.60 (1H, m, ArH), 7.79 (1H, d, ArH), 8.25 (2H, m, ArH)

Similarly were prepared:

N-Methyl-C-(3-nitro-phenyl)-methanesulfonamide $^1$H NMR DMSO 2.64 (3H, d, NHCH$_3$), 4.60 (2H, s, CH$_2$), 7.05 (1H, q, NH), 7.74 (1H, m, ArH), 7.87 (1H d, ArH), 8.27 (1H, m, ArH), 8.31 (1H, s, ArH)

N,-2-methoxyethyl-C-(3-nitro-phenyl)-methanesulfonamide $^1$H NMR CDCl$_3$ 3.24 (2H, t, CH$_2$), 3.34 (3H, S, OCH$_3$), 3.46 (2H, t, CH$_2$), 4.41 (2H, S, CH$_2$), 7.57 (1H, t, ArH), 7.79 (1H, d, ArH), 8.20 (1H, d, ArH), 8.30 (1H, s, ArH)

Intermediates of Step D)

C-(3-Amino-phenyl)-N,N-dimethyl-methanesulfonamide

To a stirred mixture of iron powder (0.5 g), ethanol (20 ml), water (1 ml) and concentrated hydrochloric acid (5 drops) at reflux was added N,N-Dimethyl-C-(3-nitro-phenyl)-methanesulfonamide (0.5 g). The mixture was then heated under reflux for a further 2 hours then basified with excess sodium carbonate solution, cooled to 60° C., then filtered. The filter cake washed with ethanol and the filtrate evaporated. The crude product was partitioned between ethyl acetate and water, separation and evaporation of the organic phase gave C-(3-Amino-phenyl)-N,N-dimethyl-methanesulfonamide, 0.4 g, sufficiently pure to use.

$^1$H NMR CDCl$_3$, 7.75 (6H, s, N(CH$_3$)$_2$, 3.72 (2H, br s, NH$_2$), 4.15 (2H, s, CH$_2$), 6.68 (1H, d, ArH), 6.75 (2H, m, ArH), 7.15 (1H, t, ArH)

Similarly were prepared:

C-(3-Amino-phenyl)-N-methyl-methanesulfonamide $^1$H NMR CDCl$_3$ 2.73 (3H, d, CH$_3$), 3.75 (2H, br s, NH$_2$), 4.05 (1H, br s, NH), 4.18 (2H, 5, CH$_2$, 6.72 (3H, m, ArH), 7.18 (1H, t, ArH)

C-(3-Amino-phenyl)-N-(2-methoxy-ethyl)-methanesulfonamide $^1$H NMR CDCl$_3$ 3.15 (2H, m, CH$_2$), 3.31 (3H, s, CH$_3$), 3.40 (2H, m, CH$_2$), 3.75 (2H, br 5, NH$_2$), 4.18 (2H, s, CH$_2$), 4.56 (1H, br t, NH), 6.67 (1H, d, ArH), 6.76 (2H, m, ArH), 7.15 (1H, t, ArH)

C-(3-Amino-phenyl)-methanesulfonamide, is commercially available.

Example 72

I. Behavioral Animal Models for the Analysis of Inflammatory and Neuropathic Pain Several animal models for the analysis of inflammatory and neuropathic pain are known. Said models share the common feature that after e.g., induction of a nerve lesion (e.g., spared nerve injury, SNI) or after exposing experimental animals to a noxious stimulus (e.g., injection of formalin or carrageenan), the signs of pain as induced by said interventions are measured by quantifiable behavioral components such as, e.g., paw withdrawal threshold to mechanical stimulation with von Frey hairs (or to thermal stimulation using a laser source or licking behaviour). These reactions are interpreted as being equivalent to mechanical and thermal allodynia (hypersensitivity to mechanical stimuli) or hyperalgesia in humans.

The spared nerve injury model (SNI model, as developed by Decosterd and Woolf (2000), see FIG. 1) is characterized by the induction of clinically relevant nerve lesions and after surgical intervention, subsequent behavioral experiments (e.g., von Frey Assay). Said model constitutes a common nerve injury model which consists of ligation and section of two branches of the sciatic nerve (namely tibial and common peroneal nerves) leaving the sural nerve intact. The SNI model results in early (less than 24 hours), prolonged and substantial changes in mechanical and cold sensitivity that closely mimic the features of clinical neuropathic pain. Animals with these types of nerve injury have been shown to develop abnormal pain sensations and hypersensitivity to mechanical stimuli (allodynia) similar to those reported by neuropathic pain patients.

Alternatively, the formalin assay in mice is a valid and reliable behavioral model of nociception in inflammatory and neuropathic pain. It is sensitive to various classes of analgesic drugs (Hunskaar S, Hole K, Pain. 1987 July; 30(1):103-14.) The noxious stimulus consists of an injection of 10 µl diluted formalin (2% in saline) under the skin of the dorsal surface of the left hindpaw (subcutaneous or interplantar into the left hindpaw). The response is licking and flinching of the injected paw.

For the carrageenan assay a subcutaneous injection of 25 µl of 1% carrageenan (in saline) into a single hind paw (ipsi-lateral paw) of mice is applied. Subsequent inflammation results in long lasting swelling and hypersensitivity (against mechanical and thermal stimuli) of the paw. The carrageenan assay is a standard laboratory assay used to predict anti-inflammatory activity of test compounds. Paw edema measurements and Hargreaves Assay (withdrawal of paws due to thermal stimulation via a light source) are used for read out.

Regarding the present invention, the effect of administration of cyclin-dependent kinase (CDK)-inhibiting compounds according to any one of Formulae (I) to (III) (including formula (IIIa)) on the development of inflammatory and neuropathic pain is assayed in a SNI model, in a carrageenan and in a formalin assay. The experimental procedure and results are described in detail below.

Example 73

A. Spared Nerve Injury (SNI)—Model of Chronic Neuropathic Pain

As outlined above, the spared nerve injury (SNI) model (see FIG. 1) involves a lesion of two of the three terminal branches of the sciatic nerve (tibial and common peroneal nerves) of experimental animals, leaving the sural nerve intact. SNI results in mechanical and thermal allodynia in the non-injured sural nerve skin territory (Decosterd and Woolf, Pain 2000; 87:149-158. (2) Tsujino et al., Mol. Cel. Neurosci. 2000; 15:170-182).

1. Induction of Spared Nerve Injury (Nerve Lesion) in Wildtype Mice

Wildtype mice (strain C3HeB/FeJ) (age, sex and weight matched) were anesthetized with Hypnorm (0.315 mg/ml fentanyl citrate+10 mg/ml fluanisone; Janssen)/Hypnovel (5 mg/ml midazolam; Roche Applied Sciences)/water at a ratio of 1:1:2 at 4 µl/g prior to surgical preparation.

Subsequently, an incision was made under aseptic precautions in the ipsi-lateral right hind leg of all mice just above the level of the knee, exposing the three terminal branches of the sciatic nerve: the common peroneal, tibial, and sural nerves. The common peroneal and tibial nerves were ligated tightly with 7/0 silk and sectioned distal to the ligation removing ≈2 mm of distal nerve stump. The sural branch remained untouched during the procedure (denoted herein "SNI ipsi"). The overlying muscle and skin was sutured, and the animals were allowed to recover and to permit wound healing. In the same mice the sciatic nerve branches of the contra-lateral left hind leg were exposed but not lesioned (denoted herein "SNI contra-lateral"). Mice that underwent spared nerve injury are hereinafter denoted "SNI mice".

2. Administration of CDK-inhibiting Compounds to SNI Mice

After recovery from surgery and wound healing, SNI mice received per oral (p.o.) injections of CDK-inhibiting compounds. In this example, compound 43 was administered.

30 mg/kg of a CDK inhibitor, dissolved in 400 µl of 2% Hydroxprolylcellulose; 0.25% Lactic Acid (85% solution) was administered via per oral application 30 min prior to von Frey measurements (mechanical allodynia). As a negative control, the same amount (400 µl) of 2% Hydroxprolylcellulose; 0.25% Lactic Acid (85% solution) vehicle was administered by a single per oral application 30 min prior to von Frey measurements.

Injection of inhibitor or vehicle, and subsequent measurements of paw withdrawal threshold to mechanical stimulation in von Frey assays were performed at day 107 post SNI. Reflex nociceptive responses to mechanical stimulation were measured in a von Frey assay 30 min after each injection.

The effect of administration of CDK inhibitors to SNI mice on the development of mechanical allodynia was analyzed in a von Frey assay, as described below.

3. Behavioral Testing of SNI Mice after Administration of CDK-inhibiting Compounds (von Frey Assay)

Mice that underwent SNI and subsequent administration of the compounds of the present invention were tested for signs of mechanical allodynia post nerve injury and post administration in a von Frey assay (Decosterd and Woolf, Pain 2000; 87:149-158). This assay determines the mechanical threshold upon which a stimulus, which normally is not painful, is recognized by an animal as uncomfortable or painful. SNI ipsi and SNI contra baselines, respectively, were established.

Mechanical thresholds of SNI mice were quantified using the up-down method based on Chaplan et al. (1994) and Malmberg and Basbaum (1998).

Mice were placed in plexiglass cylinders of about 9.5 cm in diameter, 14 cm high with four vent holes toward the top and a plexiglass lid. The cylinders were placed on an elevated mesh surface (7×7 mm squares). Prior to the day of testing, the mice were acclimated to the testing cylinders for 1-2 hours. On the day of testing the mice were acclimated to the cylinders for about an hour, wherein the acclimation time depends on factors such as the strain of the mouse and the number of times they have been tested previously. In general, testing may begin once the mice are calm and stop exploring the new environment.

For testing mice, filaments 2.44, 2.83, 3.22, 3.61, 3.84, 4.08, and 4.31 (force range=0.04 to 2.0 g) were used. The 3.61 mN filament was applied first. Said filament was gently applied to the plantar surface of one paw, allowed to bend, and held in position for 2-4 seconds. Whenever a positive response to the stimulus (flexion reaction) occurred the next weaker von Frey hair was applied; whenever a negative response (no reaction) occurred the next stronger force was applied. The test was continued until the response to 4 more stimuli after the first change in response had been obtained. The highest force tested was 4.31. The cut-off threshold was 2 g.

The series of scores (i.e, "flexion reaction" and "no reaction") and the force of the last filament applied were used to determine the mechanical threshold as described in Chaplan et al., Journal of Neuroscience Methods. 53(1):55-63, 1994 Jul. The threshold determined is that to which the animal would be expected to respond to 50% of the time. Mice were sacrificed after von Frey measurements were accomplished.

4. Effects of Administration of Compound # 43 on the Development of Neuropathic Pain Compound # 43 was administered to SNI mice as described above. Von Frey measurements were performed as described above. Compound # 43 had a hypoalgesic effect on SNI mice. The results of administration of compound # 43 on SNI mice are shown in FIG. 5.

Figure 5:
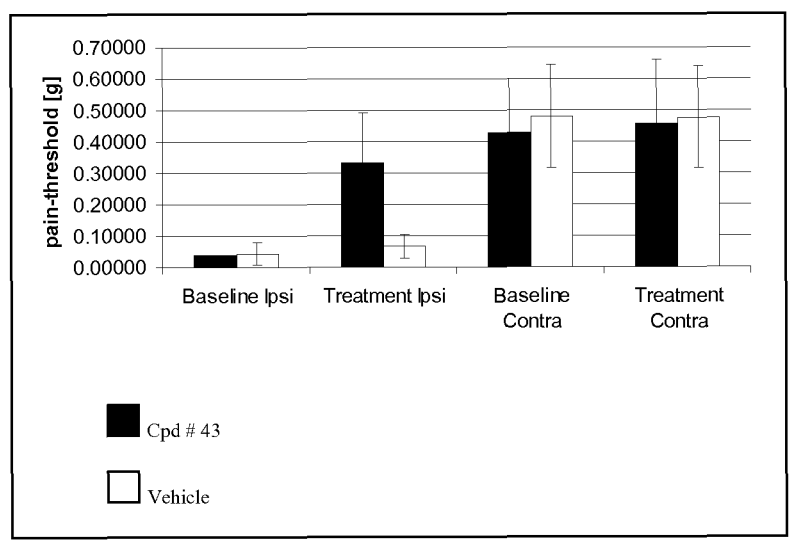
FIG. 5 shows reduced tactile allodynia in SNI mice after administration of CDK inhibiting compounds.

FIG. 5 depicts the results of von Frey measurements performed with SNI mice. Von Frey measurements were performed at ipsi-lateral and contra-lateral paws of the animals at day 107 after surgery. "Baseline" represents behavioral measurements without pharmacological treatment after SNI surgery. These measurements show a stable allodynia even at day 107 after SNI surgery. "Treatment" depicts groups that received per os treatment with 30 mg/kg compound # 43 or vehicle, respectively, at day 107.

In the "baseline" measurements animals from both treatment groups display high allodynia (=low threshold) in response to a mechanical stimulus. At day 107, however, per os treatment with 30 mg/kg compound # 43, applied 30 minutes prior to measurements did show an amelioration of allodynia. Animals treated with compound # 43-treated displayed a significant increase of threshold values indicating reduced sensitivity to mechanical stimuli (reduced allodynia). In comparison, animals treated with vehicle per os alone displayed low thresholds indicating high allodynia.

These findings signify that compound # 43 is effective as a hypoalgesic drug in models of chronic neuropathic pain.

Example 74

Formalin Assay—Model of Inflammatory Processes/Inflammatory and Chronic Neuropathic Pain The formalin assay in mice is a valid and reliable behavioral model of nociception and is sensitive to various classes of analgesic drugs (Hunskaar S, Hole K, Pain. 1987 July; 30(1):103-14.) The noxious stimulus is an injection of 10 µl diluted formalin (2% in saline) subcutaneous or intraplantar into the left hind paw. The response is licking and flinching of the injected paw. The response shows two phases, which reflect different parts of the inflammatory process (Abbott et al 1995), an early/acute phase 0-5 min post-injection, and a late/chronic phase 5-30 min post-injection. The following protocol describes one possible way to conduct the experiment:

1. Injection of Formalin and Administration of CDK-inhibiting Compound

Age, sex and weight matched wildtype mice (C3HeB/FeJ) are used in this assay. Prior to formalin injection the animals are randomly subdivided into experimental groups of 10 animals each. Thirty minutes prior to formalin injection, a suitable dose of a CDK inhibitor dissolved in (400 µl) of 2% Hydroxprolylcellulose; 0.25% Lactic Acid (85° A) solution)) can be administered by i.p. injection. Similarly, Iκ Kinase (IKK) inhibitor (30 mg/kg) in (400 µl) of 2% Hydroxprolylcellulose; 0.25% Lactic Acid (85% solution) (positive control), or vehicle alone ((400 µl) of 2% Hydroxprolylcellulose; 0.25% Lactic Acid (85% solution)) (negative control) can be administered by i.p. injection 30 min before formalin injection.

For formalin injection the mouse is held with a paper towel, in order to avoid disturbance of the injection by movements. The injected hind paw is held between thumb and forefinger and 10 µl of Formalin (2%) is injected subcutaneously (s.c.) between the two front tori into the plantar hind paw using a Hamilton syringe. The behavior of the formalin- and inhibitor-treated mice is analyzed as described below.

2. Behavioral Analysis of Mice after Injection of Formalin and Administration of CDK-inhibiting Compound The behaviour of the formalin-treated mice, i.e. licking and flinching, is monitored by an automated tracking system (Ethovision 3.0 Color Pro, Noldus, Wageningen, Netherlands) over a defined period of time: measurement is initiated 5 min after formalin injection and terminated 30 min after formalin injection. This time frame covers phase II of formalin-induced nociception (pain), which is hyperalgesia.

Two different fluorescent dyes are used for topically marking the injected hind paw (yellow dye) (Lumogenyellow; BASF Pigment, Cologne, Germany) and the contralateral paw (blue dye) (Lumogenviolet; Kremer Pigmente, Aichstetten, Germany) respectively. To determine licking behaviour, mice are monitored with a CCD camera. After monitoring and recording, the video is analyzed using the EthoVision software (Ethovision 3.0 Color Pro, Noldus, Wageningen, Netherlands) or by manual analysis. Fluorescent dot sizes and fluorescence intensities were measured and reduction of fluorescent dot size through licking and biting was calculated. The overall licking time intensity was automatically calculated by comparison of dot size reduction of treated versus untreated paws.

As another variant of assay read out the licking behaviour of the individual animals was tracked manually based on video files. Licking times were recorded over 30 minutes after formalin injection and subdivided for three different licking zones (dorsum, plantar, toes). Overall licking times can be calculated for each animal as well as each experimental group and be used as a parameter for determination of compound efficacy.

As a result it was found that mice receiving vehicle treatment prior to formalin injection (negative control) displayed a prolonged licking time and a significant reduction of fluorescent dot size at the formalin-treated paw.

Figure 2:
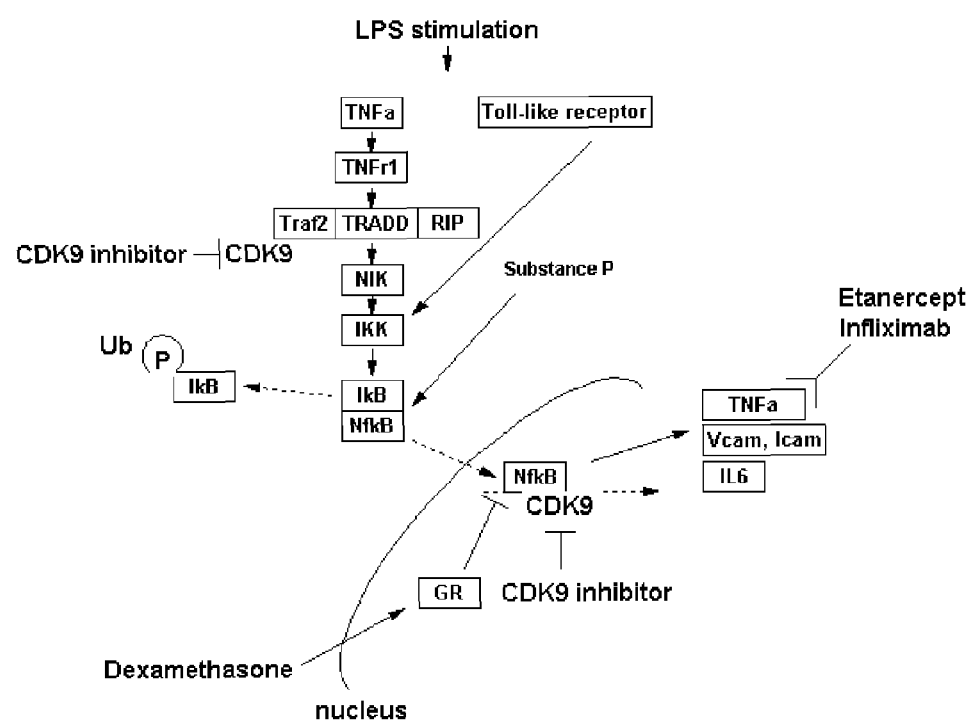
FIG. 2 schematically depicts a possible role of CDK9 as a target in the development of pain.

In contrast, a reduction in licking time and in consequence no significant reduction of fluorescent dot size of the formalin-treated paw could be observed in test compound/formalin-treated mice. The same effect, i.e. a reduction in licking time and a minor change in fluorescent dot size, was observed in control mice treated with Ikappa kinase inhibitor (IKK; for function of IKK see FIG. 2, positive control).

This observation is indicative for reduced inflammatory/chronic inflammatory pain perception in CDK9 inhibitor-treated mice and for a hypoalgesic effect of the tested compound.

Example 75

Carrageenan Assay in Mice—Model of Inflammation and Inflammatory Pain

The model of carrageenan induced paw edema is a standard laboratory assay used to predict anti-inflammatory activity and reduction of inflammation-induced pain perception of respective compounds. The following protocol describes one possible way to conduct the experiment.

The basic measurement constitutes in the measurement of edema and mechanical as well as thermal hypersensitivity in response to irritants, such as carrageenan.

Inflammation and resulting inflammatory pain is induced by subcutaneous injection of 25 µl of 1% carrageenan (in saline) into mice hind paw (ipsi-lateral paw). Each group of 10 mice receives administration of a compound according to general formulae (I) to (III)(including formula (IIIa)), 30 mg/kg body weight, vehicle ((400 µl) of 2 Hydroxprolylcellulose; 0.25% Lactic Acid (85% solution)) and saline (physiol. NaCl) by i.p. injection 30 min prior to carrageenan injection. Contra-lateral paws do not receive carrageenan injection.

1.1 Effects of Administration of a CDK-inhibiting Compound on Carrageenan-Treated Mice Paw edema induced by carrageenan injection are detected by increased paw size measured from dorsal to plantar at the metatarsus region of the injected (ipsi-lateral) paws. Sizes of ipsi- and contra-lateral paws serve as surrogate markers for inflammation and are measured at several time points after carrageenan injection: before injection (−1), 2 h (2), 3 h (3) 4 h (4), 5 h (5), 6 h (6), 24 h (24) after injection.

The paw size of all mice may increase, e.g., by 2 to 3 mm (+10%) within the first hour after carrageenan injection, independent of the type of treatment substance injected 30 minutes prior to carrageenan. During the time course, mice which received treatment with a CDK-inhibiting compound prior to carrageenan injection may display a reduction of the edema until 24 h after carrageenan injection: the increase in paw size could drop e.g. from 10% down to 8%. In contrast, the paw size of the control mice could increase by 30% in average at this time point. After 24 h post carrageenan injection, the size of all paws treated with carrageenan may increase to reach its maximum at 96 h after injection.

As a read-out of the carrageenan assay, a Hargreaves Assay may be performed, wherein said assay allows the measuring of thermal sensitivity to radiant heat. The Hargreaves assay (Hargreaves et al., 1988) measures nociceptive sensitivity in a freely moving animal by focusing a radiant heat source on the plantar surface of an animal's hindpaw as it stands in a plexiglass chamber. Specifically, the lower side of a paw is exposed to a luminous source, generating a temperature of, e.g. 55° C. Thermal sensitivity is measured as latency between start of exposure and lifting/pulling the exposed paw.

Mice treated with a CDK9 inhibitor as disclosed herein and carrageenan, or with Naproxen and carrageenan, or with solvent and carrageenan, respectively, are subjected to a Hargreaves assay. Mice treated with a CDK inhibitor and carrageenan could display a longer latency, compared to negative control mice. This observation would be indicative for a hypoalgesic effect of the CDK inhibitors as disclosed herein.

Example 76

Carrageenan Assay in Rats—Model of Inflammation and Inflammatory Pain

The following depicts one possible way of performing the carrageenan assay in rats.

Said assay detects analgesic/anti-inflammatory activity in rats with inflammatory pain, following the protocol as described by Winter et al (Proc. Soc. Exp. Biol. Med., 111, 544-547, 1962).

Rats (200-250 g) are injected with a suspension of carrageenan into the lower surface of the right hindpaw (0.75 mg per paw in 0.05 ml physiological saline). Two hours later rats are submitted consecutively to tactile and thermal stimulation of both hindpaws.

For tactile stimulation, the animal is placed under an inverted acrylic plastic box (18×11.5×13 cm) on a grid floor. The tip of an electronic Von Frey probe (Bioseb, Model 1610) is then applied with increasing force first to the non-inflamed and then the inflamed hindpaw and the force required to induce paw-withdrawal is automatically recorded. This procedure is carried out 3 times and the mean force per paw is calculated.

For thermal stimulation, the apparatus (Ugo Basile, Reference: 7371) consists of individual acrylic plastic boxes (17×11×13 cm) placed upon an elevated glass floor. A rat is placed in the box and left free to habituate for 10 minutes. A mobile infrared radiant source (96±10 mW/cm$^2$) is then focused first under the non-inflamed and then the inflamed hindpaw and the paw-withdrawal latency is automatically recorded. In order to prevent tissue damage the heat source is automatically turned off after 45 seconds.

After the behavioral measures, the paw edema is evaluated by measuring the volume of each hindpaw using a digital plethysmometer (Letica, Model 7500), which indicates water displacement (in ml) induced by paw immersion.

10 rats are studied per group. The test is performed blind.

The test substance, such as a CDK inhibitor according to any one of Formulae (I) to (III) (including formula (IIIa)) as presented herein, will be evaluated at 2 doses (10 and 30 mg/kg), administered p.o. 60 minutes before the test, and compared with a vehicle control group.

Morphine (128 mg/kg p.o.) and acetylsalicylic acid (512 mg/kg p.o.), administered under the same experimental conditions, will be used as reference substances.

The experiment will therefore include 6 groups. Data will be analyzed by comparing treated groups with vehicle control using unpaired Student's t tests.

Rats treated with a CDK9 inhibitor as disclosed herein and carrageenan, or with Naproxen and carrageenan, or with solvent and carrageenan, respectively, are subjected to a Hargreaves assay. Rats treated with a CDK inhibitor and carrageenan should display a longer latency, compared to negative control rats. This observation would be indicative for a hypoalgesic effect of the CDK inhibitors as disclosed herein.

Example 77

A. LPS In Vivo Assay (LPS)—Model of Cytokine Repression In Vivo

For the LPS induced model of septic shock, mice receive an intraperitoneal (i.p.) injection of 30 µg bacterial Lipopolysaccharide (LPS; L2630 SIGMA) in saline. Said LPS-mediated initiation of the inflammatory signalling cascade results in increasing blood serum concentrations of cytokines such as e.g. TNFα, IL-6 and IL1β. Blood can be taken from these animals at defined time points. Thereafter, serum will be separated and the samples can be stored at −80° C. until cytokine concentrations are measured using commercial ELISA assays. (AL Moreira et al., Braz J Med Biol Res 1997; 30:1199-1207).

It has been recognized that inflammatory mediators such as the cytokines TNFα, IL6 and IL1β can contribute to persistent pain states as well as inflammatory disorders. After being released from immune cells like macrophages in peripheral and microglia in CNS tissues, these mediators seem to play a pivotal role not only in inflammatory and neuropathic pain but also in inflammatory disorders such as rheumatoid arthritis (F Marchand et al., Nat Rev Neurosci 2005; 6 (7); 521-532). Thus, inhibition of tumor necrosis factor α (TNFα) represents a relevant target for the treatment of inflammatory diseases as well [Lavagno et al., Eur J Pharmacol 2004; 501, 199-208].

The LPS in vivo assay can be used as a powerful model to address repression of cytokine expression by pharmacological treatments.

1. Induction of Cytokine Expression in Wildtype Mice

Wildtype mice (strain C3HeB/FeJ) (age, sex and weight matched) were injected with 30 µg LPS (SIGMA) intraperitoneally. 90 minutes after LPS administration these animals were anaesthetized with 0.1 ml/10 g bodyweight Ketamine-Rompun (50/20 mg/ml) and blood for serum preparation was taken via cardiac puncture.

2. Administration of CDK-inhibiting Compounds to LPS Mice

Pharmacological treatment groups (n=4) of LPS mice received per os (p.o.) injections of CDK-inhibiting compounds or the vehicle (negative control), respectively. In particular, compounds 1, 5, 10, and 84 were administered.

10 or 30 mg/kg (compound per bodyweight) of a CDK inhibitor, dissolved in 20% DMSO, 5% Tween 80, 10% Tris 1M pH8, 20% PEG400, 45% PBS was administered as a single p.o. dosage 30 min prior to LPS stimulation. Vehicle control was administered in the same manner.

90 minutes (min) after LPS stimulation, blood samples were taken from the mice. Previously, the 90 min time point had been identified as the peak of TNF alpha expression in this animal model by a time course experiment.

The effect of pharmacological treatment with CDK inhibitors on cytokine levels in LPS mice was analyzed in commercial ELISA assays as described below.

3. Determination of Cytokine Blood Serum Concentrations in LPS Mice after Administration of CDK-inhibiting Compounds Blood samples (~500 µl/animal) from the LPS animals were incubated on wet ice for 30 min after cardiac puncture. Afterwards the samples were centrifuged for 15 min at 13.000 rpm. Serum was separated from the clot and stored frozen at −80° C.

Serum concentrations of TNF alpha and IL6 within the samples were measured by using commercial ELISA Kits (Natutec) according to the manufacturers instructions.

Figure 3:
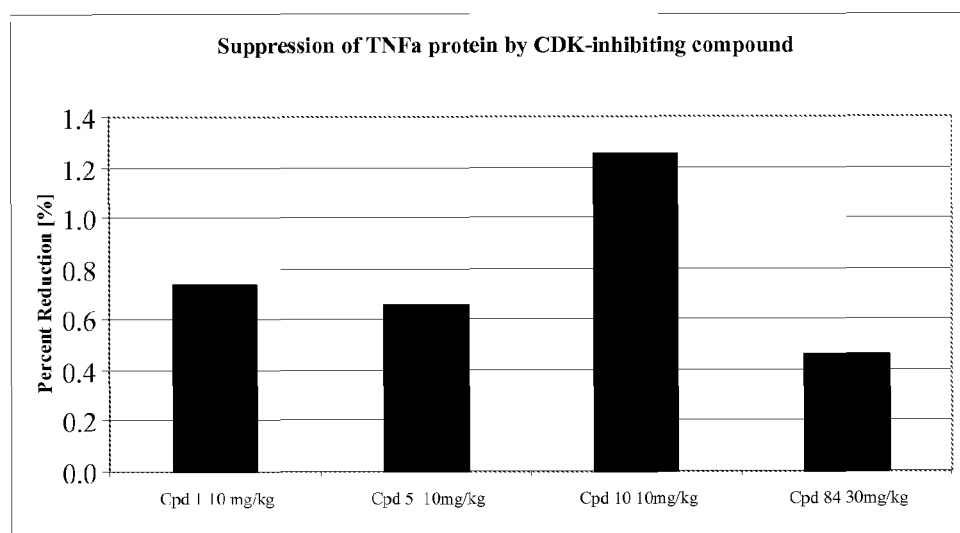
FIG. 3 depicts protein expression of TNFα displayed as % inhibition in LPS-mice after treatment with CDK-inhibiting compounds compared to vehicle treated mice

4. Effects of Administration of Compounds 1, 5, 10, and 84 on the Protein Expression of Cytokines Compounds 1, 5, 10, and 84 were administered to LPS mice as described above. ELISA based determinations of cytokine serum concentrations were performed as described above. Comparison of compounds 1, 5, 10, and 84 treated versus vehicle treated control animals displayed a significant repressive effect on TNFα and IL6 protein concentration in the blood serum. The results of administration of compounds 1, 5, 10, and 84 on LPS induced mice are shown in FIG. 3, which depicts the results of cytokine measurements (TNFalpha) performed with LPS induced mice.

These findings indicate that compounds 1, 5, and 84 are effective suppressive drugs of cytokines TNF alpha and IL6 in models of cytokine expression.

Example 78

A. In Vitro THP-1 Assay—In Vitro Model of Cytokine Inhibition

The human THP-1 cell line can be utilized as an in vitro model of cytokine expression as mediated by Lipopolysaccharide (LPS) or Tumor Necrosis Factorα [TNFα].

Monocytic THP-1 cells (ATCC; TIB-202) can be differentiated into macrophage-like cells expressing pro-inflammatory cytokines like TNFα, IL6 and IL1β upon induction with LPS or by TNFα (autocrine induction) itself.

It has been recognized that inflammatory mediators such as the cytokines TNFα, IL6 and IL1β can contribute to persistent pain states as well as to inflammatory disorders. After being released from immune cells like macrophages in peripheral and microglia in CNS tissues, these mediators seem to play a pivotal role not only in inflammatory and neuropathic pain but also in inflammatory disorders such as rheumatoid arthritis (F Marchand et al., Nat Rev Neurosci 2005; 6 (7); 521-532). Hence inhibition of tumor necrosis factor α (TNFα) represents a relevant target in the treatment of inflammatory disorders as well [Lavagno et al., Eur J Pharmacol 2004; 501, 199-208].

Therefore, the THP-1 in vitro assay can be used as a powerful screening model to address pharmacological inhibition of cytokine expression (U Singh et al, Clin Chem 2005; 51 (12); 2252-6], K Rutault et al., J Biol Chem 2001; 276 (9); 6666-74].

1. Growth and Differentiation of THP-1 Cells

THP-1 cells are grown in modified RPMI-1640 medium (ATCC, Cat. No. 30-2001) supplemented with 10% FCS and 1% Pen/Strep. For cytokine inhibition assays, cells are seeded at a density of $5 \times 10^5$ cells/ml into 6-well plates in standard growth medium supplemented with 100 ng/ml PMA (Sigma, P1585) to induce differentiation into macrophage-like cells. After 24 hours, the medium is replaced with standard growth medium (without PMA) and the cells are incubated for another 48 hours to complete differentiation.

2. Treatment of Differentiated THP-1 Cells with CDK-inhibiting Compounds and LPS Stimulation After 72 h of differentiation, the medium is replaced with serum free growth medium, and CDK-inhibiting compounds as well as reference compounds such as positive and negative controls, each dissolved in DMSO are added at concentrations ranging from 0.5 to 5 µM (final concentration of DMSO in the well is 0.1%). Cells are incubated for 60 min with compounds prior to stimulation with 100 ng/ml LPS (Sigma, L2630) for another 4-48 hours. Supernatants are collected and assayed immediately for cytokine expression, e.g. for TNFα, IL-6 and IL-1b using commercially available sandwich ELISA assays (eBioscience, Cat. No 88-7346, 88-7066, 88-7010) or kept frozen at 20° C. until evaluation.

3. Determination of Cytokine Concentrations in THP-1 Supernatant after Administration of CDK-inhibiting Compounds Concentrations of TNFα, IL6 and IL1β within the cell culture supernatants are measured by using commercial ELISA Kits (eBioscience) according to the manufacturer's instructions.

4. Effects of Treatment with CDK-inhibiting Compounds on the Protein Expression of Cytokines in THP-1 Cell Supernatants CDK-inhibitory compounds # 1, 2, 3, 5, 16, 18, 19 and 32 were administered to differentiated THP-1 cells in triplicates as described above (see section 2.). After 60 min of pre-incubation with test or reference compound (SB203580, a p38 inhibitor and BMS345541, an IKK-inhibitor) alone, cells were stimulated with LPS. After incubation for 4-48 h, supernatants were collected and ELISA based determinations of cytokine supernatant concentrations were performed as described in section 3, supra.

Comparison of cells treated with compounds # 1, 2, 3, 5, 16, 18, 19, 32 and reference compounds versus cells treated with vehicle (DMSO) displayed a significant inhibitory effect of compound # 1, 3, 16, 18, 19 and 32 on TNFα, and IL6 protein concentration in the cell supernatant. Compared to reference compounds SB203580 or BMS3455541, these compounds exhibited a similar or better inhibition of TNFα/Il-6 expression.

Figure 4A:
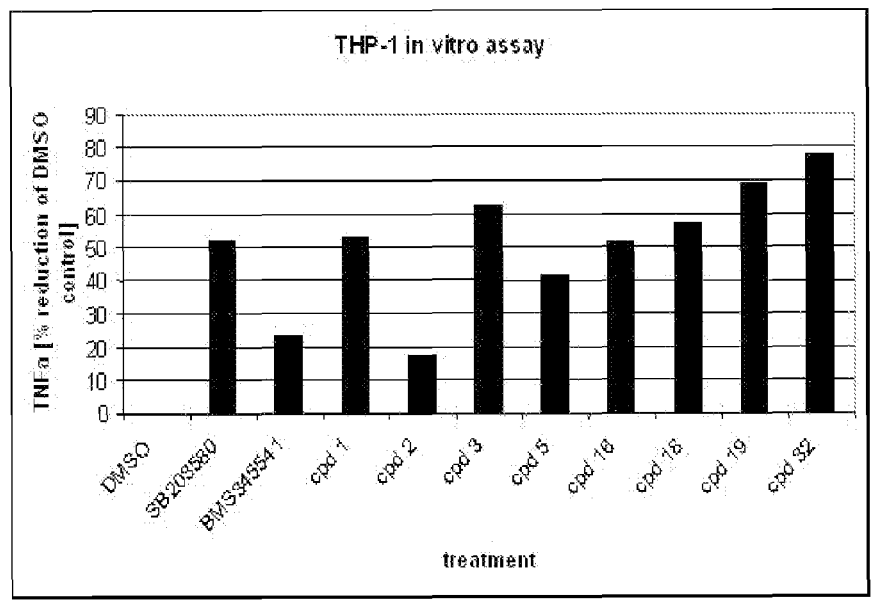
FIG. 4A depicts the results of cytokine measurements performed with LPS-induced THP-1 macrophages. TNFα expression displayed as % inhibition compared to the DMSO control. Cells treated with compounds 1, 3, 16, 18, 19 or 32 show a significant inhibition of TNFα expression in the supernatant compared to the vehicle (DMSO). Compared to reference compounds SB203580 (p38-inhibitor) and BMS345541 (IKK-inhibitor) these compounds exhibit a similar or better inhibition of TNFα expression in this assay.
Figure 4B:
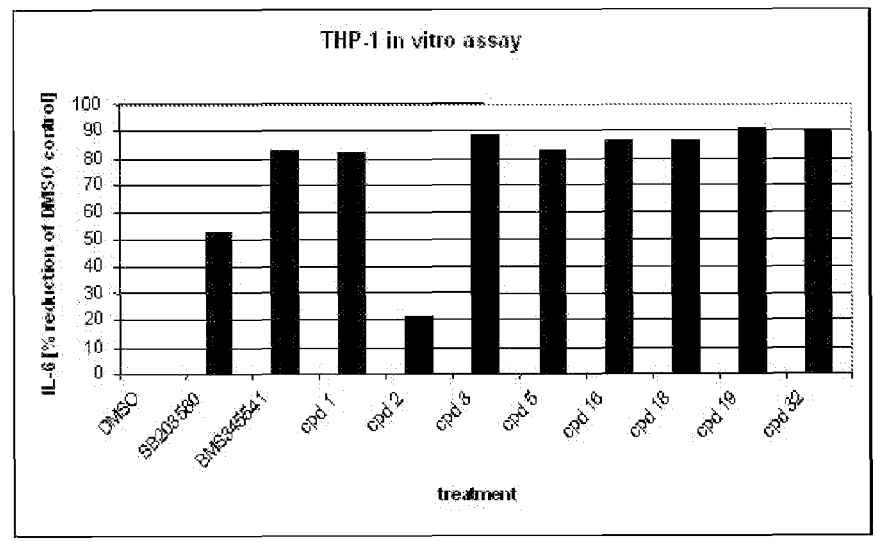
FIG. 4B shows IL6 expression displayed as % inhibition compared to the DMSO control. Cells treated with compounds 1, 3, 5, 16, 18, 19 or 32 show a significant inhibition of IL6 expression in the supernatant compared to the vehicle (DMSO). Compared to reference compounds SB203580 or BMS345541 these compounds exhibit a similar or better inhibition of IL6 expression in this assay.

The effects of administration of compounds # 1, 2, 3, 5, 16, 18, 19 and 32 on expression of TNFα and IL-6 in LPS induced THP-1 macrophages are shown in FIGS. 4A and 4B. FIG. 4A shows the results of TNFα-measurements in LPS-induced THP-1 macrophages, while FIG. 4B shows the results of IL-6 measurements in LPS-induced THP-1 macrophages.

These findings indicate that CDK-inhibitory compounds # 1, 3, 5, 16, 18, 19 and 32 are effective suppressors of expression of cytokines TNFα and IL-6.

Example 79

A. In Vitro Kinase Inhibition Assays

IC50 profiles of compounds 1-84 were determined for cyclin-dependent kinases CDK2/CycA, CDK4/CycD1, CDK5/p35NCK, CDK6/CycD1 and CDK9/CycT in enzymatic kinase inhibition assays in vitro. IC50 values as obtained in these assays were used for evaluating the specific selectivity and potency of the compounds with respect to CDK9 inhibition.

Results obtained in these assays were used to select compounds displaying specificity for CDK9. Specifically, it was intended to distinguish the CDK9-specific compounds from other compounds having significant inhibitory potency also with regard to other CDKs, i.e. on some or all of CDKs 2, 4, 5, and 6. This separation is essential in order to avoid adverse (cytostatic/cytotoxic) effects, which may occur upon inhibition of cell cycle relevant CDKs 2, 4, 5, and 6.

Furthermore, these data were used to establish structure activity relationships (SAR) supporting the design of new and even improved structures/compounds with respect to potency and selectivity.

1. Test Compounds

Compounds were used as $1\times10^{-02}$ M stock solutions in 100% DMSO, 100 µl each in column 2 of three 96-well V-shaped microtiterplates (in the following, said plates are referred to as "master plates").

Subsequently, the $1\times10^{-02}$ M stock solutions in column 2 of the master plates were subjected to a serial, semi-logarithmic dilution using 100% DMSO as a solvent, resulting in 10 different concentrations, the dilution endpoint being $3\times10^{-07}$ M/100% DMSO in column 12. Column 1 and 7 were filled with 100% DMSO as controls. Subsequently, 2×5 µl of each well of the serial diluted copy plates were aliquoted in 2 identical sets of "compound dilution plates", using a 96-channel pipettor.

On the day of the kinase inhibition assay, 45 µl H$_2$O were added to each well of a set of compound dilution plates. To minimize precipitation, the H$_2$O was added to the plates only a few minutes before the transfer of the compound solutions into the assay plates. The plates were shaken thoroughly, resulting in "compound dilution plates/10% DMSO" with a concentration of $1\times10^{-03}$ M/10% DMSO to $3\times10^{-08}$ M/10% DMSO in semilog steps. These plates were used for the transfer of 5 µl compound solution into the "assay plates". The compound dilution plates were discarded at the end of the working day. For the assays (see below), 5 µl solution from each well of the compound dilution plates were transferred into the assay plates. The final volume of the assay was 50 µl. All compounds were tested at 10 final assay concentrations in the range from $1\times10^{-04}$ M to $3\times10^{-09}$ M. The final DMSO concentration in the reaction mixtures was 1 in all cases.

2. Recombinant Protein Kinases

For the determination of inhibitory profiles, the following 5 protein kinases were used: CDK2/CycA, CDK4/CycD1, CDK5/p35NCK, CDK6/CycD1 and CDK9/CycT. Said protein kinases were expressed in Sf9 insect cells as human recombinant GST-fusion proteins or His-tagged proteins by means of the baculovirus expression system. Kinases were purified by affinity chromatography using either GSH-agarose (Sigma) or Ni-NTH-agarose (Qiagen). The purity of each kinase was determined by SDS-PAGE/silver staining and the identity of each kinase was verified by western blot analysis with kinase specific antibodies or by mass spectroscopy.

3. Protein Kinase Assay

All kinase assays were performed in 96-well FlashPlates™ from Perkin Elmer/NEN (Boston, Mass., USA) in a 50 µl reaction volume. The reaction mixture was pipetted in four steps in the following order:

20 µl of assay buffer (standard buffer)

5 µl of ATP solution (in H$_2$O)

5 µl of test compound (in 10% DMSO)

10 µl of substrate/10 µl of enzyme solution (premixed)

The assay for all enzymes contained 60 mM HEPES-NaOH, pH 7.5, 3 mM MgCl$_2$, 3 mM MnCl$_2$, 3 µM Na-Orthovanadate, 1.2 mM DTT, 50 µg/ml PEG20000, 1 µM [-$^{33}$P]-ATP (approx. 5×1005 cpm per well).

The following amounts of enzyme and substrate were used per well:

| # Kinase | Kinase Lot # | Kinase ng/50 µl | Substrate | Substrate ng/50 µl |
|---|---|---|---|---|
| 1. CDK2/CycA | SP005 | 100 | Histone H1 | 250 |
| 2. CDK4/CycD1 | SP005 | 50 | Rb-CTF (Lot 009) | 500 |
| 3. CDK5/p35NCK | SP001 | 50 | Rb-CTF (Lot 009) | 1000 |
| 3. CDK6/CycD1 | SP003 | 400 | Rb-CTF (Lot 009) | 500 |
| 4. CDK9/CycT | 003 | 100 | Rb-CTF (Lot 009) | 1000 |

Reaction mixtures were incubated at 30° C. for 80 minutes. The reaction was stopped with 50 µl of 2% (v/v) H$_3$PO$_4$, plates were aspirated and washed two times with 200 µl H$_2$O or 200 µl 0.9% (w/v) NaCl. Incorporation of $^{33}$P was determined with a microplate scintillation counter (Microbeta, Wallac).

All assays were performed with a BeckmanCoulter/Sagian robotic system.

4. Evaluation of Raw Data

The median value of the counts in column 1 (n=8) of each assay plate was defined as "low control". This value reflects unspecific binding of radioactivity to the plate in the absence of a protein kinase but in the presence of the substrate. The median value of the counts in column 7 of each assay plate (n=8) was taken as the "high control", i.e. full activity in the absence of any inhibitor. The difference between high and low control was referred to as 100% activity. As part of the data evaluation, the low control value from a particular plate was subtracted from the high control value as well as from all 80 "compound values" of the corresponding plate. The residual activity (in %) for each well of a particular plate was calculated by using the following formula:

Res. Activity (%)=100×[(cpm of compound−low control)/(high control−low control)]

The residual activities for each concentration and the compound IC50 values were calculated using Quattro Workflow V2.0.1.3 (Quattro Research GmbH, Munich, Germany; www.quattro-research.com). The model used was "Sigmoidal response (variable slope)" with parameters "top" fixed at 100% and "bottom" at 0%.

It turns out that the IC50 values of compounds 1-84 are all comprised between 1 nM and 10 µM.

Example 80

A. Cloning and Purification of CDK9 and Cyclin T1:

Both cDNA fragments were cloned by PCR into pDONR201 vectors using the gateway recombination system (Invitrogen) according to the manufacturer's recommendations. The fragments were subcloned into a gateway-adapted shuttle vector (pPM7) for production of recombinant adenovirus. All plasmids were verified by restriction digests and sequencing analysis.

Expression and purification of CDK9/Cyclin T1 proteins was in principle performed as described by Cotten et al. (M. Cotten et al., Nucleic acids research, 2003, 31(28), 128).

Kinase assays using CDK9/Cyclin T1 were performed in principle as described by Cotten et al. (M. Cotten et al., Nucleic acids research, 2003, 31(28), 128).

Results:

CDK9/CyclinT1 complexes from HEK293 cells (ATCC number: CRL-1573) were completely solubilised. CDK9/CyclinT1 proteins were almost completely precipitated by and eluted from streptavidin beads (data not shown). Enrichment was verified from blots stained with PonceauS. CDK9/CyclinT1 proteins can be seen in the eluate whereas they are not visible within the cells or extract. Probing nitrocellulose with antibodies against CDK2 and CDK4 revealed that those kinases do not contaminate the purifications (data not shown).

Increasing amounts of CDK9 wt proteins incubated with substrates (ATP and GST-CTDII) resulted in incorporation of radioactive phosphate. As expected, mutation of critical kinase domain residues (K48R and D167N) within CDK9 revealed no phosphate incorporation, confirming that these mutations render the kinase inactive. Additionally, EDTA pre-incubation completely inhibited activity.

These results show that purification of CDK9/CyclinT1 proteins using adenovirus leads to an active and pure enzyme. A putative contamination with other protein kinases can be ruled out because purification of mutated CDK9 resulted in negligible kinase activity.

B. Kinase Assays:

Kinase assays determining CDK2/CyclinA and CDK5/p35 activity were performed as described by the manufacturer's recommendations (ProQinase (Freiburg, Germany) for CDK2/CyclinA and Upstate for CDK5/p35).

General Kinase Assay:

The inhibitory effect of compounds according to the present invention on the activity of protein kinases can be measured according to the following protocol:

Reaction Volume: 40 µl
Reaction Time: 60 min
Reaction Temperature: room temperature
Assay Plate: 96 well U bottom plate (Greiner, 650161)
MultiScreen-PH Plate: 96 well MAPH Filter Plates (Millipore, MAPHNOB50)
Filter Washing Solution: 0.75% $H_3PO_4$
Scintillation Liquid Supermix Liquid Scintillator (PerkinElmer, 1200-439)
Controls:
Negative Control (C−): 100 mM EDTA (Ethylenediaminetetraacetic acid), no Inhibitor
Positive Control (C+): no Inhibitor
Reaction Buffer:
20 mM Tris (Tris(hydroxymethyl)aminomethane hydrochloride), pH 7.5
10 mM $MgCl_2$
1 mM DTT
Final Assay Concentrations:
Kinase: Use kinase conc. yielding 10% ATP turn over.
ATP: 1 µM
Adenosine 5'-[-$^{33}$P]triphosphate:12.5 µCi/ml (Amersham Biosciences, BF1000)
Substrate: Myelin Basic Protein 10 µM (Invitrogen, 13228-010)

Pipetting Sequence:
1) Add 10 µl 4 fold concentrated Substrate+4 fold concentrated ATP in 3 fold concentrated Reaction Buffer to each well of Assay Plate
2) Add 10 µl 4 fold concentrated inhibitor in 4% DMSO in $H_2O$ to each well except to C− and C+wells
3) Add 10 µl 4% DMSO in $H_2O$ to C− and C+wells
4) Add 10 µl 500 mM EDTA in $H_2O$ to C− wells
5) Add 10 µl 50 µCi/ml Adenosine 5'-[-$^{33}$P]triphosphate in $H_2O$ to each well
6) Add 10 µl 4 fold concentrated kinase in Reaction Buffer to each well
7) Incubate 1 hr at room temperature
8) Add 10 µl 50 mM EDTA in $H_2O$ to each well except to C− wells
9) Prepare MAPH plates by adding 200 µl 0.75% $H_3PO_4$ to each well
10) Exhaust 0.75% $H_3PO_4$ using Millipore vacuum station
11) Add 60 µl 0.75% $H_3PO_4$ to each well of MAPH Filter Plate
12) Transfer 30 µl sample per well from Assay Plate to corresponding well of MAPH Filter Plate
13) Incubate 30 min at room temperature
14) Wash each well of MAPH Filter Plates 3× with 200 µl 0.75% $H_3PO_4$ using Millipore vacuum station.
15) Add 20 µl Scintillation Liquid to each well of MAPH Filter Plate
16) Seal MAPH Filter Plate
17) Store MAPH Filter Plate 30 min in darkness
18) Quantify radioactivity Results:

$IC_{50}$s were calculated for each kinase based on serial dilutions. Table 6 shows the inhibitory effect of selected compounds according to the present invention on the activity of certain protein kinases.

TABLE 6

$IC_{50}$s of selected compounds according to the present invention

|  | CDK1/CycB | CDK2/CycA | CDK4/CycD1 | CDK5/p35 | CDK6/CycD3 | CDK9/CycT1 |
|---|---|---|---|---|---|---|
| Compound 20 | <5 | <2 | n.a. | <5 | n.a. | <0.5 |
| Compound 85 | <10 | <10 | <10 | <5 | <10 | <0.1 |
| Compound 49 | <5 | <2 | <10 | <5 | <10 | <0.1 |
| Compound 86 | <10 | <10 | >10 | <10 | n.a. | <0.5 |

(all data in µM; n.a. = not available).

These data show that compounds according to the present invention, do have an inhibitory effect on the protein kinase activity of various protein kinases, such as CDK1/CycB, CDK2/CycA, CDK4/CycD1, CDK5/p35, CDK6/CycD3 and CDK9/CycT1.

Example 81

Determination of RNA Polymerase II C-terminal Domain Phosphorylation:

The phosphorylation status of RNA polymerase II C-terminal domain is determined by western blot techniques. PM1 cells (obtainable from the National Institute of Allergy and Infectious Diseases; Division of AIDS via the NIH AIDS Research & Reference Reagent Program), are seeded in 6-well plates at a density of about 5×10⁵ per well. After over night incubation cells are treated with compounds of the present invention. Cells are pelleted and lysed with 300 µL 3× Laemmli buffer followed by 30 min denaturing at 65° C. After separation of equal lysate volumes by SDS-PAGE the proteins are transferred to nitrocellulose membranes (Schleicher&Schuell) and probed with anti-SER2 (H5), anti-SER5 (H14) or RNA Poll II-antibodies purchased from Eurogentec and Santa Cruz, respectively. The amount of reactive protein is visualized by ECL detection methods (Amersham).
Results:

In order to see, if the compounds of the present invention do have the intrinsic capacity to penetrate cells and act against cellular target proteins, such as CDK9, the effect of the compounds of the present invention on CDK9-dependent phosphorylation of RNA-polymerase II is investigated. Probing blots with antibodies against the phosphorylated forms of RNA polymerase II show, that specifically serine 2 phosphorylation is decreased, whereas antibodies recognizing serine 5 phosphorylation do not show any differences. These results indicate that kinases being responsible for the phosphorylation of this site, for example CDK7 are not touched. Additionally, a reduction in the molecular weight of RNA polymerase II is observed indicating that phosphorylation is decreased.

Example 82

Growth Assay Using Alamar Blue™:

Cells were seeded in 384-well plates (white, Greiner: 781080) at a density of 30,000-40,000 cells per well in medium (RPMI+10% FCS).

Cells were incubated in 25 µl medium/well and were grown over night at 37° C., 6% $CO_2$. On the following day compounds were added in DMSO in serial fold dilutions in fresh medium. Negative control wells were incubated without cells. Positive control wells were incubated with cells but without inhibitors (DMSO only). These wells served as data points to determine relative growth (given in % of the DMSO control [=100%]). The cell number was determined by addition of 5 µL Alamar Blue™ (Biosource DAL1100) to each well. Fluorescence was measures with an Analyst GT machine (Molecular Devices) at an excitation wavelength of 560 nm and an emission wavelength of 590 nm.

The following cell lines were used: A2780 (ECACC order number 93112519; human ovarian carcinoma; Semin Oncol (1984) 11:285; Cancer Res (1987) 47:414), B16F1 (ATCC order number CRL-6323; melanoma; Nat. New Biol. 242: 148-149, 1973); HCT116 (ATCC order number CCL-247; Colorectal carcinoma; Cancer Res (1981) 41:1751; Cancer (1995) 76:201), HT29 (ATTC order number HTB-38; colorectal adenocarcinoma; J. Biol. Chem. 271: 9490-9496, 1996) HepG2 (ATCC order number HB-8065; hepatocellular carcinoma; J. Biol. Chem. 271: 10073-10078, 1996), J774 (ATCC order number TIB-67; reticulum cell sarcoma; J. Biol. Chem. 271: 18431-18436, 1996); MCF7 (ATCC order number HTB-22; Breast carcinoma; J Natl Cancer Inst (1973) 51:1409; Cancer Res (1993) 53:5193), PM1 (obtainable from the National Institute of Allergy and Infectious Diseases; Division of AIDS via the NIH AIDS Research & Reference Reagent Program; Lusso P et al (1995), J Virol 69: 3712-3720) and U373-MAGI-CCR5 (obtainable from the National Institute of Allergy and Infectious Diseases; Division of AIDS via the NIH AIDS Research & Reference Reagent Program; Kensinger R D et al (2004), Antimicrob Agents Chemother 48: 1614-1623).

Results:

$IC_{50}$s were calculated for each cell line based on serial dilutions. Table 7 shows the $IC_{50}$s of selected compounds according to the present invention against various cell lines.

TABLE 7

$IC_{50}$s of selected compounds according to the present invention against various cell lines (all data in µM; n.a. = not available).

| Cell line | Compound 20 | Compound 85 | Compound 49 | Compound 86 |
|---|---|---|---|---|
| A2780 |  | <10 |  |  |
| B16F1 |  | <10 |  |  |
| HCT116 | <5 | <2 | <2 | <5 |
| HT29 |  | <5 |  |  |
| HepG2 |  | <10 | >10 |  |
| J774 |  | <10 |  |  |
| MCF7 |  | <10 |  |  |
| PM1 |  | <5 | <5 |  |
| U373-MAGI-CCR5E |  | <10 | <10 |  |

These data show, that compounds according to the present invention exhibit growth inhibitory activity against all cell lines tested.

Example 83

HIV Replication Assay:

PM1 cells are seeded in 12-well plates at a density of about 1.5×10⁵ per well with RPMI 1640 containing 10% FCS, 1% L-Glutamine and 1% Na-Pyruvate (Sigma). Cells were previously infected with HIV-1 BaL for 3 h at a concentration of about 5×10⁸ µg p24/cell. After addition of the compounds of the present invention cells are incubated for 6 to 10 days. During this incubation the cells are passaged and compound-containing medium is renewed. The concentration of p24 in the cellular supernatants is determined at each of this time points using a previously described ELISA assay (Bevec et al., Proceedings of the National Academy of Sciences U.S.A. 1992, 89(20), 9870-9874).
Results:

The growth of PM1 cells is not generally affected by compounds of the present invention. No correlation between CDK9 inhibition and toxicity is observed.

Compounds of the present invention are potent inhibitors of HIV replication.

Example 84

NFκB-dependent Transcriptional Activity:

The used NIH 3T3 75E11/300D8 cell line is described elsewhere (J. Eickhoff et al., Journal of Biological Chemistry, 2004, 279(10), 9642-9652).
Results:

It is known, that CDK9 regulates NF B-dependent transcriptional activity. The compounds of the present invention are able to affect TNF-stimulated NF B-dependent promoter activity. Under non-stimulated conditions no inhibition is observed.

Example 85

HBV-replication:

To test the anti-HBV-activity of compounds of the present invention the HBV-producing cell line HepG2-2.2.15 (M. A. Sells, PNAS 1987, 84, 1005-1009) is used. About 1.0×10⁴ cells are seeded in 96-well microtiter plates in DMEM medium supplemented with 10% FCS. After incubation at 37° C. in 5% $CO_2$ atmosphere for 24 hours the medium is replaced with fresh medium containing the appropriately diluted compounds of the present invention. 3 days later medium is replaced by freshly prepared compound-containing medium and the cells are incubated for further 3 days. Subsequently 200 µl lysis buffer (50 mM Tris-Cl 7.5; 1 mM EDTA 8.0; 0.5% NP40) per well is added. To remove cell debris and nucleic acids, lysate is centrifuged (15000 rpm, 10 min, 4° C.).

Cellular and viral RNA is removed by addition of 2 µl of RNase. 100 µl of the samples are spotted onto an uncharged nylon membrane pre-wetted with PBS (phosphate-buffered saline) using a 96 well-blotting chamber (MINIfold Dot-Blot, Schleicher&Schüll). After further washing with 200 µl PBS per well the membrane is treated twice with 0.5M NaOH, 1.5M NaCl (2 min) and 4 times with 0.5M Tris 7.5, 3M NaCl (1 min). The nucleic acids are fixed by UV-treatment and is used for hybridisation with a radioactive HBV-fragment prepared from the overlength HBV genome plasmid pT-HBV1.3 (L. G. Guidotti et al., Journal of Virology 1995, 69(10), 6158-6169).

The fixed membrane is pre-hybridized in a standard hybridisation buffer (50% formamide, 5×SSPE, 10×Denhards, 1% SDS, 100 µg/ml salmon sperm DNA) for at least 3 hours at 42° C. and hybridised overnight against the labelled HBV-fragment. The preparation of the HBV-fragment with the "Random primers DNA labelling system" (Invitrogen) is done according to the manufacturer's instructions. Hybridized filter are washed at room temperature with 2×SSC, at 62° C. with 2×SSC, 0.5% SDS and at 62° C. with 0.5×SSC, 0.5% SDS. Each washing step is carried out twice. The intensity of the HBV-DNA is quantified using a phosphoimager (Fuji). To test the cell viability 0.5×10$^4$ HepG2-2.2.15-cells are seeded in 96-well-microtiter plates in DMEM medium supplemented with 10% fetal bovine serum. After incubation at 37° C. for 24 hours the medium is replaced by fresh compound-containing medium. 3 days later medium is replaced again by freshly prepared medium containing the compounds of the present invention and the cells are incubated for further 3 days at 37° C. After the incubation period 1/10 volume of Alamar Blue (Serotec) solution containing a growth dependant indicator is added and the cells are incubated for 3 h at 37° C. Absorbance is monitored at 570 nm and 600 nm wavelength.

Results:
Compounds according to the present invention are tested in a HBV replication assay. Some compounds of the present invention inhibit HBV replication without affecting viability in those cells. Some compounds of the present invention are inactive in those assays indicating that other protein kinase targets than CDK9 (especially further CDKs) might be important for HBV replication. This is underlined by flavopiridol, which inhibits replication, but is known to be a more or less unspecific inhibitor of CDKs.

Example 86

HCMV Replication:
Human foreskin fibroblasts (HFF) cell culture is grown in DMEM containing 10% FCS. For HCMV-replication assays, HFF cells are infected with HCMV strain AD169 producing EGFP (HCMV AD169-GFP; 27). 1 h post infection, medium is changed with medium containing compounds of the present invention. After incubation of 7 days cells are lysed (in 25 mM Tris, pH 7.5, 2 mM DTT, 1% Triton X-100 and 10% glycerol) and analysed for EGFP content in a Wallac Victor fluorescence detector.

Results:
Compounds of the present invention are identified as potent inhibitors of HCMV replication in cell culture: some compounds according to the present invention show inhibition of HCMV replication (using strain AD 169 in HFF cells).

Example 87

HCV Replicon Assay:
Compounds of the present invention are tested for activity in the HCV replicon system described by Bartenschlager and coworkers (Lohmann et al, Replication of subgenomic hepatitis C virus RNAs in a hepatoma cell line. Science 285, 110, 1999).

References

Barboric M. et al., NfkB Binds P-TEFb to Stimulate Transcriptional Elongation by RNA Polymerase II. Molecular Cell, 2001, Vol. 8, 327-337

Besson J. M., The neurobiology of pain. Lancet, 1999, 353 (9164), 1610-1615

Brower, New paths to pain relief. Nat Biotechnol, 2000, 18(4), 387-391

Chao S. H. and Price D. H., Flavopiridol inactivates P-TEFb and blocks most RNA polymerase II transcription in vivo. J Biol Chem, 2001, 276(34), 31793-9

Chaplan S R, Bach F W, Pogrel J W, Chung J M, and Yaksh, T L. (1994) Quantitative assessment of tactile allodynia in the rat paw. J Neurosci Methods 53: 55-63.

Dai Y. and Grant S., Cyclin-dependent kinase inhibitors. Curr Opin Pharmacol, 2003, 3(4), 362-370

Falco G. D. et al., CDK9, a member of the cdc2-like family of kinases, binds to gp130, the receptor of the IL-6 family of cytokines. Oncogene, 2002, 21(49), 7464-7470

Feldmann and Maini, NatMed, 2003, 9 (10); 356-61

Firestein, 2003, Nature 423, 356-361

Han et al.; 2003, Autoimmunity, 28, 197-208

Hargreaves, K: Pain 32(1) (1988 January) 77-88

Huwe et al., Small molecules as inhibitors of cyclin-dependent kinases. Angew Chem Int Ed Engl, 2003, 42(19), 2122-2138

Kim et al., Phosphorylation of the RNA polymerase II carboxyl-terminal domain by CDK9 is directly responsible for human immunodeficiency virus type 1 Tat-activated transcriptional elongation. Mol Cell Biol, 2002, 22(13), 4622-4637.

Koltzenburg M, Neural mechanisms of cutaneous nociceptive pain. Clin J Pain, 2000, 16(3 Suppl), 131-138

Laufer S., Gay S. And Brune K., Inflammation and Rheumatic Diseases—The molecular basis of novel therapies, Thieme, 2003

Lee K. M. et al., Spinal NfkB activation induces COX-2 upregulation and contributes to inflammatory pain hypersensitivity. European Journal of Neuroscience, 2004, Vol. 19, 3375-3381

Liu H. and Herrmann C., Differential Localization and Expression of the CDK9 42k and 55k Isoforms. J Cell Physiol, 2004, 203, 251-260

MacLachlan T. K. et al., Binding of CDK9 to TRAF2. J Cell Biochem, 1998, 71(4), 467-478

Malmberg A B and Basbaum A I. (1998) Partial sciatic nerve injury in the mouse as a model of neuropathic pain: behavioral and neuroanatomical correlates. Pain 76: 215-2

Meijer L, Leclerc S., Leost M., Properties and potential applications of chemical inhibitors of cyclin-dependent kinases, Pharmacol Ther 1999, 82(2-3):279-284

Sausville, E. A. Trends Molec. Med. 2002, 8, S32-S37

Tian B. et al., Identification of direct genomic targets downstream of the NfkB transcription factor mediating TNF signaling. *JBC*, 2005, as manuscript M500437200

Wang D, et al., Inhibition of human immunodeficiency virus type 1 transcription by chemical cyclin-dependent kinase inhibitors. J. Virol. 2001; 75: 7266-7279

Watkins L. R. et al., Glial proinflammatory cytokines mediate exaggerated pain states: implications for clinical pain. *Adv Exp Med. Biol.*, 2003, 521, 1-21

West et al.; 2001, Journal of Virology 75(18), 8524-8537

Zhou M. et al., Coordination of transcription factor phosphorylation and histone methylation by the P-TEFb Kinase during human immunodeficiency virus type I transcription, J. Virol 2004, 78(24):13522-13533

The invention claimed is:
1. A compound according to the general Formula (I)

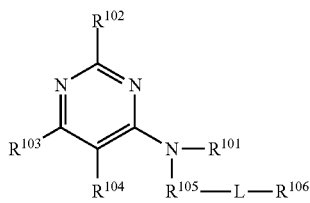

(I)

wherein
$R^{101}$ is selected from the group consisting of:
hydrogen, linear or branched $C_1$-$C_6$ substituted or unsubstituted alkyl, linear or branched $C_2$-$C_6$ alkenyl, and linear or branched $C_2$-$C_6$ alkynyl;
$R^{102}$ is selected from the group consisting of:
hydrogen, linear or branched substituted or unsubstituted $C_1$-$C_6$ alkyl, linear or branched $C_2$-$C_6$ alkenyl, linear or branched $C_2$-$C_6$ alkynyl, —F, —Cl, —Br, —I, —CN, —NH$_2$, N(C$_1$-C$_4$alkyl)$_2$, and —NO$_2$;
$R^{104}$ is selected from the group consisting of:
hydrogen, linear or branched substituted or unsubstituted $C_1$-$C_6$ alkyl, linear or branched $C_2$-$C_6$ alkenyl, linear or branched $C_2$-$C_6$ alkynyl, —F, —Cl, —Br, —I, —CN, —NH$_2$ and —NO$_2$;
$R^{103}$ is selected from substituted or unsubstituted phenyl or pyridine, wherein each substituent is independently selected from the group consisting of linear or branched $C_1$-$C_6$ substituted or unsubstituted alkyl, linear or branched substituted or unsubstituted $C_1$-$C_6$ alkoxy, linear or branched $C_2$-$C_6$ alkenyl, substituted or unsubstituted $C_{2-4}$ alkenyloxy, linear or branched $C_2$-$C_6$ alkynyl, substituted or unsubstituted $C_{3-7}$cycloalkyl, substituted or unsubstituted heterocycloalkyl, substituted or unsubstituted —O—heterocycloalkyl, substituted or unsubstituted $C_{1-4}$alkylsulfonyl, substituted or unsubstituted mono- and di-(C$_1$-C$_4$alkyl)sulfonamido, —F, —Cl, —Br, —I, —COOH, —CN, —NH$_2$, —OH, —NO$_2$, —NR$^{20}$R$^{21}$, —CO—R$^{20}$, —CO—O—R$^{20}$, and —CO—NR$^{20}$R$^{21}$, wherein R$^{20}$ and R$^{21}$ are independently of each other selected from the group consisting of hydrogen, linear or branched substituted or unsubstituted $C_1$-$C_6$ alkyl, acetyl, and substituted or unsubstituted amino;
$R^{105}$ is selected from the group consisting of substituted or unsubstituted phenyl or pyridine, wherein each substituent is independently selected from the group consisting of linear or branched $C_1$-$C_6$ substituted or unsubstituted alkyl, linear or branched substituted or unsubstituted $C_1$-$C_6$ alkoxy, linear or branched $C_2$-$C_6$ alkenyl, linear or branched $C_2$-$C_6$ alkynyl, —F, —Cl, —Br, —I, —CN, —NH$_2$, —NO$_2$, —NR$^{20}$R$^{21}$, —CO—R$^{20}$, and —CO—NR$^{20}$R$^{21}$, wherein R$^{20}$ and R$^{21}$ are independently of each other selected from the group consisting of hydrogen, linear or branched substituted or unsubstituted $C_1$-$C_6$ alkyl, acetyl, and substituted or unsubstituted amino;
$R^{106}$ is selected from the group consisting of hydrogen, linear or branched substituted or unsubstituted $C_1$-$C_8$ alkyl, substituted or unsubstituted $C_{3-4}$alkenyl, substituted or unsubstituted $C_{3-8}$-cycloalkyl, substituted or unsubstituted aryl, substituted or unsubstituted heteroaryl, substituted or unsubstituted heterocyclyl, substituted or unsubstituted $C_3$-$C_8$ cycloalkyl, and
—(CH$_2$)$_q$—A, wherein q is an integer selected from 0 to 5 and A is selected from the group consisting of hydrogen, —F, —Cl, —Br, —I, —CN, —NH$_2$, —NO$_2$, linear or branched substituted or unsubstituted $C_1$-$C_6$ alkyl, linear or branched substituted or unsubstituted $C_1$-$C_6$ alkoxy, linear or branched $C_2$-$C_6$ alkenyl, linear or branched $C_2$-$C_6$ alkynyl, substituted or unsubstituted heterocyclyl, substituted or unsubstituted cycloalkyl, and carboxamido substituted with one or two $C_1$-$C_6$ alkyl; or
$R^{106}$, when M is —NR$^{140}$—, can form a heterocyclic structure when taken together with the nitrogen of M and R$^{140}$;
L is —CR$^{150}$R$^{151}$—SO$_2$—M—,
wherein R$^{150}$ and R$^{151}$ are independently selected from the group consisting of hydrogen, linear $C_1$-$C_3$ alkyl and fluorine, wherein M is a bond or —NR$^{140}$—;
$R^{140}$ is selected from the group consisting of hydrogen, linear or branched substituted or unsubstituted $C_1$-$C_8$ alkyl, and substituted or unsubstituted $C_3$-$C_8$ cycloalkyl;
or, alternatively, —L—R$^{106}$, when taken together, is selected from the group consisting of:

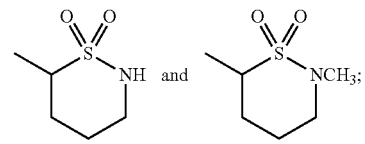

and tautomeric forms,
N-oxides, individual stereoisomers and mixtures of stereoisomers thereof;
and the pharmaceutically acceptable salts of such compounds.

2. The compound of claim 1, wherein:
$R^{101}$ is selected from the group consisting of:
hydrogen, linear or branched $C_1$-$C_6$ substituted or unsubstituted alkyl, linear or branched $C_2$-$C_6$ alkenyl, and linear or branched $C_2$-$C_6$ alkynyl;
$R^{102}$ and $R^{104}$ are independently selected from the group consisting of:
hydrogen, linear or branched substituted or unsubstituted $C_1$-$C_6$ alkyl, linear or branched $C_2$-$C_6$ alkenyl, linear or branched $C_2$-$C_6$ alkynyl, —F, —Cl, —Br, —I, —CN, —NH$_2$, and —NO$_2$;
$R^{103}$ and $R^{105}$ are independently selected from the group consisting of substituted or unsubstituted phenyl and substituted or unsubstituted pyridine, wherein each substituent is independently selected from the group consisting of linear or branched $C_1$-$C_6$ substituted or unsubstituted alkyl, linear or branched substituted or unsubstituted $C_1$-$C_6$ alkoxy, linear or branched $C_2$-$C_6$ alkenyl, linear or branched $C_2$-$C_6$ alkynyl, —F, —Cl, —Br, —I, —CN, —NH$_2$, —NO$_2$, —NR$^{20}$R$^{21}$, —CO—R$^{20}$, and —CO—NR$^{20}$R$^{21}$, wherein R$^{20}$ and R$^{21}$ are independently of each other selected from the group consisting of hydrogen, linear or branched substituted or unsubstituted $C_1$-$C_6$ alkyl, acetyl, and substituted or unsubstituted amino;

R$^{106}$ is selected from the group consisting of hydrogen, linear or branched substituted or unsubstituted $C_1$-$C_8$ alkyl, substituted or unsubstituted aryl, substituted or unsubstituted heteroaryl, substituted or unsubstituted heterocyclyl, substituted or unsubstituted $C_3$-$C_8$ cycloalkyl, and —(CH$_2$)$_q$-A, wherein q is an integer selected from 0 to 5 and A is selected from the group consisting of hydrogen, —F, —Cl, —Br, —I, —CN, —NH$_2$, —NO$_2$, linear or branched substituted or unsubstituted $C_1$-$C_6$ alkyl, linear or branched substituted or unsubstituted $C_1$-$C_6$ alkoxy, linear or branched $C_2$-$C_6$ alkenyl, linear or branched $C_2$-$C_6$ alkynyl, substituted or unsubstituted heterocyclyl, substituted or unsubstituted cycloalkyl, and carboxamido substituted with one or two $C_1$-$C_6$ alkyl; or R$^{106}$, when M is —NR$^{140}$—, can form a heterocyclic structure when taken together with the nitrogen of M and R$^{140}$;

L is —CR$^{150}$R$^{151}$—SO$_2$—M—, wherein R$^{150}$ and R$^{151}$ are independently selected from the group consisting of hydrogen, linear $C_1$-$C_3$ alkyl, and fluorine, wherein M is a bond or —NR$^{140}$—; and R$^{140}$ is selected from hydrogen, linear or branched substituted or unsubstituted $C_1$-$C_8$ alkyl, and substituted or unsubstituted $C_3$-$C_8$ cycloalkyl;

and tautomeric forms and pharmaceutically acceptable salts thereof.

3. The compound of claim 2 having the general Formula (II)

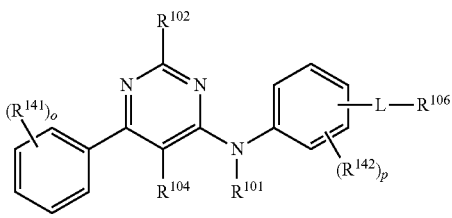

wherein:

R$^{101}$ and R$^{104}$ are hydrogen;

R$^{102}$ is hydrogen or —NH$_2$;

R$^{106}$ is selected from the group consisting of hydrogen, linear or branched substituted or unsubstituted $C_1$-$C_8$ alkyl, substituted or unsubstituted aryl, substituted or unsubstituted heteroaryl, substituted or unsubstituted heterocyclyl, substituted or unsubstituted $C_3$-$C_8$ cycloalkyl, and —(CH$_2$)$_q$—A, wherein q is an integer selected from 0 to 5 and A is selected from the group consisting of hydrogen, —F, —Cl, —Br, —I, —CN, —NH$_2$, —NO$_2$, linear or branched substituted or unsubstituted $C_1$-$C_6$ alkyl, linear or branched substituted or unsubstituted $C_1$-$C_6$ alkoxy, linear or branched $C_2$-$C_6$ alkenyl, linear or branched $C_2$-$C_6$ alkynyl, substituted or unsubstituted heterocyclyl, substituted or unsubstituted cycloalkyl, and carboxamido substituted with one or two $C_1$-$C_6$ alkyl; or R$^{106}$, when M is —NR$^{140}$—, can form a heterocyclic structure when taken together with the nitrogen of M and R$^{140}$;

L is —CR$^{150}$R$^{151}$—SO$_2$—M—, wherein R$^{150}$ and R$^{151}$ are independently selected from the group consisting of hydrogen, linear $C_1$-$C_3$ alkyl, and fluorine, wherein M is a bond or —NR$^{140}$—;

R$^{140}$ is selected from the group consisting of hydrogen, linear or branched substituted or unsubstituted $C_1$-$C_8$ alkyl, and substituted or unsubstituted $C_3$-$C_8$ cycloalkyl;

o is an integer selected from 0 to 5;

p is an integer selected from 0 to 4;

each R$^{141}$ and R$^{142}$ is independently selected from the group consisting of linear or branched $C_1$-$C_6$ substituted or unsubstituted alkyl, linear or branched substituted or unsubstituted $C_1$-$C_6$ alkoxy, linear or branched $C_2$-$C_6$ alkenyl, linear or branched $C_2$-$C_6$ alkynyl, —F, —Cl, —Br, —I, —CN, —NH$_2$, and —NO$_2$;

and tautomeric forms and pharmaceutically acceptable salts thereof.

4. The compound of claim 3 wherein at least one R$^{141}$ is methoxy.

5. The compound of claim 3, wherein at least one R$^{141}$ is in the ortho position.

6. The compound of claim 5, wherein the R$^{141}$ in the ortho-position is methoxy.

7. The compound of claim 3 wherein R$^{150}$ and R$^{151}$ are both hydrogen.

8. The compound of claim 3 wherein M is —NR$^{140}$ and R$^{140}$ is selected from the group consisting of hydrogen, methyl, ethyl, and isopropyl.

9. The compound of claim 8 wherein R$^{140}$ is hydrogen.

10. The compound of claim 8 wherein R$^{140}$ is methyl.

11. The compound of claim 3, wherein R$^{106}$ is selected from the group consisting of hydrogen, linear or branched substituted or unsubstituted $C_1$-$C_8$ alkyl, and —(CH$_2$)$_q$A, wherein q is an integer selected from 0 to 5 and A is selected from the group consisting of linear or branched substituted or unsubstituted $C_1$-$C_6$ alkoxy, substituted or unsubstituted heterocyclyl, substituted or unsubstituted heteroaryl, and carboxamido substituted with one or two $C_1$-$C_6$ alkyl.

12. The compound of claim 11, wherein R$^{106}$ is hydrogen.

13. The compound of claim 11, wherein R$^{106}$ is linear or branched unsubstituted $C_{1-5}$ alkyl.

14. The compound of claim 3 wherein L is linked to the phenyl group of the compound in the meta-position.

15. The compound of claim 1 having the general Formula (III)

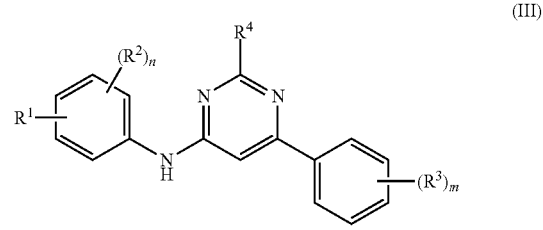

wherein

R$^1$ is —XSO$_2$NR$^5$R$^6$ or —XSO$_2$R$^8$;

X is methylene;

R$^5$ and R$^6$ independently of each other are selected from the group consisting of hydrogen, $C_{1-4}$alkyl, hydroxy-$C_{1-4}$alkyl or $C_{3-4}$alkenyl, $C_{3-8}$-cycloalkyl, $C_{3-8}$-cycloalkyl-$C_{1-4}$alkyl, $C_{4-7}$-heterocycloalkyl-$C_{0-4}$alkyl, $C_{4-7}$-aryl-$C_{0-4}$alkyl, and $C_{4-7}$-heteroaryl-$C_{0-4}$alkyl or wherein $R^5$ and $R^6$ together with the N-atom to which they are bound also form a 5- to 8-membered heterocycloalkyl, wherein said cycloalkyl, heterocycloalkyl, aryl, heteroaryl or alkyl is further optionally substituted by up to 2 radicals selected from the group consisting of halo, hydroxy, aminocarbonyl, $C_{1-4}$alkyl, hydroxy-$C_{1-4}$alkyl, $C_{1-4}$ alkyl—O—$C_{1-4}$alkyl, $C_{1-4}$alkyl—O—, and —$NR^5R^6$;

or —$XSO_2NR^5R^6$ is:

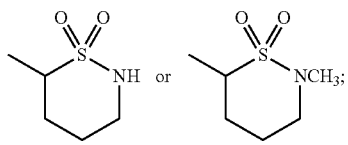

$R^8$ is $C_{1-4}$alkyl, hydroxy-$C_{2-4}$alkyl or $C_{3-4}$alkenyl, $C_{3-8}$-cycloalkyl, $C_{3-8}$-cycloalkyl-$C_{1-4}$alkyl, and $C_{4-7}$-heterocycloalkyl-$C_{0-4}$ alkyl;

wherein said cycloalkyl, heterocycloalkyl or alkyl is further optionally substituted by up to 2 radicals selected from the group consisting of halo, hydroxy, $C_{1-4}$ alkyl, hydroxy-$C_{1-4}$ alkyl, $C_{1-4}$alkyl—O—$C_{1-4}$ alkyl, $C_{1-4}$ alkyl-O, and —$NR^5R^6$;

n is selected from 0, 1 and 2;

$R^2$ is independently selected from halo;

m is selected from 0, 1, 2 and 3;

$R^3$ is independently selected from the group consisting of: halo, hydroxy, $C_{1-4}$alkyl, $C_{3-7}$cycloalkyl, $C_{1-4}$ alkyl-cycloalkyl, $C_{1-4}$ alkyl-heterocycloalkyl, —O-heterocycloalkyl, $C_{1-4}$ alkoxy, $C_{2-4}$ alkenyloxy, —$OCF_3$, $C_{2-4}$ alkanoyl, $C_{1-4}$alkylsulfonyl, mono- and di-($C_1$-$C_4$alkyl)sulfonamido, aminocarbonyl, mono- and di-($C_1$-$C_4$alkyl)aminocarbonyl, aryl-$C_{1-4}$ alkoxy, heteroaryl-$C_{1-4}$ alkoxy, heterocycloalkyl-$C_{1-4}$ alkoxy, heterocycloalkyl-$C_{1-4}$ alkyl, heteroaryl-$C_{1-4}$-alkyl, $C_{1-4}$ alkyloxymethyl, hydroxy-$C_{14}$alkyloxymethyl, cyano, —COOH, and $C_1$-$C_4$ alkoxycarbonyl, wherein the above mentioned substituents can be further substituted by radicals selected from the group of $C_{1-4}$-alkyl, hydroxyl-$C_{0-4}$-alkyl, $C_{1-4}$-alkoxy, aminocarbonyl, halo, and $NR^5R^6$; and $R^4$ is hydrogen, $C_{1-4}$ alkyl or —NR'R", wherein R' and R" are each independently selected from the group consisting of hydrogen and $C_{1-4}$ alkyl.

16. The compound of claim 15, wherein $R^1$ is —$XSO_2NR^5R^6$, $R^6$ is hydrogen or methyl and $R^5$ is selected from the group consisting of ethyl, 2-hydroxyethyl, isopropyl, cyclopropyl, cyclobutyl, cyclopentyl, cyclohexyl, n-propyl, tert-butyl, 3-methoxy-propyl, 2-dimethylaminoethyl, 3-dimethylaminopropyl, piperidinyl, pyridinyl, pyrrolidinyl, tetrahydrofuranyl, tetrahydro-furan-2-ylmethyl, 4-chlorobenzyl, and thiophen-2-yl-methyl, or $R^5$ and $R^6$ are both hydrogen, methyl or ethyl, or $R^5$ and $R^6$ together with the N-atom to which they are bound form morpholine, 4-aminocarbonyl-piperidine or azepane, or —$XSO_2NR^5R^6$ is:

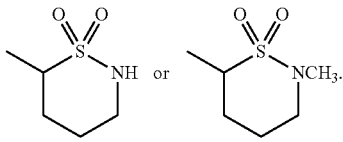

17. The compound of claim 15, wherein $R^1$ is —$XSO_2R^8$ and $R^8$ is $C_{1-4}$ alkyl or hydroxy $C_{2-4}$ alkyl.

18. The compound of claim 15, wherein m is selected from 1, 2 and 3, $R^3$ is independently selected from the group consisting of hydrogen, halo, hydroxy, $C_{1-4}$alkyl, $C_{1-4}$ alkoxy, $C_{2-4}$ alkenyloxy, —$OCF_3$, $C_{2-4}$ alkanoyl, $C_{1-4}$alkylsulfonyl, mono- and di-($C_1$-$C_4$alkyl)sulfonamido, aminocarbonyl, mono- and di-($C_1$-$C_4$alkyl)aminocarbonyl, $C_{1-4}$ alkyloxymethyl, hydroxy-$C_{1-4}$alkyloxymethyl, cyano, —COOH, and $C_1$-$C_4$ alkoxycarbonyl; or one substituent selected from $C_{3-7}$cycloalkyl, $C_{1-4}$ alkyl -cycloalkyl, $C_{1-4}$ alkyl -heterocycloalkyl, —O—heterocycloalkyl, aryl-$C_{1-4}$ alkoxy, heterocycloalkyl-$C_{1-4}$ alkoxy, heterocycloalkyl-$C_{1-4}$-alkyl, heteroaryl-$C_{1-4}$ alkoxy, and heteroaryl-$C_{1-4}$-alkyl; wherein said substituents can be further substituted by one or more radicals selected from the group of $C_{1-4}$-alkyl, hydroxyl-$C_{0-4}$-alkyl, $C_{1-4}$-alkoxy, halo, aminocarbonyl, and $NR^5R^6$.

19. The compound of claim 18 wherein $R^3$ is selected from the group consisting of methyl, ethyl, hydroxymethyl, hydroxy, methoxy, ethoxy, isopropoxy, benzyloxy, hydrogen, fluoro, chloro, trifluoromethyl, 2-methoxy-ethoxy, methoxymethyl, 2-methoxy-ethyl, tetrahydro-furan-3-yloxy, tetrahydro-furan-2-yl-methoxy, —$N(CH_3)SO_2CH_3$, piperidin-1-yl-methyl, 2-hydroxymethyl-piperidin-1-yl-methyl, 3-hydroxymethyl-piperidin-1-yl-methyl, 3-(2-hydroxyethyl)-piperidin-1-yl-methyl, 3-aminocarbonyl-piperidin-1-yl-methyl, dimethylaminomethyl, diethylaminomethyl, (ethyl-isopropyl-amino)-methyl, morpholin-4-ylmethyl, 4-methyl-piperazin-1-yl-methyl, [1,2,4]triazol-1-yl-methyl, pyridine-3-yl-methoxy, and pyridine-4-yl-methoxy.

20. The compound of claim 15, wherein X is methylene.

21. The compound of claim 15, wherein the compound has a structure according to Formula (IIIa),

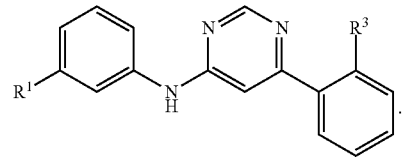

22. The compound of claim 1, which is selected from the group consisting of:
{3-[6-(2-Ethoxy-phenyl)-pyrimidin-4-ylamino]-phenyl}-methanesulfonamide (Compound 1);
{3-[6-(2,3-Dimethoxy-phenyl)-pyrimidin-4-ylamino]-phenyl}-methanesulfonamide (Compound 2);
{3-[6-(4-Fluoro-2-methoxy-phenyl)-pyrimidin-4-ylamino]-phenyl}-methanesulfonamide (Compound 3);
{3-[6-(2-Ethoxy-5-fluoro-phenyl)-pyrimidin-4-ylamino]-phenyl}-methanesulfonamide (Compound 4);
{3-[6-(2-Isopropoxy-phenyl)-pyrimidin-4-ylamino]-phenyl}-methanesulfonamide (Compound 5);
{3-[6-(3-Fluoro-phenyl)-pyrimidin-4-ylamino]-phenyl}-methanesulfonamide (Compound 6);
{3-[6-(4-Fluoro-phenyl)-pyrimidin-4-ylamino]-phenyl}-methanesulfonamide (Compound 7);

{3-[6-(3-Ethoxy-phenyl)-pyrimidin-4-ylamino]-phenyl}-methanesulfonamide (Compound 8);

{3-[6-(3-Benzyloxy-phenyl)-pyrimidin-4-ylamino]-phenyl}-methanesulfonamide (Compound 9);

N-Isopropyl-C-{3-[6-(2-methoxy-phenyl)-pyrimidin-4-ylamino]-phenyl}-methanesulfonamide (Compound 10);

N-Cyclopropyl-C-{3-[6-(2-methoxy-phenyl)-pyrimidin-4-ylamino]-phenyl}-methanesulfonamide (Compound 11);

C-{3-[6-(2-Ethoxy-phenyl)-pyrimidin-4-ylamino]-phenyl}-N-propyl-methanesulfonamide (Compound 12);

N-Cyclopentyl-C-{3-[6-(2-ethoxy-phenyl)-pyrimidin-4-ylamino]-phenyl}-methanesulfonamide (Compound 13);

C-{3-[6-(2-Methoxy-phenyl)-pyrimidin-4-ylamino]-phenyl}-N-propyl-methanesulfonamide (Compound 14);

N-tert-Butyl-C-{3-[6-(2-methoxy-phenyl)-pyrimidin-4-ylamino]-phenyl}-methanesulfonamide (Compound 15);

N-Cyclopentyl-C-{3-[6-(2-methoxy-phenyl)-pyrimidin-4-ylamino]-phenyl}-methanesulfonamide (Compound 16);

C-{3-[6-(2-Ethoxy-phenyl)-pyrimidin-4-ylamino]-phenyl}-N-isopropyl-methanesulfonamide (Compound 17);

N-Cyclopropyl-C-{3-[6-(2-ethoxy-phenyl)-pyrimidin-4-ylamino]-phenyl}-methanesulfonamide (Compound 18);

N-tert-Butyl-C-{3-[6-(2-ethoxy-phenyl)-pyrimidin-4-ylamino]-phenyl}-methanesulfonamide (Compound 19);

C-{3-[6-(2-Methoxy-phenyl)-pyrimidin-4-ylamino]-phenyl}-N,N-dimethyl-methanesulfonamide (Compound 20);

C-{3-[6-(2-Benzyloxy-phenyl)-pyrimidin-4-ylamino]-phenyl}-N-propyl-methanesulfonamide (Compound 21);

C-{3-[6-(2-Benzyloxy-phenyl)-pyrimidin-4-ylamino]-phenyl}-N-isopropyl-methanesulfonamide (Compound 22);

C-{3-[6-(2-Benzyloxy-phenyl)-pyrimidin-4-ylamino]-phenyl}-N-cyclopropyl-methanesulfonamide (Compound 23);

C-{3-[6-(2-Benzyloxy-phenyl)-pyrimidin-4-ylamino]-phenyl}-N,N-dimethyl-methanesulfonamide (Compound 24);

C-{3-[6-(3-Benzyloxy-phenyl)-pyrimidin-4-ylamino]-phenyl}-N,N-dimethyl-methanesulfonamide (Compound 25);

{3-[6-(2-Ethyl-phenyl)-pyrimidin-4-ylamino]-phenyl}-methanesulfonamide (Compound 26);

C-{3-[6-(3-Ethoxy-phenyl)-pyrimidin-4-ylamino]-phenyl}-N,N-dimethyl-methanesulfonamide (Compound 27);

C-{3-[6-(2-Ethoxy-phenyl)-pyrimidin-4-ylamino]-phenyl}-N,N-dimethyl-methanesulfonamide (Compound 28);

C-{3-[6-(2-Benzyloxy-phenyl)-pyrimidin-4-ylamino]-phenyl}-N-cyclopentyl-methanesulfonamide (Compound 29);

C-{3-[6-(2-Benzyloxy-phenyl)-pyrimidin-4-ylamino]-phenyl}-N-tert-butyl-methanesulfonamide (Compound 30);

C-{3-[6-(3-Benzyloxy-phenyl)-pyrimidin-4-ylamino]-phenyl}-N-isopropyl-methanesulfonamide (Compound 31);

{3-[6-(2-Benzyloxy-phenyl)-pyrimidin-4-ylamino]-phenyl}-methanesulfonamide (Compound 32);

C-{3-[6-(2-Methoxy-phenyl)-pyrimidin-4-ylamino]-phenyl}-N-(3-methoxy-propyl)-methanesulfonamide (Compound 33);

N-Cyclohexyl-C-{3-[6-(2-methoxy-phenyl)-pyrimidin-4-ylamino]-phenyl}-methanesulfonamide (Compound 34);

C-{3-[6-(2-Methoxy-phenyl)-pyrimidin-4-ylamino]-phenyl}-N-(tetrahydro-furan-2-ylmethyl)-methanesulfonamide (Compound 35);

N-(4-Chloro-benzyl)-C-{3-[6-(2-methoxy-phenyl)-pyrimidin-4-ylamino]-phenyl}-methanesulfonamide (Compound 36);

C-{3-[6-(2-Methoxy-phenyl)-pyrimidin-4-ylamino]-phenyl}-N-thiophen-2-ylmethyl-methanesulfonamide (Compound 37);

N,N-Diethyl-C-{3[6-(2-methoxy-phenyl)-pyrimidin-4-ylamino]-phenyl}-methanesulfonamide (Compound 38);

N-(2-Hydroxy-ethyl)-C-{3-[6-(2-methoxy-phenyl)-pyrimidin-4-ylamino]-phenyl}-N-methyl-methanesulfonamide (Compound 39);

1-{3-[6-(2-Methoxy-phenyl)-pyrimidin-4-ylamino]-phenylmethanesulfonyl}-piperidine-4-carboxylic acid amide (Compound 40);

[6-(2-Methoxy-phenyl)-pyrimidin-4-yl]-[3-(morpholine-4-sulfonylmethyl)-phenyl]-amine (Compound 41);

[3-(Azepane-1-sulfonylmethyl)-phenyl]-[6-(2-methoxy-phenyl)-pyrimidin-4-yl]-amine (Compound 42);

C-{3-[6-(2-Ethoxy-phenyl)-pyrimidin-4-ylamino]-phenyl}-N-methyl-methanesulfonamide (Compound 43);

C-{3-[6-(2-Benzyloxy-phenyl)-pyrimidin-4-ylamino]-phenyl}-N-methyl-methanesulfonamide (Compound 44);

N-Ethyl-C-{3-[6-(2-methoxy-phenyl)-pyrimidin-4-ylamino]-phenyl}-methanesulfonamide (Compound 45);

N-(2-Hydroxy-ethyl)-C-{3-[6-(2-methoxy-phenyl)-pyrimidin-4-ylamino]-phenyl}-methanesulfonamide (Compound 46);

C-{3-[6-(2-Benzyloxy-phenyl)-pyrimidin-4-ylamino]-phenyl}-N,N-diethyl-methanesulfonamide (Compound 47);

C-{3-[6-(2-Benzyloxy-phenyl)-pyrimidin-4-ylamino]-phenyl}-N-(2-hydroxy-ethyl)-N-methyl-methanesulfonamide (Compound 48);

C-{3-[6-(2-Methoxy-phenyl)-pyrimidin-4-ylamino]-phenyl}-N-methyl-methanesulfonamide (Compound 49);

[3-(6-Phenyl-pyrimidin-4-ylamino)-phenyl]-methanesulfonamide (Compound 50);

{3-[6-(2-Chloro-phenyl)-pyrimidin-4-ylamino]-phenyl}-methanesulfonamide (Compound 51);

2-[6-(3-Methanesulfonylmethyl-phenylamino)-pyrimidin-4-yl]-phenol (Compound 52);

[6-(2-Benzyloxy-phenyl)-pyrimidin-4-yl]-(3-methanesulfonylmethyl-phenyl)-amine (Compound 53);

{3-[6-(2-Hydroxy-phenyl)-pyrimidin-4-ylamino]-phenyl}-methanesulfonamide (Compound 54);

{3-[6-(2-Hydroxymethyl-phenyl)-pyrimidin-4-ylamino]-phenyl}-methanesulfonamide (Compound 55);

{2-[6-(3-Methanesulfonylmethyl-phenylamino)-pyrimidin-4-yl]9-phenyl}-methanol (Compound 56);

(3-Methanesulfonylmethyl-phenyl)-{6[2-(2-methoxy-ethoxy)-phenyl]-pyrimidin-4-yl}-amine (Compound 57);

[6-(2-Benzyloxy-phenyl)-pyrimidin-4-yl]-(3-methanesulfonylmethyl-phenyl)-amine (Compound 58);

(3-Methanesulfonylmethyl-phenyl)[6-(2-methoxy-phenyl)-pyrimidin-4-yl]-amine (Compound 59);

(3-Methanesulfonylmethyl-phenyl)-{6-[2-(tetrahydro-furan-3-yloxy)-phenyl]-pyrimidin-4-yl}-amine (Compound 60);

{3-[6-(2-Fluoro-phenyl)-pyrimidin-4-ylamino]-phenyl}-methanesulfonamide (Compound 61);

{3-[6-(4-Methoxy-phenyl)-pyrimidin-4-ylamino]-phenyl}-methanesulfonamide (Compound 62);

{3-[6-(3-Trifluoromethyl-phenyl)-pyrimidin-4-ylamino]-phenyl}-methanesulfonamide (Compound 63);

(3-Methanesulfonylmethyl-phenyl)-{6-[2-(tetrahydro-furan-2-ylmethoxy)-phenyl]-pyrimidin-4-yl}-amine (Compound 64);

(3-{6-[2-(Tetrahydro-furan-3-yloxy)-phenyl]-pyrimidin-4-ylamino}-phenyl)-methanesulfonamide (Compound 65);

{3-[2-Amino-6-(2-methoxy-phenyl)-pyrimidin-4-ylamino]-phenyl}-methanesulfonamide (Compound 66);

[3-(1,1-Dioxo-[1,2]thiazinan-6-yl)-phenyl]-[6-(2-methoxy-phenyl)-pyrimidin-4-yl]-amine (Compound 67);

[6-(2-Methoxy-phenyl)-pyrimidin-4-yl]-[3-(2-methyl-1,1-dioxo-[1,2]thiazinan-6-yl)-phenyl]-amine (Compound 68);

{3-[6-(3-Hydroxymethyl-phenyl)-pyrimidin-4-ylamino]-phenyl}-methanesulfonamide (Compound 69);

(3-{6-[3-(2-Hydroxymethyl-piperidin-1-ylmethyl)-phenyl]-pyrimidin-4-ylamino}-phenyl)-methanesulfonamide (Compound 70);

(3-{6-[3-(3-Hydroxymethyl-piperidin-1-ylmethyl)-phenyl]-pyrimidin-4-ylamino}-phenyl)-methanesulfonamide (Compound 71);

[3-(6-{3-[3-(2-Hydroxy-ethyl)-piperidin-1-ylmethyl]-phenyl}-pyrimidin-4-ylamino)-phenyl]-methanesulfonamide (Compound 72);

1-{3[6-(3-Sulfamoylmethyl-phenylamino)-pyrimidin-4-yl]-benzyl}-piperidine-3-carboxylic acid amide (Compound 73);

{3-[6-(3-Dimethylaminomethyl-phenyl)-pyrimidin-4-ylamino]-phenyl}-methanesulfonamide (Compound 74);

{3-[6-(3-Diethylaminomethyl-phenyl)-pyrimidin-4-ylamino]-phenyl}-methanesulfonamide (Compound 75);

[3-(6-{3-[(Ethyl-isopropyl-amino)-methyl]-phenyl}-pyrimidin-4-ylamino)-phenyl]-methanesulfonamide (Compound 76);

{3-[6-(3-Morpholin-4-ylmethyl-phenyl)-pyrimidin-4-ylamino]-phenyl}-methanesulfonamide (Compound 77);

(3-{6-[3-(4-Methyl-piperazin-1-ylmethyl)-phenyl]-pyrimidin-4-ylamino}-phenyl)-methanesulfonamide (Compound 78);

{3-[6-(3-[1,2,4]Triazol-1-ylmethyl-phenyl)-pyrimidin-4-ylamino]-phenyl}-methanesulfonamide (Compound 79);

C-{3-[6-(2-Methoxymethyl-phenyl)-pyrimidin-4-ylamino]-phenyl}-N-methyl-methanesulfonamide (Compound 80);

(3-{6-[2-(2-Methoxy-ethoxy)-phenyl]-pyrimidin-4-ylamino}-phenyl)-methanesulfonamide (Compound 81);

(3-{6-[2-(Tetrahydro-furan-2-ylmethoxy)-phenyl]-pyrimidin-4-ylamino}-phenyl)-methanesulfonamide (Compound 82);

(3-{6-[2-(2-Methoxy-ethoxy)-phenyl]-2-methyl-pyrimidin-4-ylamino}-phenyl)-methanesulfonamide (Compound 83);

[3-(3-Dimethylamino-propane-1-sulfonylmethyl)-phenyl]-[6-(2-methoxy-phenyl)-pyrimidin-4-yl]-amine (Compound 84);

C-{3-[6-(2-Methoxy-phenyl)-pyrimidin-4-ylamino]-phenyl}-methanesulfonamide (Compound 85); and N-(2-Methoxy-ethyl)-C-{3-[6-(2-methoxy-phenyl)-pyrimidin-4-ylamino]-phenyl}-methanesulfonamide (Compound 86).

23. A pharmaceutical composition containing the compound of claim 1, together with a pharmaceutically acceptable carrier.

24. C-{3-[6-(2-Methoxy-phenyl)-pyrimidin-4-ylamino]-phenyl}-methanesulfonamide.

* * * * *